United States Patent
Lin et al.

(10) Patent No.: US 11,325,937 B2
(45) Date of Patent: May 10, 2022

(54) GLYCOSIDE COMPOUND AND PREPARATION METHOD THEREFOR, COMPOSITION, APPLICATION, AND INTERMEDIATE

(71) Applicant: SHANGHAI HUTCHISON PHARMACEUTICALS LIMITED, Shanghai (CN)

(72) Inventors: Guoqiang Lin, Shanghai (CN); Jiange Zhang, Shanghai (CN); Ping Tian, Shanghai (CN); Chenguo Feng, Shanghai (CN); Changsen Zhan, Shanghai (CN); Junjie Zhou, Shanghai (CN)

(73) Assignee: SHANGHAI HUTCHISON PHARMACEUTICALS LIMITED, Shanghai (CN)

( * ) Notice: Subject to any disclaimer, the term of this patent is extended or adjusted under 35 U.S.C. 154(b) by 0 days.

(21) Appl. No.: 17/054,124

(22) PCT Filed: May 7, 2019

(86) PCT No.: PCT/CN2019/085823
§ 371 (c)(1),
(2) Date: Nov. 9, 2020

(87) PCT Pub. No.: WO2020/001166
PCT Pub. Date: Jan. 2, 2020

(65) Prior Publication Data
US 2021/0115082 A1 Apr. 22, 2021

(30) Foreign Application Priority Data

Jun. 27, 2018 (CN) .......................... 201810680576.5

(51) Int. Cl.
*C07H 15/18* (2006.01)
*C07H 15/26* (2006.01)
*C07H 5/10* (2006.01)

(52) U.S. Cl.
CPC ............... *C07H 15/26* (2013.01); *C07H 5/10* (2013.01); *C07H 15/18* (2013.01)

(58) Field of Classification Search
None
See application file for complete search history.

(56) References Cited

U.S. PATENT DOCUMENTS 5,674,987 A * 10/1997 Gray .................. C07H 15/20
536/18.6

FOREIGN PATENT DOCUMENTS

| CN | 1631895 A | 6/2005 |
|---|---|---|
| CN | 101255178 A | 9/2008 |
| CN | 102238983 A | 11/2011 |
| CN | 102772423 A | 11/2012 |
| CN | 105687216 A | 6/2016 |
| CN | 107460220 A | 12/2017 |

OTHER PUBLICATIONS

Wolff, Manfred E. "Burger's Medicinal Chemistry, 5ed, Part I", John Wiley & Sons, 1995, pp. 975-977. (Year: 1995).*
Banker, G.S. et al, "Modern Pharmaceutics, 3ed.", Marcel Dekker, New York, 1996, p. 596 (Year: 1996).*
AN 2009:1074039; Hao et al., Sichuan Daxue Xuebao, Ziran Kexueban, 2009, 46(3), pp. 697-702. (Year: 2009).*
RN 167019-03-06, RN 174408-86-7, RN 1053724-87-0, etc. STN Registry, Feb. 22, 2010.
Parchornik, A. et al., "Universal Standard Reagents. The Use of 3-(2,4,-Dinitro-Anilino)Propanol(DNAO) and 1-(2,4,-Dinitrophenyl1)-4-Hydroxypiperidine (DNPP) in Glycosylation and Selective Hydrolysis of Ester Glucosides" Heterocycle , vol. 51, No. (6), Dec. 31, 1999 pp. 1243-1256.
Boysen, et al., "Synthesis of Selectively Functionalized Carbosilane Dendrimers with a Carbohydrate Core", Institute of Organic Chemistry, Sep. 17, 1999, pp. 1925-1927.
Matsuoka, et al., "Carbosilane Dendrimers Bearing Globotriaoses: Construction of a Series of Carbosilane Dendrimers Bearing Globotriaoses", Biomacromolecules 2006, 7, pp. 2284-2290.
Matsuoka, et al., "Carbosilane Dendrimers Bearing Globotriaoses: Syntheses of Globotrioasyl Derivative and Introduction into Carbosilane Dendrimers", Biomacromolecules 2006, 7, pp. 2274-2283.
Azefu, et al., "Facile Synthesis of Stable Lipid Analogues Possessing a Range of Alkyl Groups: Application to Artificial Glycolipids", Bioorganic & Medicinal Chemistry 10 (2002) pp. 4013-4022.
Zhao Y, Thorson JS. Chemoenzymatic synthesis of the *Salmonella* group E1 core trisaccharide using a recombinant beta-(1-->4)-mannosyltransferase. Carbohydr Res. Jun. 30, 1999;319(1-4):184-91.
Zhao, et al., "Acceptor Specificity of *Salmonella* GDP-Man:α | Rhal→3α d d Gal- PP -Und β1→4-Mannosyltransferase: A Simplified Assay Based on Unnatural Acceptors", J Am. Chem. Soc. 1998, 120, pp. 12986-12987.
Matsuoka, et al., "Synthetic assembly of trisaccharide moieties of globotriaosyl ceramide using carbosilane dendrimers as cores. A new type of functional glyco-material", Tetrahedron Letters, vol. 40, Issue 44, Oct. 1999, pp. 7839-7842.
Hao et al., "The Effect of Several Structures for Salidroside on its Antioxidation Activity", Journal of Sichuan University, vol. 46 No. 3, May 2009, pp. 697-702.

(Continued)

Primary Examiner — Traviss C McIntosh, III
(74) Attorney, Agent, or Firm — Dilworth IP, LLC

(57) ABSTRACT

The present invention discloses a glycoside compound represented by Formula III, and a preparation method, a composition, use and an intermediate thereof. The glycoside compound provided in the present invention has simple preparation method, can significantly increase the expression of VEGF-A mRNA, and is effective in promoting the angiogenesis. This provides a reliable guarantee for the development of drugs with pro-angiogenic activity for treating cerebral infarction cerebral stroke, myocardial infarction, and ischemic microcirculatory disturbance of lower limbs.

28 Claims, 11 Drawing Sheets

(56) References Cited

OTHER PUBLICATIONS

Gloe TE, Müller A, Ciuk A, Wrodnigg TM, Lindhorst TK. Synthesis of AB4-type carbohydrate scaffolds as branching units in the glycosciences. Carbohydr Res. Apr. 29, 2016;425: pp. 1-9.
Arimitsu K, Kimura H, Kajimoto T, Ono M, Ohmomo Y, Yamashita M, Node M, Saji H. Novel design and synthesis of a radioiodinated glycolipid analog as an acceptor substrate for N-acetylglucosaminyltransferase V. J Labelled Comp Radiopharm. Sep. 2013;56(11): pp. 562-572.
Cao Qiongdan et al., "Effect of Astragaloside IV on Oxidative Stress Induced by High Glucose in Neonatal Rats Myocardial Cells", 2015, 5 pages.

\* cited by examiner

GLYCOSIDE COMPOUND AND PREPARATION METHOD THEREFOR, COMPOSITION, APPLICATION, AND INTERMEDIATE

BACKGROUND

Technical Field

The present invention relates to a glycoside compound, and a preparation method, a composition, use and an intermediate thereof.

Related Art

In recent years, research on drugs directed against angiogenesis has attracted more and more attention, and angiogenesis has become a potential biological target for drug intervention in the treatment of cancers, vascular diseases and chronic inflammation. The development of drugs, such as anti-angiogenesis inhibitors intended to reduce tumor angiogenesis, has become a successful way for treatment of many advanced and aggressive cancers. The discovery of pro-angiogenesis has provided a new direction for the effective treatment of ischemic vascular diseases, and it has also become a research hotspot in the medical field. By means of pro-angiogenesis, it is expected to ameliorate major diseases that endanger human health, for example, cardio-cerebrovascular diseases (such as angina pectoris, myocardial infarction, cerebral infarction, and stroke) and lower limb ischemia (such as diabetic lower limb vascular diseases, and thromboangiitis obliterans) caused by microcirculatory disturbance.

Cerebrovascular diseases refer to a group of diseases in which pathological changes occur to cerebral arteries or carotid arteries that dominate the brain, causing the intracranial blood circulation disturbance and damage to brain tissue. Clinically, the main manifestations are sudden fainting, unconsciousness, or accompanying deviated mouth and eyes, slurring of speech, and hemiparalysis. Ischemic cerebrovascular diseases mainly refer to cerebral thrombosis, cerebral embolism, and multiple cerebral infarction, etc. The diseases are characterized by sudden attack, rapid progress, and critical condition. Because the diseases are often found in the elderly and tend to be complicated by multiple organ damage, the prognosis is poor and the mortality rate is high. Ischemic cerebrovascular diseases are known as cerebral infarction due to ischemic necrosis of the brain tissue in a corresponding area resulting from sharp interruption of blood flow in the cerebral arteries.

Cerebral stroke, also known as "stroke" and cerebralvascular accident (CVA), is one of the most notorious fatal diseases in the world. It is a group of diseases where brain tissue damage is caused by the sudden rupture of blood vessels in the brain or the failure of blood to flow to the brain due to blocked blood vessels, and includes ischemic and hemorrhagic stroke. The incidence of ischemic stroke is higher than that of hemorrhagic stroke. Ischemic stroke is ischemic-hypoxic injury and necrosis of the brain tissue caused by blood supply disorders in local brain tissue region due to a variety of causes, which in turn leads to such clinical manifestations as corresponding neurologic deficits, and severely affects the quality of life of patients.

The research focus on pathological intervention of ischemic injury is mainly to improve the cerebral blood circulation and neuroprotection. Among them, the measure to improve cerebral blood circulation is mainly antithrombotic therapy at present. Antithrombotic drugs include thrombolytic drugs, platelet aggregation inhibitors and anticoagulants. Existing neuroprotective drugs mainly include calcium antagonists, glutamate antagonists, glutamate release inhibitors, GABA receptor agonists, free radical scavengers, cell membrane stabilizers, and others.

The discovery of pro-angiogenesis in recent years has provided a new direction for the effective treatment of ischemic vascular diseases, and it has also become a research hotspot in the medical field. Angiogenesis can promote the neuron survival after cerebral stroke, and improve the neurological deficits and quality of life of the patients after stroke. However, the influencing factors and regulatory mechanisms of angiogenesis after cerebral stroke are complicated. Recent studies have found that PAR1 is involved in microangiogenesis and nerve repair after stroke. Angiogenesis refers to the formation of new capillaries by germination and/or non-germination on the basis of original blood vessels. Angiogenesis mainly includes the process of increase of vascular permeability; production of proteolytic enzymes to degrade the extracellular matrix, and promote endothelial cell proliferation; detachment of endothelial cells from the basement membrane and migration to the Virchow-Robin space to form a three-dimensional lumen through adhesion, proliferation, and reconstruction; differentiation into new capillaries; and interstitial cells entering the vessel wall as induced by an intermediary molecule, to make the blood vessels stable and mature. Under normal physiological conditions, once the blood vessels are formed in the body, they remain highly stable, and are regulated by many key molecules that have positive or negative regulatory effects (that is, pro-angiogenic and anti-angiogenic factors). The initiation of angiogenesis is only turned on briefly with the appearance of the stimulus signal, and then turned off, to maintain a dynamic balance between angiogenesis and decline. Factors affecting microangiogenesis after cerebral stroke include: local blood and oxygen supply; changes in thrombin and its concentration; and levels of pro-angiogenic factors, such as hypoxia-inducible factor 1a (HIF-1a), vascular endothelial growth factor (VEGF), matrix metalloproteinases (MMPs), angiopoietin 1 (Ang-1), and angiopoietin 2 (Ang-2), etc. PAR1 usually interacts with pro-angiogenic factors and plays a role in promoting angiogenesis. VEGF is currently recognized as a factor that plays a key role in angiogenesis. Normally, VEGF is expressed only at a low level to maintain the blood vessel density and permeability under physiological conditions. Some pathological processes such as inflammation, tumors, wound healing, ischemia, and hypoxia can promote the VEGF expression. In patients with cerebral stroke, neurons and glial cells around the focus have increased expression of VEGF. By specifically binding to cell surface receptors on endothelial cells, VEGF can promote the proliferation and migration of vascular endothelial cells, increase the vascular permeability, and enhance the expression of factors that degrade extracellular matrix, thereby promoting microangiogenesis.

However, drugs with clear therapeutic angiogenesis are still in the stage of transition from laboratory to clinical trial. For example, the product Generx available from Cardium Therapeutics is an angiogenic FGF4 gene therapy for the treatment of myocardial microvascular dysfunction. It is currently in the phase III clinical trial.

Therefore, how to find a simple, stable and effective drug with pro-angiogenic activity is a research hotspot and challenge for those skilled in the art.

SUMMARY

To solve the technical problem in the prior art that drugs with clear therapeutic angiogenesis are not available in the market and the preparation of drugs is difficult, the present invention provides a glycoside compound, and a preparation method, a composition, use and an intermediate thereof. The glycoside compound provided in the present invention has simple preparation method, can significantly increase the expression of VEGF-A mRNA, and is useful in the preparation of pro-angiogenic drugs. This provides a reliable guarantee for the development of drugs with pro-angiogenic activity for treating ischemic cardio-cerebrovascular diseases, particularly cerebral infarction (cerebral stroke), myocardial infarction, and ischemic microcirculatory disturbance of lower limbs.

The above technical problems are solved in the present invention through the following technical solutions.

The present invention provides a glycoside compound represented by Formula III below, or a tautomer, an optical isomer, a solvate, a polymorph, a pharmaceutically acceptable salt or ester, or a pharmaceutically acceptable prodrug or derivative thereof:

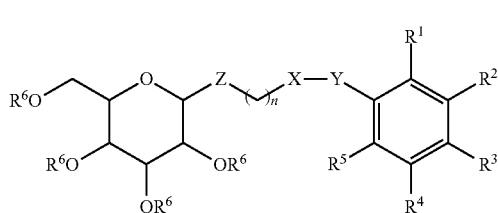

III in which $R^1$, $R^2$, $R^1$, $R^4$ and $R^5$ are each independently selected from the group consisting of hydrogen, hydroxyl, mercapto, a substituted or unsubstituted $C_1$-$C_{20}$ alkoxy group, nitro or halo;

or any adjacent two of $R^1$, $R^2$, $R^3$, $R^4$ and $R^5$ form, together with carbon atoms on the phenyl ring to which they are attached, a 5- to 7-membered heterocyclic ring having a heteroatom that is O or S, where one or more heteroatoms may be present, and when more than one heteroatoms are present, the heteroatoms may be the same or different, where the substituent in the substituted or unsubstituted $C_1$-$C_{20}$ alkoxy group is selected from the group consisting of a $C_3$-$C_{20}$ cycloalkyl group, a $C_1$-$C_{20}$ alkenyl group, a substituted or unsubstituted $C_6$-$C_{20}$ aryl group, halo, a substituted or unsubstituted $C_2$-$C_{20}$ heteroaryl group, a $C_3$-$C_6$ cycloalkoxy group, a $C_1$-$C_{20}$ alkoxy group, or a $C_1$-$C_{20}$ alkyl group, in which the substituent in the substituted or unsubstituted $C_6$-$C_{20}$ aryl group and the substituted or unsubstituted $C_2$-$C_{20}$ heteroaryl group is each independently halo or a halo-substituted $C_1$-$C_{20}$ alkyl group;

X is $CH_2$, $NR^7$, O or S;
Y is $CH_2$, $NR^8$, O or S;
Z is O or S;
$R^1$ and $R^8$ are each independently hydrogen, an aryl-substituted $C_1$-$C_6$ alkoxycarbonyl group, or a $C_1$-$C_6$ alkoxycarbonyl group;
each $R^6$ is independently hydrogen or glycosyl; and
n is 2, 3 or 4.
Preferably:
when X is $CH_2$, Y is $CH_2$, and n=2, 3 or 4, $R^1$-$R^5$ are not all H;

when n=2, $R^1$, $R^4$ and $R^5$ are H, $R^2$ and $R^3$ are not both OCH; and OH;

when n=2, $R^1$, $R^2$ and $R^5$ are H, $R^3$ and $R^5$ are not both OH and $OCH_3$;

when n=2, $R^2$, $R^4$ and $R^5$ are H, $R^1$ and $R^3$ are not both OH; and when n=2, $R^1$, $R^2$ and $R^4$ are H, $R^3$ and $R^5$ are not both OH.

The present invention provides a glycoside compound represented by Formula I below, or a tautomer, an optical isomer, a solvate, a polymorph, a pharmaceutically acceptable salt or ester, or a pharmaceutically acceptable prodrug or derivative thereof:

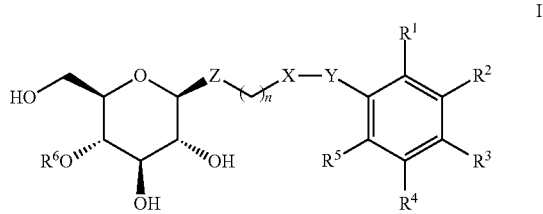

I $R^1$, $R^2$, $R^3$, $R^4$ and $R^5$ are each independently selected from the group consisting of hydrogen, hydroxyl, mercapto, a substituted or unsubstituted $C_1$-$C_{20}$ alkoxy group (for example, a substituted or unsubstituted $C_1$-$C_{10}$ alkoxy group, such as a substituted or unsubstituted $C_1$-$C_6$ alkoxy group), nitro, or halo;

or any adjacent two of $R^1$, $R^2$, $R^3$, $R^4$ and $R^5$ form, together with carbon atoms on the phenyl ring to which they are attached, a 5- to 7-membered heterocyclic ring (for example, $R^2$ and $R^3$ form a 5- to 7-membered heterocyclic ring) having a heteroatom that is O or S (for example, O), where one or more (for example, two) heteroatoms may be present, and when more than one heteroatoms are present, the heteroatoms may be the same or different, in which the substituent in the substituted or unsubstituted $C_1$-$C_{20}$ alkoxy group is selected from the group consisting of a $C_3$-$C_{20}$ cycloalkyl group (for example, a $C_3$-$C_{10}$ cycloalkyl group, such as a $C_3$-$C_6$ cycloalkyl group), a $C_2$-$C_{20}$ alkenyl group (for example, a $C_2$-$C_6$ alkenyl, such as a $C_2$-$C_4$ alkenyl, for example

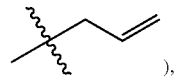 [SMILES: *CC=C]

), a substituted or unsubstituted $C_6$-$C_{20}$ aryl group (for example, a substituted or unsubstituted $C_6$-$C_{10}$ aryl group, such as substituted or unsubstituted aryl or naphthyl), halo (for example, fluoro, chloro, bromo or iodo), a substituted or unsubstituted $C_2$-$C_{20}$ heteroaryl group in which the heteroatom is one or more selected from the group consisting of N, S and O (for example, 1 heteroatom is present; for example, the heteroatom is N; for example, the substituted or unsubstituted $C_2$-$C_{20}$ heteroaryl group is a monocyclic heteroaryl group).

(for example, a substituted or unsubstituted $C_2$-$C_{10}$ heteroaryl group, such as a substituted or unsubstituted $C_2$-$C_6$ heteroaryl group), a $C_3$-$C_6$ cycloalkoxy group (e.g.

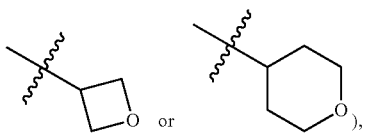 [SMILES: *C1COC1 ; *C1CCOCC1]

a $C_1$-$C_{20}$ alkoxy group (for example, a $C_1$-$C_{10}$ alkoxy group, such as a $C_1$-$C_6$ alkoxy group, for example, methoxy, ethoxy or propoxy) or a $C_1$-$C_{20}$ alkyl group (for example, a $C_1$-$C_{10}$ alkyl group, such as a $C_1$-$C_6$ alkyl group, for example a $C_1$-$C_3$ alkyl group), where the substituent in the substituted or unsubstituted $C_1$-$C_{20}$ aryl group and the substituted or unsubstituted $C_2$-$C_{20}$ heteroaryl group is each independently selected from halo (for example, fluoro, chloro, bromo or iodo) or a halo (for example, fluoro, chloro, bromo or iodo)-substituted $C_1$-$C_{20}$ alkyl group (where one or more substituents may be present in the halo-substituted $C_1$-$C_{20}$ alkyl group, and when more than one heteroatoms are present, the heteroatoms may be the same or different; for example, a halo-substituted $C_1$-$C_{10}$ alkyl group, for example, a halo-substituted $C_1$-$C_6$ alkyl group, for example, a halo-substituted $C_1$-$C_3$ alkyl group, for example, —$CF_3$, —$CHF_2$ or —$CH_2F$);

X is $CH_2$, $NR^7$, O or S;
Y is $CH_2$, $NR^8$, O or S;
Z is O or S;
$R^7$ and $R^8$ are each independently hydrogen, an aryl-substituted $C_1$-$C_6$ alkoxycarbonyl group (e.g. benzoxycarbonyl) or a $C_1$-$C_6$ alkoxycarbonyl group (e.g. tert-butoxycarbonyl);
$R^6$ is hydrogen or

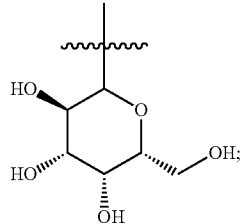

and
n is 2, 3 or 4.
Preferably:
when X is $CH_2$, Y is $CH_2$, and n=2, 3 or 4, $R^1$-$R^5$ are not all H;
when n=2, $R^1$, $R^4$ and $R^5$ are H, $R^2$ and $R^3$ are not both $OCH_3$ and OH; and
when n=2, $R^1$, $R^2$ and $R^5$ are H, $R^3$ and $R^4$ are not both OH and $OCH_3$.

In the present invention, the substituted or unsubstituted $C_2$-$C_{20}$ heteroaryl group may be substituted or unsubstituted pyrrolyl, substituted or unsubstituted furyl, substituted or unsubstituted thienyl, substituted or unsubstituted pyrazolyl, substituted or unsubstituted imidazolyl, substituted or unsubstituted oxazolyl, substituted or unsubstituted thiazolyl, substituted or unsubstituted isoxazolyl, substituted or unsubstituted pyridinyl, substituted or unsubstituted pyridazinyl, substituted or unsubstituted pyrimidinyl, or substituted or unsubstituted pyrazinyl, for example, substituted or unsubstituted pyridinyl.

In the present invention, the unsubstituted $C_1$-$C_{20}$ alkoxy group may be

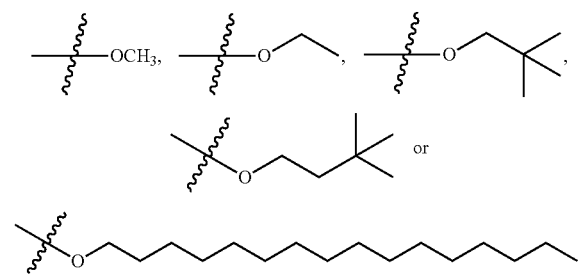

In the present invention, the $C_3$-$C_{20}$ cycloalkyl group may be cyclopropyl, cyclobutyl, cyclopentyl or cyclohexyl.

In the present invention, the substituted $C_6$-$C_{20}$ aryl group may be

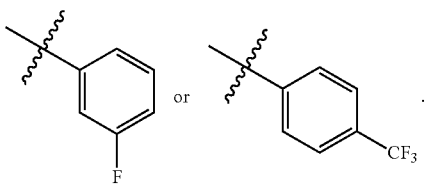 [SMILES: *c1cccc(F)c1 ; *c1ccc(C(F)(F)F)cc1]

In the present invention, the substituted $C_1$-$C_{20}$ alkoxy group may be

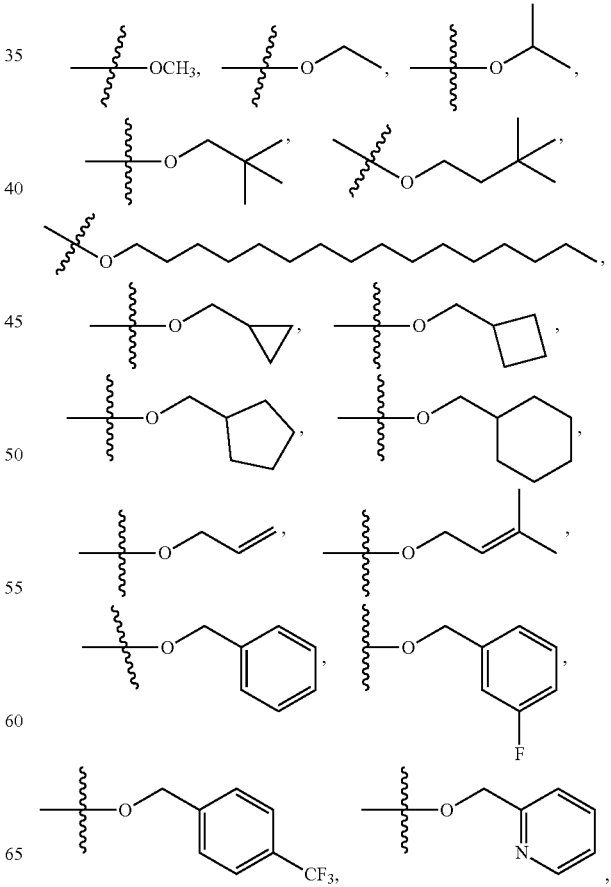

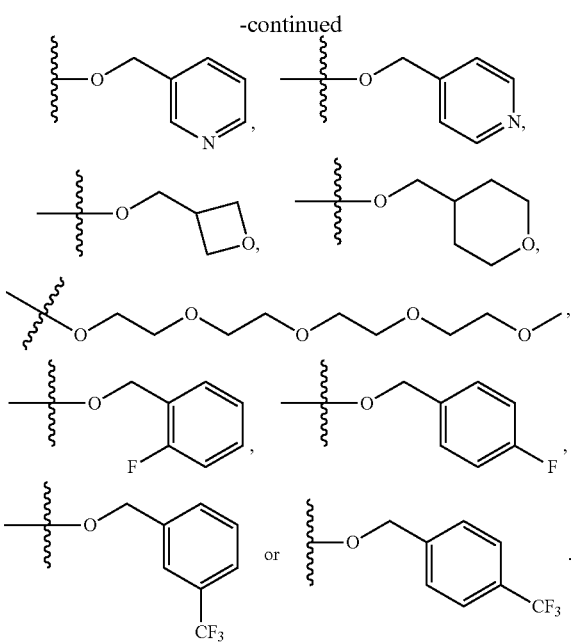

In the present invention, the unsubstituted $C_2$-$C_{20}$ heteroaryl group may be

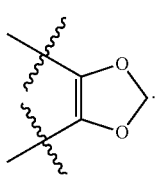 [SMILES: *C1=C(*)OCO1]

In the present invention, the 5- to 7-membered heterocyclic ring may be

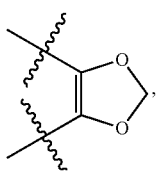 [SMILES: *C1=C(*)OCO1]

In the present invention, $R^1$ may be hydrogen.

In the present invention, $R^2$ may be hydrogen, or a substituted or unsubstituted $C_1$-$C_{20}$ alkoxy group, or $R^2$ and $R^3$ form

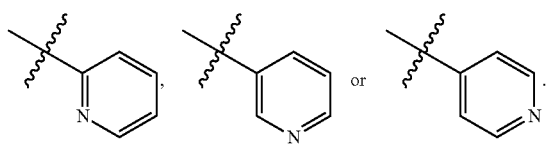

where the substituted or unsubstituted $C_1$-$C_{20}$ alkoxy group and substituents thereof are as defined above.

In the present invention, $R^3$ may be hydrogen, hydroxyl, mercapto, a substituted or unsubstituted $C_1$-$C_{20}$ alkoxy group, hydroxyl, nitro or halo, where the substituted or unsubstituted $C_1$-$C_{20}$ alkoxy group and substituents thereof, and halo are as defined above.

In the present invention, $R^4$ may be hydrogen, or a substituted or unsubstituted $C_1$-$C_{20}$ alkoxy group, where the substituted or unsubstituted $C_1$-$C_{20}$ alkoxy group and substituents thereof are as defined above.

In the present invention, $R^5$ may be hydrogen.

In an embodiment of the present invention, the definitions of various groups are as follows (the definitions of the unmentioned groups are as described above). X is $CH_2$; and Y is $CH_2$, $NR^8$, S or O, in which $R^4$ is hydrogen, an aryl-substituted alkoxycarbonyl group or an alkoxycarbonyl group.

In an embodiment of the present invention, the definitions of various groups are as follows (the definitions of the unmentioned groups are as described above). X is $NR^7$; and Y is $CH_2$, in which $R^7$ is hydrogen, an aryl-substituted alkoxycarbonyl group, or an alkoxycarbonylgroup.

In an embodiment of the present invention, the definitions of various groups are as follows (the definitions of the unmentioned groups are as described above). X is O or S; and Y is $CH_2$.

In the present invention, when $R^1$, $R^2$, $R^3$, $R^4$ and $R^5$ are each independently selected from hydrogen, hydroxyl, mercapto, a substituted or unsubstituted $C_1$-$C_{20}$ alkoxy group, nitro or halo, one or more (for example, 1, 2, or 3, such as 1) substituted or unsubstituted $C_1$-$C_{20}$ alkoxy groups may be present.

In the present invention,

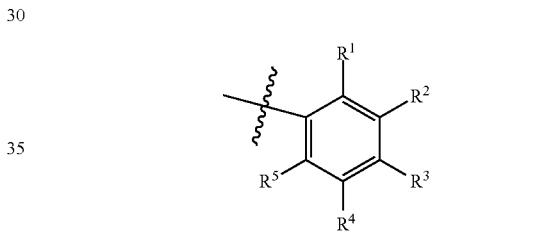

may have any of the following structures:

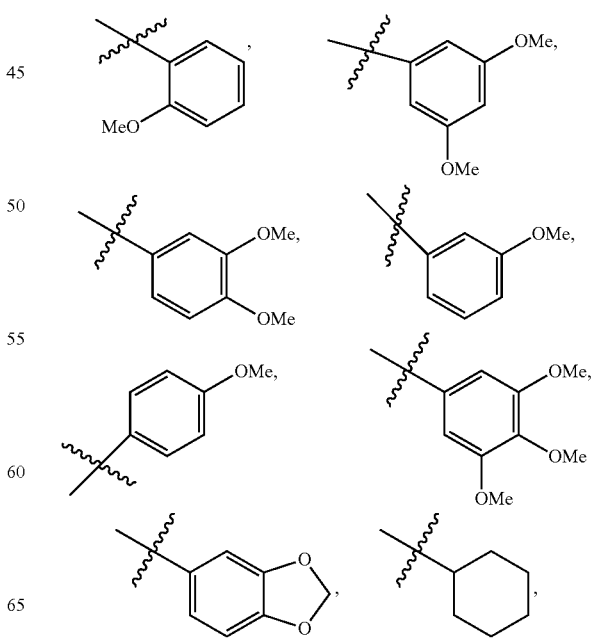

-continued
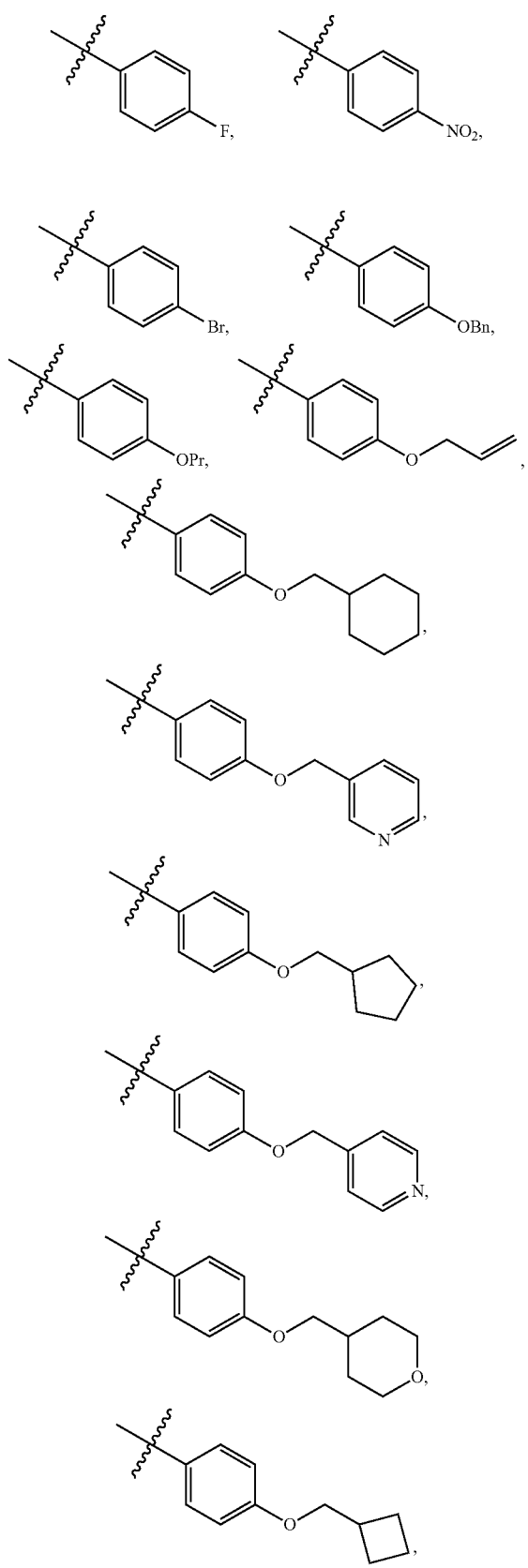
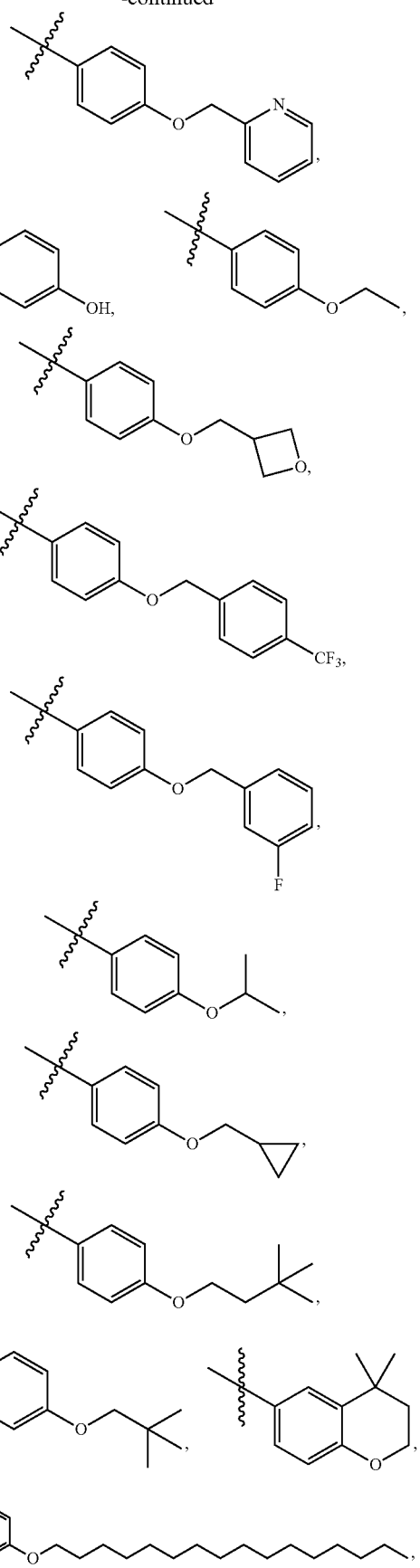

-continued

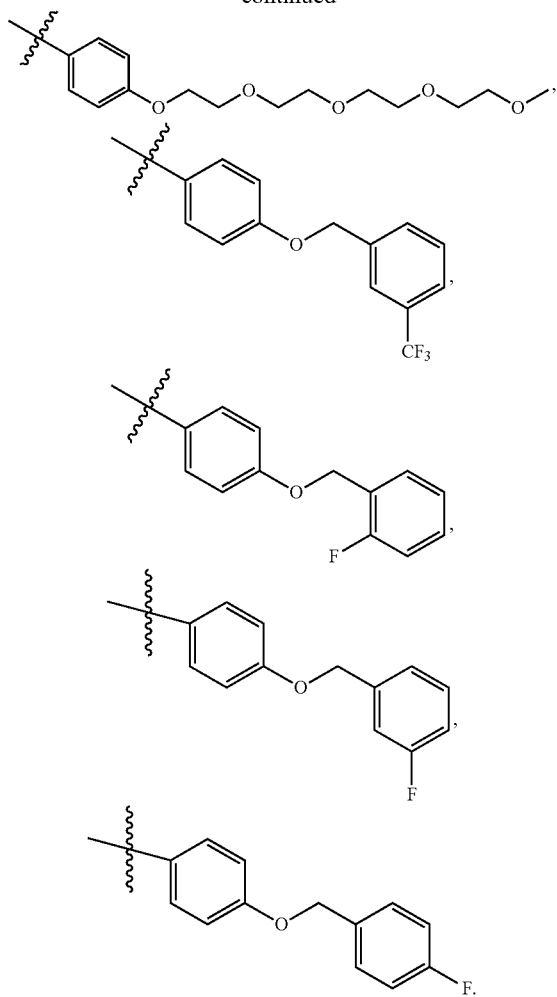

In the present invention, preferably, n=2.

In the present invention, preferably, $R^1$, $R^2$, $R^3$, $R^4$ and $R^5$ are each independently selected from hydrogen, a substituted or unsubstituted $C_1$-$C_{20}$ alkoxy group, nitro or halo.

In the present invention, preferably, $R^6$ is hydrogen.

In the present invention, preferably, the optical isomer of

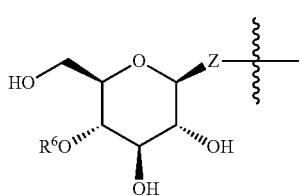

in the compound represented by Formula I may be:

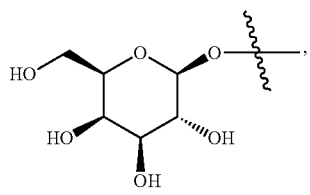 [SMILES: *O[C@@H]1O[C@H](CO)[C@H](O)[C@H](O)[C@H]1O]

-continued

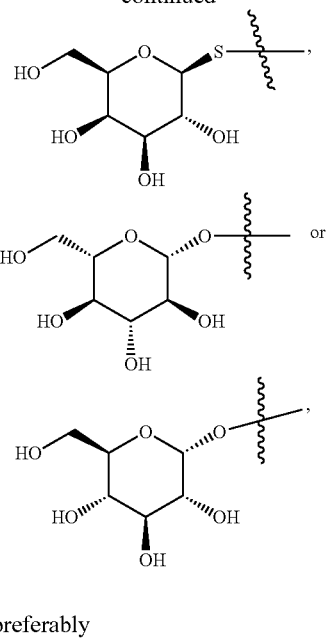

and further preferably

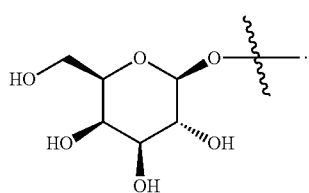

In a certain embodiment of the present invention, the substituents in the compound of Formula I may be the following (the definitions of the unmentioned groups are as described above):

n is 2, 3 or 4; and

X is $CH_2$, $NR^7$, O or S.

In a certain embodiment of the present invention, the substituents in the compound of Formula I may be the following (the definitions of the unmentioned groups are as described above):

n is 2, 3 or 4; and

Y is $CH_2$, NR, O or S.

In a certain embodiment of the present invention, the substituents in the compound of Formula I may be the following (the definitions of the unmentioned groups are as described above):

$R^1$ is hydrogen;

$R^2$ is hydrogen, or a substituted or unsubstituted $C_1$-$C_{20}$ alkoxy group, or $R^2$ and W form

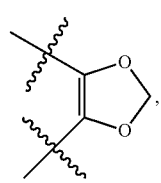 [SMILES: *C1=C(*)OCO1]

where the substituted or unsubstituted $C_1$-$C_{20}$ alkoxy group and substituents thereof are as defined above;

$R^3$ is hydrogen, hydroxyl, mercapto, a substituted or unsubstituted $C_1$-$C_{20}$ alkoxy group, hydroxyl, nitro or halo, where the substituted or unsubstituted $C_1$-$C_{20}$ alkoxy group and substituents thereof, and halo are as defined above;

$R^4$ is hydrogen, or a substituted or unsubstituted $C_1$-$C_{20}$ alkoxy group, where the substituted or unsubstituted $C_1$-$C_{20}$ alkoxy group and substituents thereof are as defined above; and $R^5$ is hydrogen.

In a certain embodiment of the present invention, the substituents in the compound of Formula I may be the following (the definitions of the unmentioned groups are as described above):

n is 2;
when X is $CH_2$, Y is $CH_2$, $NR^3$, S or O;
when X is $NR^7$, Y is $CH_2$; and
when X is O or S, Y is $CH_2$.

The present invention also provides compounds of any of the following structures:

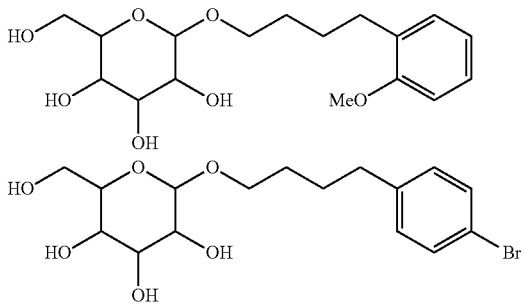
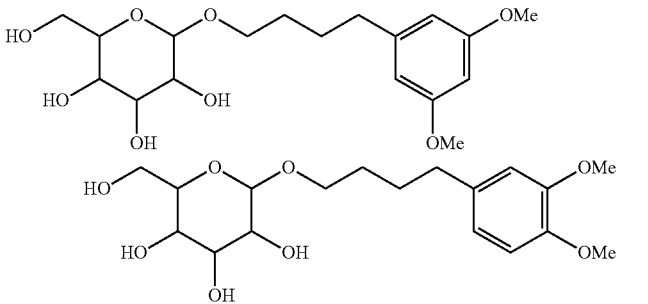
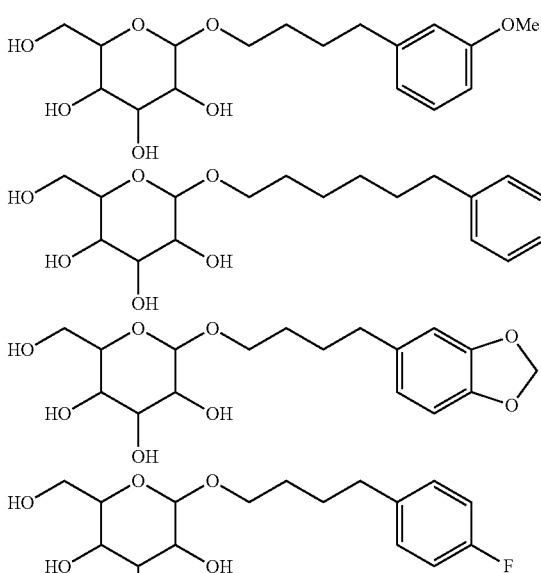
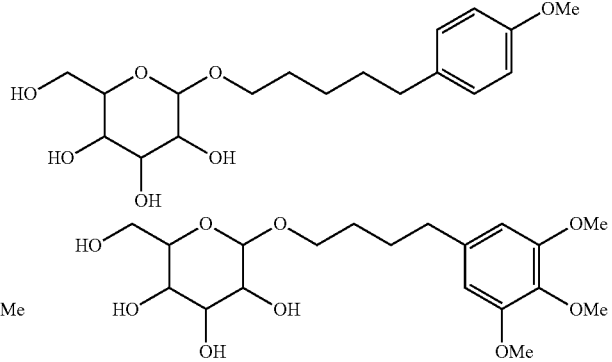
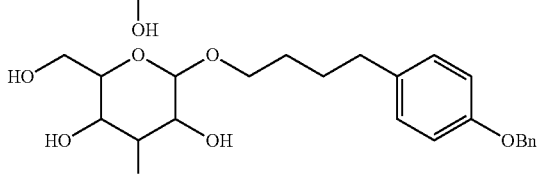
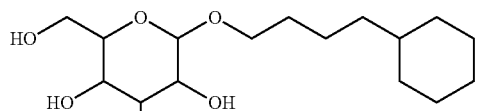
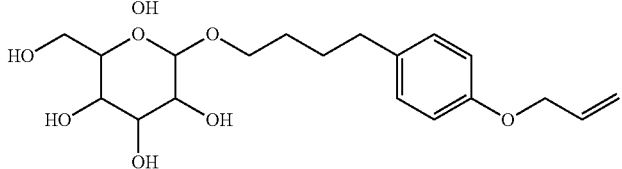
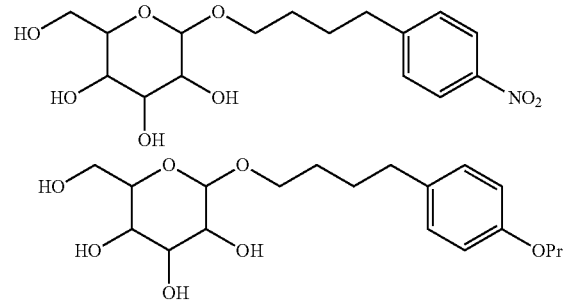
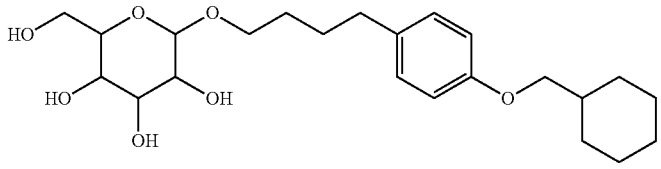
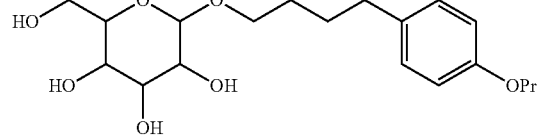

-continued
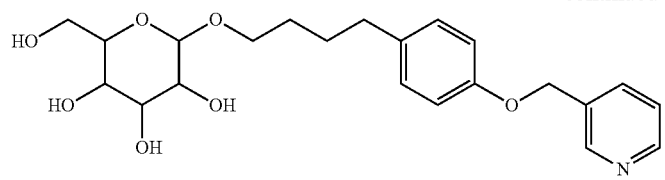
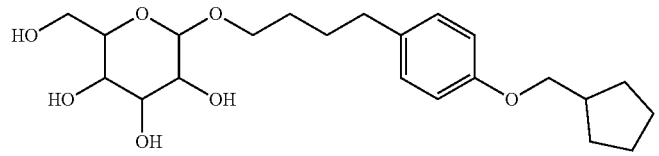
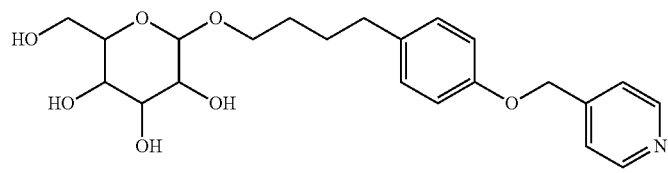
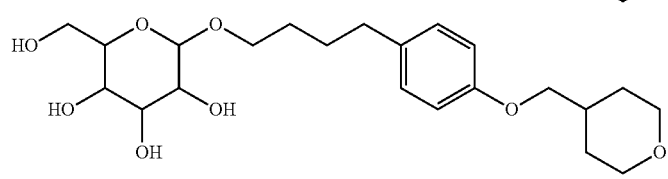
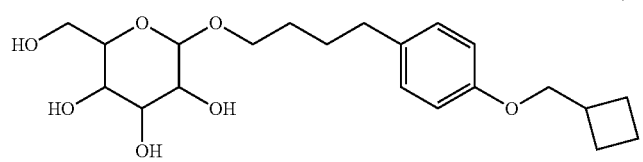
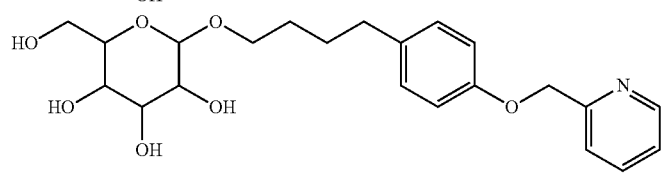
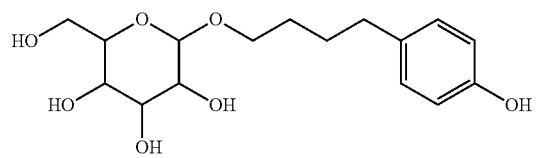
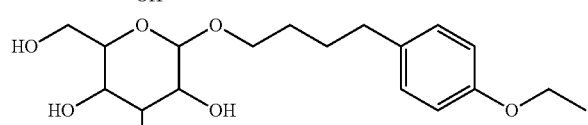
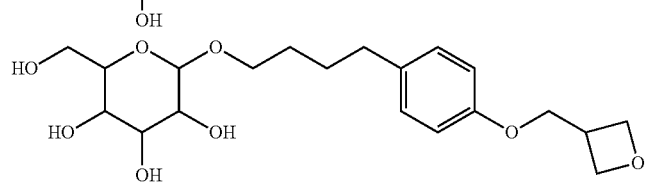
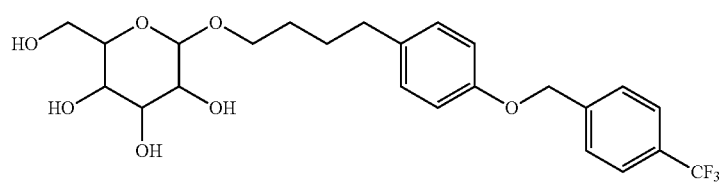

-continued
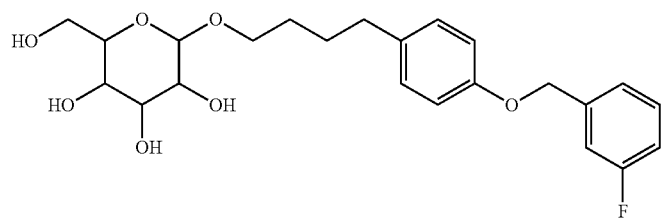
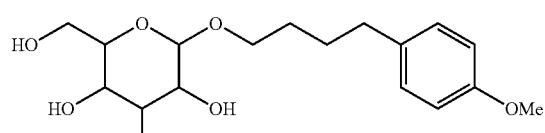
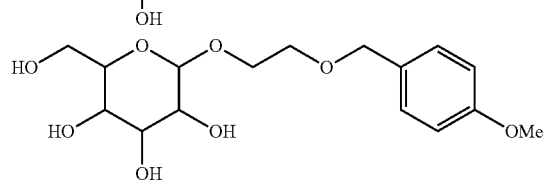
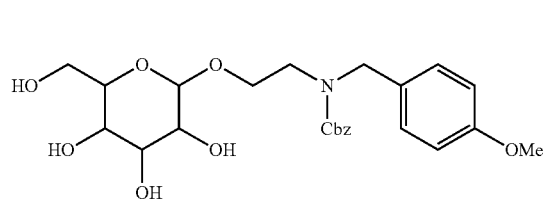
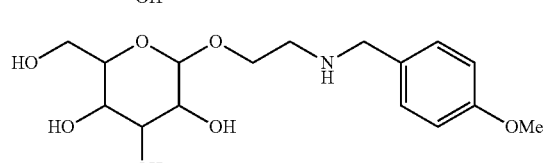
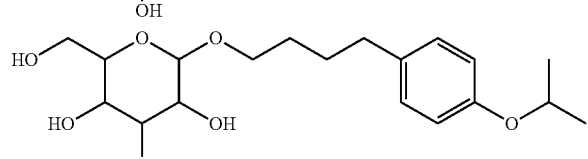
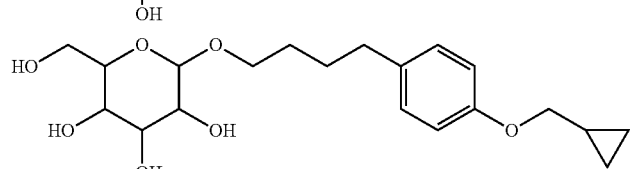
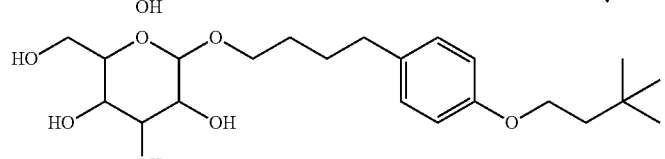
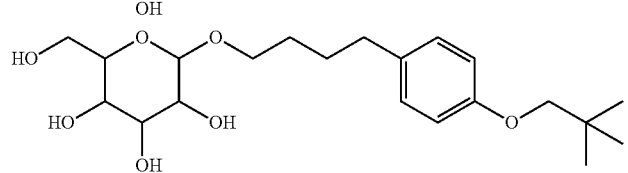
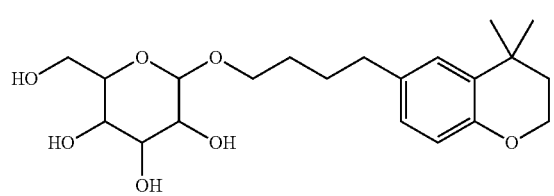

19 20
-continued
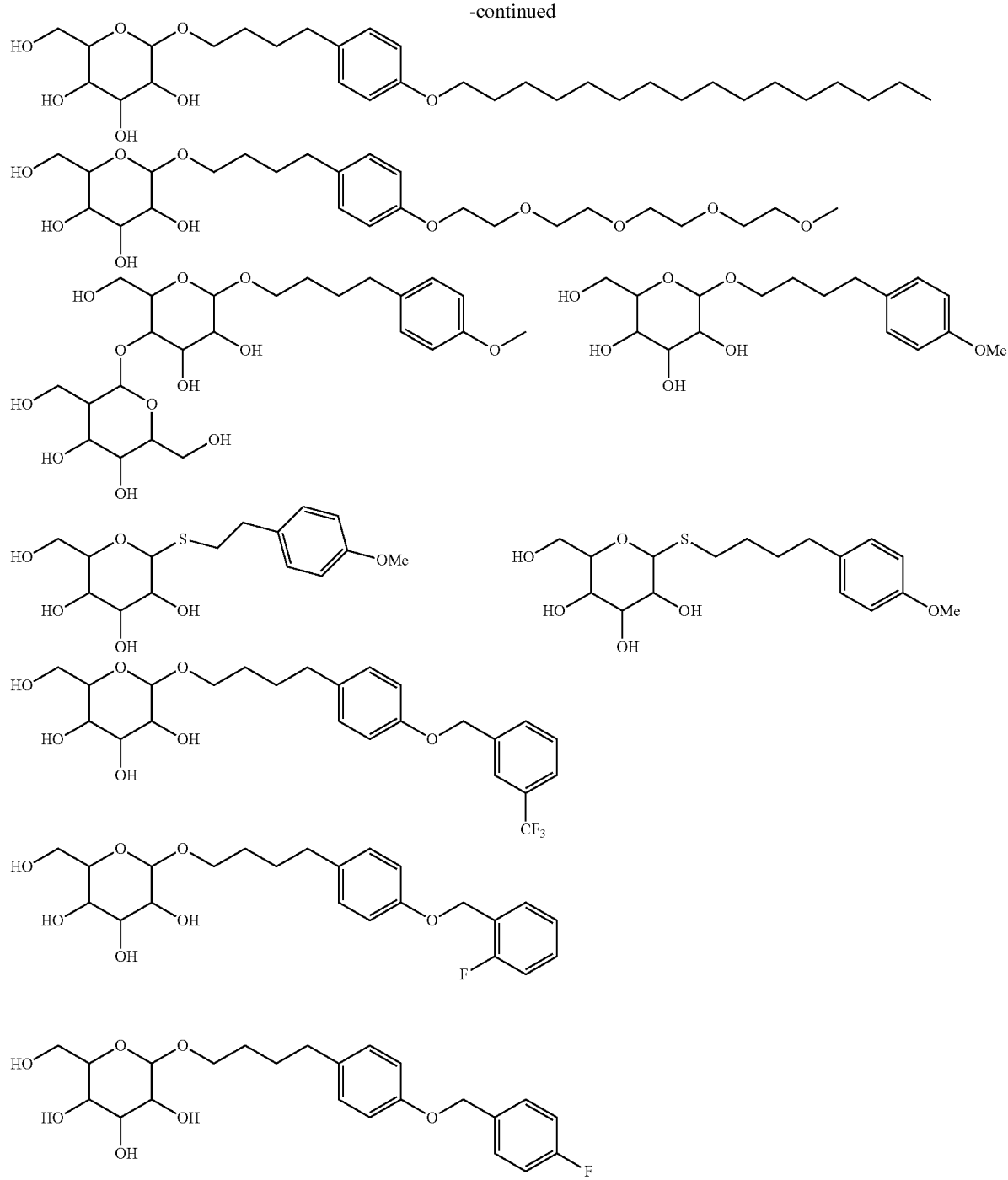
Preferably, these compounds are:
TG-001                TG-002
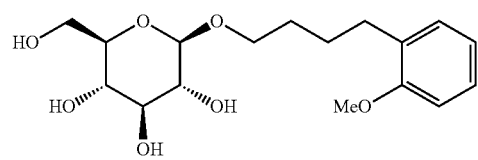 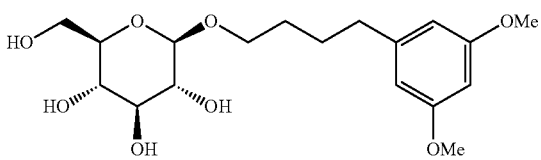

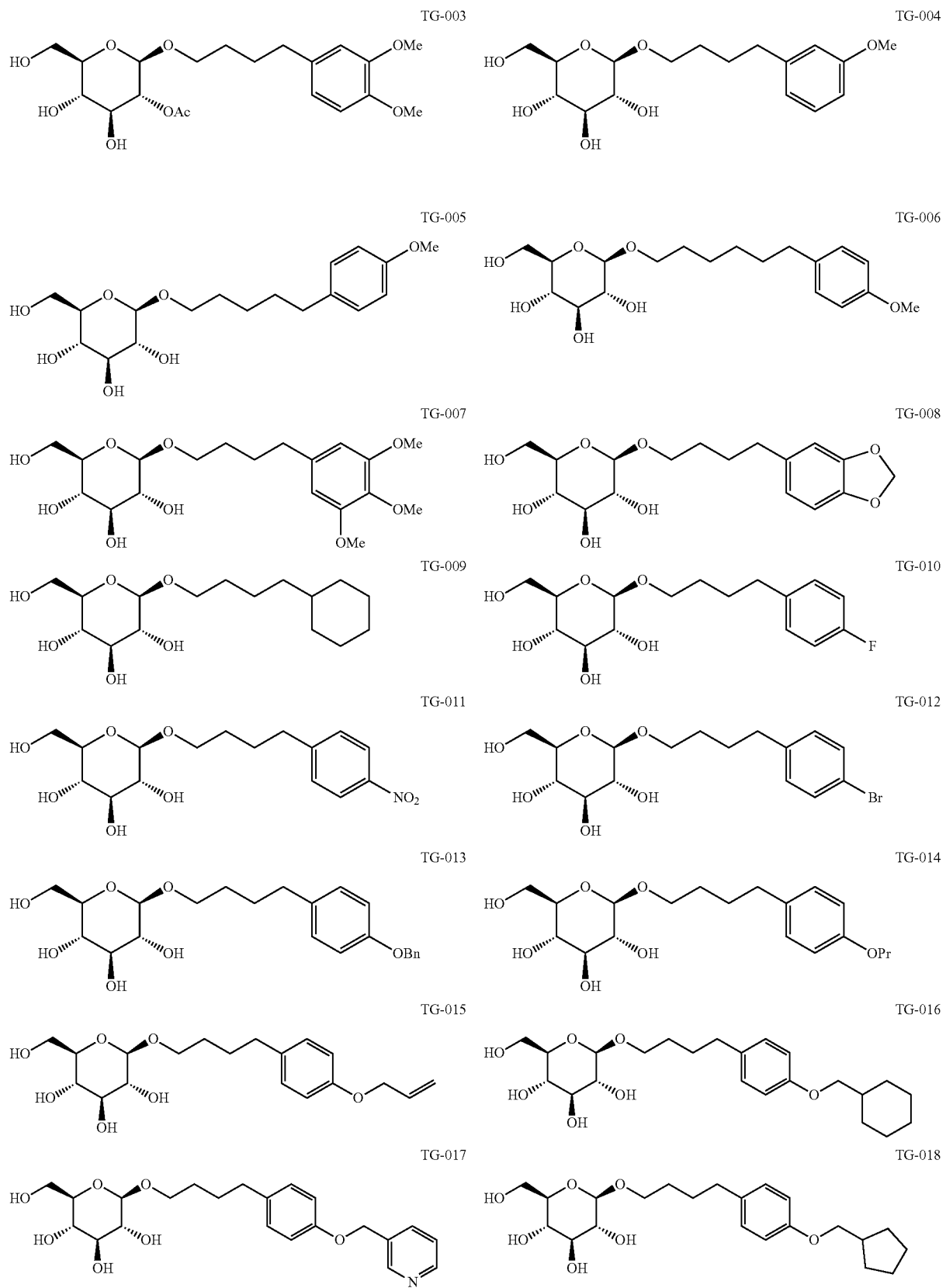

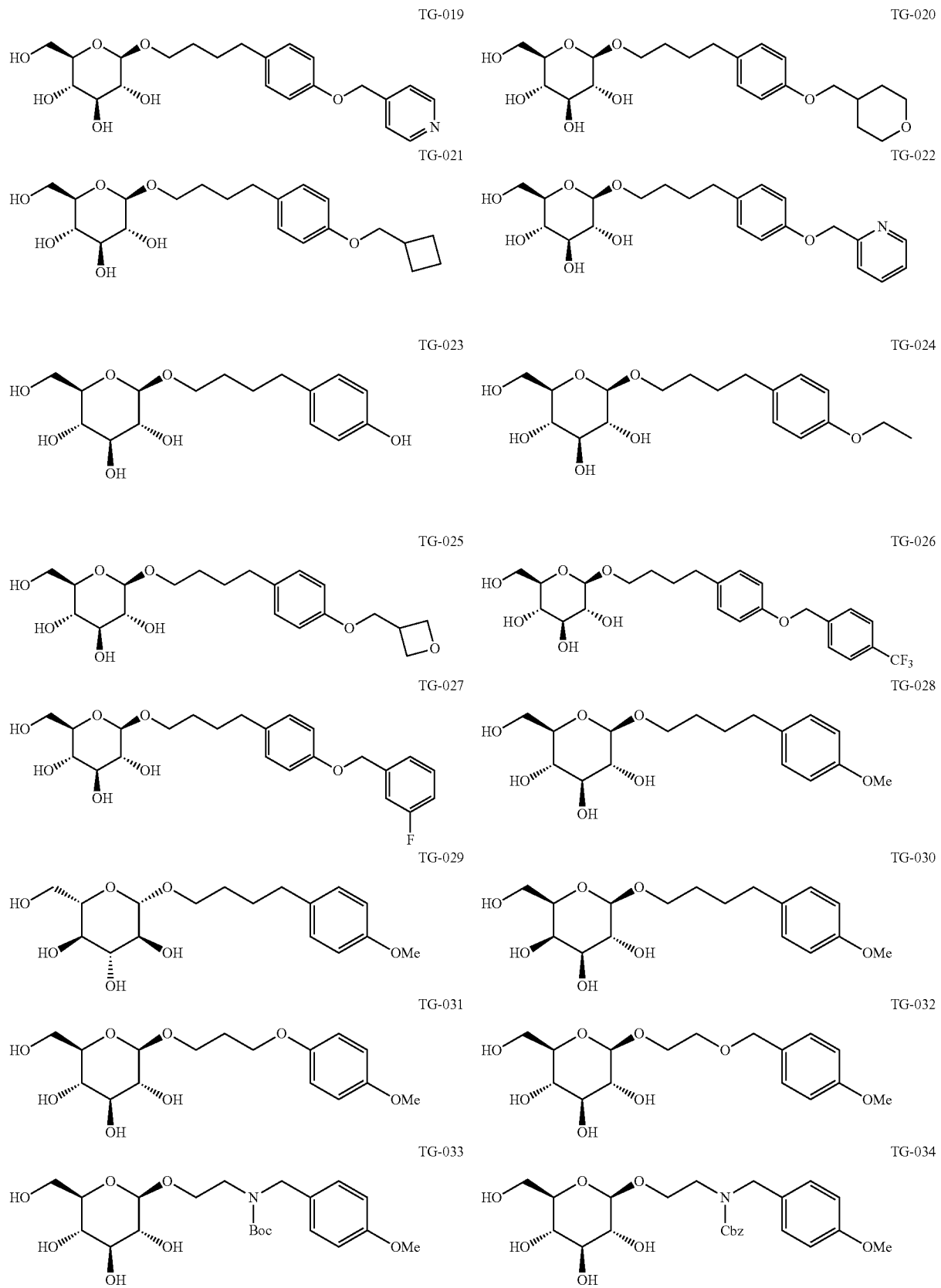

TG-035
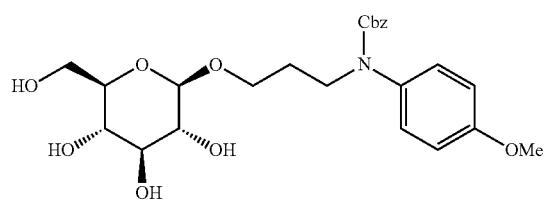
TG-036
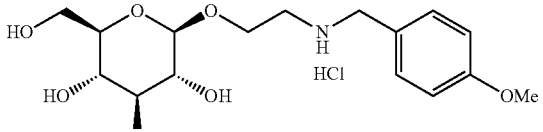
TG-037
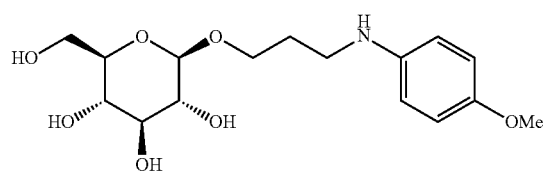
TG-038
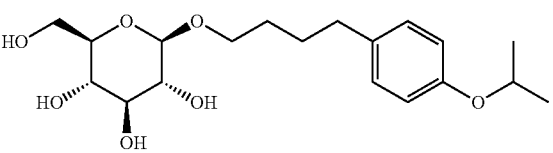
TG-039
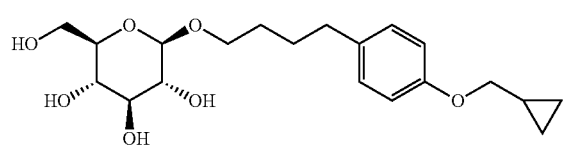
TG-040
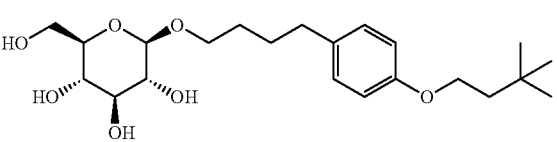
TG-041
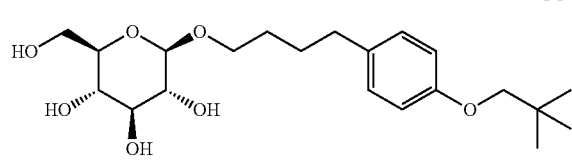
TG-042
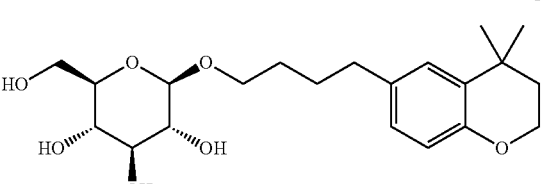
TG-043
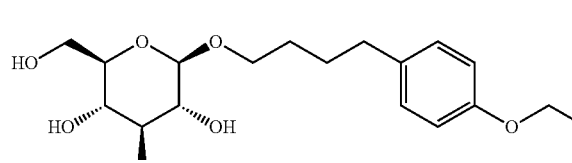
TG-044
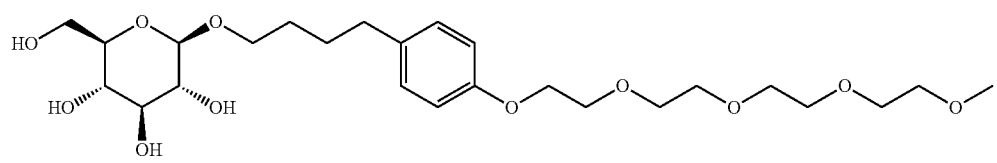
TG-045
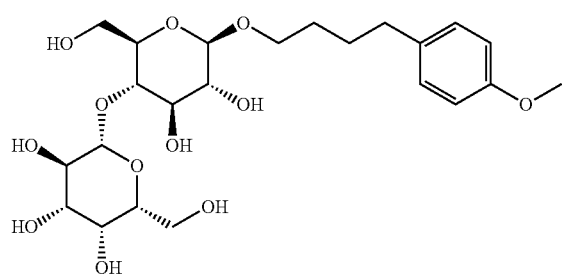
TG-046
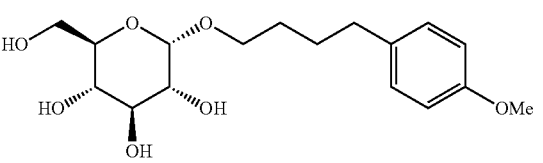
TG-047
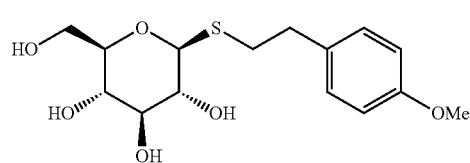
TG-048
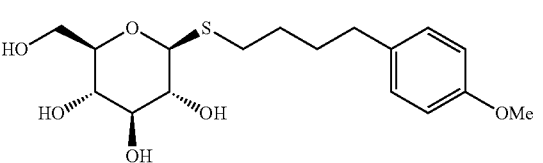

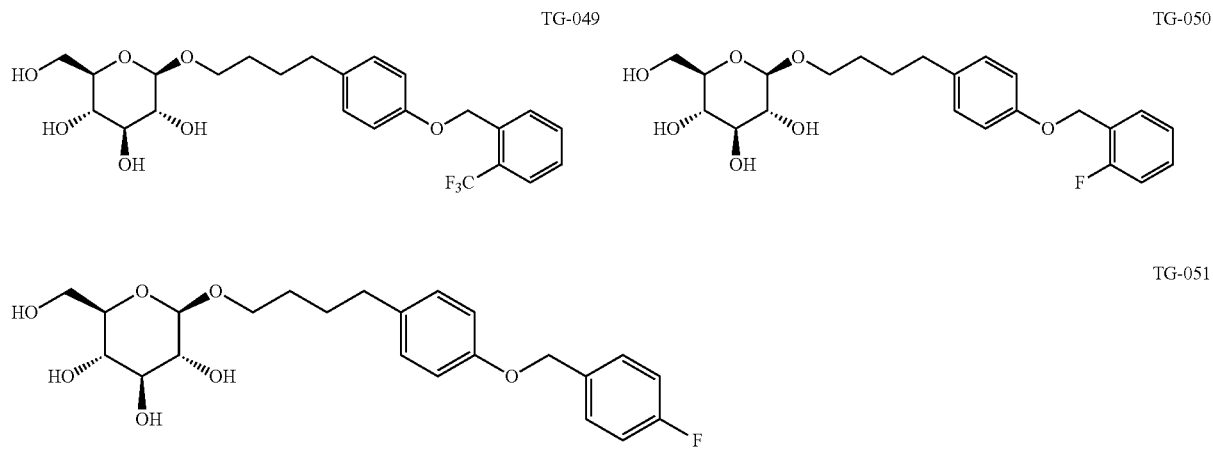

The present invention also provides a method for preparing a glycoside compound, which comprises the steps of reducing a compound represented by Formula V in a solvent to obtain a compound represented by Formula VI:

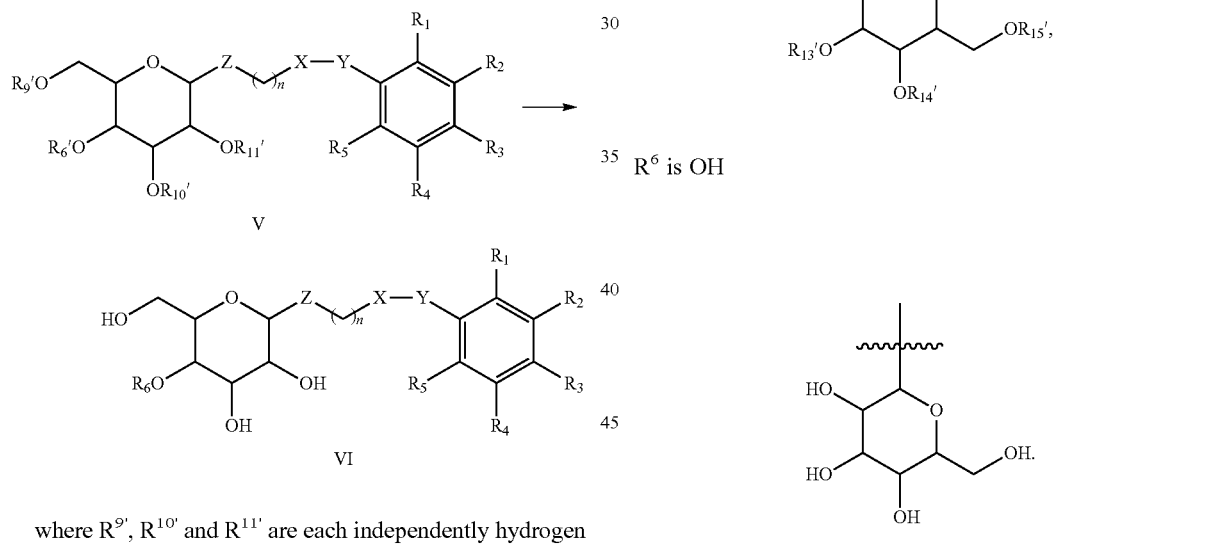

where $R^{9'}$, $R^{10'}$ and $R^{11'}$ are each independently hydrogen or Ac, and at least one of them is Ac; $R^{6'}$ is hydrogen, Ac or $R^{12'}$, $R^{13'}$, $R^{14'}$, and $R^{15'}$ are each independently hydrogen, Bz or Ac; n, X, Y, Z, $R^1$, $R^2$, $R^3$, $R^4$, $R^5$ and $R^6$ are as defined above; when $R^{6'}$ is hydrogen or Ac, $R^6$ is hydrogen; and when $R^{6'}$ is $R^6$ is OH The present invention also provides a method for preparing a compound represented by Formula I, which comprises the steps of: reducing a compound represented by Formula II in a solvent to obtain the compound represented by Formula I:

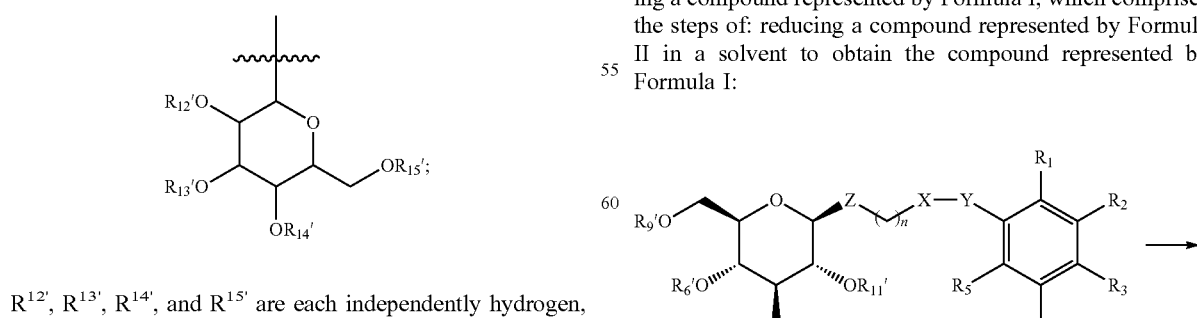

-continued

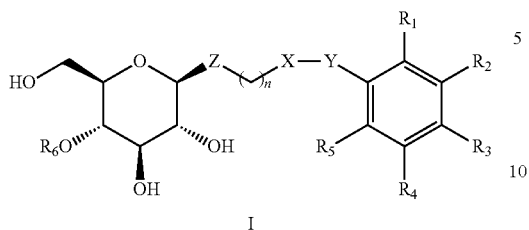

I where $R^{9'}$, $R^{10'}$ and $R^{11'}$ are each independently hydrogen or Ac, and at least one of them is Ac; $R^6$ is hydrogen, Ac or

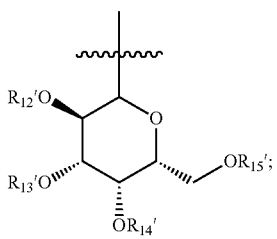

$R^{12'}$, $R^{13'}$, $R^{14'}$, and $R^{15'}$ are each independently hydrogen, Bz or Ac; n, X, Y, Z, $R^1$, $R^2$, $R^3$, $R^4$, $R^5$ and $R^6$ are as defined above; when $R^{6'}$ is hydrogen or Ac, $R^6$ is hydrogen; and when $R^{6'}$ is

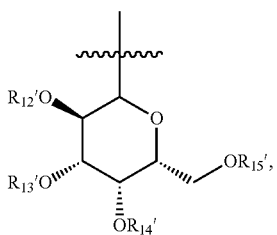

$R^6$ is OH

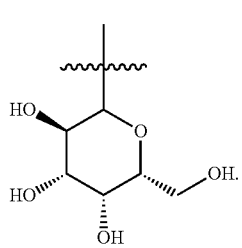

The present invention also provides use of the glycoside compound, or a compound below, or a tautomer, an optical isomer, a solvate, a polymorph, a pharmaceutically acceptable salt or ester, or a pharmaceutically acceptable prodrug or derivative thereof, in the preparation of pro-angiogenic drugs:

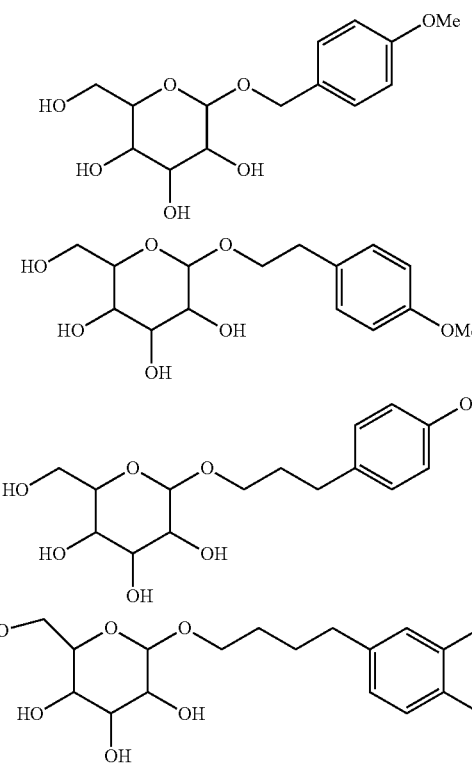

The present invention also provides use of the glycoside compound represented by Formula I, Compound TG-052, Compound TG-053, Compound TG-054 or TG-057, or a tautomer, an optical isomer, a solvate, a polymorph, a pharmaceutically acceptable salt or ester, or a pharmaceutically acceptable prodrug or derivative thereof, in the preparation of pro-angiogenic drugs:

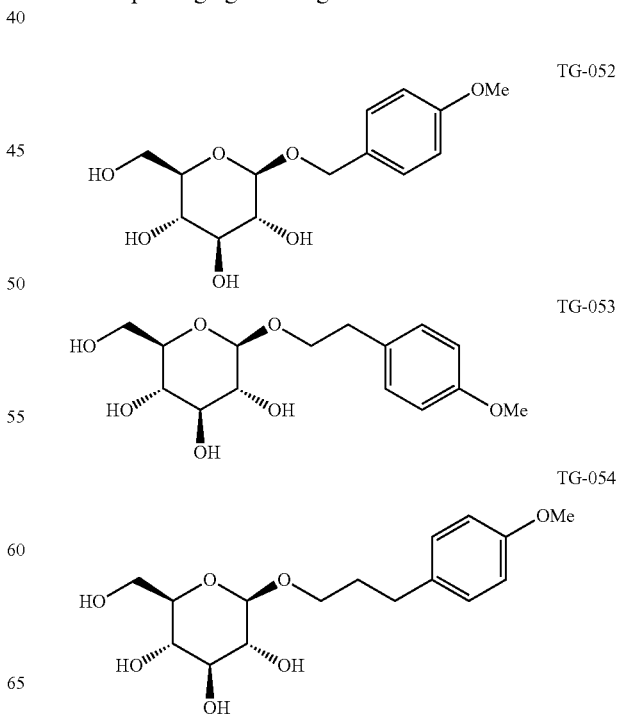

-continued

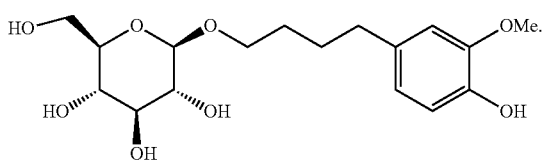

TG-057

The present invention also provides use of the glycoside compound, or a compound below, or a tautomer, an optical isomer, a solvate, a polymorph, a pharmaceutically acceptable salt or ester, or a pharmaceutically acceptable prodrug or derivative thereof, in the preparation of drugs for treating ischemic cardio-cerebrovascular diseases, particularly cerebral infarction (cerebral stroke) and myocardial infarction, and ischemic microcirculatory disturbance of lower limbs:

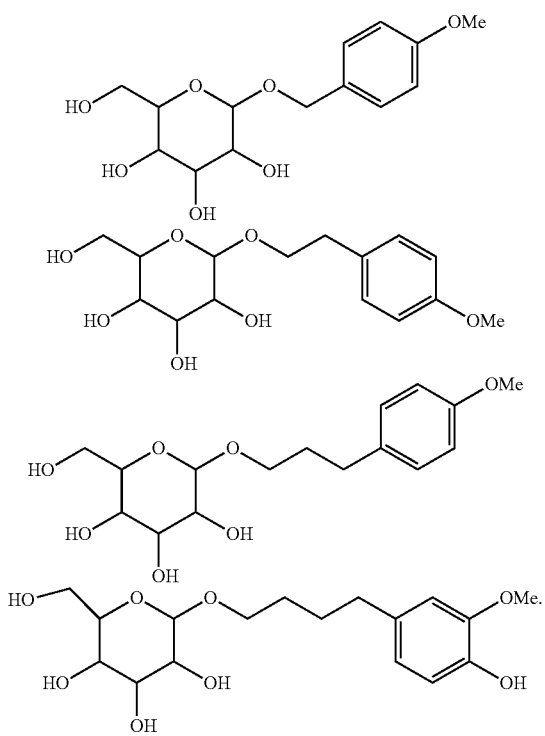

The present invention also provides use of the glycoside compound represented by Formula I, Compound TG-052, Compound TG-053, or Compound TG-054, or a tautomer, an optical isomer, a solvate, a polymorph, a pharmaceutically acceptable salt or ester, or a pharmaceutically acceptable prodrug or derivative thereof, in the preparation of drugs for treating ischemic cardio-cerebrovascular diseases, particularly cerebral infarction (cerebral stroke) and myocardial infarction, and ischemic microcirculatory disturbance of lower limbs:

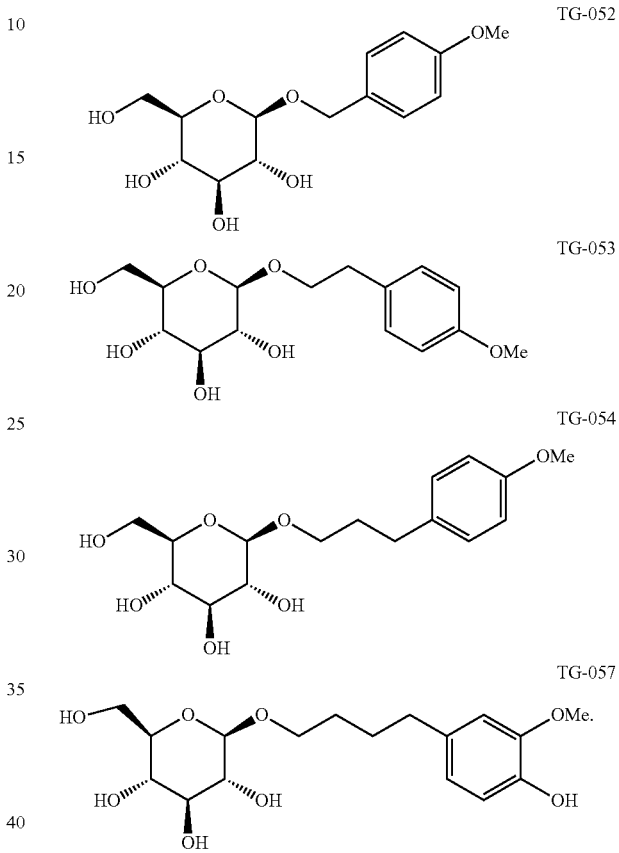

The ischemic cardio-cerebrovascular diseases involve vascular wall lesions, and all symptoms and/or pathological changes in the early to late stages of tissue ischemia of heart and brain, such as cerebral infarction (cerebral stroke) or myocardial infarction, caused by vascular lesions due to changes in blood composition and/or hemodynamic changes.

The present invention also provides an intermediate of the glycoside compound shown above:

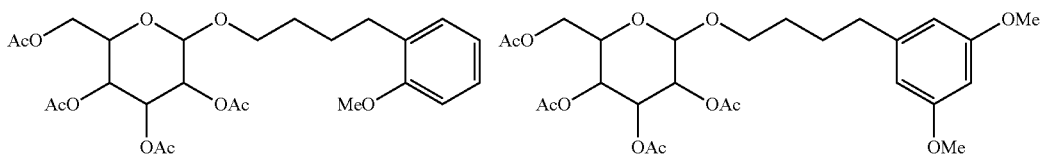

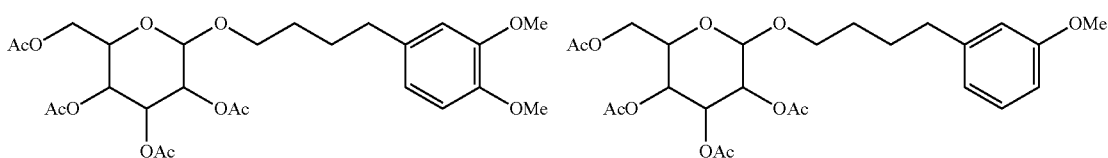

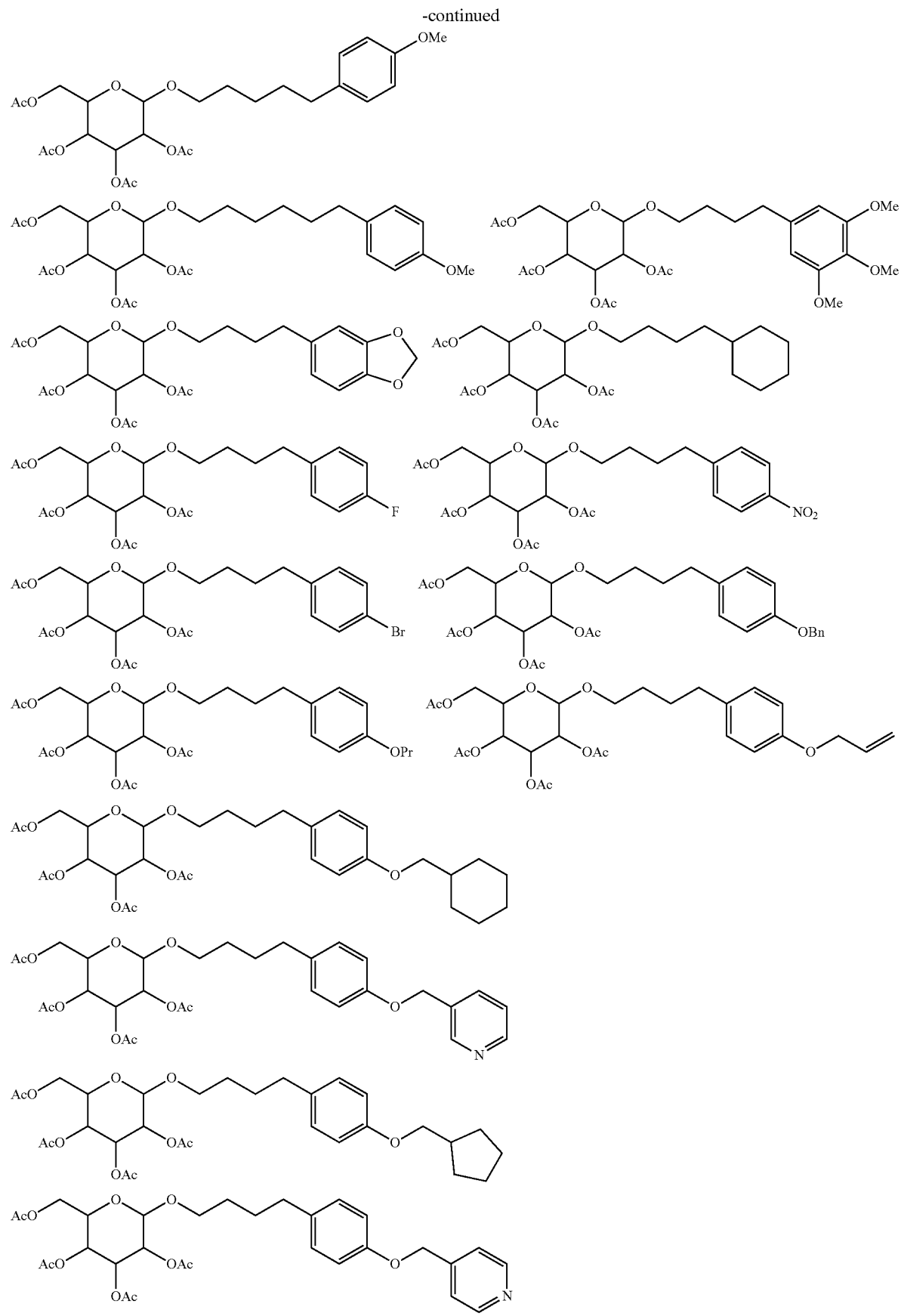

-continued
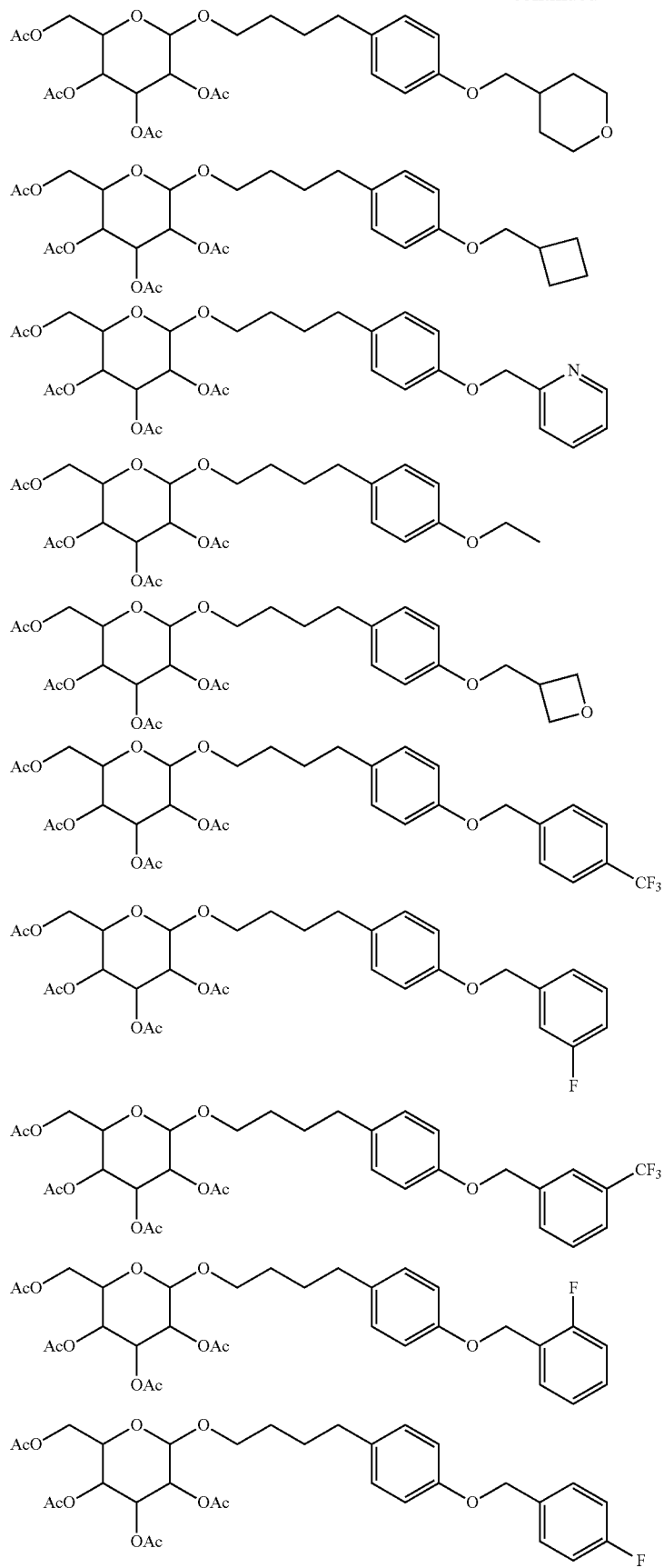

37
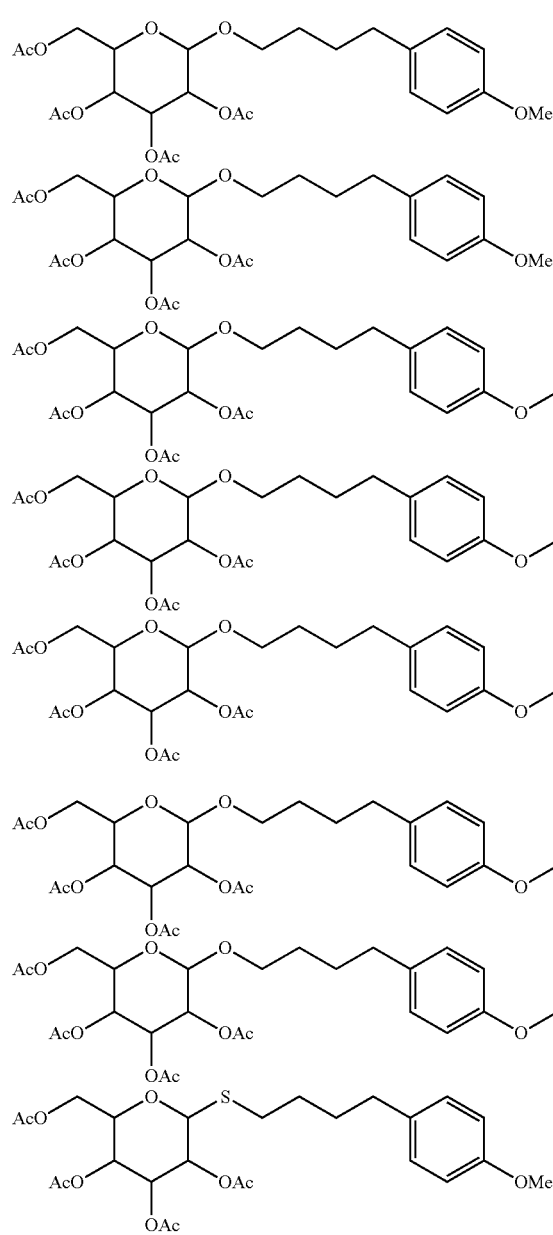
38
-continued
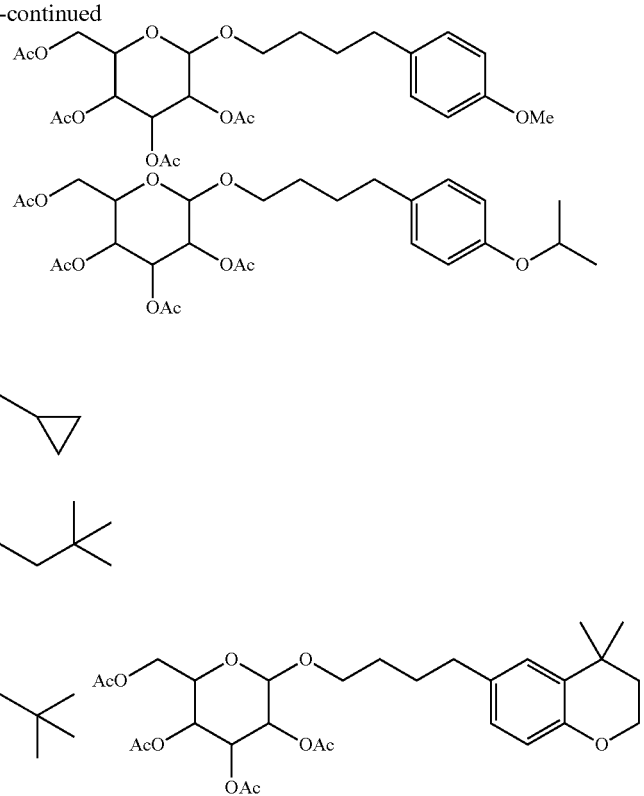
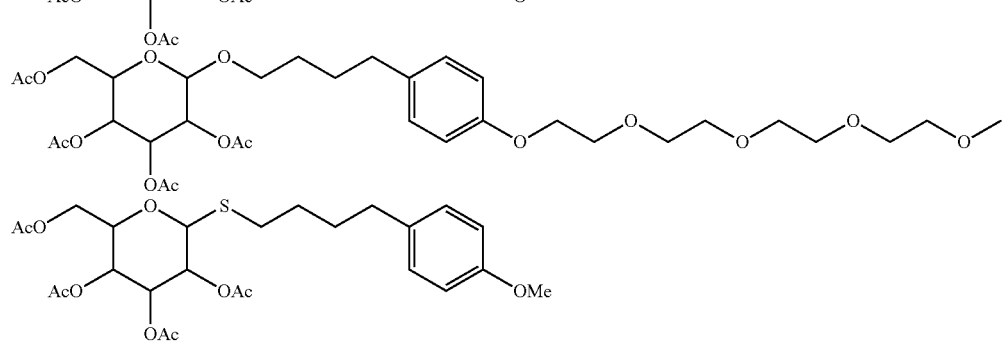
The present invention also provides an intermediate of the glycoside compound represented by Formula I:
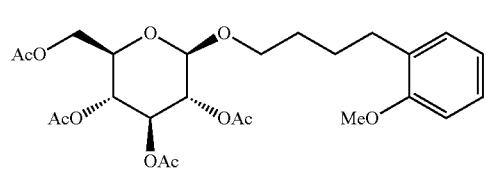 10a 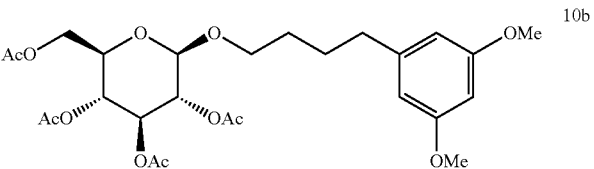 10b
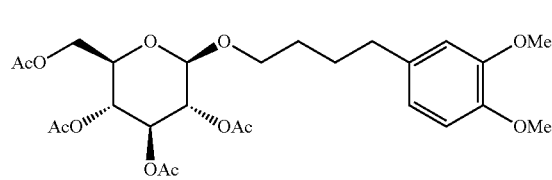

-continued
10e
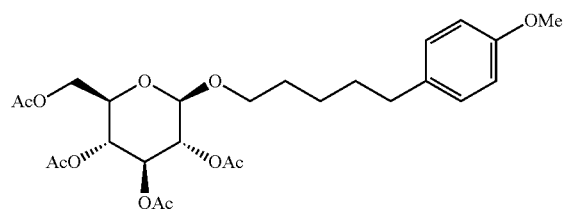
10f
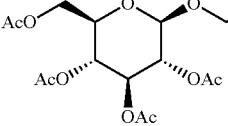
10g
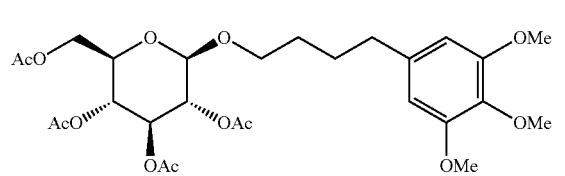
10h
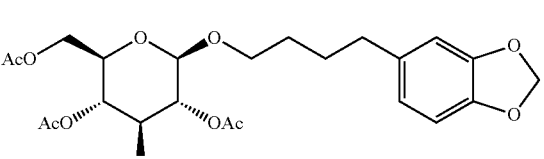
10i
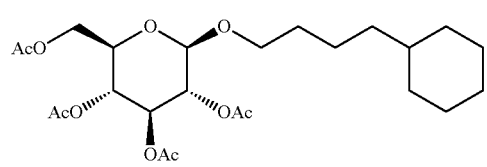
10j
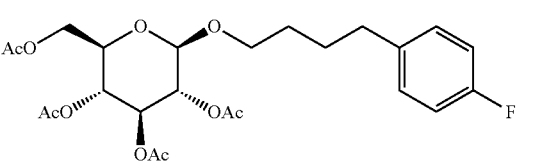
10k
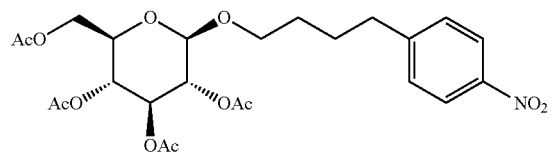
10l
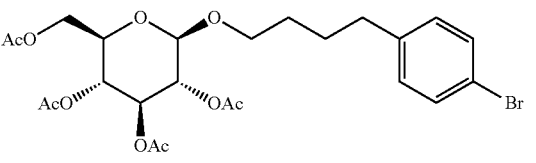
18a
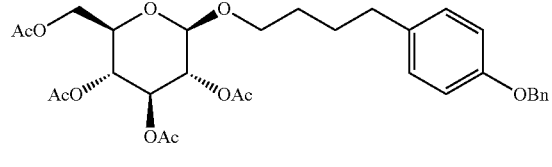
18b
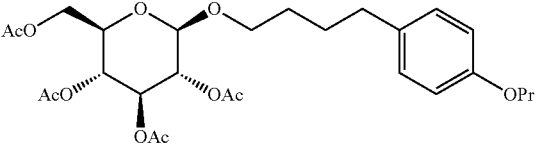
18c
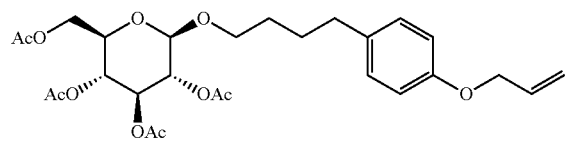
18d
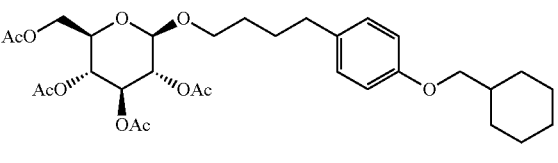
18e
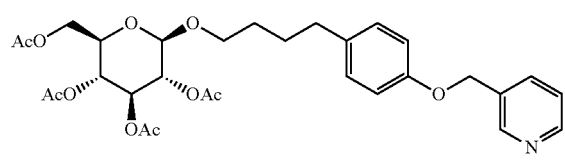
18f
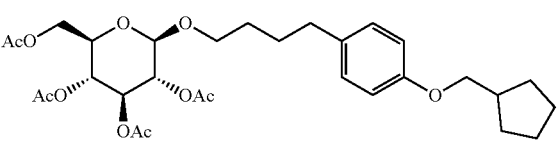
18g
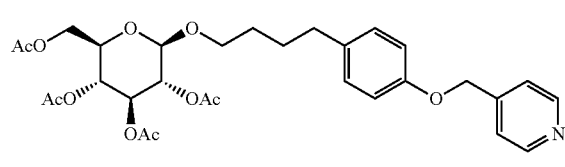
18h
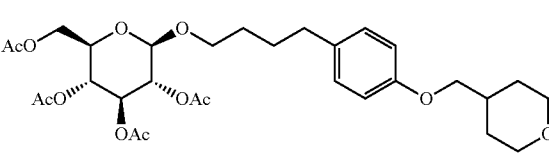
18i
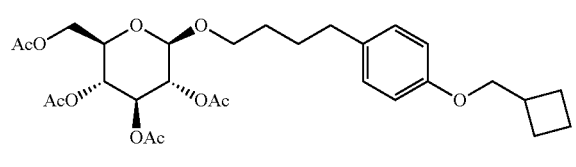
18j
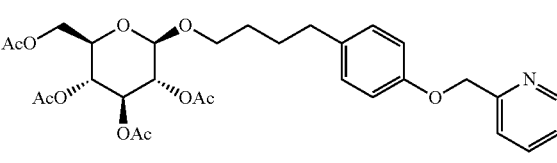

-continued
| 18k | 18l |
|---|---|
| 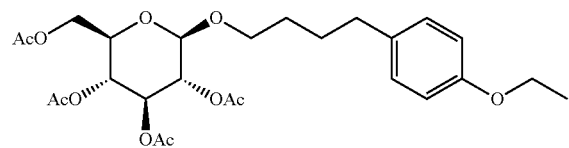 | 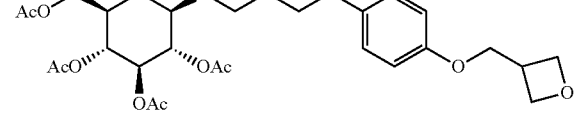 |
| 18m | 18n |
| 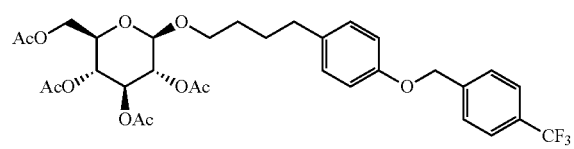 | 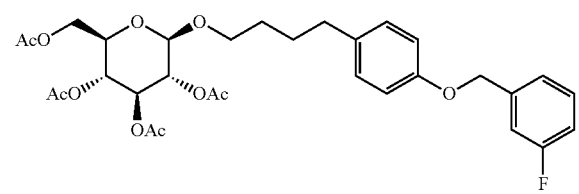 |
| 18o | 18p |
| 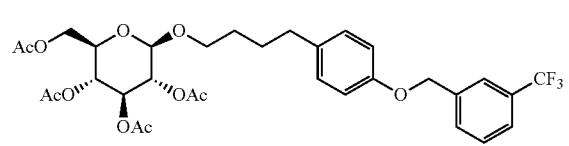 | 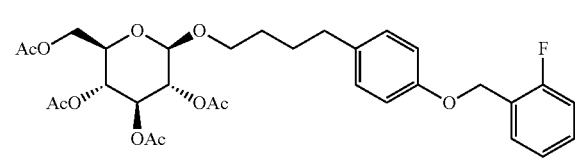 |
| 18q | 22a |
| 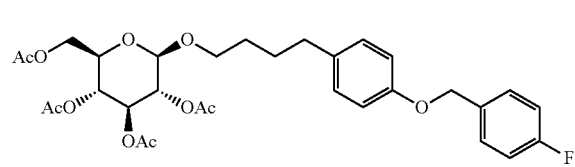 | 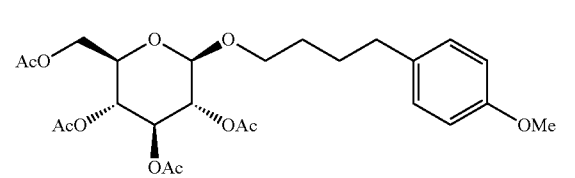 |
| 22b | 22c |
| 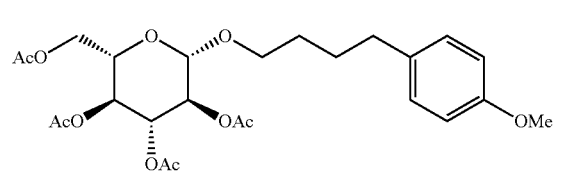 | 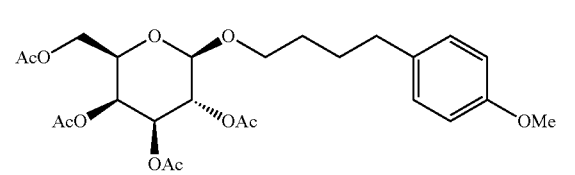 |
| 39a | 39b |
| 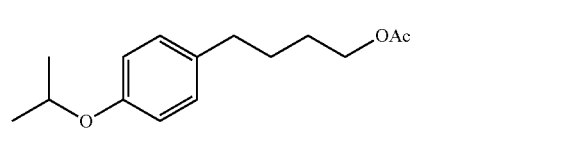 | 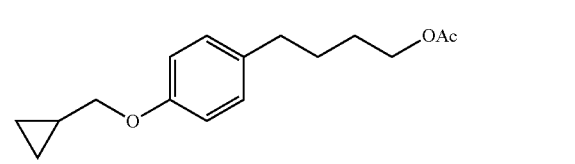 |
| 39c | 39d |
| 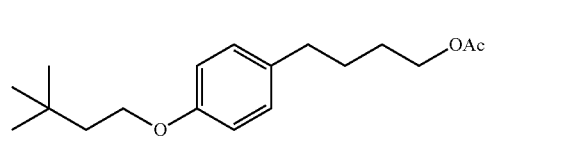 | 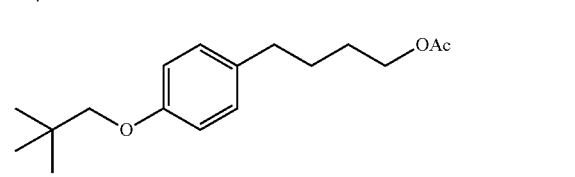 |
| 39e | |
| 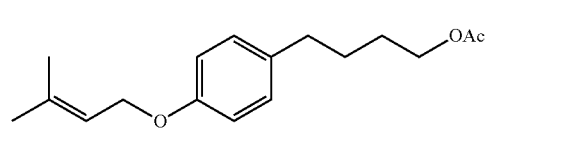 |  39f |
| | 39g |
| 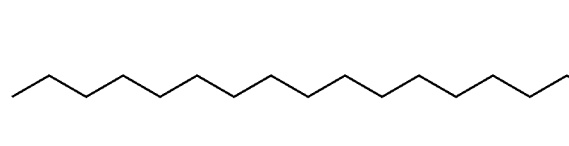 | 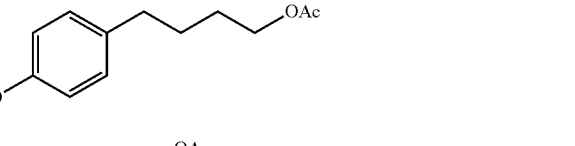 |

43 | 44
-continued
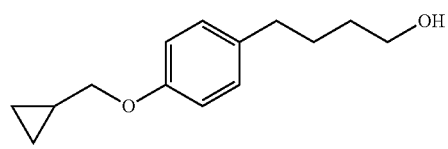
40b
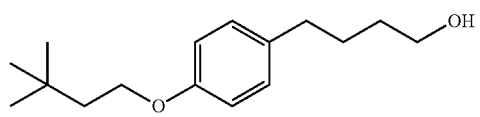
40c
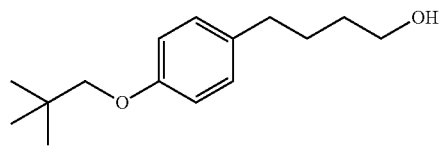
40d
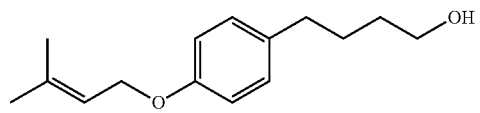
40e
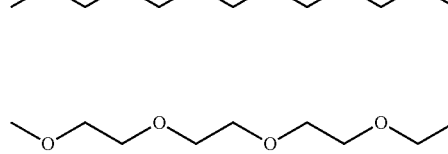
40f
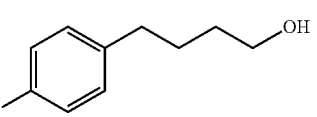
40g
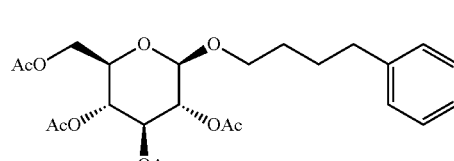
43a
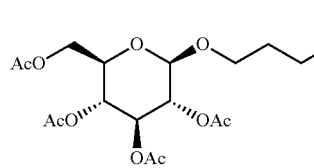
43b
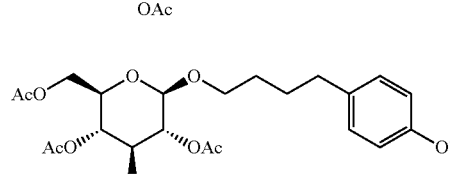
43c
43d
43e
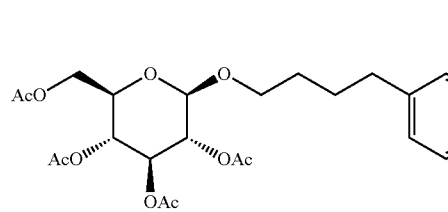
43f
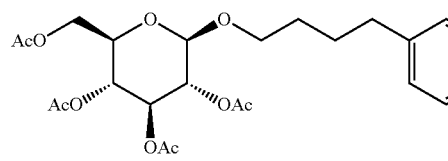
43g
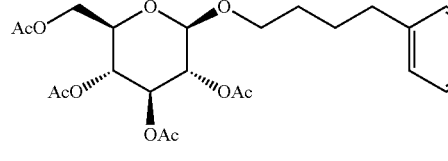
55
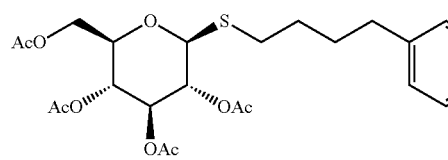

The present invention further provides use of the glycoside compound, or a tautomer, an optical isomer, a solvate, a polymorph, a pharmaceutically acceptable salt or ester, or a pharmaceutically acceptable prodrug or derivative thereof, in pro-angiogenic drugs for the prevention and/or treatment of preferably ischemic vascular diseases, and further preferably ischemic cardio-cerebrovascular diseases, particularly cerebral infarction (cerebral stroke) and myocardial infarction, and ischemic microcirculatory disturbance of lower limbs. In one aspect, this can be implemented as use of the glycoside compound, or a compound below, or a tautomer, an optical isomer, a solvate, a polymorph, a pharmaceutically acceptable salt or ester, or a pharmaceutically acceptable prodrug or derivative thereof, in the preparation of drugs that are used to prevent and/or treat ischemic vascular diseases in mammals, including humans, by promoting angiogenesis. They are further preferably used in ischemic cardio-cerebrovascular diseases, particularly cerebral infarction (cerebral stroke), myocardial infarction, and ischemic diseases of lower limbs. In another aspect, this can be implemented as a method for promoting angiogenesis in a patient in need thereof, preferably a method for treating and/or preventing a mammal (including human) having or susceptible to ischemic vascular disease, and further preferably a method for treating and/or preventing a mammal (including human) having or susceptible to ischemic cardio-cerebrovascular diseases, particularly cerebral infarction (cerebral stroke), myocardial infarction, and ischemic microcirculatory disturbance of lower limbs. The method comprises administering, to the patient, a therapeutically effective amount of the glycoside compound of the present invention, or a tautomer, an optical isomer, a solvate, a polymorph, a pharmaceutically acceptable salt or ester, or a pharmaceutically acceptable prodrug or derivative thereof, together with a pharmaceutically acceptable excipient or carrier.

Further, use of the glycoside compound of the present invention, or a tautomer, an optical isomer, a solvate, a polymorph, a pharmaceutically acceptable salt or ester, or a pharmaceutically acceptable prodrug or derivative thereof, in the prevention and/or treatment of ischemic vascular diseases is provided. Examples of ischemic cerebrovascular diseases include cerebral stroke, atherosclerotic cerebral thrombosis, cardiogenic cerebral embolism, acute ischemic cerebrovascular syndrome, small vessel disease (also known as lacunar stroke), multiple cerebral infarction, massive cerebral infarction, cerebral watershed infarction, hemorrhagic infarction, asymptomatic cerebral infarction, cerebral venous and cerebral venous sinus thrombosis, Moyamoya disease, and ischemic cerebral stroke due to other causes.

In a preferred embodiment, the ischemic cerebrovascular disease is atherosclerotic cerebral thrombosis, which is occlusion of the lumen caused by thrombus formed on the basis of atherosclerosis and various vascular diseases such as arteritis, causing clinical syndromes such as ischemia, hypoxia, necrosis, and softening of brain tissues.

In another preferred embodiment, the ischemic cerebrovascular disease is cardiogenic cerebral embolism, which is cerebral infarction caused by vascular occlusion due to the distal migration of cardiogenic emboli to the cerebral artery system through the blood flow path.

In another preferred embodiment, the ischemic cerebrovascular disease is acute ischemic cerebrovascular syndrome, which includes transient ischemic attack, reversible ischemic neurological deficit and cerebral stroke with full recovery.

In another preferred embodiment, the cerebrovascular disease is cerebral stroke. It is a group of diseases where brain tissue damage is caused by the sudden rupture of blood vessels in the brain or the failure of blood to flow to the brain due to blocked blood vessels, and includes ischemic and hemorrhagic stroke.

Preferably, a therapeutically effective amount of the glycoside compound of the present invention, or a tautomer, an optical isomer, a solvate, a polymorph, a pharmaceutically acceptable salt or ester, or a pharmaceutically acceptable prodrug or derivative thereof is administered to a patient in need thereof through a common route of administration in a conventional pharmaceutical composition (comprising an effective amount of the active ingredient and a suitable pharmaceutical carrier) and dosage form formulated for administration according to methods known in the art.

A "therapeutically effective amount" refers to an amount of the active ingredient which, when administered, is sufficient to prevent the development of, or to a certain extent alleviate one or more symptoms of the disease of interest. The specific dose of the compound administered according to the present invention is determined by the specific conditions of the case, including the compound administered, the route of administration, the specific status being treated, and similar considerations. In particular, a "therapeutically effective amount of a compound" refers to an amount of a compound sufficient to prevent or to some extent alleviate one or more ischemic vascular diseases. The ischemic vascular diseases are particularly cerebral infarction (cerebral stroke), myocardial infarction, and ischemic diseases of the lower limbs, etc. Further, the ischemic cerebrovascular diseases include cerebral stroke, atherosclerotic cerebral thrombosis, cardiogenic cerebral embolism, acute ischemic cerebrovascular syndrome, small vessel disease (also known as lacunar stroke), multiple cerebral infarction, massive cerebral infarction, cerebral watershed infarction, hemorrhagic infarction, asymptomatic cerebral infarction, cerebral venous and cerebral venous sinus thrombosis, Moyamoya disease, and ischemic cerebral stroke due to other causes.

Depending on the type and severity of the ischemic vascular disease to be treated and the response of specific patient to the drug treatment, the single dose and daily dose are different. Therefore, an accurate single dose will be determined based on standard medical principles under the guidance of a doctor.

An effective daily dose of the glycoside compound according to the present invention of 0.01 mg to about 1000 mg, about 1 mg to about 500 mg, or about 10 mg to about 200 mg, and optionally about 0.01 mg to about 2000 mg, about 10 mg to about 1000 mg, about 100 mg to about 800 mg, or about 200 mg to about 600 mg of an additional active agent in an oral dosage form are used in the treatment of ischemic vascular diseases.

The glycoside compound of the present invention, or a tautomer, an optical isomer, a solvate, a polymorph, a pharmaceutically acceptable salt or ester, or a pharmaceutically acceptable prodrug or derivative thereof may be used alone or in combination, or in a combined therapy with other therapeutic agents.

In an embodiment of the present invention, the glycoside compound, or a tautomer, an optical isomer, a solvate, a polymorph, a pharmaceutically acceptable salt or ester, or a pharmaceutically acceptable prodrug or derivative thereof, is used in the prevention and/or treatment of ischemic vascular diseases, where the prevention or treatment includes administration to use as a sole active ingredient.

In another embodiment of the present invention, the glycoside compound, or a tautomer, an optical isomer, a solvate, a polymorph, a pharmaceutically acceptable salt or ester, or a pharmaceutically acceptable prodrug or derivative thereof, is used in the prevention and/or treatment of ischemic vascular diseases, where the prevention or treatment includes administration in a combined therapy with a therapeutic agent selected from the group consisting of another glycoside compound or the present invention or a tautomer, an optical isomer, a solvate, a polymorph, a pharmaceutically acceptable salt or ester, or a pharmaceutically acceptable prodrug or derivative thereof, antihypertensive drugs, lipid-lowering drugs, thrombolytic drugs, platelet aggregation inhibitors, anticoagulants, neuroprotective drugs, calcium antagonists, glutamate antagonists, glutamate release inhibitors, GABA receptor agonists, free radical scavengers, and cell membrane stabilizers. In a preferred embodiment of the present invention, the additional therapeutic agent is selected from the group consisting of another glycoside compound of the present invention or a tautomer, an optical isomer, a solvate, a polymorph, a pharmaceutically acceptable salt or ester, or a pharmaceutically acceptable prodrug or derivative thereof, Reteplase, Lanoteplase, Monteplase, Douchi Fibrinolytic Enzyme, new earthworm fibrinolytic enzyme, Nattokinase, snake venom plasminogen activator, Aspirin, Ticlopidine, Clopidogrel, Prasugrel, Ticagrelor, Cangrelor, sarpogrelate hydrochloride, vorapaxar, atopaxar, heparin, low molecular weight heparin, warfarin, Rivaroxaban, Bivalirudin, Pradaxa, Edaravone, and Statins.

As will be apparent to those skilled in the art, a combination of the present invention comprising a glycoside compound of the present invention or a tautomer, an optical isomer, a solvate, a polymorph, a pharmaceutically acceptable salt or ester, or a pharmaceutically acceptable prodrug or derivative thereof and an additional therapeutic agent is effective not only when these active ingredients are used in a single composition, but also when they are used in two different compositions (administered simultaneously, sequentially or separately after a period of time). In addition, it will be appreciated by those skilled in the art that the glycoside compound of the present invention or a tautomer, an optical isomer, a solvate, a polymorph, a pharmaceutically acceptable salt or ester, or a pharmaceutically acceptable prodrug or derivative thereof, can be prescribed to use in a combined therapy with an additional active ingredients, to prevent and/or treat ischemic vascular diseases.

In a particular embodiment, the combined therapy comprises simultaneously, sequentially or separately administering the glycoside compound of the present invention or a tautomer, an optical isomer, a solvate, a polymorph, a pharmaceutically acceptable salt or ester, or a pharmaceutically acceptable prodrug or derivative thereof, and the additional therapeutic agent, to a subject. Alternatively, the combined therapy comprises administering the glycoside compound of the invention or a tautomer, an optical isomer, a solvate, a polymorph, a pharmaceutically acceptable salt or ester, or a pharmaceutically acceptable prodrug or derivative thereof, and an additional therapeutic agent in a single composition, to a subject.

In an embodiment of the present invention, the glycoside compound of the present invention or a tautomer, an optical isomer, a solvate, a polymorph, a pharmaceutically acceptable salt or ester, or a pharmaceutically acceptable prodrug or derivative thereof can be conveniently administered to a patient. Therefore, the compound used for the purpose of the present invention can be in the form of a pharmaceutical composition comprising an effective amount of the glycoside compound of the present invention or a tautomer, an optical isomer, a solvate, a polymorph, a pharmaceutically acceptable salt or ester, or a pharmaceutically acceptable prodrug or derivative thereof in combination with a pharmaceutically acceptable excipient or carrier. This aspect can also be implemented as a composition comprising an effective amount of the glycoside compound of the present invention or a tautomer, an optical isomer, a solvate, a polymorph, a pharmaceutically acceptable salt or ester, or a pharmaceutically acceptable prodrug or derivative thereof in combination with a pharmaceutically acceptable excipient or carrier, which is used in the prevention and/or treatment of cerebral infarction, cerebral stroke, atherosclerotic cerebral thrombosis, cardiogenic cerebral embolism, acute ischemic cerebrovascular syndrome, small vessel disease (also known as lacunar stroke), multiple cerebral infarction, massive cerebral infarction, cerebral watershed infarction, hemorrhagic infarction, asymptomatic cerebral infarction, cerebral venous and cerebral venous sinus thrombosis, Moyamoya disease, and ischemic cerebral stroke due to other causes.

In one embodiment of the present invention, the compound used can be administered in the form of a unit dosage preparation comprising a pharmaceutically acceptable conventional carrier through a route of administration including oral, injection, subcutaneous, intratracheal, transdermal, parenteral, rectal, topical, intravenous, and intramuscular administration, or others. The pharmaceutical composition can be formulated into any medicinal form, such as tablets, granules, injections, gels, pills, capsules, suppositories, implants, nano-preparations, and powder injections. Some dosage forms such as tablets and capsules can be subdivided into suitable unit dosage forms comprising an appropriate amount of the active ingredient, such as an effective amount to achieve the desired purpose.

In another embodiment, the glycoside compound of the present invention used for the purpose of the present invention, or a tautomer, an optical isomer, a solvate, a polymorph, a pharmaceutically acceptable salt or ester, or a pharmaceutically acceptable prodrug or derivative thereof is in an injectable preparation to be administered to a patient to be treated. Suitable injectable preparations in the present invention include a sterilized or sterile solution, emulsion or suspension made of a drug and a suitable solvent or dispersion medium for injection into a human, and a sterile powder preparation for being formulated into a solution or suspension before use. The injectable preparation includes an injectable solution (where a large-volume injectable solution for intravenous drip is also known as an intravenous infusion), a sterile powder for injection and a concentrated solution for injection.

The carrier includes excipients and diluents, which need to have a sufficiently high purity and a very low toxicity to make them suitable for being administered to a patient to be treated. The carrier can be inert or have pharmaceutical benefits itself.

The types of carriers include, but are not limited to, diluents such as fillers and bulking agents, binders, lubricants, anti-caking agents, disintegrants, sweeteners, buffers, preservatives, solubilizers, isotonic agents, suspending agents and dispersants, wetting or emulsifying agents, flavoring and fragrances, thickeners, and vehicles. Some carriers can be listed in more than one category, for example, vegetable oils can be used as a lubricant in some preparations and as a diluent in other preparations. Exemplary pharmaceutically acceptable carriers include sugar, starch, cellulose, malt, gelatin, talc and vegetable oils. Optional active agents can be contained in the pharmaceutical composition, which do not substantially affect the activity of the compound of the present invention.

The present invention has the following positive effects. The glycoside compound provided in the present invention has simple preparation method, can significantly increase the expression of VEGF-A mRNA, and is useful in the preparation of pro-angiogenic drugs. This provides a reliable guarantee for the development of drugs with pro-angiogenic activity for treating cerebral infarction cerebral stroke, myocardial infarction, and ischemic microcirculatory disturbance of lower limbs.

The compound or its salt of the present application may be the sole active agent administered or may be administered in conjunction with other active agents.

Definition of Terms

"Stereoisomers", "optical isomers" or "optically active isomers" are compounds that have the same chemical composition but different arrangements of atoms or groups in space. They include "diastereomers" and "enantiomers".

"Diastereomers" are stereoisomers that have two or more centers of chirality and whose molecules are not mirror images of each other. Diastereomers have different physical properties, such as melting point, boiling point, spectral characteristics and reactivity. In the presence of a resolving agent or chromatography, a mixture of diastereomers can be separated by a high-resolution analytical step such as electrophoresis and crystallization using, for example, a chiral HPLC column.

"Enantiomers" refer to two stereoisomers of a compound that are not overlapping mirror images of each other. A 50:50 mixture of enantiomers is called a racemic mixture or a racemate, which may occur during a chemical reaction or a treatment process when no stereoselectivity or stereospecificity is available.

"Alkyl" includes both branched and linear saturated aliphatic hydrocarbon groups, and has a specified number of carbon atoms, typically 1 to about 12 carbon atoms. The term C1-C6 alkyl group as used herein means an alkyl group having 1 to about 6 carbon atoms. When the C0-Cn alkyl group is used herein in combination with another group, for example, (phenyl)C0-C4 alkyl, in this specified group, phenyl is directly bonded through a single covalent bond (C0) or connected via an alkyl group with a specified number of carbon atoms (in this case, 1 to about 4 carbon atoms). Examples of the alkyl group include, but are not limited to: methyl, ethyl, n-propyl, isopropyl, n-butyl, 3-methylbutyl, tert-butyl, n-pentyl, and sec-pentyl.

"Alkenyl" refers to linear and branched hydrocarbon groups including one or more unsaturated carbon-carbon double bonds. The carbon-carbon double bonds may be present at any stable point along the chain. The alkenyl groups described herein typically have 2 to about 12 carbon atoms. Preferred alkenyl groups are lower alkenyl groups, having 2 to about 8 carbon atoms, for example, $C_2$-$C_8$, $C_2$-$C_6$, and $C_2$-$C_4$ alkenyl groups. Examples of alkenyl groups include ethenyl, propenyl, and butenyl.

"Alkoxy" refers to an alkyl group, as defined above, having a specified number of carbon atoms and connected via an oxygen bridge. Examples of alkoxy groups include, but are not limited to, methoxy, ethoxy, 3-hexyloxy, and 3-methylpentyloxy.

The term "heterocycle" means a 5- to 8-membered saturated ring, partially unsaturated ring, or aromatic ring containing 1 to about 4 heteroatoms selected from N, O, and S, with the remaining ring atoms being carbon; or a 7- to 11-membered saturated ring, partially unsaturated ring, or aromatic heterocyclic ring system, and a 10- to 15-membered tricyclic ring system, where the system contains at least 1 heteroatom selected from N, O and S in the polycyclic ring system and containing up to about 4 heteroatoms independently selected from N, O and S in each ring of the polycyclic ring system. Unless otherwise specified, a heterocycle may be attached to a group that is amenable to substitution and produces a stable structure at any heteroatom and carbon atom of the heterocycle. As indicated, the heterocycle described herein may be substituted on a carbon or nitrogen atom, provided that the resulting compound is stable. The nitrogen atom in a heterocyclic ring may optionally be quaternized. It is preferred that the total number of heteroatoms in the heterocyclyl group is not more than 4 and that the total number of S and O atoms in the heterocyclyl group is not more than 2, and more preferably not more than 1. Examples of heterocyclyl groups include pyridinyl, indolyl, pyrimidinyl, pyridizinyl, pyrazinyl, imidazolyl, oxazolyl, furyl, phenylthio, thiazolyl, triazolyl, tetrazolyl, isoxazolyl, quinolinyl, pyrrolyl, pyrazolyl, benz[b]thiophenyl, isoquinolinyl, quinazolinyl, quinoxalinyl, thienyl, isoindolyl, dihydroisoindolyl, 5,6,7,8-tetrahydroisoquinolinyl, pyridinyl, pyrimidinyl, furyl, thienyl, pyrrolyl, pyrazolyl, pyrrolidinyl, morpholinyl, piperazinyl, piperidinyl, and pyrrolidinyl.

"Aryl" or "heteroaryl" means a stable 5- or 6-membered monocyclic or polycyclic ring containing 1 to 4, or preferably 1 to 3 heteroatoms selected from N, O, and S, with the remaining ring atoms being carbon. When the total number of S and O atoms in the heteroaryl group exceeds 1, these heteroatoms are not adjacent to each other. Preferably the total number of S and O atoms in the heteroaryl group is not greater than 2. It is particularly preferred that the total number of S and O atoms in the heteroaryl group is not greater than 1. The nitrogen atom in a heterocyclic ring may optionally be quaternized. When indicated, these heteroaryl groups can also be substituted with carbon or non-carbon atoms or groups. Such substitution may include the fusion with a 5 to 7-membered saturated cyclic group optionally containing 1 or 2 heteroatoms independently selected from N, O and S to form for example [1,3]dioxazo[4,5-c]pyridinyl. Examples of heteroaryl groups include, but are not limited to, pyridinyl, indolyl, pyrimidinyl, pyridizinyl, pyrazinyl, imidazolyl, oxazolyl, furyl, phenylthio, thiazolyl, triazolyl, tetrazolyl, isoxazolyl, quinolinyl, pyrrolyl, pyrazolyl, benz[b]thiophenyl, isoquinolinyl, quinazolinyl, quinoxalinyl, thienyl, isoindolyl, and 5,6,7,8-tetrahydroisoquinolinyl.

"Pharmaceutically acceptable salt" or "salt of the compound" is a derivative of the disclosed compound, where the parent compound is modified by preparing a non-toxic acid or base addition salt thereof, and also refers to a pharmaceutically acceptable solvate, including a hydrate, of the compound and salt. Examples of pharmaceutically acceptable salts include, but are not limited to: inorganic or organic acid addition salts of basic residues such as amines; inorganic or organic base addition salts of acidic residues such as carboxylic acids; and a combination of one or more of the above salts. Pharmaceutically acceptable salts include non-toxic salts and quaternary ammonium salts of the parent compound formed, or example, with non-toxic inorganic or organic acids. For example, non-toxic acid salts include those derived from inorganic acids, such as: hydrochloric acid, hydrobromic acid, sulfuric acid, sulfamic acid, phosphoric acid, and nitric acid. Other acceptable inorganic salts include metal salts such as sodium salt, potassium salt, and cesium salts; alkaline earth metal salts such as calcium salts, and magnesium salts; and combinations including one or more of the above salts.

The organic salts of the compounds include salts prepared with organic acids such as acetic acid, trifluoroacetic acid, propionic acid, succinic acid, glycolic acid, stearic acid, lactic acid, malic acid, tartaric acid, citric acid, ascorbic acid, embonic acid, maleic acid, hydroxymaleic acid, phenylacetic acid, glutamic acid, benzoic acid, salicylic acid, methanesulfonic acid, ethanesulfonic acid, benzenesulfonic acid, p-aminobenzenesulfonic acid, 2-acetoxybenzoic acid, fumaric acid, p-toluenesulfonic acid, methanesulfonic acid, ethanedisulfonic acid, oxalic acid, isethionic acid, and HOOC—(CH2)n-COOH; organic amine salts, such as triethylamine salt, pyridine salt, picoline salt, ethanolamine salt, triethanolamine salt, dicyclohexylamine salt, and N,N'-dibenzylethylenediamine salt; amino acid salts, such as: arginine salt, aspartate salt, and glutamate salt; and combinations of one or more of the above salts.

"Glycosyl" includes monoglycosyl, diglycosyl, oligoglycosyl, and polyglycosyl, etc. Monoglycosyl includes, but is not limited to, erythrosyl, threitolyl, arabinosyl, ribosyl, xylosyl, lyxosyl, glucosyl, mannosyl, fructosyl, galactosyl, etc. Diglycosyl includes, but is not limited to, sucrosyl, maltosyl, cellobiosyl, isomaltosyl, gentiobiosyl, trehalosyl and lactosyl.

"Prodrug" refers to a compound that is metabolized, for example by hydrolysis or oxidation, in the host to produce a compound of the present invention. Typical examples of the prodrug include compounds that have a biologically unstable protective group on the functional group of the active compound. The prodrug can be oxidized, reduced, aminated, deaminated, hydroxylated, dehydroxylated, hydrolyzed, dehydrated, alkylated, dealkylated, acylated, deacylated, phosphorylated, dephosphorylated to produce an active compound.

"Derivative" refer to a more complex product derived from the substitution of hydrogen atom(s) or atomic group(s) of the compound with additional atom(s) or atomic group(s).

DETAILED DESCRIPTION

Figure 1:
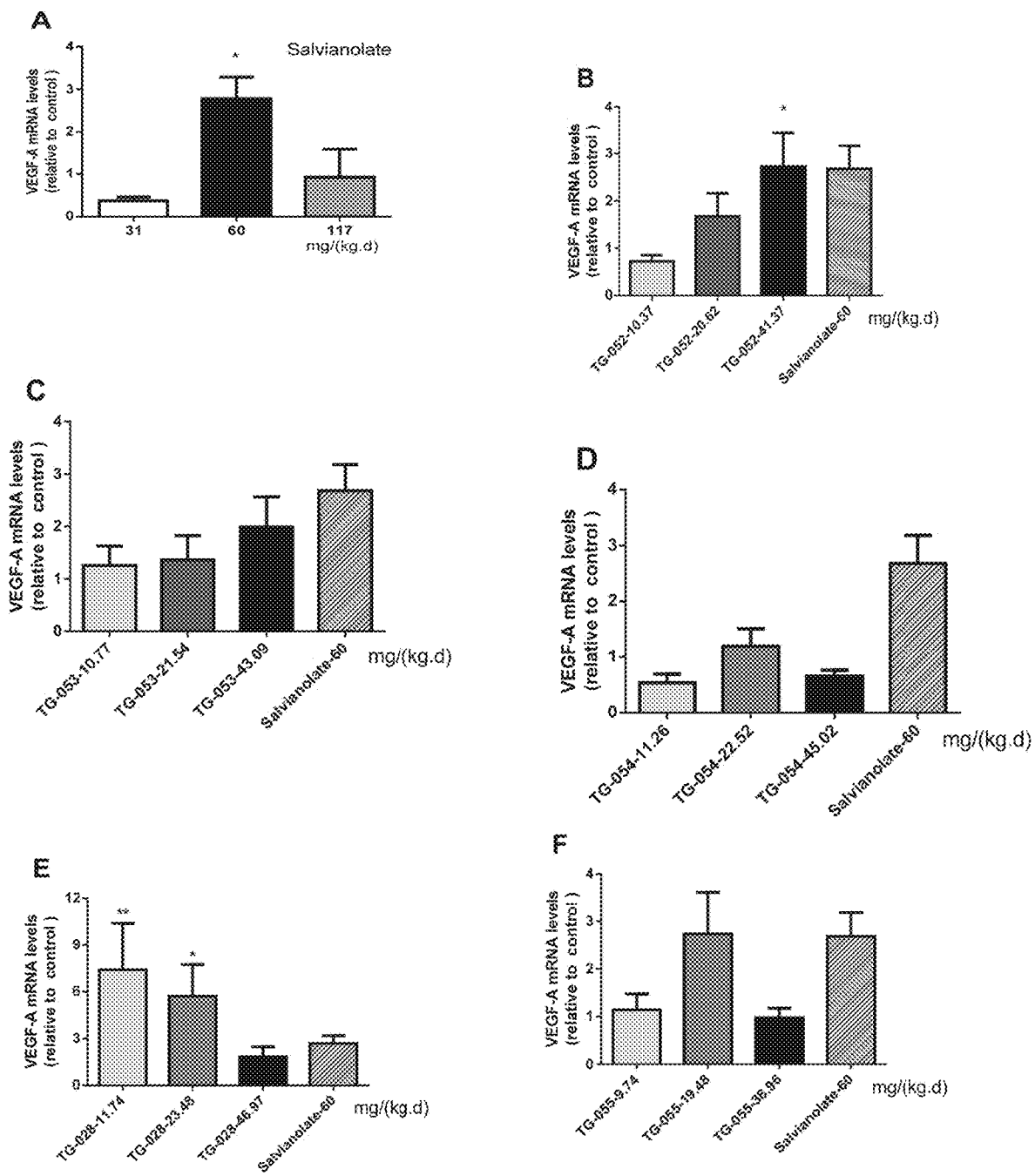
FIG. 1 is a schematic diagram showing the effects of compounds on VEGF-A mRNA expression in a sponge implanted animal model.

The present invention will be further described by way of examples below; however, the present invention is not limited thereto. In examples below where no specific conditions are given in the experimental methods, the experimental conditions are selected according to conventional methods and conditions, or according to the product instructions.

Route A: Synthesis of Compounds TG-001, TG-002, TG-003, TG-004, TG-005, TG-006, TG-007, TG-008, and TG-057

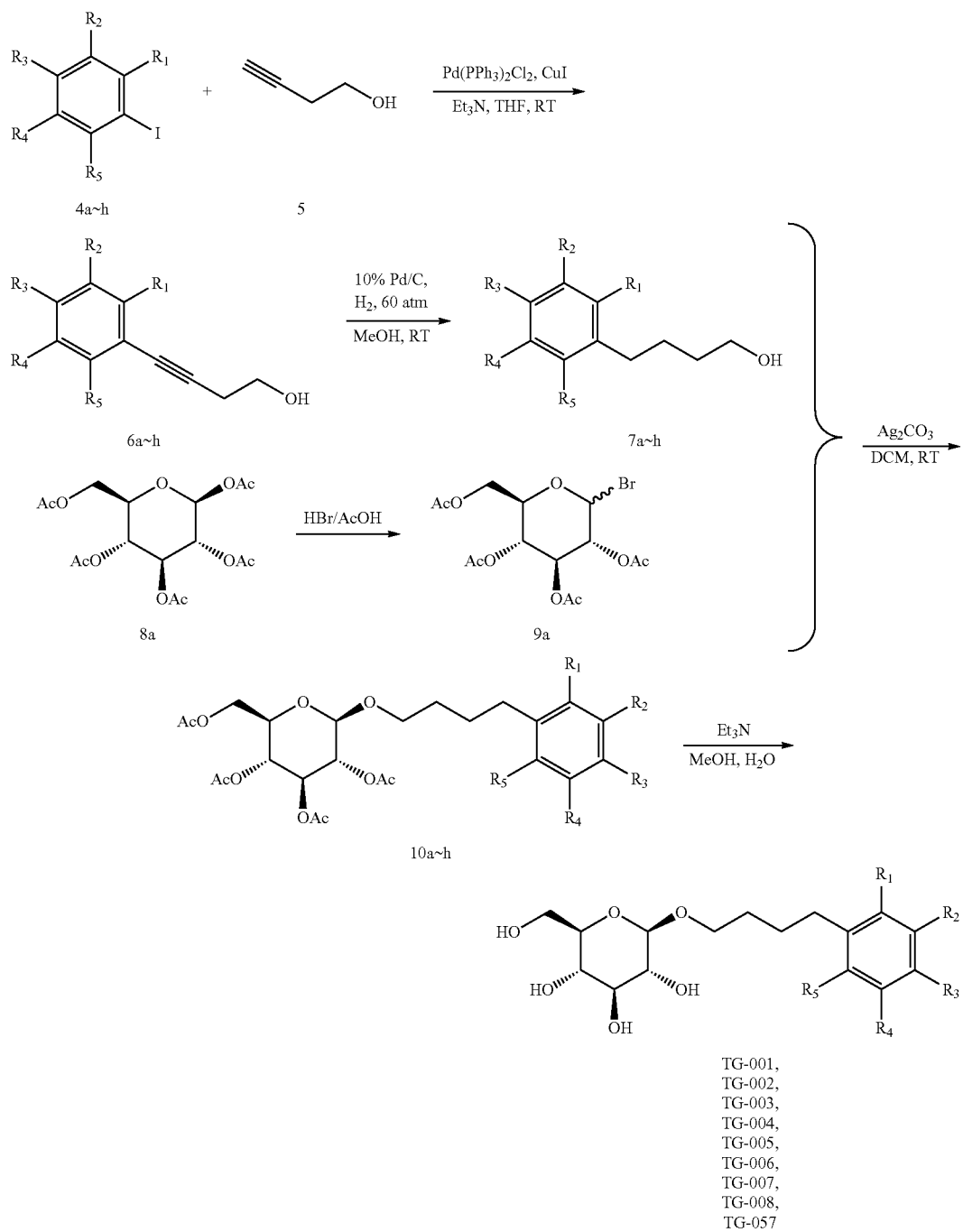

Experimental operations of Route a:

Compound 4a (1 eq), Pd(PPh$_3$)$_2$Cl$_2$ (2 mol %), and CuI (2 mol %) were added to a reaction flask. Under a N$_2$ atmosphere, THF (0.2 M), Compound 5 (1.2 eq), and Et$_3$N (9.6 eq) were sequentially added to the system, and then reacted for 20 h at room temperature. After filtering through celite (Shanghai Dahe Chemical Co., Ltd. analytical pure AR), the reaction solution was directly spin-dried, and then separated by chromatography (petroleum ether/ethyl acetate=2:1), to obtain Compound 6a (yield 89%). Compound 6a (1 eq), and Pd/C (10%) were added to MeOH (0.1 M), and reacted at room temperature for 20 h under 60 atm of H$_2$. After filtering through celite, the reaction solution was concentrated under reduced pressure and purified by column chromatography on silica gel to obtain Compound 7a (yield 94%).

33% HBr/AcOH (4 eq) solution was added dropwise to Compound 8a (1 eq), and reacted at room temperature for 4 h. The reaction solution was directly spin-dried, and recrystallized in Et$_2$O and n-hexane to obtain Compound 9a (76 g, yield 98%).

Compounds 7a (1 eq) and 9a (1.2 eq) were added to a reaction flask. Under a N$_2$ atmosphere, dichloromethane (0.3 M) was added to the system, and reacted for 30 min at room temperature. Ag$_2$CO$_3$ (1.2 eq) was added to the system, and reacted at room temperature for 20 h. After filtration, the reaction solution was directly spin-dried and separated by chromatography (Eluent: petroleum ether/ethyl acetate=4:1) to obtain Compound 10a (yield 40%). Compound 10a (1 eq) was added to a reaction flask, and then MeOH (4 M), H$_2$O (4 M), and Et$_3$N (2 eq) were respectively added, reacted at room temperature for 20 h, concentrated under reduced pressure, and purified by column chromatography on silica gel (Eluent: dichloromethane:methanol=9:1), to obtain Compound TG-001 (yield 70%).

Compounds TG-002, TG-003, TG-004, TG-005, TG-006, TG-007, TG-008, and TG-057 have a synthesis route similar to that for Compound TG-001, and have structures show below:

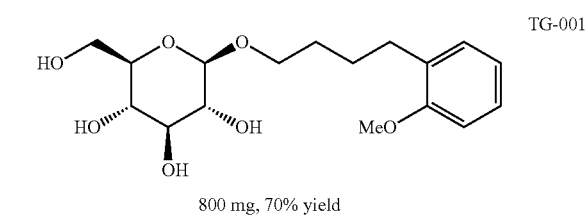

TG-001

800 mg, 70% yield

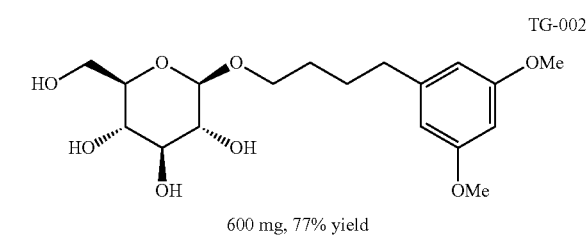

TG-002

600 mg, 77% yield

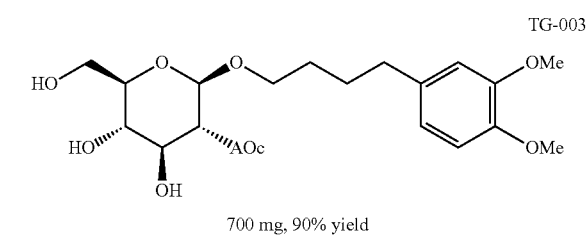

TG-003

700 mg, 90% yield

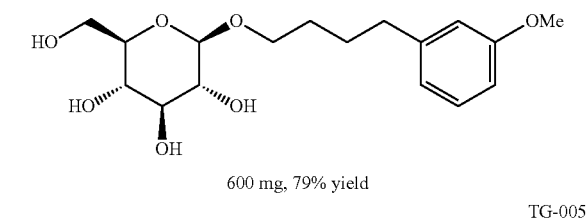

TG-004

600 mg, 79% yield

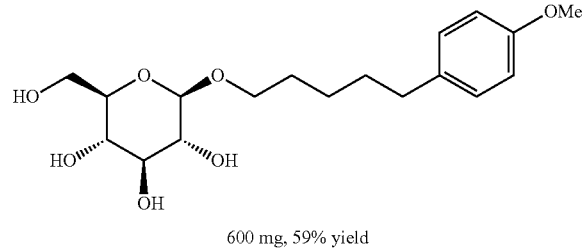

TG-005

600 mg, 59% yield

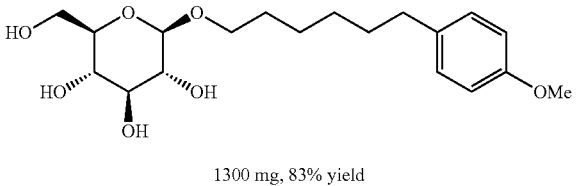

TG-006

1300 mg, 83% yield

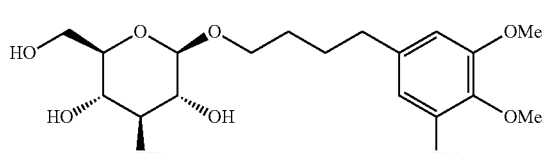

TG-007

900 mg, 71% yield

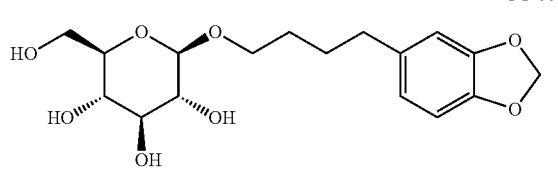

TG-008

1400 mg, 80% yield

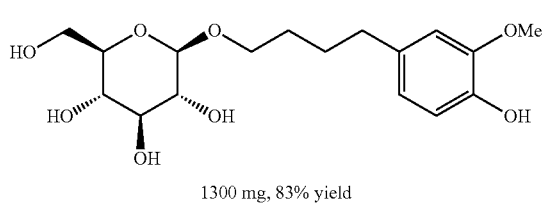

TG-057

1300 mg, 83% yield

The identification data for structures of Compounds TG-001, TG-002, TG-003, TG-004, TG-005, TG-006, TG-007, TG-008, and TG-057 are shown below: Identification data for TG-001:

$^1$H NMR (400 MHz, CD$_3$OD) δ (ppm) 7.17-7.06 (m, 2H), 6.88 (d, J=8.0 Hz, 1H), 6.82 (td, J=7.4, 0.9 Hz, 1H), 4.23 (d, J=7.8 Hz, 1H), 3.91 (m, 1H), 3.85 (dd, J=11.9, 2.0 Hz, 1H), 3.80 (s, 3H), 3.66 (dd, J=11.9, 5.3 Hz, 1H), 3.55 (m, 1H), 3.37-3.21 (m, 3H), 3.19-3.12 (m, 1H), 2.61 (t, J=7.0 Hz, 2H), 1.64 (m, 4H).

LRMS (ESI): [M+Na]$^+$ 365.1; HRMS (ESI): [M+H]$^+$ calculated C$_{17}$H$_{27}$O$_7^+$ 343.1751, found 343.1748.

Data for TG-002

$^1$H NMR (400 MHz, CD$_3$OD) δ (ppm) 6.35 (d, J=2.2 Hz, 2H), 6.28 (t, J=2.2 Hz, 1H), 4.24 (d, J=7.8 Hz, 1H), 3.96-3.91 (m, 1H), 3.85 (dd, J=11.8, 1.7 Hz, 1H), 3.74 (s, 6H), 3.66 (dd, J=11.9, 5.2 Hz, 1H), 3.58-3.53 (m, 1H), 3.38-3.21 (m, 3H), 3.19-3.11 (m, 1H), 2.57 (t, J=7.3 Hz, 2H), 1.75-1.58 (m, 4H).

LRMS (ESI): [M+Na]$^+$ 395.1; HRMS (ESI): [M+NH$_4$]$^+$ calculated C$_{18}$H$_{32}$O$_8$N$^+$ 390.2122, found 390.2122.

Data for TG-003

$^1$H NMR (400 MHz, CD$_3$OD) δ (ppm) 6.84 (d, J=8.2 Hz, 1H), 6.79 (d, J=1.9 Hz, 1H), 6.72 (dd, J=8.1, 1.9 Hz, 1H), 4.24 (d, J=7.8 Hz, 1H), 3.98-3.88 (m, J H), 3.86 (dd, J=11.9, 1.9 Hz, 1H), 3.81 (s, 3H), 3.79 (s, 1H), 3.66 (dd, J=11.9, 5.3 Hz, 1H), 3.61-3.51 (m, 1H), 3.38-3.21 (m, 3H), 3.20-3.12 (m, 1H), 2.58 (t, J=7.2 Hz, 2H), 1.75-1.56 (m, 4H).

LRMS (ESI): [M+Na]$^+$ 395.1; HRMS (ESI): [M+NH$_4$]$^+$ calculated C$_{18}$H$_{32}$O$_8$N$^+$ 390.2122, found 390.2118.

Data for TG-005:

¹H NMR (400 MHz, CD₃OD) δ (ppm) 7.07 (d, J=8.8 Hz, 2H), 6.80 (d, J=8.8 Hz, 2H), 4.23 (d, J=7.8 Hz, 1H), 3.93-3.82 (m, 2H), 3.75 (s, 3H), 3.66 (dd, J=11.9, 5.3 Hz, 1H), 3.52 (dt, J=9.5, 6.7 Hz, 1H), 3.38-3.22 (m, 3H), 3.20-3.12 (m, 1H), 2.54 (t, J=7.6 Hz, 2H), 1.68-1.61 (m, 4H), 1.47-1.31 (m, 2H).

LRMS (ESI): [M+Na]⁺ 375.1; HRMS (ESI): [M+H]⁺ calculated $C_{18}H_{29}O_7^+$ 357.1908, found 357.1906.

Data for TG-006:

¹H NMR (400 MHz, CD₃OD) δ (ppm) 7.06 (d, J=8.6 Hz, 2H), 6.84-6.80 (d, J=8.6 Hz, 2H), 4.23 (d, J=7.8 Hz, 1H), 3.93-3.82 (m, 2H), 3.75 (s, 3H), 3.66 (dd, J=11.9, 5.2 Hz, 1H), 3.52 (dt, J=9.5, 6.7 Hz, 1H), 3.38-3.21 (m, 3H), 3.20-3.11 (m, 1H), 2.53 (t, J=7.6 Hz, 2H), 1.68-1.50 (m, 4H), 1.47-1.25 (m, 4H).

LRMS (ESI): [M+Na]⁺ 393.1; HRMS (ESI): [M+NH₄]⁺ calculated $C_{19}H_{34}O_7N^+$ 388.2330, found 388.2327.

Data for end product TG-004:

¹H NMR (400 MHz, CD₃OD) δ (ppm) 7.15 (t, J=7.8 Hz, 1H), 6.79-6.67 (m, 3H), 4.24 (d, J=7.8 Hz, 1H), 3.92 (dt, J=9.4, 6.4 Hz, 1H), 3.85 (dd, J=11.9, 1.8 Hz, 1H), 3.76 (s, 3H), 3.66 (dd, J=11.9, 5.2 Hz, 1H), 3.60-3.51 (m, 1H), 3.39-3.21 (m, 3H), 3.19-3.12 (m, 1H), 2.60 (t, J=7.3 Hz, 2H), 1.78-1.56 (m, 4H).

LRMS (ESI): [M+Na]⁺ 365.1; HRMS (ESI): [M+NH₄]⁺ calculated $C_7H_{30}O_7N^+$ 360.2017, found 360.2016.

Data for TG-007:

¹H NMR (400 MHz, CD₃OD) δ (ppm) 6.49 (s, 2H), 4.24 (d, J=7.8 Hz, 1H), 3.97-3.83 (m, 2H), 3.81 (s, 6H), 3.72 (s, 3H), 3.69-3.52 (m, 2H), 3.37-3.21 (m, 3H), 3.20-3.13 (m, 1H), 2.59 (t, J=7.3 Hz, 2H), 1.79-1.55 (m, 4H).

LRMS (ESI): [M+Na]⁺ 425.1; HRMS (ESI): [M+NH₄]⁺ calculated $C_{19}H_{34}O_9N^+$ 420.2228, found 420.2226.

Data for TG-008:

¹H NMR (400 MHz, CD₃OD) δ (ppm) 6.71-6.67 (m, 2H), 6.65-6.61 (m, 1H), 5.87 (s, 2H), 4.23 (d, J=7.8 Hz, 1H), 3.95-3.88 (m, 1H), 3.85 (m, 1H), 3.66 (dd, J=11.8, 5.2 Hz, 1H), 3.60-3.48 (m, 1H), 3.38-3.20 (m, 3H), 3.19-3.12 (m, 1H), 2.55 (t, J=7.1 Hz, 2H), 1.73-1.53 (m, 4H).

LRMS (ESI): [M+Na]⁺ 379.0; HRMS (ESI): [M+Na]⁺ calculated $C_{17}H_{24}O_8Na^+$ 379.1374, found 379.1362.

Data for TG-057

¹H NMR (400 MHz, CDCl₃) δ (ppm) 6.83 (d, 1H, J=7.6 Hz), 6.70-6.64 (m, 2H), 6.26 (br, 1H), 4.83 (br, 8H), 4.00 (s, 1H), 3.88 (s, 3H), 3.74 (t, 2H, J=6.4 Hz), 3.55 (s, 2H), 2.58 (t, 2H, J=7.2 Hz), 1.69-1.62 (m, 4H).

LRMS (ESI): [M+Na]⁺ 381.2.

The structure of each reaction intermediate during the experiment is shown below:

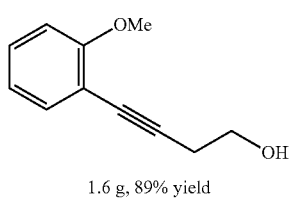

1.6 g, 89% yield

6a

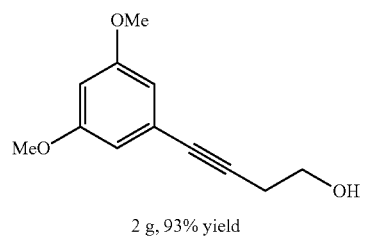

2 g, 93% yield

6b

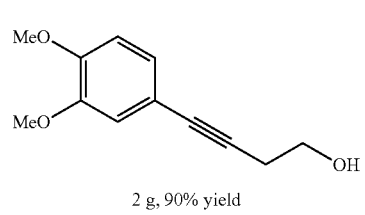

2 g, 90% yield

6c

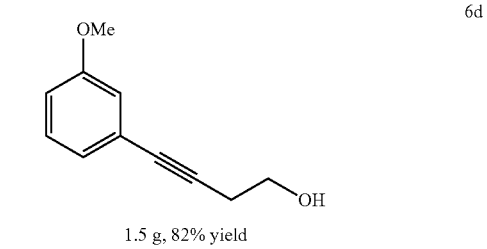

1.5 g, 82% yield

6d

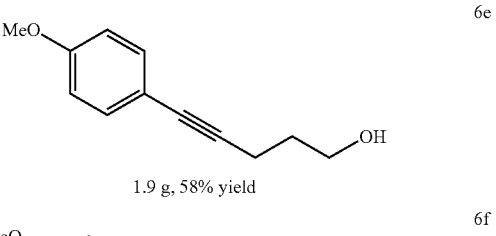

1.9 g, 58% yield

6e

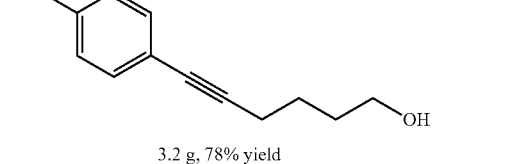

3.2 g, 78% yield

6f

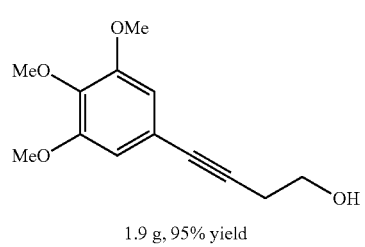

1.9 g, 95% yield

6g

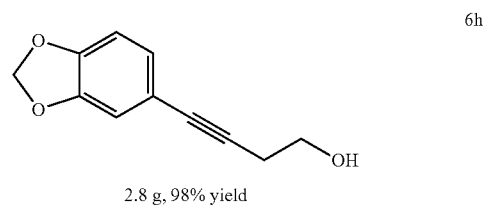

2.8 g, 98% yield

6h

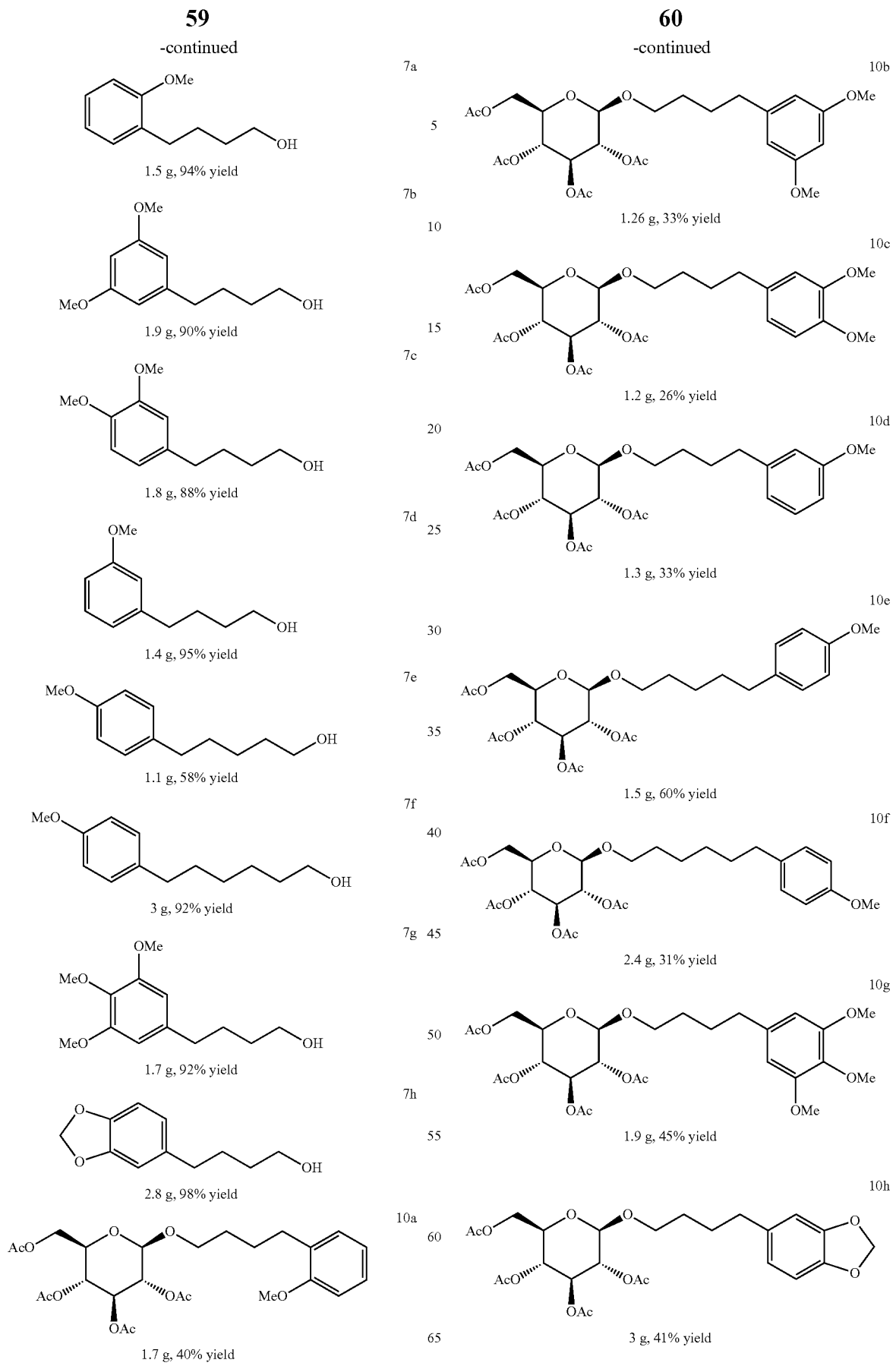

The identification data for Intermediates 10a-10h is:

10a:
1H NMR (400 MHz, CDCl$_3$) δ 6.32 (d, J=2.2 Hz, 2H), 6.29 (t, J=2.2 Hz, 1H), 5.20 (t, J=9.5 Hz, 1H), 5.08 (t, J=9.7 Hz, 1H), 4.98 (dd, J=9.6, 8.0 Hz, 1H), 4.48 (d, J=8.0 Hz, 1H), 4.26 (dd, J=12.3, 4.7 Hz, 1H), 4.13 (dd, J=12.3, 2.3 Hz, 1H), 3.89 (d, J=9.5 Hz, 1H), 3.78 (s, 6H), 3.68 (dd, J=9.9, 2.2 Hz, 1H), 3.49 (d, J=9.4 Hz, 1H), 2.55 (t, J=6.6 Hz, 2H), 2.08 (s, 3H), 2.05-1.97 (m, 9H), 1.63 (dd, J=11.5, 4.3 Hz, 4H).

LRMS (ESI): [M+Na]$^+$ 533.5.

10b:
$^1$H NMR (400 MHz, CDCl$_3$) 6.34-6.28 (m, 3H), 5.20 (t, J=9.5 Hz, 1H), 5.08 (t, J=9.7 Hz, 1H), 4.98 (dd, J=9.6, 8.0 Hz, 1H), 4.48 (d, J=8.0 Hz, 1H), 4.26 (dd, J=12.3, 4.7 Hz, 1H), 4.13 (dd, J=12.3, 2.3 Hz, 1H), 3.89 (d, J=9.5 Hz, 1H), 3.78 (s, 6H), 3.68 (dd, J=9.9, 2.2 Hz, 1H), 3.49 (d, J=9.4 Hz, 1H), 2.55 (t, J=6.6 Hz, 2H), 2.10-2.07 (s, 3H), 2.03 (s, 3H), 2.00 (m, 6H), 1.63 (dd, J=11.5, 4.3 Hz, 4H).

LRMS (ESI): [M+Na]$^+$ 563.5.

10c:
$^1$H NMR (300 MHz, CDCl$_3$) δ 6.82-6.59 (m, 3H), 5.27-4.83 (m, 3H), 4.46 (d, J=7.9 Hz, 1H), 4.32-3.99 (m, 2H), 3.83 (m, 7H), 3.74-3.35 (m, 2H), 2.53 (m, 2H), 1.99 (m, 12H), 1.59 (m, 4H).

LRMS (ESI): [M+Na]$^+$ 563.5.

10d:
$^1$H NMR (300 MHz, CDCl$_3$) δ 7.19 (t, J=8.1 Hz, 1H), 6.81-6.65 (m, 3H), 5.28-4.88 (m, 3H), 4.48 (d, J=8.0 Hz, 1H), 4.32-4.06 (m, 2H), 3.88 (m, 1H), 3.80 (s, 3H), 3.68 (d, J=8.2 Hz, 1H), 3.51 (m, 1H), 2.59 (m, 2H), 2.03 (m, 12H), 1.64 (m, 4H).

LRMS (ESI): [M+Na]$^+$ 533.5.

10e:
$^1$H NMR (300 MHz, CDCl$_3$) δ 7.08 (d, J=6.9 Hz, 2H), 6.82 (d, J=6.8 Hz, 2H), 5.69 (d, J=4.2 Hz, 1H), 5.19 (m, 1H), 4.91 (d, J=9.3 Hz, 1H), 4.30 (m, 1H), 4.20 (m, 2H), 3.96 (m, 1H), 3.79 (s, 3H), 3.46 (t, J=5.7 Hz, 2H), 2.55 (t, J=7.0 Hz, 2H), 2.09 (m, 9H), 1.71 (s, 3H), 1.66-1.48 (m, 4H), 1.36 (d, 0.1=6.7 Hz, 2H).

LRMS (ESI): [M+Na]$^+$ 547.5.

10f:
$^1$H NMR (400 MHz, CDCl$_3$) δ 7.08 (d, J=8.6 Hz, 2H), 6.83 (t, J=5.7 Hz, 2H), 5.20 (t, J=9.5 Hz, 1H), 5.08 (t, J=9.7 Hz, 1H), 4.98 (dd, J=9.6, 8.0 Hz, 1H), 4.48 (d, J=8.0 Hz, 1H), 4.26 (dd, J=12.3, 4.7 Hz, 1H), 4.12 (m, 1H), 3.86 (dt, J=9.6, 6.3 Hz, 1H), 3.79 (s, 3H), 3.68 (ddd, J=9.9, 4.6, 2.4 Hz, 1H), 3.46 (dt, J=9.5, 6.8 Hz, 1H), 2.58-2.49 (m, 2H), 2.08 (s, 3H), 2.02 (m, 9H), 1.62-1.49 (m, 4H), 1.36-1.28 (m, 4H).

LRMS (ESI): [M+Na]$^+$ 561.5.

10g:
LRMS (ESI): [M+Na]$^+$ 593.5.

10h:
LRMS (ESI): [M+Na]$^+$ 547.5.

Route B: Synthesis of Compounds TG-009, TG-010, TG-011, and TG-012

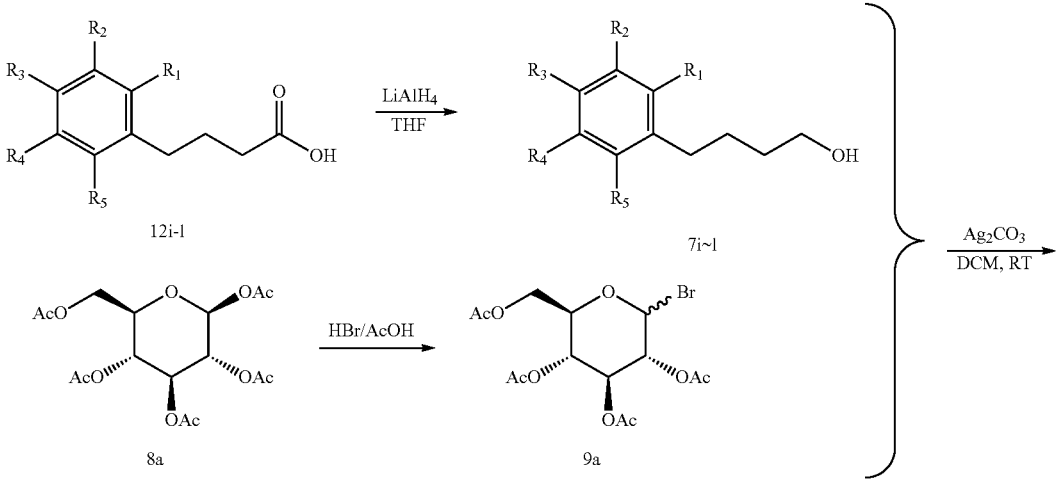

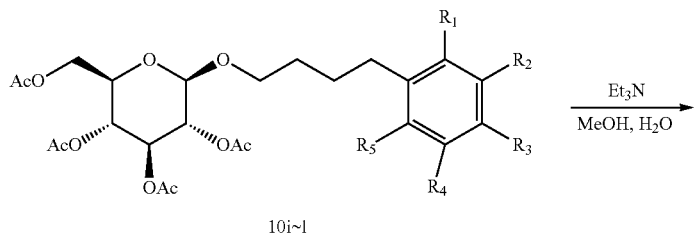

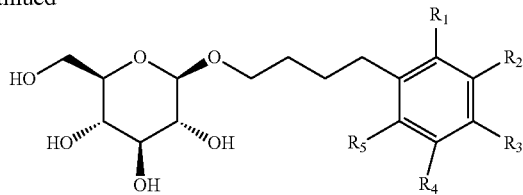

TG-009,
TG-010,
TG-011,
TG-012

Experimental Operations of Route B:

Compound 12i (1 eq) was dissolved in THF (0.2 M), and then LiAlH$_4$ (2 eq) was slowly added to the system at 0° C., and reacted at room temperature for 2-20 h. At 0° C., H$_2$O (1 time the volume of the solvent THF), 15% NaOH solution (1 time the volume of the solvent THF), and H$_2$O (3 times the volume of the solvent THF) were slowly added to the system in sequence. The solution was extracted with ethyl acetate, and the extracts were combined, washed with saturated brine and dried over anhydrous sodium sulfate. After the solvent was distilled off under reduced pressure, the residue was purified by column chromatography on silica gel (Eluent: petroleum ether/ethyl acetate=4:1) to obtain Compound 7i (yield 98%).

Compounds 7i (1 eq) and 9a (1.2 eq) were added to a reaction flask. Under a N$_2$ atmosphere, dichloromethane (0.3 M) was added to the system, and reacted for 30 min at room temperature. Ag$_2$CO$_3$ (1.2 eq) was added to the system, and reacted at room temperature for 20 h. After filtering through celite, the reaction solution was concentrated under reduced pressure and purified by column chromatography on silica gel to obtain Compound 10i (yield 26%). Compound 10i (1 eq) was added to a reaction flask, and then MeOH (4 M), H$_2$O (4 M), and Et$_3$N (2 eq) were respectively added, reacted at room temperature for 20 h, and purified by column chromatography on silica gel (Eluent: dichloromethane:methanol=9:1), to obtain Compound TG-009 (yield 75%).

Compounds TG-010, TG-011, and TG-012 have a synthesis route similar to that for Compound TG-009. The structures and identification data for Compounds TG-009, TG-010, TG-011, and TG-012 are shown below:

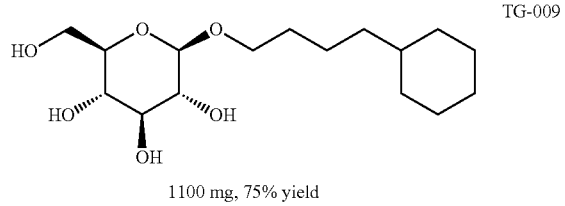

1100 mg, 75% yield

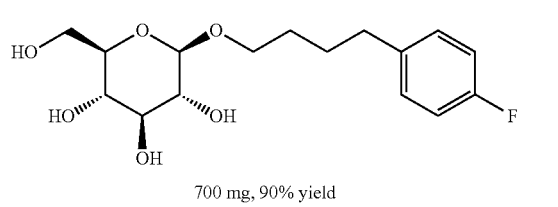

700 mg, 90% yield

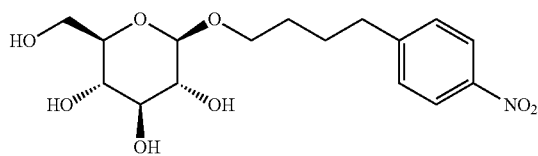

550 mg, 73% yield

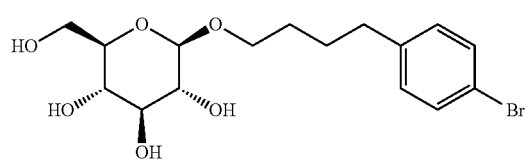

1000 mg, 79% yield

Data for TG-009

$^1$H NMR (400 MHz, CD$_3$OD) δ (ppm) 4.24 (d, J=7.8 Hz, 1H), 3.95-3.81 (m, 2H), 3.66 (dd, J=11.9, 5.2 Hz, 1H), 3.53 (dt, J=9.5, 6.7 Hz, 1H), 3.38-3.21 (m, 3H), 3.20-3.11 (m, 1H), 1.81-1.51 (m, 7H), 1.46-1.08 (m, 8H), 0.95-0.80 (m, 2H).

LRMS (ESI): [M+Na]$^+$ 341.1; HRMS (ESI): [M+Na]$^+$ calculated C$_{16}$H$_{30}$O$_6$Na$^+$ 341.1946, found 341.1934.

Data for TG-012

$^1$H NMR (400 MHz, CD$_3$OD) δ (ppm) 7.38 (d, J=8.3 Hz, 2H), 7.12 (d, J=8.3 Hz, 2H), 4.24 (d, J=7.8 Hz, 1H), 3.92 (dt, J=9.5, 6.4 Hz, 1H), 3.85 (dd, J=11.9, 1.6 Hz, 1H), 3.66 (dd, J=11.8, 5.2 Hz, 1H), 3.56 (dt, J=9.6, 6.3 Hz, 1H), 3.31 (m, 3H), 3.19-3.11 (m, 1H), 2.61 (t, J=7.4 Hz, 2H), 1.77-1.55 (m, 4H).

LRMS (ESI): [M+Na]$^+$ 414.9; HRMS (ESI): [M+Na]$^+$ calculated C$_{16}$H$_{23}$O$_6$BrNa$^+$ 413.0570, found 413.0568.

Data for TG-011

$^1$H NMR (400 MHz, CD$_3$OD) δ (ppm) 8.14 (d, J=8.7 Hz, 2H), 7.45 (d, J=8.7 Hz, 2H), 4.25 (d, J=7.8 Hz, 1H), 4.00-3.82 (m, 2H), 3.70-3.50 (m, 2H), 3.37-3.22 (m, 3H), 3.21-3.12 (m, 1H), 2.78 (t, J=7.6 Hz, 2H), 1.85-1.57 (m, 4H).

LRMS (ESI): [M+Na]$^+$ 380.0; HRMS (ESI): [M+Na]$^+$ calculated C$_{16}$H$_{23}$O$_6$NNa$^+$ 380.1327, found 380.1314.

Data for TG-010

$^1$H NMR (400 MHz, CD$_3$OD) δ (ppm) 7.18 (dd, J=8.5, 5.6 Hz, 2H), 7.00-6.91 (m, 2H), 4.24 (d, J=7.8 Hz, 1H), 3.92 (dt, J=9.6, 6.3 Hz, 1H), 3.87-3.82 (m, 1H), 3.66 (dd, J=11.8, 5.2 Hz, 1H), 3.56 (dt, J=9.5, 6.3 Hz, 1H), 3.37-3.22 (m, 3H), 3.20-3.11 (m, 1H), 2.62 (t, J=7.3 Hz, 2H), 1.78-1.54 (m, 4H).

LRMS (ESI): [M+COOH]⁻ 375.0; HRMS (ESI): [M+Cl]⁻ calculated C₆H₂₃O₆FCl⁻ 365.1173, found 365.1173.

The structure of each reaction intermediate during the experiment is shown below:

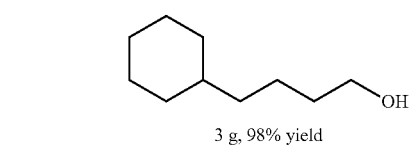

3 g, 98% yield

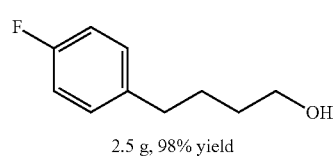

2.5 g, 98% yield

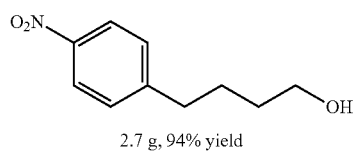

2.7 g, 94% yield

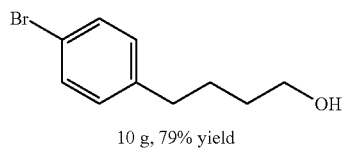

10 g, 79% yield

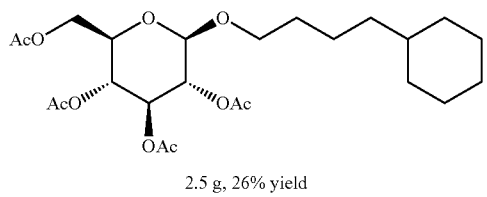

2.5 g, 26% yield

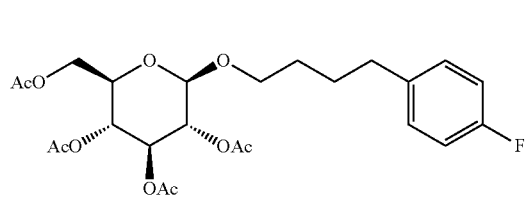

1.3 g, 17% yield

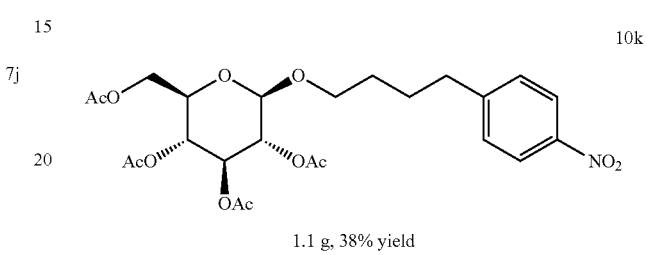

1.1 g, 38% yield

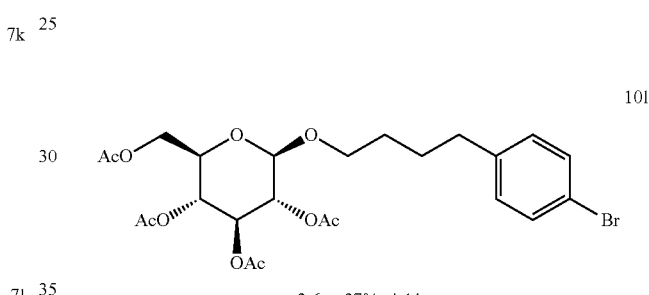

3.6 g, 27% yield

The identification data for Intermediates 10i-10l is:

10i:
LRMS (ESI): [M+Na]⁺ 509.5.
10j:
LRMS (ESI): [M+Na]⁺ 521.5.
10k:
LRMS (ESI): [M+Na]⁺ 548.5.
10l:
LRMS (ESI): [M+Na]⁺ 582.4.

Route of C: Synthesis of Compounds TG-013, TG-014, TG-015, TG-016, TG-017, TG-018, TG-019, TG-020, TG-021, TG-022, TG-024, TG-025, TG-026, TG-027, TG-049, TG-050, TG-051, and TG-023

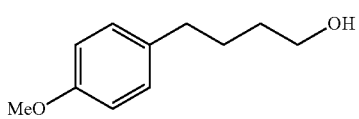 

-continued

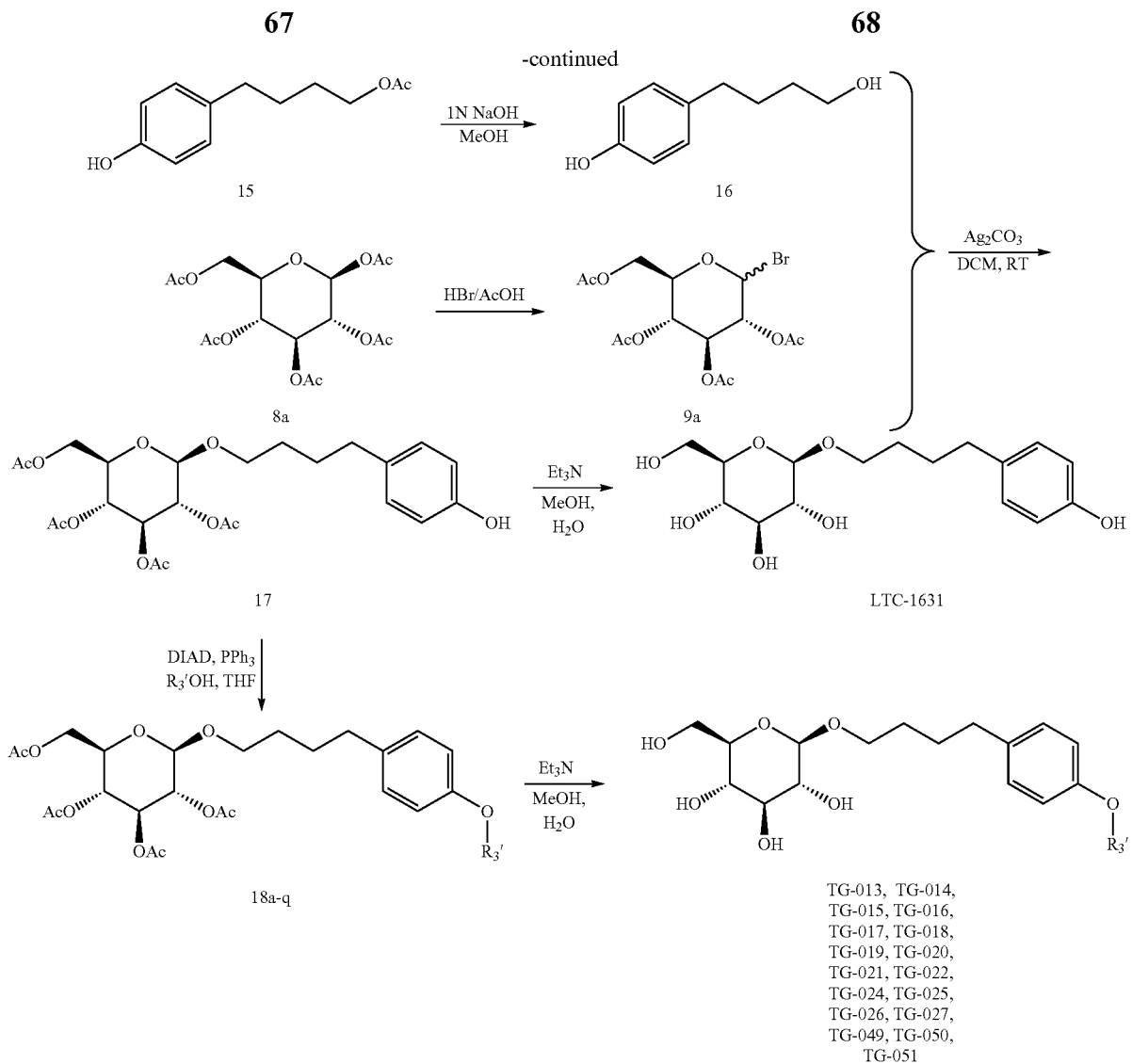

Experimental Operations of Route C

Compound 13 (1 eq) and Et₃N (1.5 eq) were added to dichloromethane (0.5 M), and then Ac₂O (1.2 eq) was added dropwise at 0° C., reacted for 20 h at 0° C. to room temperature, washed separately with saturated NH₄Cl and NaCl solution, dried with anhydrous Na₂SO₄, and concentrated under reduced pressure to obtain Compound 14 (16 g, yield 92%).

Compound 14 (1 eq) was added to dichloromethane (0.5 M). 1M BBr₃/dichloromethane (2.5 eq) was slowly added dropwise at −78° C., reacted at 0° C. for 5 h, quenched with saturated NaHCO₃ solution, extracted with dichloromethane, dried over anhydrous Na₂SO₄, concentrated under reduced pressure, and purified by column chromatography on silica gel (Eluent: petroleum ether/ethyl acetate=2:1), to obtain Compound 15 (8.7 g, yield 78%).

Compound 15 (1 eq) was added to MeOH (0.5 M), and then 1 M NaOH solution (3 eq) was added to the system, and reacted at room temperature for 2 h. The reaction solution was adjusted to pH 3 with 2 N HCl, extracted with ethyl acetate, dried over anhydrous Na₂SO₄, concentrated under reduced pressure, and purified by column chromatography on silica gel (Eluent: petroleum ether/ethyl acetate=1:1), to obtain Compound 16 (6 g, yield 85%).

Compounds 16 (1 eq) and 9a (1.2 eq) were added to a reaction flask. Under a N₂ atmosphere, dichloromethane (0.3 M) was added to the system, and reacted for 30 min at room temperature. Ag₂CO₃ (2.2 eq) was added to the system, and reacted at room temperature for 20 h. After filtering through celite, the reaction solution was concentrated under reduced pressure, and the residue was purified by column chromatography on silica gel (Eluent: petroleum ether/ethyl acetate=1:2) to obtain Compound 17 (7.6 g, yield 32%).

Compound 17 (1 eq) and PPh₃ (1.5 eq) were added to a reaction flask, and DIAD (1.5 eq) was slowly added dropwise to the system at room temperature, and reacted continuously for another 30 min. R³′OH (1.2 eq) was added dropwise to the system, and reacted at 65° C. for 2-10 h. The reaction solution was concentrated under reduced pressure and purified by column chromatography on silica gel to obtain Compounds 18a-j (yield 55-90%).

Compound 18a or 17 (1 eq) was added to a reaction flask, and then MeOH (4 M), H₂O (4 M), and Et₃N (2 eq) were respectively added, and reacted at room temperature for 20 h. The reaction solution was concentrated under reduced pressure, and purified by column chromatography on silica gel (Eluent: dichloromethane:methanol=9:1), to obtain Compounds TG-013 (yield 59%) and TG-023 (yield 13%) respectively.

Compounds TG-014, TG-015, TG-016, TG-017, TG-018, TG-019, TG-020, TG-021, TG-022, TG-024, TG-025, TG-026, TG-027, TG-049, TG-050, TG-051, and TG-023 have a synthesis route similar to that for Compound TG-013.

Structures and identification data for Compounds TG-013, TG-014, TG-015, TG-016, TG-017, TG-018, TG-019, TG-020, TG-021, TG-022, TG-024, TG-025, TG-026, TG-027, TG-049, TG-050, TG-051, and TG-023 are shown below.

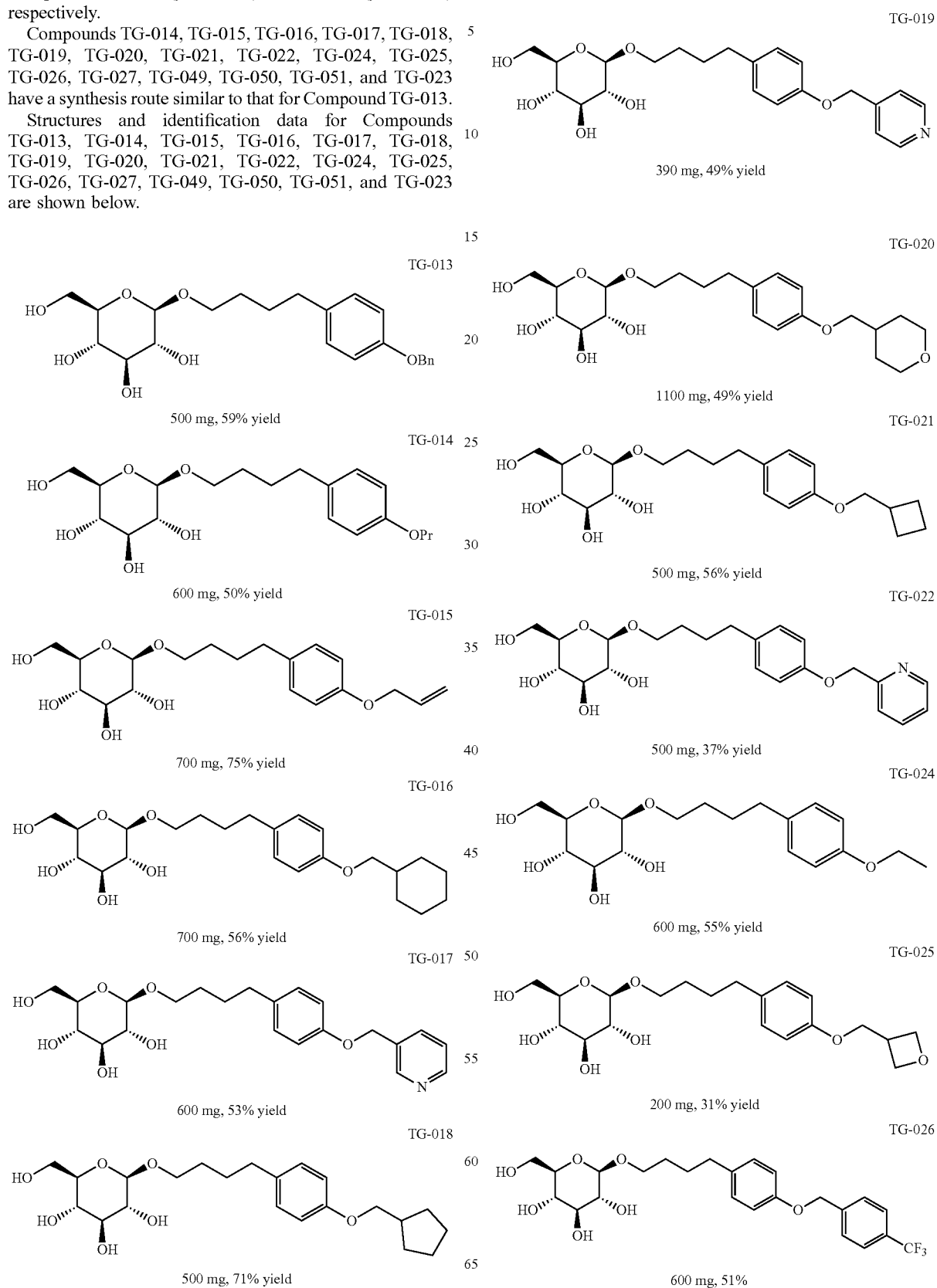

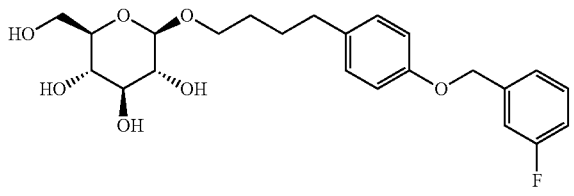

TG-027

200 mg, 19%

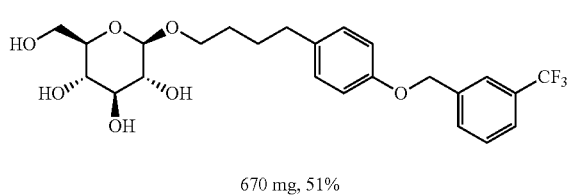

TG-049

670 mg, 51%

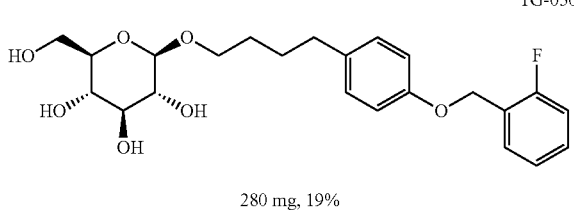

TG-050

280 mg, 19%

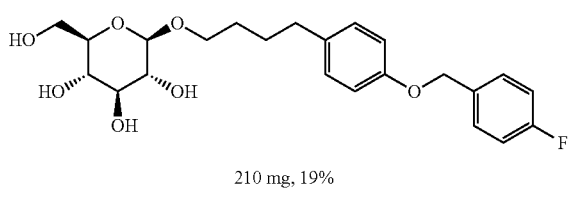

TG-051

210 mg, 19%

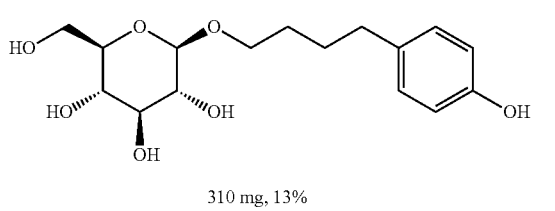

TG-023

310 mg, 13%

Data for TG-013

$^1$H NMR (400 MHz, CD$_3$OD) δ (ppm) 7.34 (m, 5H), 7.09 (d, J=8.3 Hz, 2H), 6.88 (d, J=8.4 Hz, 2H), 5.03 (s, 2H), 4.23 (d, J=7.8 Hz, 1H), 4.01-3.82 (m, 2H), 3.66 (dd, J=11.8, 5.0 Hz, 1H), 3.59-3.47 (m, 1H), 3.39-3.22 (m, 3H), 3.16 (t, J=8.3 Hz, 1H), 2.56 (t, J=6.9 Hz, 2H), 1.65 (d, J=4.1 Hz, 4H).

LRMS (ESI): [M+Na]$^+$ 441.1; HRMS (ESI): [M+Na]$^+$ calculated C$_{23}$H$_{30}$O$_7$Na$^+$ 441.1884, found 441.1880.

Data for TG-015

$^1$H NMR (400 MHz, CD$_3$OD) δ (ppm) 7.08 (d, J=8.6 Hz, 2H), 6.82 (d, J=8.6 Hz, 2H), 6.12-5.96 (m, 1H), 5.37 (dd, J=17.3, 1.6 Hz, 1H), 5.22 (dd, J=10.6, 1.4 Hz, 1H), 4.55-4.44 (m, 2H), 4.23 (d, J=7.8 Hz, 1H), 3.97-3.80 (m, 2H), 3.66 (dd, J=11.9, 5.2 Hz, 1H), 3.60-3.50 (m, 1H), 3.38-3.21 (m, 3H), 3.20-3.12 (m, 1H), 2.56 (t, J=7.1 Hz, 2H), 1.73-1.55 (m, 4H).

LRMS (ESI): [M+Na]$^+$ 391.0; HRMS (ESI): [M+Na]$^+$ calculated C$_{19}$H$_{28}$O$_7$Na$^+$ 391.1727, found 391.1726.

Data for TG-016

$^1$H NMR (400 MHz, CD$_3$OD) δ (ppm) 7.06 (d, J=8.5 Hz, 2H), 6.78 (d, J=8.6 Hz, 2H), 4.23 (d, J=7.8 Hz, 1H), 3.95-3.82 (m, 2H), 3.72 (d, J=6.4 Hz, 2H), 3.66 (dd, J=11.9, 5.2 Hz, 1H), 3.59-3.50 (m, 1H), 3.37-3.20 (m, 3H), 3.19-3.12 (m, 1H), 2.56 (t, J=7.1 Hz, 2H), 1.86 (d, J=13.1 Hz, 2H), 1.81-1.57 (m, 8H), 1.38-1.16 (m, 3H), 1.09 (m, 2H).

LRMS (ESI): [M+Na]$^+$ 447.2; HRMS (ESI): [M+Na]$^+$ calculated C$_{23}$H$_{36}$O$_7$Na$^+$ 447.2353, found 447.2352.

Data for TG-017

$^1$H NMR (400 MHz, CD$_3$OD) δ (ppm) 8.65 (d, J=1.2 Hz, 1H), 8.52 (dd, J=4.9, 1.2 Hz, 1H), 7.96 (d, J=7.9 Hz, 1H), 7.48 (dd, J=7.8, 5.0 Hz, 1H), 7.14 (d, J=8.5 Hz, 2H), 6.94 (d, J=8.6 Hz, 2H), 5.14 (s, 2H), 4.27 (d, J=7.8 Hz, 1H), 3.99-3.85 (m, 2H), 3.69 (dd, J=11.9, 5.2 Hz, 1H), 3.58 (dt, J=9.4, 6.2 Hz, 1H), 3.43-3.24 (m, 3H), 3.23-3.16 (m, 1H), 2.60 (t, J=7.1 Hz, 2H), 1.76-1.60 (m, 4H).

LRMS (ESI): [M+Na]$^+$ 442.1; HRMS (ESI): [M+Na]$^+$ calculated C$_{22}$H$_{29}$O$_7$NNa$^+$ 442.1836, found 442.1834.

Data for TG-018

$^1$H NMR (400 MHz, CD$_3$OD) δ (ppm) 7.10 (d, J=8.5 Hz, 2H), 6.82 (d, J=8.6 Hz, 2H), 4.27 (d, J=7.8 Hz, 1H), 3.99-3.86 (m, 2H), 3.83 (d, J=6.9 Hz, 2H), 3.69 (dd, J=11.8, 5.2 Hz, 1H), 3.62-3.54 (m, 1H), 3.41-3.24 (m, 3H), 3.21-3.17 (m, 1H), 2.59 (t, J=7.0 Hz, 2H), 2.40-2.30 (m, 1H), 1.93-1.78 (m, 2H), 1.76-1.57 (m, 8H), 1.47-1.35 (m, 2H).

LRMS (ESI): [M+Na]$^+$ 433.2; HRMS (ESI): [M+Na]$^+$ calculated C$_{22}$H$_{34}$O$_7$Na$^+$ 433.2197, found 433.2192.

Data for TG-019

$^1$H NMR (400 MHz, CD$_3$OD) δ (ppm) 8.66-8.44 (m, 2H), 7.54 (d, J=5.9 Hz, 2H), 7.15 (d, J=8.6 Hz, 2H), 6.93 (d, J=8.6 Hz, 2H), 5.18 (s, 2H), 4.26 (d, J=7.8 Hz, 1H), 3.95 (dt, J=9.5, 6.3 Hz, 1H), 3.89 (dd, J=11.9, 1.9 Hz, 1H), 3.69 (dd, J=11.8, 5.2 Hz, 1H), 3.62-3.54 (m, 1H), 3.41-3.24 (m, 3H), 3.23-3.16 (m, 1H), 2.61 (t, J=7.1 Hz, 2H), 1.77-1.58 (m, 4H).

LRMS (ESI): [M+H]$^+$ 420.2; HRMS (ESI): [M+H]$^+$ calculated C$_{22}$H$_{30}$O$_7$N$^+$ 420.2017, found 420.2014.

Data for TG-020

$^1$H NMR (400 MHz, CD$_3$OD) δ (ppm) 7.11 (d, J=8.5 Hz, 2H), 6.83 (d, J=8.5 Hz, 2H), 4.27 (d, J=7.8 Hz, J H), 4.05-3.86 (m, 4H), 3.82 (d, J=6.3 Hz, 2H), 3.69 (dd, J=11.8, 5.2 Hz, 1H), 3.58 (dt, J=9.5, 6.2 Hz, 1H), 3.49 (td, J=12.0, 1.7 Hz, 2H), 3.40-3.24 (m, 3H), 3.19 (t, J=8.4 Hz, 1H), 2.60 (t, J=7.1 Hz, 2H), 2.14-1.98 (m, 1H), 1.85-1.60 (m, 6H), 1.47 (qd, J=12.3, 4.5 Hz, 2H).

LRMS (ESI): [M+Na]$^+$ 449.2; HRMS (ESI): [M+H]$^+$ calculated C$_{22}$H$_{35}$O$_8$$^+$ 427.2326, found 427.2323.

Data for TG-021

$^1$H NMR (400 MHz, CD$_3$OD) δ (ppm) 7.10 (d, J=8.5 Hz, 2H), 6.83 (d, J=8.5 Hz, 2H), 4.27 (d, J=7.8 Hz, 1H), 3.99-3.85 (m, 4H), 3.69 (dd, J=11.8, 5.2 Hz, 1H), 3.58 (dt, J=9.4, 6.2 Hz, 1H), 3.41-3.24 (m, 3H), 3.19 (t, J=8.4 Hz, 1H), 2.85-2.71 (m, 1H), 2.59 (t, J=7.1 Hz, 2H), 2.24-2.08 (m, 2H), 2.08-1.85 (m, 4H), 1.70 (m, 4H).

LRMS (ESI): [M+Na]$^+$ 419.2.

Data for TG-014

$^1$H NMR (400 MHz, CD$_3$OD) δ (ppm) 7.07 (d, J=8.5 Hz, 2H), 6.79 (d, J=8.6 Hz, 2H), 4.23 (d, J=7.8 Hz, 1H), 3.96-3.80 (m, 4H), 3.66 (dd, J=11.9, 5.2 Hz, 1H), 3.59-3.49 (m, 1H), 3.38-3.21 (m, 3H), 3.20-3.11 (m, 1H), 2.56 (t, J=7.1 Hz, 2H), 1.75 (m, 2H), 1.70-1.57 (m, 4H), 1.02 (t, J=7.4 Hz, 3H).

LRMS (ESI): [M+Na]$^+$ 393.1; HRMS (ESI): [M+Na]$^+$ calculated C$_{19}$H$_{30}$O$_7$Na$^+$ 393.1884, found 393.1880.

Data for TG-022

$^1$H NMR (400 MHz, CD$_3$OD) δ 8.53 (d, J=4.4 Hz, 1H), 7.86 (td, J=7.8, 1.6 Hz, 1H), 7.59 (d, J=7.9 Hz, 1H), 7.36 (dd, J=7.0, 5.4 Hz, 1H), 7.10 (d, J=8.6 Hz, 2H), 6.90 (d,

J=8.6 Hz, 2H), 5.13 (s, 2H), 4.23 (d, J=7.8 Hz, 1H), 3.95-3.88 (m, 1H), 3.85 (dd, J=11.9, 1.7 Hz, 1H), 3.66 (dd, J=11.9, 5.2 Hz, 1H), 3.59-3.51 (m, 1H), 3.35-3.12 (m, 4H), 2.57 (t, J=7.1 Hz, 2H), 1.81-1.52 (m, 4H).

LRMS (ESI): [M+Na]⁺ 442.0; HRMS (ESI): [M+Na]⁺ calculated C₂₂H₂₉O₇NNa⁺ 442.1836, found 442.1834.

Data for TG-024

¹H NMR (400 MHz, CD₃OD) δ 7.10 (d, J=8.5 Hz, 2H), 6.82 (d, J=8.6 Hz, 2H), 4.27 (d, J=7.8 Hz, 1H), 4.02 (q, J=7.0 Hz, 2H), 3.98-3.92 (m, 1H), 3.89 (dd, J=11.8, 1.6 Hz, 1H), 3.69 (dd, J=11.8, 5.2 Hz, 1H), 3.58 (dt, J=9.5, 6.2 Hz, 1H), 3.41-3.29 (m, 3H), 3.23-3.13 (m, 1H), 2.59 (t, J=7.1 Hz, 2H), 1.78-1.56 (m, 4H), 1.39 (t, J=7.0 Hz, 3H).

LRMS (ESI): [M+Na]⁺ 379.1.

Data for TG-025

¹H NMR (400 MHz, CD₃OD) δ 7.13 (d, J=8.5 Hz, 2H), 6.88 (d, J=8.6 Hz, 2H), 4.97-4.83 (m, 2H), 4.62 (t, J=6.0 Hz, 2H), 4.27 (d, J=7.8 Hz, 1H), 4.19 (d, J=6.4 Hz, 2H), 3.95 (dt, J=6.3, 3.3 Hz, 1H), 3.89 (dd, J=11.8, 1.7 Hz, 1H), 3.69 (dd, J=11.8, 5.2 Hz, 1H), 3.63-3.54 (m, 1H), 3.52-3.41 (m, 1H), 3.41-3.24 (m, 3H), 3.23-3.15 (m, 1H), 2.61 (t, J=7.1 Hz, 2H), 1.81-1.57 (m, 4H).

LRMS (ESI): [M+Na]⁺ 421.1.

Data for TG-026

¹H NMR (400 MHz, CD₃OD) δ 7.68 (dd, J=18.9, 8.3 Hz, 4H), 7.14 (d, J=8.6 Hz, 2H), 6.93 (d, J=8.6 Hz, 2H), 5.17 (s, 2H), 4.27 (d, J=7.8 Hz, 1H), 3.95 (dt, J=6.3, 3.3 Hz, 1H), 3.89 (dd, J=11.8, 1.7 Hz, 1H), 3.69 (dd, J=11.8, 5.2 Hz, 1H), 3.62-3.54 (m, 1H), 3.42-3.24 (m, 3H), 3.23-3.15 (m, 1H), 2.61 (t, J=7.1 Hz, 2H), 1.83-1.52 (m, 4H).

LRMS (ESI): [M+Na]⁺ 509.2.

Data for TG-027

¹H NMR (400 MHz, CD₃OD) δ 7.40 (dt, J=7.9, 5.9 Hz, 1H), 7.26 (d, J=7.7 Hz, 1H), 7.20 (d, J=9.9 Hz, 1H), 7.13 (d, J=8.6 Hz, 2H), 7.05 (td, J=8.5, 2.3 Hz, 1H), 6.91 (d, J=8.6 Hz, 2H), 5.09 (s, 2H), 4.27 (d, J=7.8 Hz, 1H), 3.95 (dt, J=9.4, 6.3 Hz, 1H), 3.89 (dd, J=11.9, 1.8 Hz, 1H), 3.69 (dd, J=11.9, 5.2 Hz, 1H), 3.62-3.54 (m, 1H), 3.41-3.24 (m, 3H), 3.23-3.15 (m, 1H), 2.60 (t, J=7.1 Hz, 2H), 1.90-1.55 (m, 4H).

LRMS (ESI): [M+Na]⁺ 459.2.

Identification data for TG-049:

¹H NMR (400 MHz, CD₃OD) δ 7.74 (s, 1H), 7.69 (d, J=7.4 Hz, 1H), 7.62-7.53 (m, 2H), 7.11 (d, J=8.6 Hz, 2H), 6.91 (d, J=8.6 Hz, 2H), 5.13 (s, 2H), 4.23 (d, J=7.8 Hz, 1H), 3.92 (dt, J=9.4, 6.3 Hz, 1H), 3.85 (dd, J=11.9, 1.7 Hz, 1H), 3.66 (dd, J=11.8, 5.2 Hz, 1H), 3.55 (dt, J=9.6, 6.2 Hz, 1H), 3.37-3.32 (m, 1H), 3.26 (t, J=5.9 Hz, 2H), 3.20-3.11 (m, 1H), 2.57 (t, J=7.1 Hz, 2H), 1.80-1.49 (m, 4H).

LRMS (ESI): [M+Na]⁺ 509.20

Identification data for TG-050:

¹H NMR (400 MHz, CD₃OD) δ 7.53 (td, J=7.5, 1.3 Hz, 1H), 7.42-7.34 (m, 1H), 7.21 (td, J=7.5, 1.0 Hz, 1H), 7.18-7.10 (m, 1H), 7.14 (d, J=8.6 Hz, 2H), 6.92 (d, J=8.6 Hz, 2H), 5.12 (s, 2H), 4.27 (d, J=7.8 Hz, 1H), 3.95 (dt, J=9.4, 6.3 Hz, 1H), 3.89 (dd, J=11.9, 1.8 Hz, 1H), 3.69 (dd, J=11.9, 5.2 Hz, 1H), 3.58 (dt, J=9.5, 6.3 Hz, 1H), 3.39-3.25 (m, 3H), 3.24-3.16 (m, 1H), 2.61 (t, J=7.1 Hz, 2H), 1.78-1.59 (m, 4H).

LRMS (ESI): [M+Na]⁺ 459.20

Data for TG-051

¹H NMR (400 MHz, CD₃OD) δ 7.47 (dd, J=8.5, 5.5 Hz, 2H), 7.13 (d, J=8.6 Hz, 4H), 7.14-7.09 (m, 1H), 6.91 (d, J=8.6 Hz, 2H), 5.04 (s, 2H), 4.27 (d, J=7.8 Hz, 1H), 3.95 (dt, J=9.3, 6.2 Hz, 1H), 3.89 (dd, J=11.8, 1.7 Hz, 1H), 3.69 (dd, J=11.8, 5.2 Hz, 1H), 3.58 (dt, J=9.4, 6.2 Hz, 1H), 3.0-3.24 (m, 3H), 3.23-3.14 (m, 1H), 2.60 (t, J=7.1 Hz, 2H), 1.91-1.56 (m, 4H).

LRMS (ESI): [M+Na]⁺ 459.2

Data for TG-023

¹H NMR (400 MHz, CD₃OD) δ 6.99 (d, J=8.5 Hz, 2H), 6.70-6.63 (m, 2H), 4.23 (d, J=7.8 Hz, 1H), 3.96-3.82 (m, 2H), 3.66 (dd, J=11.9, 5.2 Hz, 1H), 3.54 (dt, J=9.5, 6.1 Hz, 1H), 3.38-3.21 (m, 3H), 3.16 (dd, 1H), 2.53 (t, J=7.0 Hz, 2H), 1.70-1.56 (m, 4H).

LRMS (ESI): [M+Na]⁺ 351.1; HRMS (ESI): [M+NH₄]⁺ calculated C₁₆H₂₈O₇N⁺ 346.1860, found 346.1857.

The structure of each reaction intermediate during the experiment is shown below:

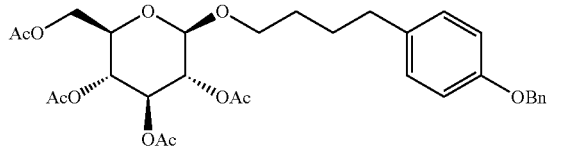

1.2 g, 66% yield

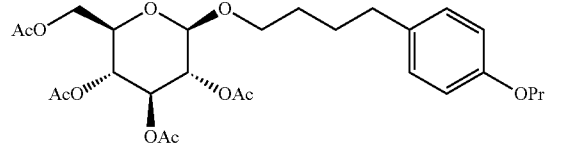

1.8 g, 90% yield

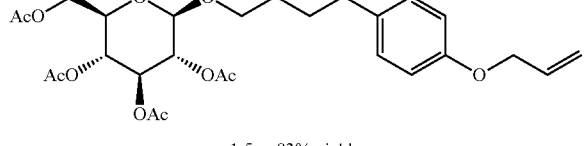

1.5 g, 83% yield

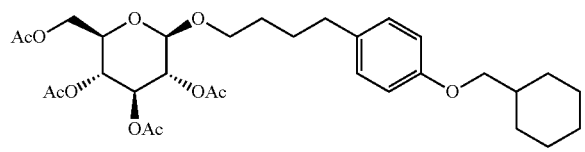

1.5 g, 82% yield

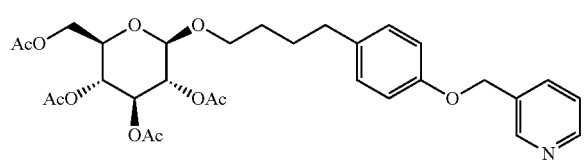

1.6 g, 80% yield

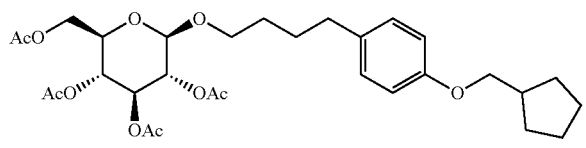

1 g, 87% yield

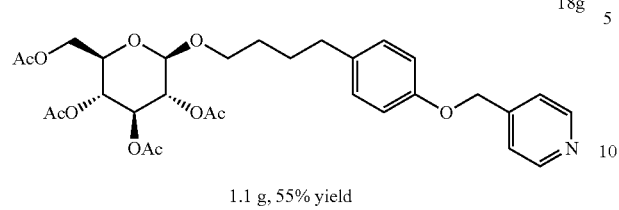

18g 1.1 g, 55% yield

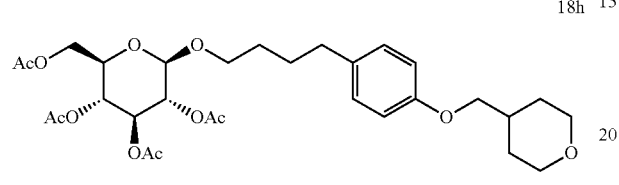

18h 3.2 g, 80% yield

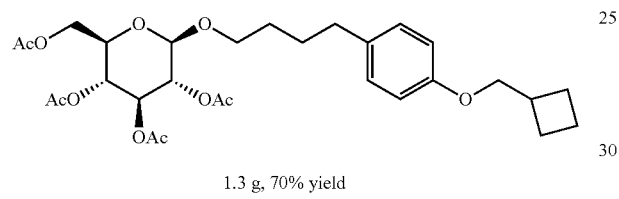

18i 1.3 g, 70% yield

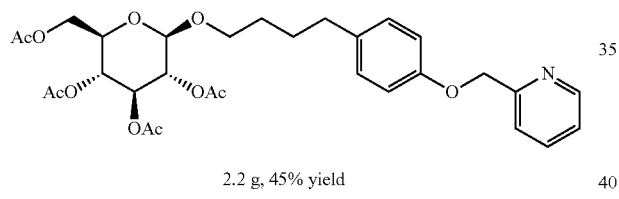

18j 2.2 g, 45% yield

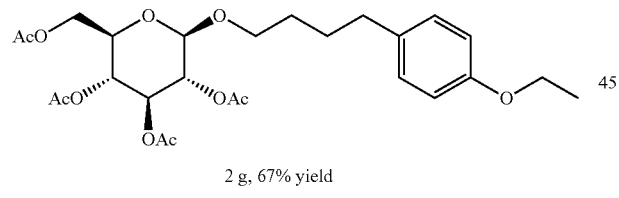

18k 2 g, 67% yield

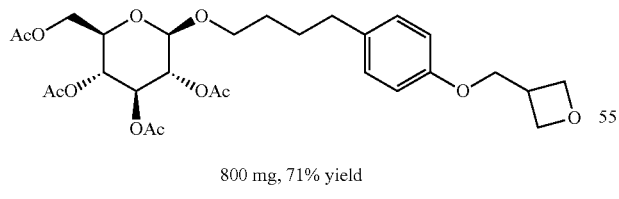

18l 800 mg, 71% yield

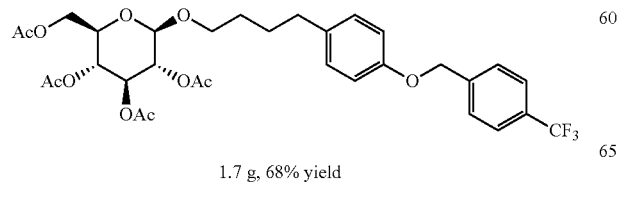

18m 1.7 g, 68% yield

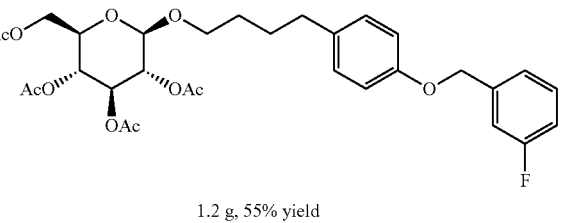

18n 1.2 g, 55% yield

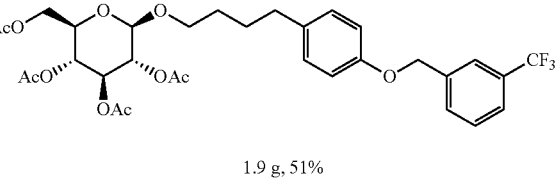

18o 1.9 g, 51%

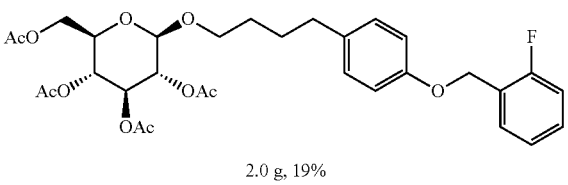

18p 2.0 g, 19%

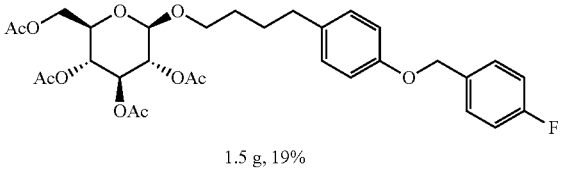

18q 1.5 g, 19%

The identification data for Intermediates 18a-18q is:
18a:
LRMS (ESI): [M+Na]$^+$ 609.6.
18b:
LRMS (ESI): [M+Na]$^+$ 561.5.
18c:
LRMS (ESI): [M+Na]$^+$ 559.5.
18d:
LRMS (ESI): [M+Na]$^+$ 615.6.
18e:
LRMS (ESI): [M+Na]$^+$ 610.6.
18f:
LRMS (ESI): [M+Na]$^+$ 601.6.
18g:
LRMS (ESI): [M+Na]$^+$ 610.6.
18h:
LRMS (ESI): [M+Na]$^+$ 617.6.
18i:
LRMS (ESI): [M+Na]$^+$ 587.6.
18j:
LRMS (ESI): [M+Na]$^+$ 610.2.
18k:
LRMS (ESI): [M+Na]$^+$ 547.2.
18l:
LRMS (ESI): [M+Na]$^+$ 589.2.
18m:
LRMS (ESI): [M+Na]$^+$ 677.2.
18n:
LRMS (ESI): [M+Na]$^+$ 627.2.

18o:
LRMS (ESI): [M+Na]+ 677.23
18p:
LRMS (ESI): [M+Na]+ 654.23
18q:
LRMS (ESI): [M+Na]+ 654.23
Route D: Synthesis of End Products TG-028, TG-029, and TG-030
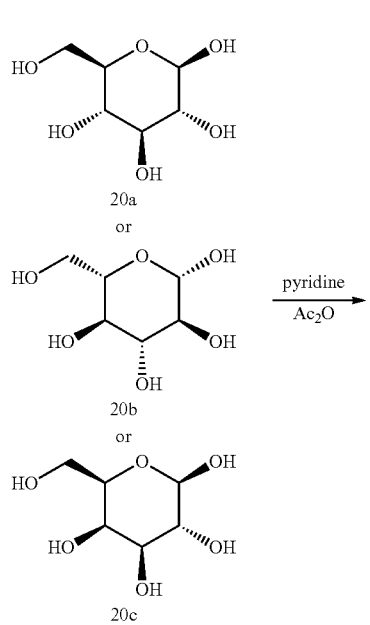
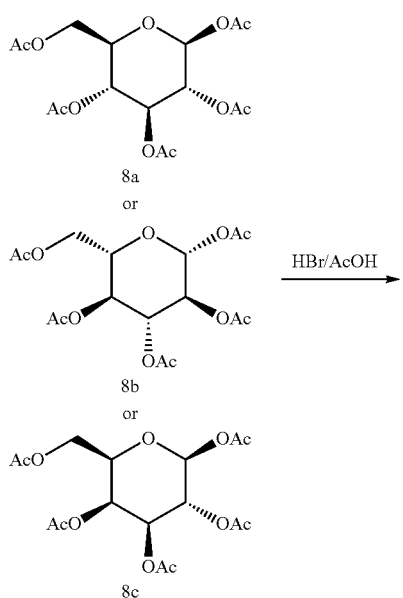
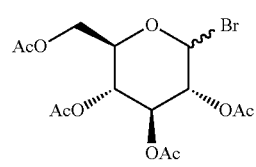
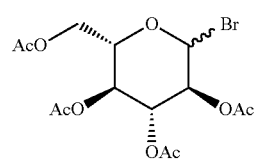
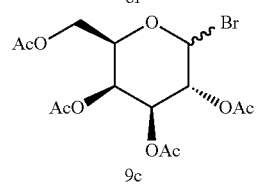
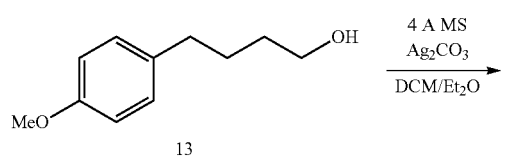
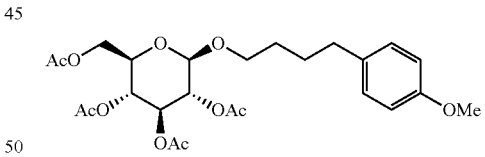
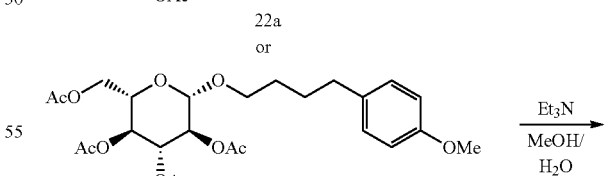
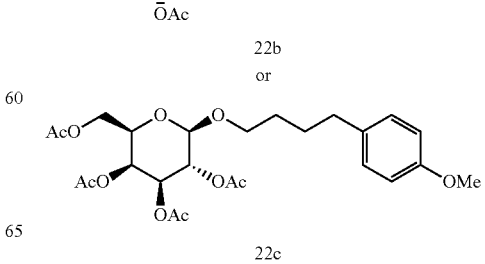

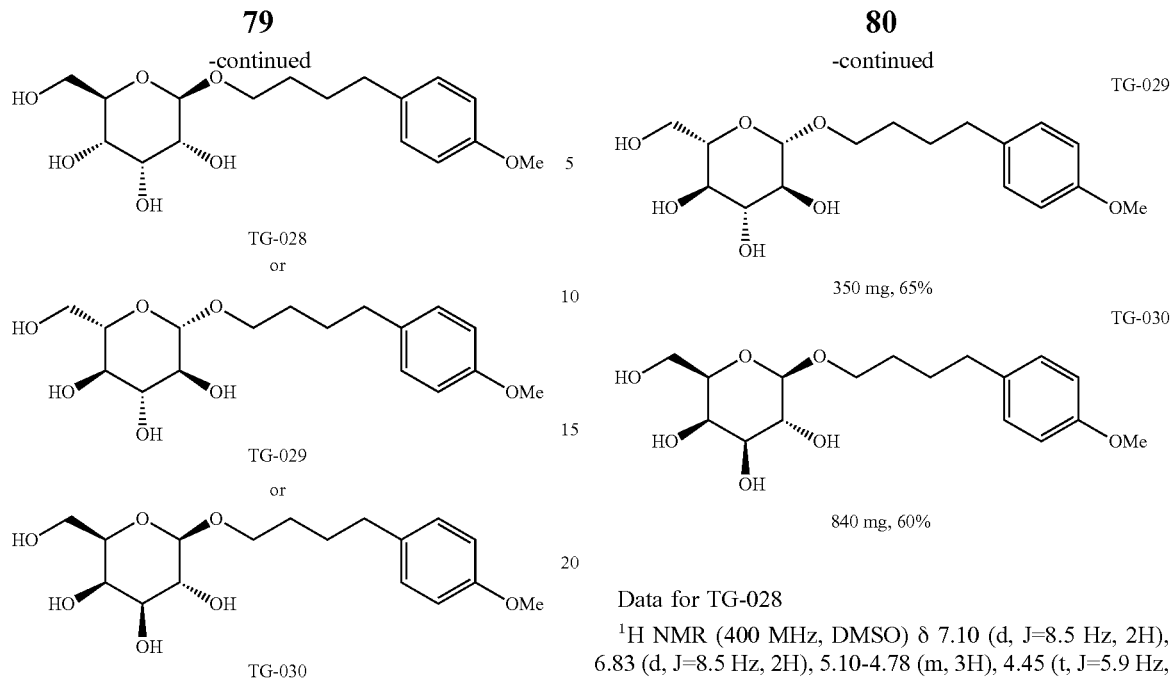

Experimental Operations of Route D:

20a (3 g, 16.7 mmol) was added to 40 ml of pyridine, and then Ac₂O was added dropwise and reacted for 3 days. The reaction solution was concentrated under reduced pressure, and purified by column chromatography on silica gel (Eluent: ethyl acetate:petroleum ether=1:4) to obtain product 8a (yield 95%). 33% HBr/AcOH (4 eq) solution was added dropwise to Compound 8a, and reacted at room temperature for 4 h. The reaction solution was concentrated under reduced pressure, and the crude product was recrystallized in Et₂O and n-hexane to obtain Compound 9a. 9a (1 eq) was added to a three-neck flask, and then a mixture of 4 Å molecular sieve and anhydrous dichloromethane/Et₂O was added. The mixed solution was stirred until uniform, and then the raw material 13 (0.95 eq) was added. After continuously stirring for 30 min, Ag₂CO₃ (1.2 eq) was added and reacted overnight. After filtering through celite, the reaction solution was concentrated under reduced pressure and purified by column chromatography on silica gel to obtain the product 22a (yield 19%).

Compound 22a (1 eq) was added to a reaction flask, and then MeOH (4 M), H₂O (4 M), and Et₃N (2 eq) were respectively added, and reacted at room temperature for 20 h. After filtering through celite, the reaction solution was concentrated under reduced pressure and purified by column chromatography on silica gel to obtain Compound TG-028 (yield 64%).

Compounds TG-029 and TG-030 have a synthesis route similar to that for Compound TG-028.

The structures and identification data for Compounds TG-028, TG-029, and TG-030 are shown below:

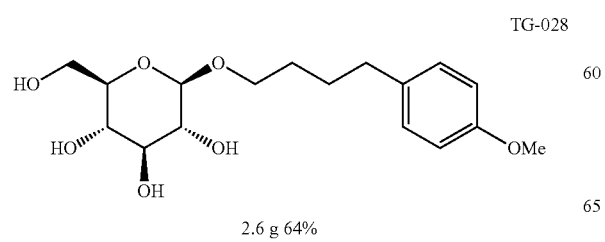

TG-028

2.6 g 64%

350 mg, 65%

840 mg, 60%

Data for TG-028

¹H NMR (400 MHz, DMSO) δ 7.10 (d, J=8.5 Hz, 2H), 6.83 (d, J=8.5 Hz, 2H), 5.10-4.78 (m, 3H), 4.45 (t, J=5.9 Hz, 1H), 4.09 (d, J=7.8 Hz, 1H), 3.77 (m, J=12.5, 6.4 Hz, 1H), 3.71 (s, 3H), 3.65 (dd, J=10.8, 6.0 Hz, 1H), 3.49-3.37 (m, 2H), 3.17-2.98 (m, 3H), 2.92 (td, J=8.3, 5.1 Hz, 1H), 2.55-2.5 (m, 2H) 1.69-1.41 (m, 4H).

LRMS (ESI): [M+Na]⁺ 365.0; HRMS (ESI): [M+Na]⁺ calculated C₇H₂₆O₇Na⁺ 365.1571, found 365.1569.

Data for TG-029

¹H NMR (400 MHz, CD₃OD) δ 7.08 (d, J=8.5 Hz, 2H), 6.80 (d, J=8.6 Hz, 2H), 4.23 (d, J=7.8 Hz, 1H), 3.91 (m, 1H), 3.85 (dd, J=11.9, 1.7 Hz, 1H), 3.76 (s, 3H), 3.66 (dd, J=11.8, 5.2 Hz, 1H), 3.55 (dt, J=9.5, 6.1 Hz, 1H), 3.37-3.1 (m, 4H), 2.56 (t, J=7.1 Hz, 2H), 1.78-1.53 (m, 4H).

LRMS (ESI): [M+Na]⁺ 365.0; RMS (ESI): [M+Na]⁺ calculated C₁₇H₂₆O₇Na⁺ 365.1571, found 365.1570.

Data for TG-030

¹H NMR (400 MHz, CD₃OD) δ 7.12 (d, J=8.3 Hz, 2H), 6.83 (d, J=8.4 Hz, 2H), 4.22 (d, J=7.3 Hz, 1H), 3.95 (dd, J=10.9, 4.9 Hz, 1H), 3.85 (d, J=2.4 Hz, 1H), 3.83-3.71 (m, 5H), 3.64-3.44 (m, 4H), 2.59 (t, J=6.9 Hz, 2H), 1.68 (d, J=3.7 Hz, 4H).

LRMS (ESI): [M+Na]⁺ 365.1; HRMS (ESI): [M+NH₄]⁺ calculated C₁₇H₃₀O₇N⁺ 360.2017, found 360.2015.

The structure of each reaction intermediate during the experiment is shown below:

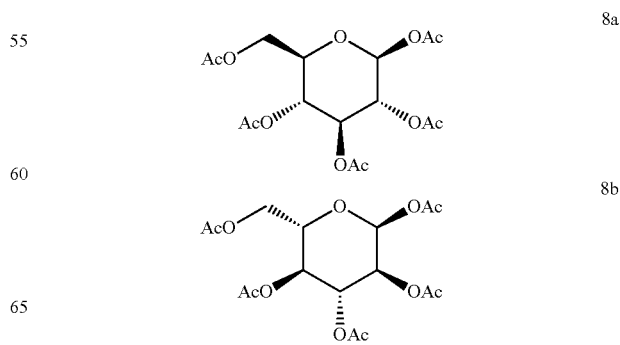

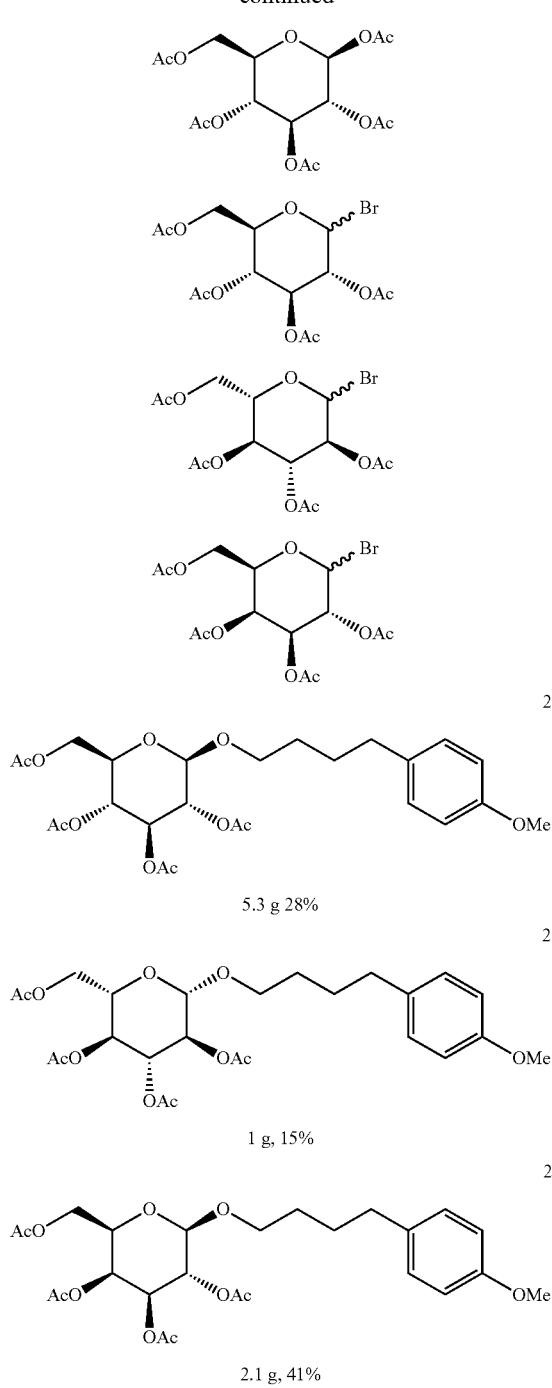
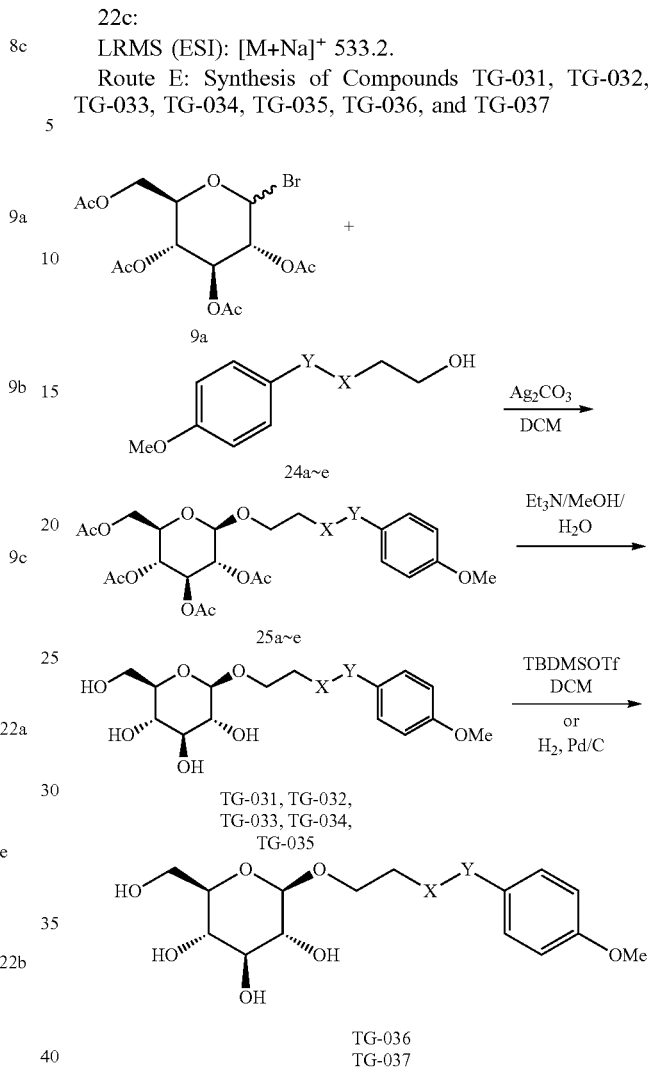
The identification data for Intermediates 22a-22c is:
22a:
$^1$H NMR (400 MHz, CDCl$_3$) δ 7.07 (d, J=8.6 Hz, 2H), 6.82 (t, J=5.7 Hz, 2H), 5.20 (t, J=9.5 Hz, 1H), 5.08 (t, J=9.7 Hz, 1H), 4.98 (t, J=9.6, 8.0 Hz, 1H), 4.48 (d, J=8.0 Hz, 1H), 4.26 (dd, J=12.3, 4.7 Hz, 1H), 4.16-4.07 (m, 1H), 3.89 (dd, J=5.8, 3.7 Hz, 1H), 3.78 (s, 3H), 3.68 (m, J=9.9, 4.6, 2.4 Hz, 1H), 3.49 (dt, J=9.4, 6.1 Hz, 1H), 2.55 (t, J=6.6 Hz, 2H), 2.08 (s, 3H), 2.05-1.96 (m, 9H), 1.68-1.52 (m, 4H).
LRMS (ESI): [M+Na]$^+$ 533.2.
22b:
LRMS (ESI): [M+Na]$^+$ 533.2.
22c:
LRMS (ESI): [M+Na]$^+$ 533.2.
Route E: Synthesis of Compounds TG-031, TG-032, TG-033, TG-034, TG-035, TG-036, and TG-037
The synthesis of Fragments 24a-e is shown below:
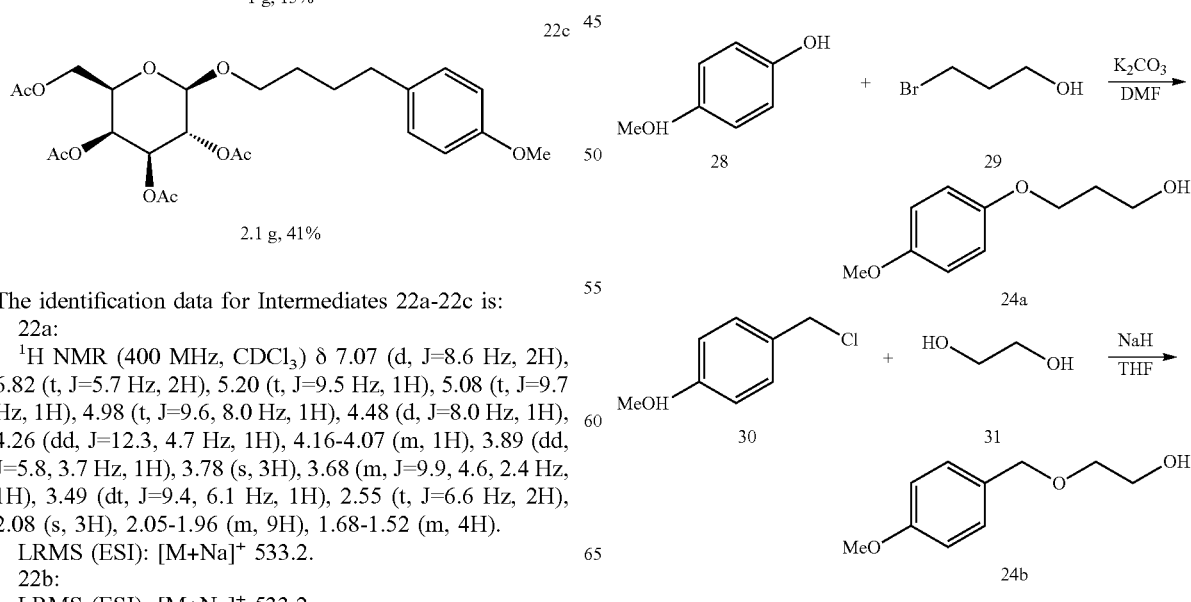

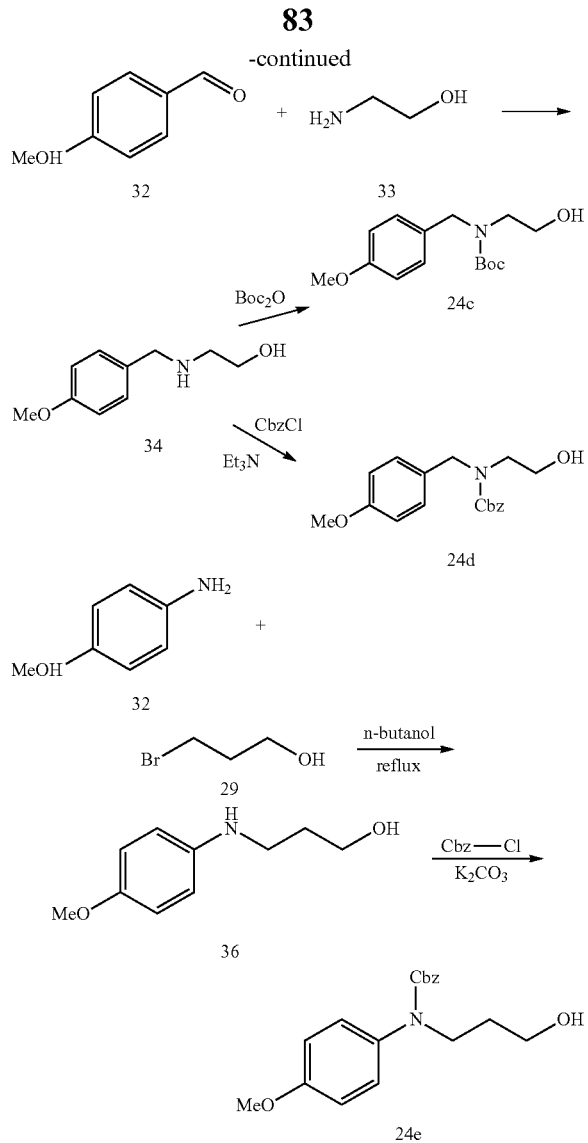

Experimental Operations of Route E:

Fragment 24a: Compounds 28 (2.48 g, 0.02 mol) and 29 (3.336 g, 0.024 mol) were respectively added to DMF (30 mL), and then $K_2CO_3$ (13.8 g, 0.1 mol) was added and stirred at room temperature for 48 hrs. Water was added, and then the solution was extracted with ethyl acetate. The extracts were combined, washed with water and dried over anhydrous sodium sulfate. The reaction solution was filtered through a sand-core glass funnel, and concentrated under reduced pressure. The residue was recrystallized in a mixture of ethyl acetate and petroleum ether to obtain 24a (3.1 g, 85% yield).

Fragment 24b: 31 (3.72 g, 60 mmol) was added to THF, then NaH (0.624 g, 26 mmol) was added batchwise, and 30 (3.132 g, 20 mmol) and $Bu_4NI$ (738 mg, 2 mmol) were added sequentially, heated to 70° C., and stirred for 5 h. The reaction solution was cooled to room temperature, washed once with saturated ammonium chloride, and concentrated under reduced pressure. Purification by column chromatography on silica gel afforded 24b (2.9 g, 80% yield).

Fragment 24c: 33 (6.1 g, 0.1 mol) was added to MeOH, and then 32 (13.6 g, 0.1 mol) was added at room temperature, heated to 70° C. and stirred overnight. After cooling to room temperature, $NaBH_4$ (3.8 g, 0.1 mol) was added batchwise, heated to 70° C. and stirred for 2 h. The reaction solution was cooled to room temperature and extracted with ethyl acetate. The extracts were combined, washed with water and dried over anhydrous sodium sulfate. The product was filtered through a sand-core glass funnel, concentrated under reduced pressure, and purified by column chromatography on silica gel to obtain 34 (13.4 g, 88% yield).

34 (3.6 g, 23.8 mmol) was added to dichloromethane, and $Boc_2O$ (6.23 g, 28.6 mmol) was added dropwise in an ice bath. Then the reaction solution was stirred overnight at room temperature, concentrated under reduced pressure, and purified by column chromatography on silica gel to obtain 24c (4.9 g, 73% yield).

Fragment 24d: 34 (3.6 g, 23.8 mmol) was added to dichloromethane, CbzCl (6.63 g, 0.39 mmol) and $Et_3N$ (4.5 g, 0.45 mmol) were sequentially added dropwise in an ice bath and stirred for 5 h. The reaction solution was washed once sequentially with water, saturated $NaHCO_3$ solution, and saturated brine. The reaction solution was dried over anhydrous sodium sulfate, concentrate under reduced pressure, and purify by column chromatography on silica gel to obtain 24d (6 g, 63.5% yield).

Fragment 24e: 35 (6.15 g, 50 mmol), 29 (13.9 g, 100 mol), and $K_2CO_3$ (13.8 g, 100 mmol) were sequentially added to n-butanol (40 mL), and then iodine (50 mg) was added, and reacted under reflux for 30 h. The reaction solution was concentrated under reduced pressure and purified by column chromatography on silica gel to obtain the product 36 (8.5 g, yield 93%). 36 (3.3 g, 18.2 mmol) was added to dichloromethane, $K_2CO_3$ (4.9 g, 36 mmol) was then added, and Cbz-C (4 g, 23.7 mmol) was added dropwise in an ice bath and stirred at room temperature overnight. The reaction solution was washed once sequentially with water and saturated saline, dried over anhydrous sodium sulfate, concentrate under reduced pressure, and purify by column chromatography on silica gel to obtain 24e (3 g, 72% yield).

9a (1 eq), 24a-e (0.95 mmol), and 4 Å molecular sieve were added to the reaction flask in sequence. Dry dichloromethane (0.25 mol/L) was added and stirred for 30 min. $Ag_2CO_3$ (1.2 eq) was added under an argon atmosphere, stirred overnight at room temperature, and filtered through celite. The filtrate was concentrated under reduced pressure and purified by column chromatography on silica gel to obtain the product 25a-e. 25a-e (1 eq) was separately added to a one-neck flask, and then MeOH (6 eq), $H_2O$ (6 eq), and $Et_3N$ (3 eq) was added to each one-neck flask and stirred overnight. The solution was concentrated under reduced pressure, and purified by column chromatography on silica gel (Eluent: methanol/dichloromethane=1:15) to obtain the products TG-031 (yield 24%), TG-032 (yield 26%), TG-033 (yield 24%), TG-034 (yield 20%), and TG-035 (yield 12%).

TG-033 (1 g, 2.25 mmol) and 2,6-Lutidine (481 mg, 4.5 mmol) were added to dichloromethane, and TBDMSOTf (893 mg, 3.38 mmol) was added dropwise in an ice bath, and stirred at 0° C. for 2 h, until TLC showed the reaction was complete. The reaction solution was adjusted to pH 5 with 0.5 M HCl, spin-dried, and purified by chromatography (methanol/dichloromethane=1:20), to obtain TG-036 (400 mg, yield 46.8%).

TG-035 (700 mg, 1.46 mmol) was added to MeOH (30 ml), and then Pd/C was added, purged with hydrogen, and stirred overnight at normal temperature under 40 atm. The reaction solution was filtered through celite, concentrated under reduced pressure, and purified by column chromatography on silica gel (Eluent: methanol/dichloromethane=1:12) to obtain the product TG-037 (320 mg, 63% yield).

The structures and identification data for Compounds TG-031, TG-032, TG-033, TG-034, TG-035, TG-036 and TG-037 are shown below:

TG-031

670 mg, 24%

TG-032

1.35 g, 26%

TG-033

1.7 g, 24%

TG-034

980 mg, 20%

TG-034

1.2 g, 12%

TG-036

400 mg, 46%

TG-037

320 mg, 63%

Data for TG-031

$^1$H NMR (400 MHz, DMSO) δ 6.89-6.81 (m, 1H), 4.90 (s, 1H), 4.46 (s, 1H), 4.46 (s, 1H), 4.13 (d, J=7.8 Hz, 1H), 3.99 (t, J=6.4 Hz, 1H), 3.90 (dt, J=9.9, 6.3 Hz, 1H), 3.66-3.55 (m, 1H), 3.43 (dd, J=11.8, 5.5 Hz, 1H), 3.08 (dq, J=23.5, 8.9 Hz, 1H), 2.94 (t, J=8.3 Hz, 1H), 1.94 (q, J=6.6 Hz, 1H).

LRMS (ESI): [M+Na]$^+$ 367.1; HRMS (ESI): [M+NH$_4$]$^+$ calculated C$_{16}$H$_{28}$O$_8$N$^+$ 362.1809, found 362.1807.

Data for TG-032

$^1$H NMR (300 MHz, CD$_3$OD) δ 7.25 (d, J=8.3 Hz, 2H), 6.86 (d, J=8.4 Hz, 2H), 4.46 (s, 2H), 4.25 (d, J=7.7 Hz, 1H), 4.06-3.91 (m, 1H), 3.87-3.54 (m, 7H), 3.36-3.10 (m, 4H).

LRMS (ESI): [M+Na]$^+$ 367.1; HRMS (ESI): [M+NH$_4$]$^+$ calculated C$_{16}$H$_{28}$O$_8$N$^+$ 362.1809, found 362.1806.

Data for TG-033

$^1$H NMR (400 MHz, DMSO) δ 7.18 (d, J=8.4 Hz, 2H), 6.90 (d, J=8.1 Hz, 2H), 5.02 (bs, 2H), 4.59-4.28 (m, 3H), 4.11 (t, 1H), 3.73 (s, 4H), 3.66 (d, J=11.6 Hz, 1H), 3.61-3.50 (m, 1H), 3.44 (dd, J=11.6, 4.7 Hz, 1H), 3.39-3.00 (m, 6H), 2.94 (t, J=8.3 Hz, 1H), 1.41 (d, J=14.2 Hz, 9H).

Data for TG-034

$^1$H NMR (300 MHz, DMSO) δ 7.35 (d, J=13.0 Hz, 5H), 7.17 (d, J=15.0 Hz, 2H), 6.88 (t, 2H), 5.09 (dd, J=14.9 Hz, 3H), 4.95 (dd, J=14.2 Hz, 2H), 4.54-4.41 (m, 3H), 4.17-4.04 (m, 1H), 3.87-3.51 (m, 5H), 3.50-3.20 (m, 4H), 3.18-2.87 (m, 5H).

LRMS (ESI): [M+Na]$^+$ 500.2; HRMS (ESI): [M+H]$^+$ calculated C$_{24}$H$_{32}$O$_9$N$^+$ 478.2072, found 478.2065.

Data for TG-035

$^1$H NMR (400 MHz, CD$_3$OD) δ 7.55-7.02 (m, 7H), 6.92 (d, J=8.9 Hz, 2H), 5.08 (s, 2H), 4.17 (d, J=7.7 Hz, 1H), 3.98-3.87 (m, 1H), 3.86-3.70 (m, 6H), 3.64 (dd, J=11.9, 5.3 Hz, 1H), 3.60-3.50 (m, 1H), 3.36-3.19 (m, 3H), 3.14 (t, J=8.4 Hz, 1H), 1.93-1.74 (m, 2H).

LRMS (ESI): [M+Na]$^+$ 500.0; HRMS (ESI): [M+Na]$^+$ calculated C$_{24}$H$_{31}$O$_9$NNa$^+$ 500.1891, found 500.1889.

Data for TG-036

$^1$H NMR (400 MHz, CD$_3$OD) δ 7.43 (d, J=8.7 Hz, 2H), 7.00 (d, J=8.7 Hz, 2H), 4.35 (d, J=7.8 Hz, 1H), 4.20 (s, 2H), 4.09 (s, 1H), 3.90 (m, J=14.0, 4.4 Hz, 2H), 3.82 (s, 3H), 3.65 (dd, J=11.7, 6.1 Hz, 1H), 3.40-3.32 (m, 2H), 3.24 (dt, J=11.5, 9.1 Hz, 4H).

LRMS (ESI): [M+H]$^+$ 344.1; HRMS (ESI): [M+H]$^+$ calculated C$_{16}$H$_{26}$O$_7$N$^+$ 344.1704, found 344.1701.

Data for TG-037

$^1$H NMR (400 MHz, CD$_3$OD) δ 6.78-6.72 (m, 2H), 6.72-6.65 (m, 2H), 4.28 (d, J=7.8 Hz, 1H), 4.07-3.96 (m, 1H), 3.87 (dd, J=11.8, 1.4 Hz, 1H), 3.70 (s, 3H), 3.69-3.63 (m, 2H), 3.34 (t, J=4.5 Hz, 1H), 3.29-3.25 (m, 2H), 3.23-3.14 (m, 3H), 1.89 (t, J=6.4 Hz, 2H).

LRMS (ESI): [M+Na]$^+$ 366.1

The structure of each reaction intermediate during the experiment is shown below:

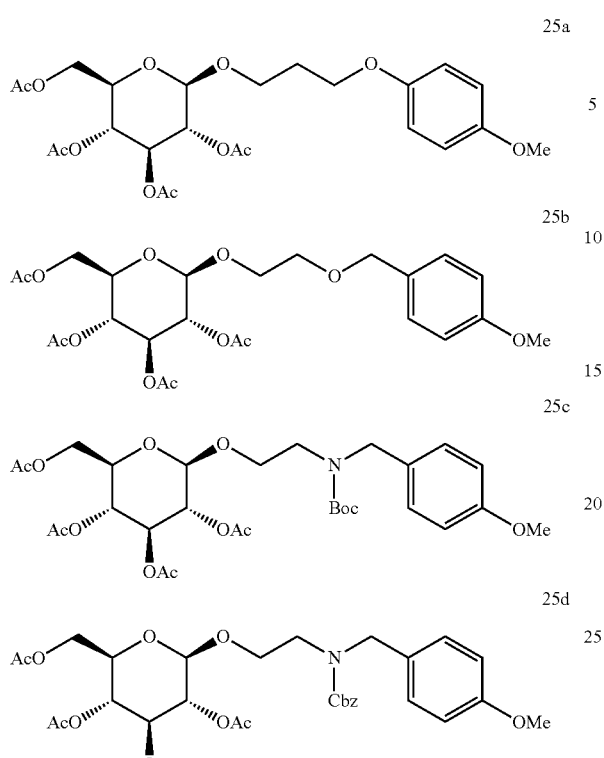
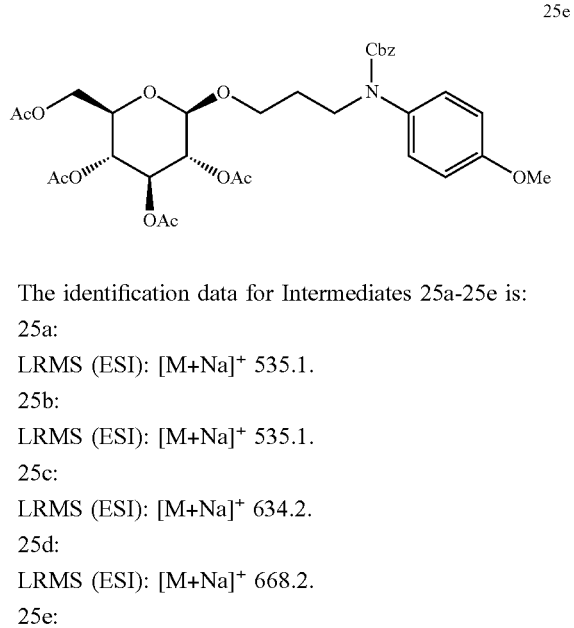
The identification data for Intermediates 25a-25e is:
25a:
LRMS (ESI): [M+Na]$^+$ 535.1.
25b:
LRMS (ESI): [M+Na]$^+$ 535.1.
25c:
LRMS (ESI): [M+Na]$^+$ 634.2.
25d:
LRMS (ESI): [M+Na]$^+$ 668.2.
25e:
LRMS (ESI): [M+Na]$^+$ 668.2.
Route F: Synthesis of Compounds TG-038, TG-039, TG-040, TG-041, TG-042, TG-043, and TG-044
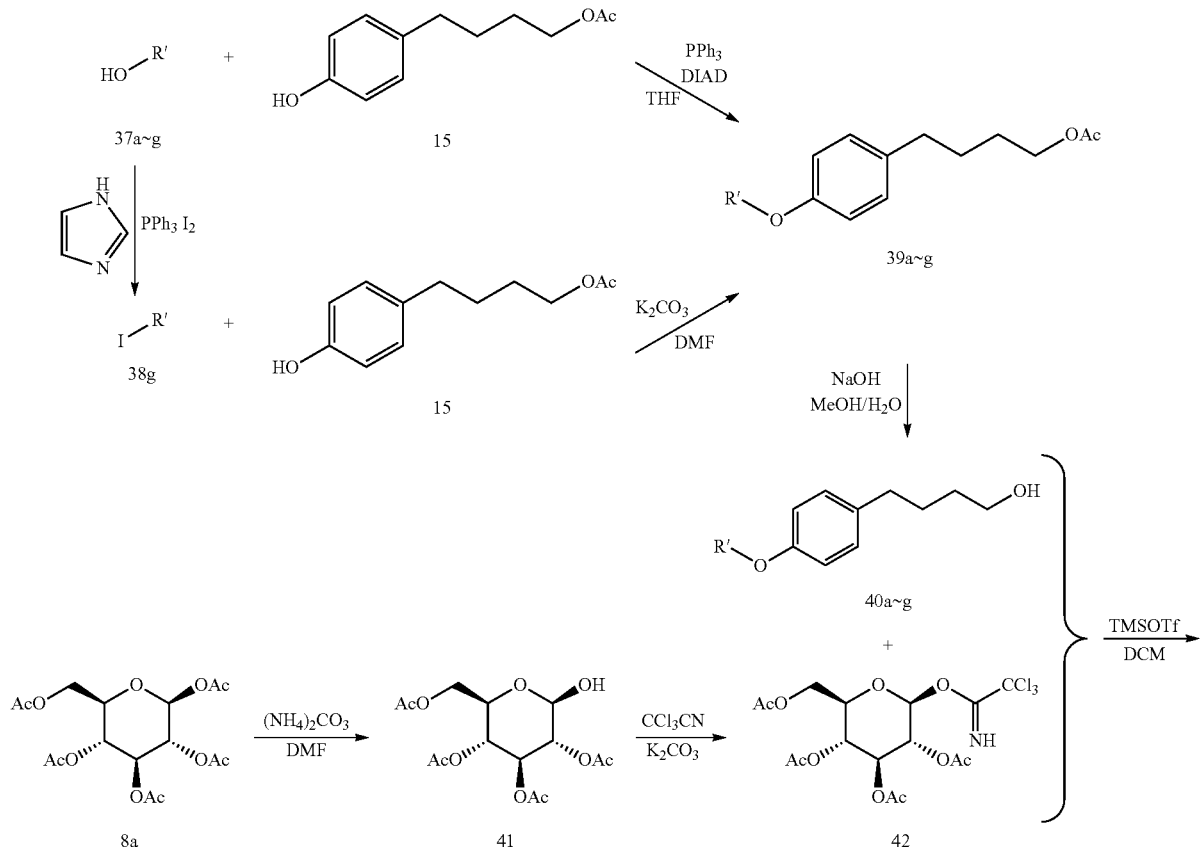

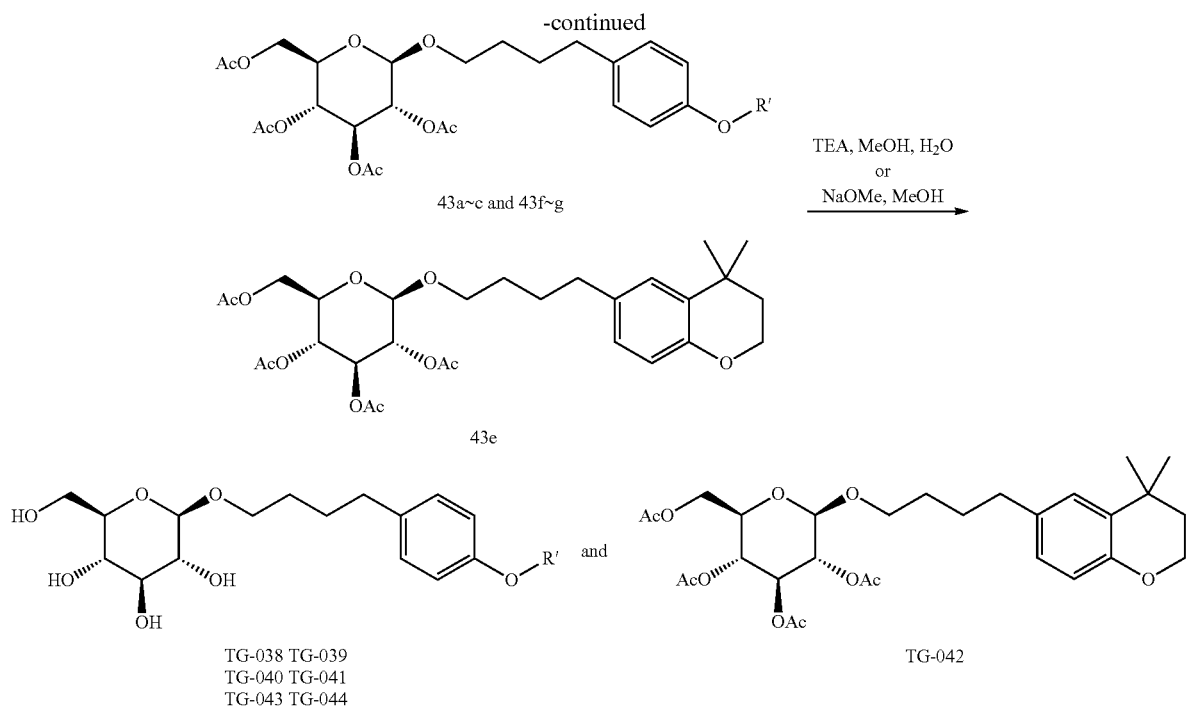

Experimental Operations of Route F:

15 (1 eq) and PPh$_3$ (1.3 eq) were added to a reaction flask, dry THF (0.5 mol/L) and then 37a-f (1 eq) were added, and DIAD (1.1 eq) was added dropwise at 0° C. The reaction solution was heated to 60° C. and stirred, until the reaction was completed as indicated by TLC. The reaction solution was concentrated under reduced pressure, and purified by column chromatography on silica gel to obtain 39a-f.

37 g (1 eq) was added to THF (0.2 mol/L), and PPh$_3$ (2 eq), imidazole (2 eq), and I$_2$ (2.5 eq) were added dropwise in an ice bath, heated to room temperature and stirred overnight. The reaction solution was filtered through celite, concentrated under reduced pressure, and purified by column chromatography on silica gel (Eluent: ethyl acetate:petroleum ether=1:9), to obtain the product 38g (5.7 g, 93% yield). 38g (1.2 eq), 15 (1 eq), and K$_2$CO$_3$ (2 eq) were added to DMF, heated to 110° C. and stirred for 10 h. The reaction solution was filtered through celite, and the filtrate was extracted with ethyl acetate. The extracts were combined, washed with water and dried over anhydrous sodium sulfate.

Concentration under reduced pressure afforded 3.8 g of crude product 39g. 39a-g (1 eq) was added to MeOH (0.5 mol/L), and then 1M aqueous NaOH solution (2.5 eq) was added dropwise at room temperature, and stirred for 4 hrs. The reaction system was neutralized with 2M HCl, and then extracted with ethyl acetate. The extract was dried over anhydrous sodium sulfate. The product was concentrated under reduced pressure and purified by column chromatography on silica gel (Eluent: ethyl acetate:petroleum ether=1:5) to obtain the product 40a-g.

8a (120 g, 0.3 mol) was added to 500 ml of DMF, (NH$_4$)$_2$CO$_3$ (60 g, 0.6 mol) was added at room temperature, and the reaction solution was heated to 45° C. and stirred for 5 h. The reaction solution was filtered through celite, and the filtrate was added with water, and then extracted with ethyl acetate. The extracts were combined, washed sequentially with water and saturated brine and dried over anhydrous sodium sulfate. After concentration under reduced pressure, the product 41 (95 g) was obtained, which was directly used in the next reaction. 41 (95 g, 0.273 mol) and K$_2$CO$_3$ (49 g, 0.355 mol) were added to dichloromethane (400 mL), and then CCl$_3$CN (157 g, 1.1 mol) was added dropwise in an ice bath, heated to room temperature, and stirred overnight. The reaction solution was filtered through celite, concentrated under reduced pressure and purified by column chromatography on silica gel to obtain 42 (95 g, yield 71%).

40a-g (1.1 eq), 42 (1 eq), and 4 A molecular sieve were added to a reaction flask, and then dry dichloromethane (0.2 mol/L) was added. The reaction was cooled to −20° C. and then TMSOTf (0.5 eq) was added dropwise. When the reaction was completed as indicated by TLC, Et$_3$N (1.5 eq) was added to quench the reaction. The reaction solution was concentrated under reduced pressure and purified by column chromatography on silica gel (Eluent: ethyl acetate:petroleum ether=1:5) to obtain the products 43a-g.

43a/43b/43e (1 eq) were respectively added to a one-neck flask, and MeOH (6 eq), H$_2$O (6 eq), and Et$_3$N (3 eq) were then added and stirred overnight. The reaction solution was concentrated under reduced pressure, and purified by column chromatography on silica gel (Eluent: methanol/dichloromethane=1:15) to obtain the product TG-038 (yield 63%)/TG-039 (yield 60%)/TG-042 (yield 36%).

43c/43d/43f/43g (1 eq) were respectively added to MeOH (0.5 mol/L), and then 0.2M MeONa (2.5 eq) was added dropwise in an ice bath, heated to room temperature, and stirred for 1 h. When the reaction was completed as indicated by TLC, the reaction solution was concentrated under reduced pressure, and purified by column chromatography on silica gel to obtain TG-040 (yield 15%)/TG-041 (yield 64%)/TG-043 (yield 55%)/TG-044 (yield 16%).

The structures and identification data for Compounds TG-038, TG-039, TG-040, TG-041, TG-042, TG-043, and TG-044 are shown below:

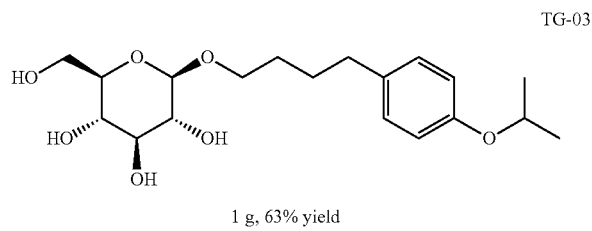

TG-038

1 g, 63% yield

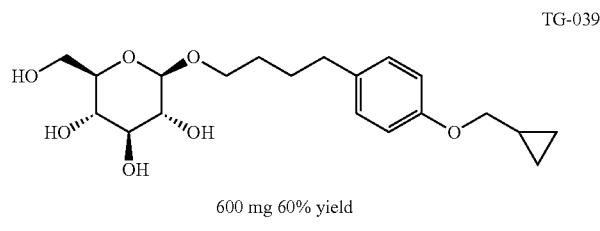

TG-039

600 mg 60% yield

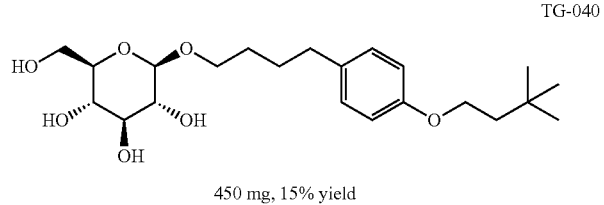

TG-040

450 mg, 15% yield

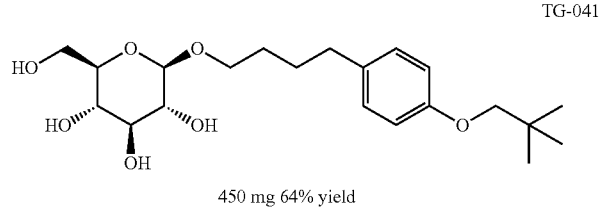

TG-041

450 mg 64% yield

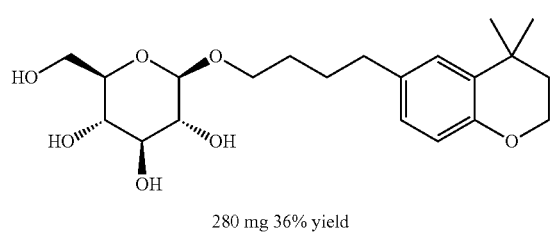

TG-042

280 mg 36% yield

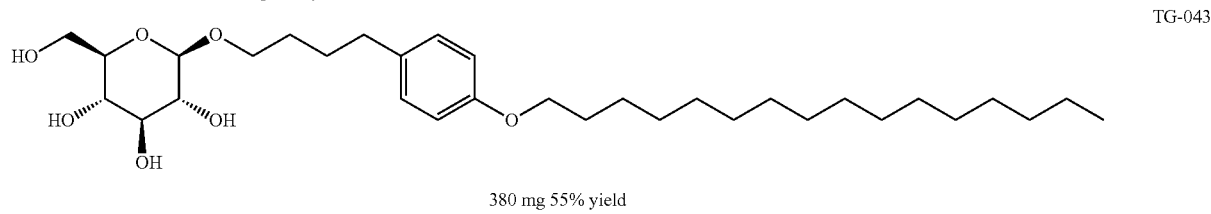

TG-043

380 mg 55% yield

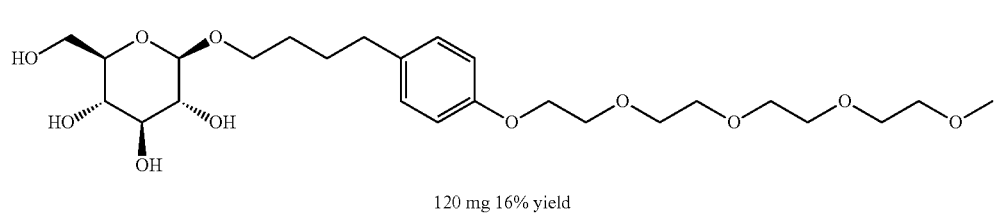

TG-044

120 mg 16% yield

Data for TG-038

$^1$H NMR (400 MHz, CD$_3$OD) δ 7.07 (d, J=8.6 Hz, 2H), 6.89-6.70 (m, 2H), 4.52 (dt, J=12.1, 6.1 Hz, 1H), 4.23 (d, J=7.8 Hz, 1H), 3.95-3.88 (m, 1H), 3.85 (dd, J=11.9, 1.9 Hz, 1H), 3.66 (dd, J=11.8, 5.3 Hz, 1H), 3.62-3.51 (m, 1H), 3.36-3.33 (m, 1H), 3.28-3.20 (m, 2H), 3.17 (dd, J=15.1, 7.2 Hz, 1H), 2.56 (t, J=7.1 Hz, 2H), 1.75-1.54 (m, 4H), 1.27 (d, J=6.0 Hz, 6H).

LRMS (ESI): [M+Na]$^+$ 393.0; RMS (ESI): [M+Na]$^+$ calculated C$_{19}$H$_{30}$O$_7$Na$^+$ 393.1884, found 393.1880.

Data for TG-039

$^1$H NMR (400 MHz, CD$_3$OD) δ 7.07 (d, J=8.6 Hz, 2H), 6.79 (d, J=8.6 Hz, 2H), 4.23 (d, J=7.8 Hz, 1H), 3.91 (m, 1H), 3.88-3.82 (m, 1H), 3.77 (d, J=6.8 Hz, 2H), 3.67 (dd, J=12.0, 5.3 Hz, 1H), 3.55 (m, 1H), 3.33-3.17 (m, 4H), 2.56 (t, J=7.1 Hz, 2H), 1.76-1.54 (m, 4H), 1.27-1.16 (m, 1H), 0.59 (dd, J=8.1, 1.4 Hz, 2H), 0.38-0.24 (m, 2H).

LRMS (ESI): [M+Na]$^+$ 405.0; HRMS (ESI): [M+Na]$^+$ calculated C$_{20}$H$_{30}$O$_7$Na$^+$ 405.1884, found 405.1883.

Data for TG-040

$^1$H NMR (400 MHz, CD$_3$OD) δ 7.07 (d, J=8.5 Hz, 2H), 6.79 (d, J=8.6 Hz, 2H), 4.23 (d, J=7.8 Hz, 1H), 3.99 (t, J=7.1 Hz, 2H), 3.91 (dt, J=9.3, 6.3 Hz, 1H), 3.85 (dd, J=11.9, 1.9 Hz, 1H), 3.67 (dd, J=11.9, 5.3 Hz, 1H), 3.57-3.52 (m, 1H), 3.26-3.11 (m, 4H), 2.56 (t, J=7.1 Hz, 2H), 1.75-1.53 (m, 6H), 0.99 (s, 9H).

LRMS (ESI): [M+Na]$^+$ 435.1; HRMS (ESI): [M+Na]$^+$ calculated C$_{22}$H$_{36}$O$_7$Na$^+$ 435.2353, found 435.2352.

Data for TG-041

$^1$H NMR (400 MHz, CD$_3$OD) δ 7.10 (d, J=8.5 Hz, 2H), 6.82 (d, J=8.5 Hz, 2H), 4.27 (d, J=7.8 Hz, 1H), 4.01-3.82 (m, 2H), 3.71 (d, J=5.2 Hz, 1H), 3.60 (m, 3H), 3.42-3.24 (m, 4H), 3.20 (t, J=8.4 Hz, 1H), 2.59 (t, J=7.0 Hz, 2H), 1.78-1.53 (m, 4H), 1.06 (s, 9H).

LRMS (ESI): [M+Na]$^+$ 421.1; HRMS (ESI): [M+Na]$^+$ calculated C$_{21}$H$_{32}$O$_7$Na$^+$ 421.2197, found 421.2194.

Data for TG-042

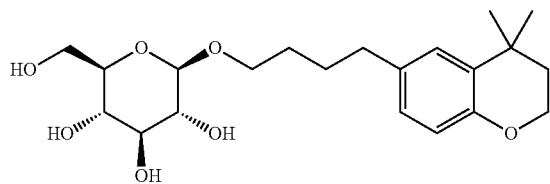 [SMILES: CC1(C)CCOc2ccc(CCCCO[C@@H]3O[C@H](CO)[C@@H](O)[C@H](O)[C@H]3O)cc21]

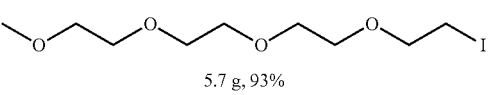

5.7 g, 93%

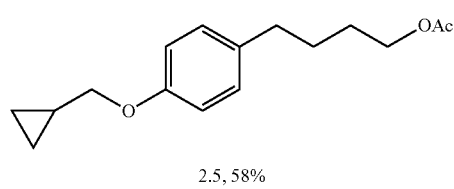

2.5, 58%

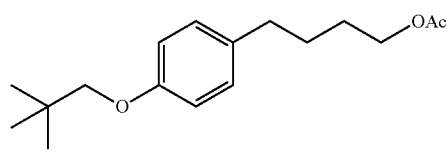

1.4 g, crude

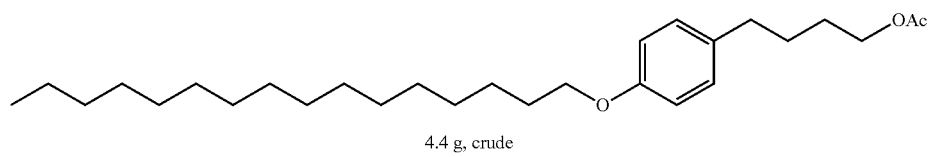

4.4 g, crude

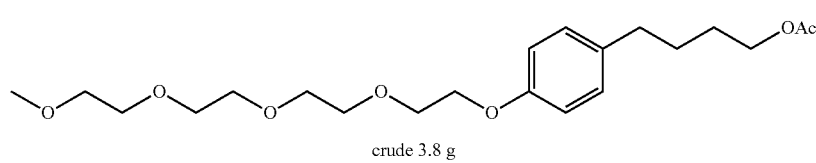

crude 3.8 g

¹H NMR (400 MHz, CD₃OD) δ 6.85 (m, 2H), 6.58 (d, J=8.9 Hz, 1H), 4.23 (d, J=7.8 Hz, 1H), 3.95-3.88 (m, 1H), 3.85 (dd, J=11.9, 1.8 Hz, 1H), 3.66 (dd, J=11.9, 5.2 Hz, 1H), 3.58-3.51 (m, 1H), 3.36-3.26 (m, 2H), 3.25-3.13 (m, 2H), 2.74 (t, J=6.8 Hz, 2H), 2.51 (t, J=6.9 Hz, 2H), 1.77 (t, J=6.8 Hz, 2H), 1.71-1.56 (m, 4H), 1.28 (s, 6H).

LRMS (ESI): [M+Na]⁺ 419.1; HRMS (ESI): [M+Na]⁺ calculated $C_{21}H_{32}O_7Na^+$ 419.2040, found 419.2041.

Data for TG-043

¹H NMR (400 MHz, CD₃OD) δ 7.07 (d, J=8.6 Hz, 2H), 6.79 (d, J=8.6 Hz, 2H), 4.23 (d, J=7.8 Hz, 1H), 3.92 (dd, J=7.9, 5.1 Hz, 2H), 3.85 (dd, J=11.9, 1.9 Hz, 1H), 3.66 (dd, J=11.9, 5.2 Hz, 1H), 3.55 (m, 1H), 3.34-3.21 (m, 4H), 2.56 (t, J=7.1 Hz, 2H), 1.70 (m, 6H), 1.45 (m, 2H), 1.41-1.20 (m, 24H), 0.99 (s, 1H), 0.89 (t, J=6.8 Hz, 3H).

LRMS (ESI): [M+Na]⁺ 575.3; HRMS (ESI): [M+Na]⁺ calculated $C_{32}H_{56}O_7Na^+$, 575.3918, found 575.3917.

Data for TG-044

¹H NMR (400 MHz, CD₃OD) δ 7.08 (d, J=8.5 Hz, 2H), 6.83 (d, J=8.6 Hz, 2H), 4.23 (d, J=7.8 Hz, 1H), 4.15-4.02 (m, 2H), 3.91 (m, 1H), 3.85 (dd, J=11.8, 1.7 Hz, 1H), 3.83-3.78 (m, 2H), 3.71-3.47 (m, 14H), 3.36-3.17 (m, 7H), 2.56 (t, J=7.0 Hz, 2H), 1.66 (m, 4H).

LRMS (ESI): [M+Na]⁺ 541.2; HRMS (ESI): [M+Na]⁺ calculated $C_{25}H_{42}O_{11}Na^+$, 541.2619, found 541.2618.

The structure of each reaction intermediate during the experiment is shown below:

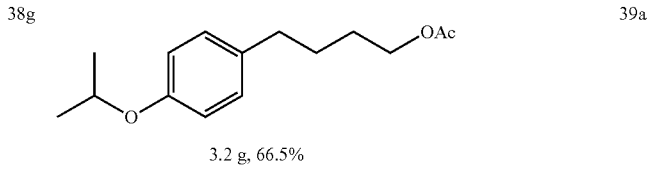

3.2 g, 66.5%

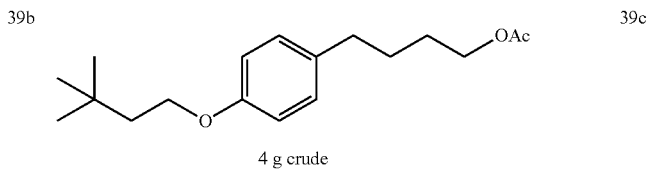

4 g crude

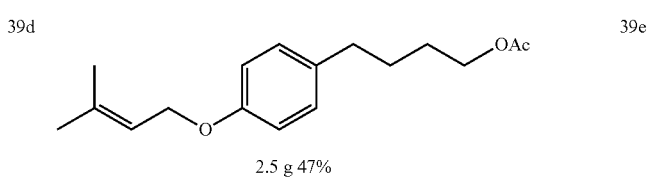

2.5 g 47%

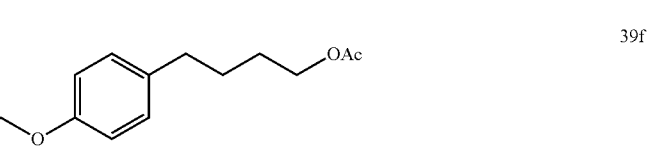

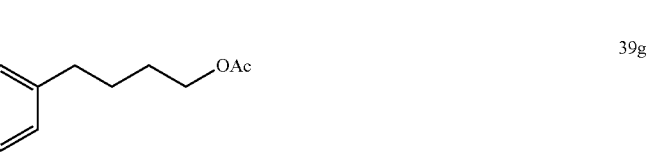

The identification data for Intermediates 39a-39f is:

39a:
LRMS (ESI): [M+Na]⁺ 273.1.
39b:
LRMS (ESI): [M+Na]⁺ 285.1.
39c:
LRMS (ESI): [M+Na]⁺ 315.2.
39d:
LRMS (ESI): [M+Na]⁺ 301.1.
39e:
LRMS (ESI): [M+Na]⁺ 299.1.
39f:
LRMS (ESI): [M+Na]⁺ 455.6.
39g:
LRMS (ESI): [M+Na]⁺ 421.2.

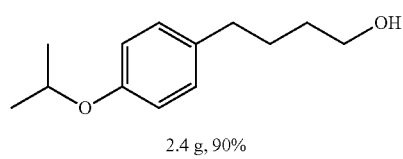
2.4 g, 90%
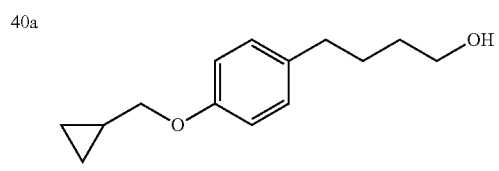
1.5 g 72%
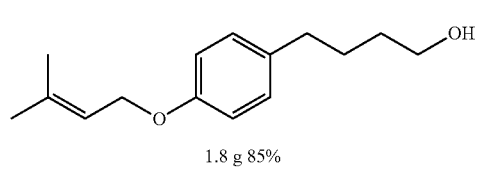
1.9 g, 38%
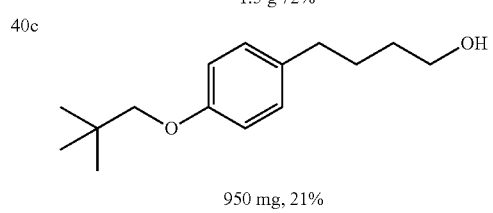
950 mg, 21%
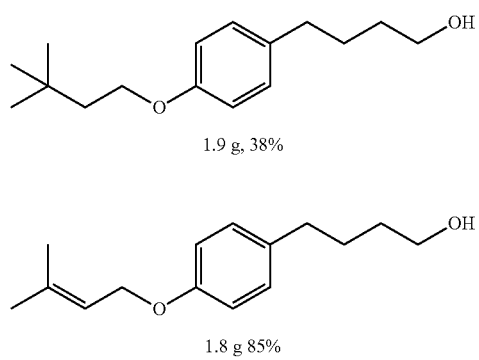
1.8 g 85%
3.9 g, 52%
2.3 g, 62%
40b:
LRMS (ESI): [M+Na]+ 243.1.
40c:
LRMS (ESI): [M+Na]+ 273.1.
40d:
LRMS (ESI): [M+Na]+ 259.1.
40e:
LRMS (ESI): [M+Na]+ 257.1.
40f:
LRMS (ESI): [M+Na]+ 413.3.
40g:
LRMS (ESI): [M+Na]+ 329.2.
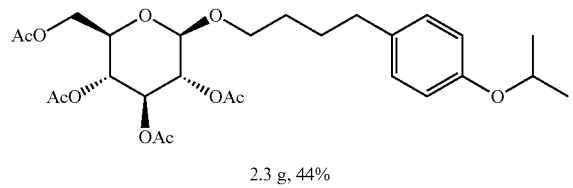
2.3 g, 44%
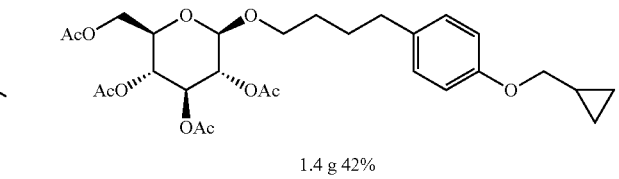
1.4 g 42%
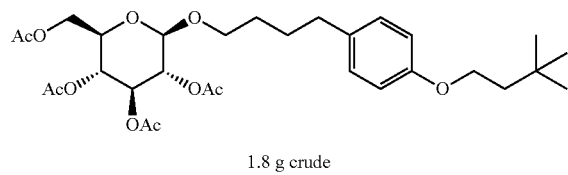
1.8 g crude
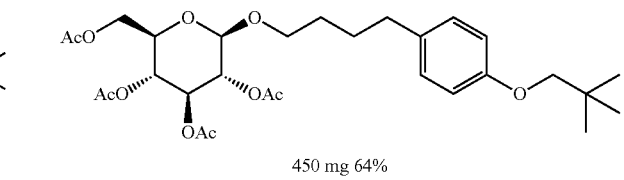
450 mg 64%

-continued
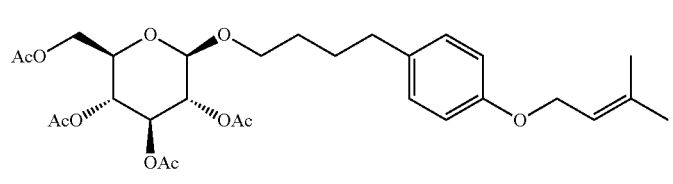
43e
1.1 g 28%
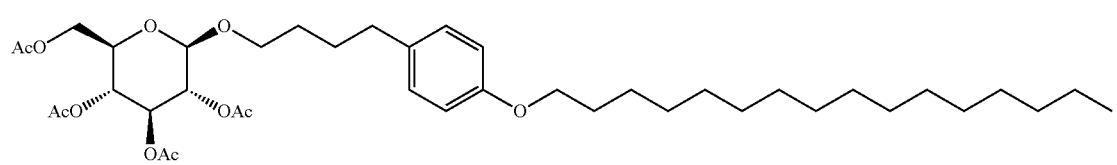
43f
0.9 g 13%
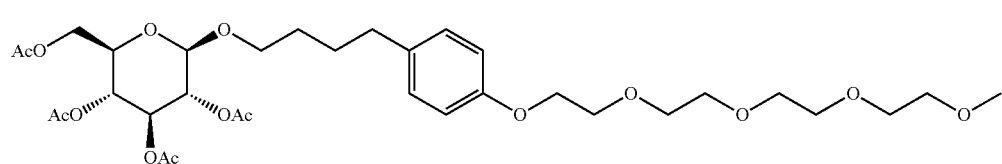
43g
1 g, 28%
43a:
LRMS (ESI): [M+Na]+ 561.2.
43b:
LRMS (ESI): [M+Na]+ 573.2.
43c:
LRMS (ESI): [M+Na]+ 603.2.
43d:
LRMS (ESI): [M+Na]+ 589.2.
43e:
LRMS (ESI): [M+Na]+ 587.2.
43f:
LRMS (ESI): [M+Na]+ 743.4.
43g:
LRMS (ESI): [M+Na]+ 709.3.
Synthesis of TG-045
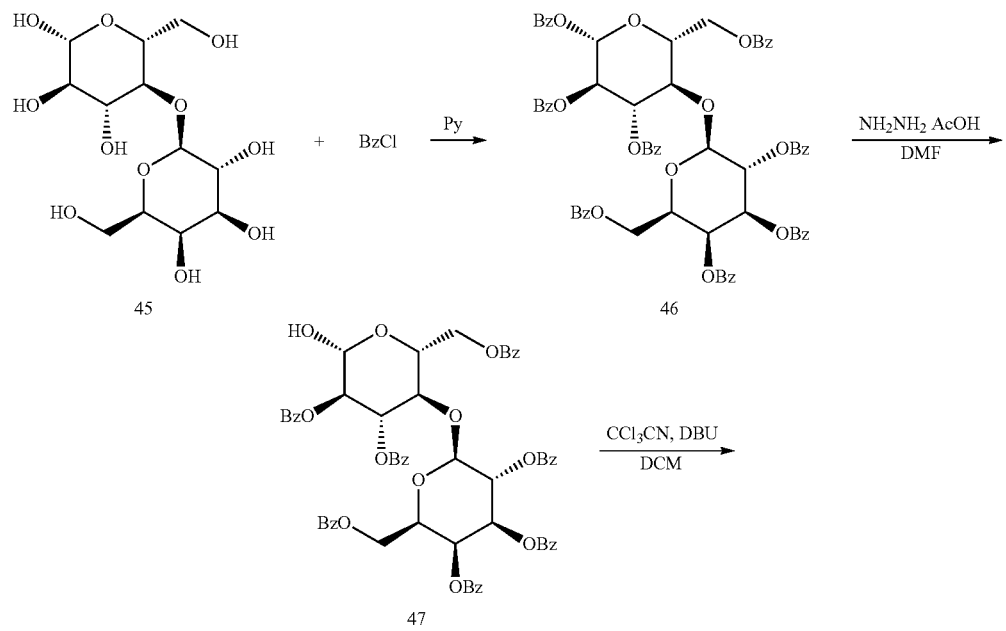

-continued

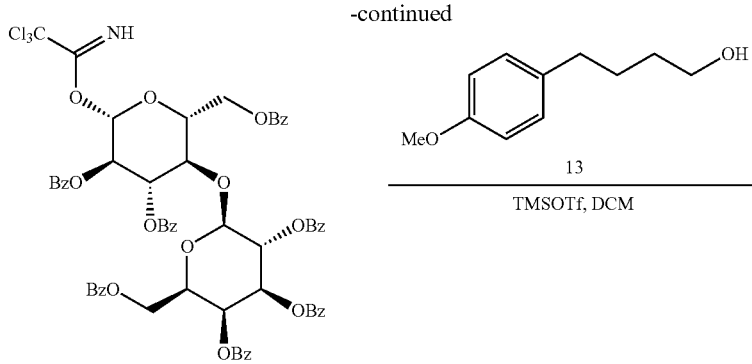

48

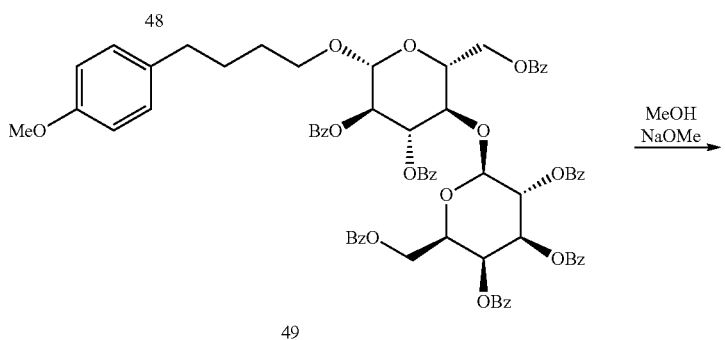

49

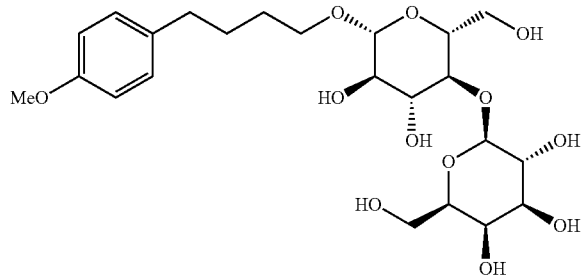

TG-045

Experimental Operations:

The raw material 45 and Py were added to the system, and stirred until dissolved. The system was cooled to 0° C. and then BzCl was added dropwise. Afterwards, the system was naturally heated to room temperature and stirred for 12 h. The solvent was distilled off under reduced pressure. A large amount of H$_2$O was added. The system was extracted 3 times with dichloromethane and then the organic phases were combined. The organic phase was washed sequentially with NaHCO$_3$ (×2), and saturated NaCl (×1), and dried over Na$_2$SO$_4$. After the solvent was distilled off under reduced pressure, the residue was purified by column chromatography on silica gel (Eluent: petroleum ether/ethyl acetate=2:1) to obtain Compound 46 as a colorless liquid (yield 100%). 46 and NH$_2$NH$_2$.AcOH were added to the system, dissolved in DMF by stirring, and then further stirred for 7 h at 60° C. A large amount of H$_2$O was added. The system was extracted 3 times with dichloromethane and then the organic phases were combined. The organic phase was washed sequentially with NaHCO$_3$ (×2), and saturated NaCl (×1), and dried over Na$_2$SO$_4$. After the solvent was distilled off under reduced pressure, the residue was purified by column chromatography on silica gel (Eluent: petroleum ether/ethyl acetate=1:1) to obtain Compound 47 as a colorless liquid (yield 78%).

47 and dichloromethane were added to the system, and then DBU, and CCl$_3$CN were sequentially added dropwise at 0° C. with stirring, naturally warmed to room temperature, and stirred for 3 h. After the solvent was distilled off under reduced pressure, the residue was purified by column chromatography on silica gel (Eluent: petroleum ether/ethyl acetate=2:1) to obtain Compound 48 as a white solid (yield 72%).

Compound 48, an alcohol 13, dichloromethane, and 4 A molecular sieve were added to the system, and stirred until dissolved. TMSOTf was added dropwise at 0° C., then naturally warmed to room temperature, and stirred for 12 h. The reaction solution was filtered under suction, and the solvent was distilled off under reduced pressure. The residue was purified by column chromatography on silica gel (Eluent: petroleum ether/ethyl acetate=5:1) to obtain Compound 49 as a colorless liquid (yield 85%).

49, and MeOH were added to the system, and stirred until dissolved. NaOMe was added at 0° C., then naturally warmed to room temperature, and stirred for 12 h. After the solvent was distilled off under reduced pressure, the residue was purified by column chromatography on silica gel (Eluent: dichloromethane/MeOH=5:1) to obtain the product TG-045 as a white solid (yield 75%).

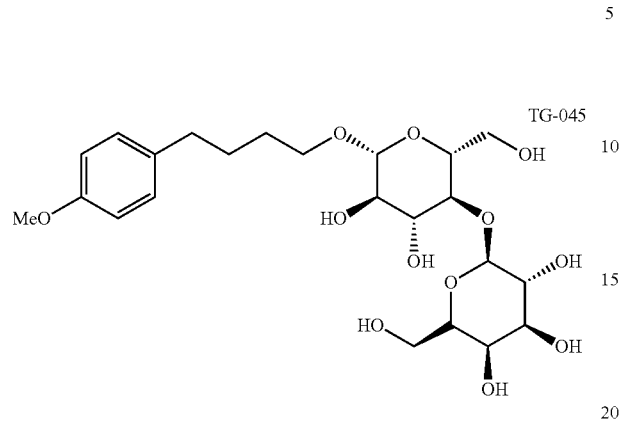

Identification data for TG-045:

$^1$H NMR (400 MHz, CD$_3$OD) δ 7.25-7.01 (m, 2H), 6.95-6.75 (m, 2H), 4.41-4.26 (m, 2H), 3.90-3.38 (m, 16H), 3.31-3.22 (m, 1H), 2.60-2.36 (m, 2H), 1.65-1.42 (m, 4H).

LRMS (ESI): [M+Na]$^+$ 527.2.

The structure of each reaction intermediate during the experiment is shown below:

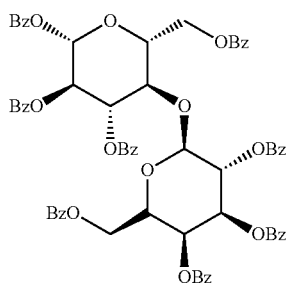

Identification data for 46:
LRMS (ESI): [M+Na]$^+$ 1197.3.

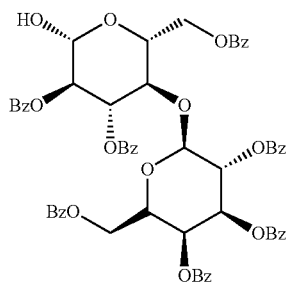

Identification data for 47:
LRMS (ESI): [M+Na]$^+$ 1093.3.

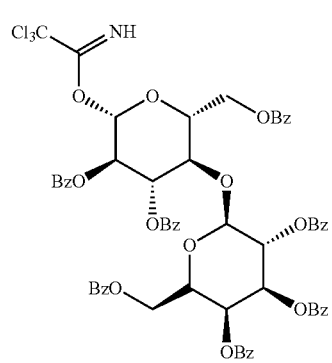

Identification data for 48:
LRMS (ESI): [M+Na]$^+$ 1236.2.

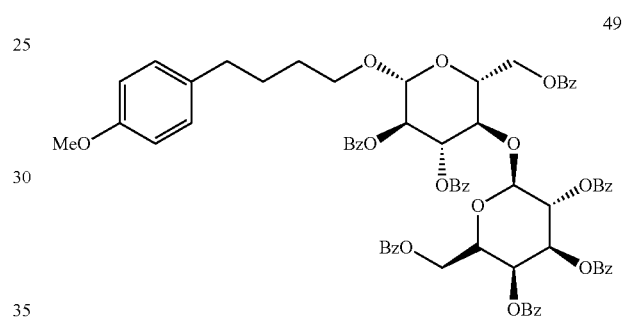

Identification data for 49
LRMS (ESI): [M+Na]$^+$ 1255.4.

Synthesis of TG-046

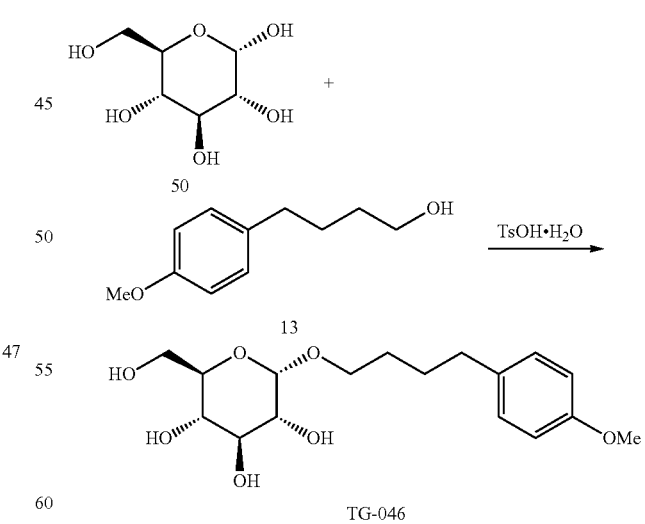

Compounds 50 (9 g, 50 mmol) and 13 (27 g, 150 mmol), and TsOH·H$_2$O (1 g, 5.26 mmol) were added to a reaction flask, heated to 80° C., and stirred for 18 h. The reaction solution was cooled to room temperature, added with H$_2$O (50 mL), stirred for 1 h, and then extracted with ethyl acetate (3×100 mL). The extracts were combined, and dried over anhydrous sodium sulfate. After the solvent was distilled off under reduced pressure, the residue was purified by column chromatography on silica gel to obtain 3.1 g of crude product, which was crystallized to obtain pure product TG-046 (500 mg).

Identification data for TG-046:

$^1$H NMR (400 MHz, CD$_3$OD) δ 7.12 (d, J=8.3 Hz, 2H), 6.84 (d, J=8.3 Hz, 2H), 4.79 (d, J=3.5 Hz, 1H), 3.88-3.73 (m, 2H), 3.78 (s, 3H), 3.73-3.64 (m, 2H), 3.62-3.54 (m, 1H), 3.53-3.45 (m, 1H), 3.41 (dd, J=9.7, 3.7 Hz, 1H), 3.29 (m, 1H), 2.63-2.59 (m, 2H), 1.75-1.63 (m, 4H).

LRMS (ESI): [M+Na]$^+$ 365.1

Synthesis of TG-047 and TG-048 was added at room temperature batchwise, and stirred at room temperature for 1 h. After the solvent was distilled off under reduced pressure, the residue was purified by column chromatography on silica gel to obtain Compound 54 (2 g).

Compounds 53 (1.2 g, 3.34 mmol) and 54 (3.674 mmol), and Et$_3$N (334 mg, 3.34 mmol) were sequentially added to acetonitrile (20 mL), stirred at room temperature for 1 h, added with 20 mL of water, extracted with ethyl acetate, washed with saturated aqueous NaCl solution, and dried over anhydrous sodium sulfate. After the solvent was distilled off under reduced pressure, the residue was purified by column chromatography on silica gel to obtain Compound 55 (1.1 g).

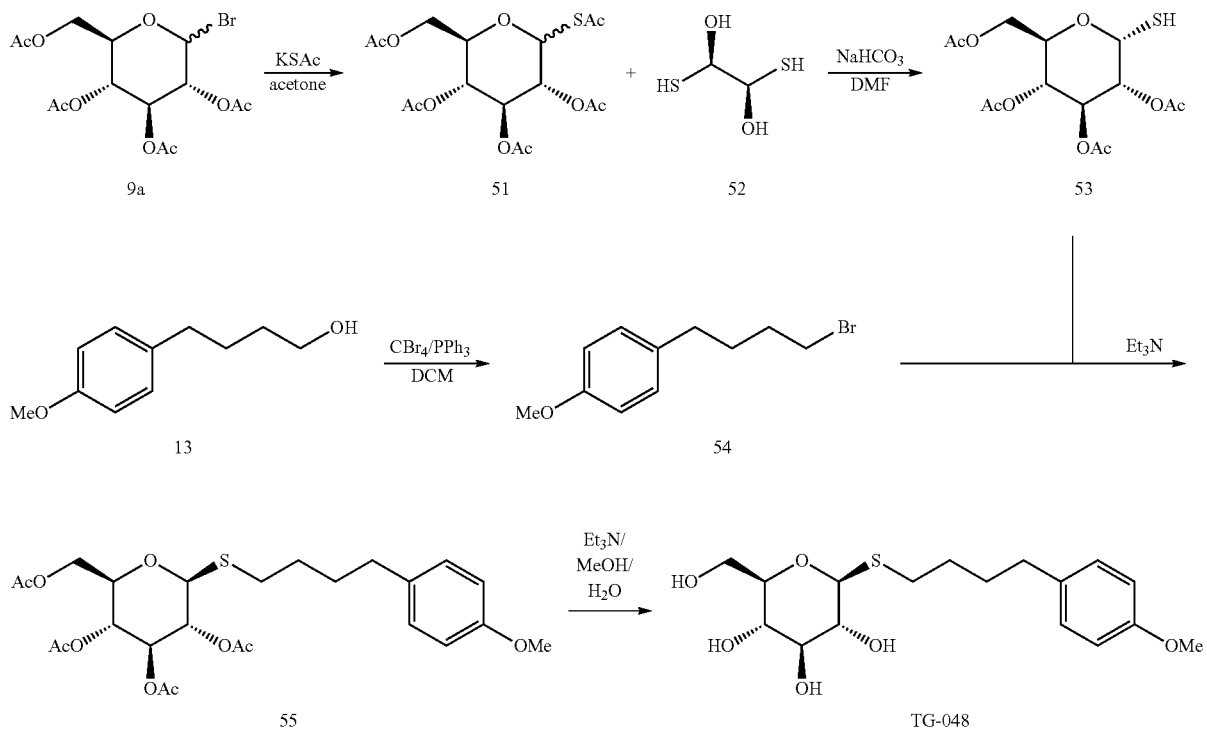

Compound 9a (16.4 g, 40 mmol) and KSAc (13.28 g, 80 mmol) were sequentially added to acetone (150 mL), and stirred for 4 h at room temperature until the reaction was substantially complete as indicated by TLC. The reaction solution was poured into 150 mL of water, and extracted with ethyl acetate. The extracts were combined, and dried over anhydrous sodium sulfate. After the solvent was distilled off under reduced pressure, the residue was purified by column chromatography on silica gel (Eluent: ethyl acetate/petroleum ether=1:6) to obtain Compound 51 (12.7 g).

Compounds 51 (12.7 g, 31.2 mmol) and 52 (6.26 g, 40.7 mmol), and NaHCO$_3$ (0.262 g, 3.12 mmol) were added to DMF (100 mL), and stirred at room temperature for 1 h. 150 mL of water was added, and then the system was extracted with ethyl acetate. The organic phases were combined, washed with aqueous sodium chloride solution, and dried over anhydrous sodium sulfate. After the solvent was distilled off under reduced pressure, the residue was purified by column chromatography on silica gel (Eluent: ethyl acetate/petroleum ether=1:4) to obtain Compound 53 (10 g).

Compound 13 (10 mmol) and PPh$_3$ (4.3 g, 13 mmol) were added to 25 mL of dichloromethane. CBr$_4$ (4.3 g, 13 mmol)

LRMS (ESI): [M+Na]$^+$ 549.2

Compound 55 (1.1 g) was added to MeOH (5 mL), and then H$_2$O (5 mL) and Et$_3$N (2.5 mL) were added and stirred overnight at room temperature, until the reaction was complete as indicated by TLC. After the solvent was distilled off under reduced pressure, the residue was purified by column chromatography on silica gel to obtain TG-048 (500 mg).

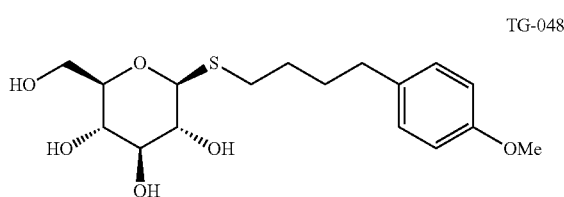 [SMILES: COc1ccc(CCCCS[C@@H]2O[C@H](CO)[C@@H](O)[C@H](O)[C@H]2O)cc1]

TG-048

Identification Data for TG-048

$^1$H NMR (400 MHz, CD$_3$OD) δ 7.12 (d, J=8.6 Hz, 2H), 6.85 (d, J=5.7 Hz, 2H), 4.35 (d, J=9.7 Hz, 1H), 3.86 (dd, J=12.0, 2.0 Hz, 1H), 3.78 (s, 3H), 3.67 (dd, J=11.8, 5.7 Hz, 1H), 3.43-3.16 (m, 4H), 2.76 (m, 2H), 2.60 (t, 1=7.2 Hz, 2H), 1.88-1.54 (m, 4H).

LRMS (ESI): [M+Na]$^+$ 381.1

The preparation method of TG-047 is similar to that for TG-048, and the structure is shown below:

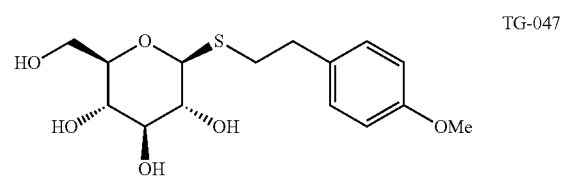 [SMILES: COc1ccc(CCS[C@@H]2O[C@H](CO)[C@@H](O)[C@H](O)[C@H]2O)cc1]

TG-047

Identification data for TG-047

1H NMR (400 MHz, CD3OD) δ 7.18 (d, J=8.6 Hz, 2H), 6.85 (d, J=8.6 Hz, 2H), 4.38 (d, J=9.5 Hz, 1H), 3.90 (dd, J=12.0, 1.8 Hz, 1H), 3.78 (s, 3H), 3.69 (dd, J=12.0, 5.4 Hz, 1H), 3.36-3.26 (m, 3H), 3.22 (t, J=8.7 Hz, 1H), 3.07-2.86 (m, 4H).

LRMS (ESI): [M+COOH]− 375.0.

EFFECT EXAMPLES

Effect Example 1. In Vitro Macrophage Experiment to Test Activity of Compounds to Promote VEGF-A mRNA Expression 1.1. Specific steps for activity screening: 1-10×10$^6$ macrophages (RAW264.7) in logarithmic growth phase were transferred to a cell culture plate. The test compounds (Compounds TG-001, TG-002, TG-003, TG-004, TG-005, TG-006, TG-007, TG-008, TG-009, TG-010, TG-011, TG-012, TG-013, TG-014, TG-015, TG-016, TG-017, TG-018, TG-019, TG-020, TG-021, TG-022, TG-023, TG-024, TG-025, TG-026, TG-027, TG-028, TG-029, TG-030, TG-031, TG-032, TG-033, TG-034, TG-035, TG-036, TG-037, TG-045, TG-039, TG-040 TG-041, TG-042, TG-043, TG-044, TG-045, TG-052, TG-053, TG-054, TG-047, TG-048, TG-046, TG-049, TG-050, TG-051, TG-055 and TG-056) were respectively diluted into various concentrations, and separately added to the cell culture plate containing macrophage. The cells were cultured for 3 h in a complete medium (RPMI 1640 medium: fetal bovine serum:tri-resistance screening agent (i.e. penicillin-streptomycin-gentamicin, Beijing Leagene Biotechnology Co., Ltd.)=89:10:1 based on volume) in a cell incubator at 37° C. and 5% CO$_2$. The cells were lyzed by Trizol (Beijing ComWin Biotech Co., Ltd) to extract RNA, and the RNA concentration was measured using a microvolume nucleic acid and protein analyzer (Nanodrop2000c). The required volume V of RNA was calculated according to the RNA concentration, and the RNA reverse transcription reaction system was prepared according to Table 1. Then RNA reverse transcription (cDNA synthesis) (RT Easy™ I (For first-strand cDNA synthesis) Reverse Transcription Kit, Chengdu ForeGene Biotechnology Co., Ltd.) was carried out according to the conditions described in Table 2. The resulting cDNA was used to prepare a fluorescence quantitative PCR reaction solution according to Table 3. The fluorescence quantitative PCR reaction conditions were set according to Table 4, and the fluorescence quantitative PCR reaction (Real time PCR Easy™-SYBR Green Fluorescence Quantification Kit, Chengdu ForeGene Biotechnology Co., Ltd.) was performed using cDNA from the reverse transcription reaction as a template. The relative expression level $2^{-\Delta\Delta Ct}$ of the target gene was calculated from the Ct value of each sample with the blank control group as a control and β-Actin as an internal reference.

Compounds TG-052, TG-053, and TG-054 can be synthesized following the method as described in Chemical & Pharmaceutical Bulletin, 2010, 58, 1627-1629.

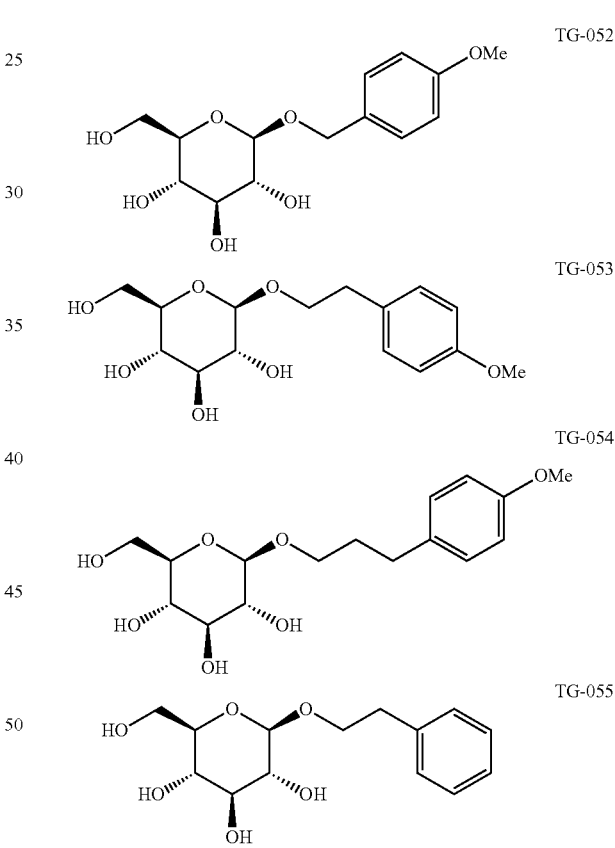

Compound TG-056 is purchased from (Shanghai Yuanye Bio-Technology Co., Ltd), and has a structure shown below:

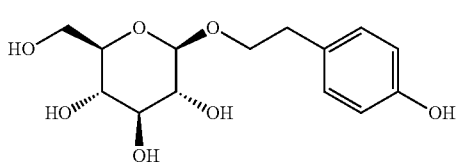 [SMILES: OC[C@H]1O[C@@H](OCCc2ccc(O)cc2)[C@H](O)[C@@H](O)[C@@H]1O]

TABLE 1

Formulation of RT reaction system

| Content added to RT-PCR reaction system | Amount |
|---|---|
| 2x RT Easy ™ Mix | 10 μL |
| Random primer (50 μM) | 1 μL |
| Template (RNA) | V μL |
| Double distilled water without RNase | (9-V) μL |
| Total volume | 20 μL |

TABLE 2

Reaction conditions for cDNA synthesis

| Step | Temperature | Time | Cycles | Description |
|---|---|---|---|---|
| 1 | 25° C. | 10 min | 1 | Preheat |
| 2 | 55° C. | 20 min | 1 | Renaturation (reverse transcription) |
| 3 | 85° C. | 5 min | 1 | Deactivation |

TABLE 3

QPCR reaction solution

| Component | Amount |
|---|---|
| cDNA template | 2.0 μL |
| Forward primer (10 μM) | 0.8 μL |
| Reverse primer (10 μM) | 0.8 μL |
| 2x Real PCR Easy ™ Mix-SYBR | 10 μL |
| DEPC water | 6.4 μL |
| Total Volume | 20 μL |

TABLE 4

QPCR reaction conditions

| Step | Temperature (° C.) | Time (s) | Cycles |
|---|---|---|---|
| Preheat | 95 | 180 | 1 |
| Three-step amplification | 95 | 5 | 40 |
|  | 60 | 10 |  |
|  | 72 | 20 |  |
| Melting | 95 | 10 | 1 |

Based on the maximum level of VEGF-A mRNA expression promoted by a drug at a certain concentration, the activity of the drug was determined. The expression level of VEGF-A mRNA in macrophages was defined as 1 when no drug was added. Using a traditional Chinese medicine injection Salvianolate that is used in the treatment of Cardio-cerebrovascular disease and promotes a maximum level of VEGF-A mRNA expression of 6 in macrophages (the results are shown in Table 5) as a judgment standard, the compound promoting a maximum level of VEGF-A mRNA expression of 4 or more in macrophage was a target compound. That is, when the maximum level of VEGF-A mRNA expression in macrophages promoted by the test compound is over 4-fold higher than the expression level of VEGF-A mRNA in macrophages without the addition of the test compound, the test compound was a preliminary target compound promoting angiogenesis. The results are shown in Table 6. The results show that most of the test compounds provided in the present invention have a good effect of promoting the expression of VEGF-A mRNA at a certain dose.

TABLE 5

Expression levels of VEGF-A mRNA in macrophages in the presence of various concentrations of Salvianolate

| Compound | Expression level of VEGF-A mRNA | | | | | |
|---|---|---|---|---|---|---|
|  | 0 | 0.5 | 1 | 2 | 3 | 4 mM |
| Salvianolat | 1 |  | 1.98 | 6.23 | 1.43 | 2.60 |

TABLE 6

Expression levels of VEGFA mRNA in macrophages in the presence of various concentrations of compounds

| Compound No. | Expression level of VEGF-A mRNA | | | | | | |
|---|---|---|---|---|---|---|---|
|  | 1 μM | 0.1 mM | 0.5 mM | 1 mM | 2 mM | 3 mM | 4 mM |
| TG-052 | — | — | 19.70 | 0.93 | 2.64 | 2.69 | 3.51 |
| TG-053 | — | — | 11.24 | 13.36 | 6.82 | 1.32 | 1.80 |
| TG-054 | — | — | 3.63 | 12.38 | 6.50 | 1.21 | 2.01 |
| TG-028 | — |  | 0.79 | 0.39 | 6.77 | 13.45 | 4.23 |
| TG-055 |  |  | 6.36 | 2.11 | 4.44 | 3.81 | 6.11 |
| TG-056 |  | 0.72 | 1.74 | 2.24 | 6.70 | 2.31 | — |
| TG-030 | 0.43 | 0.32 | 0.09 | 0.19 | 0.19 | 0.37 | — |
| TG-032 | 2.79 | 4.89 | 0.92 | 3.68 | 1.83 | 0.96 | — |
| TG-031 | 0.20 | 0.18 | 0.11 | 2.57 | 1.39 | 0.70 | — |
| TG-034 | 1.36 | 1.32 | 4.44 | 2.93 | 7.16 | 5.43 | — |
| TG-023 | 0.16 | 0.55 | 0.71 | 0.5 | 0.19 | 0.71 | — |
| TG-001 | 3.68 | 1.65 | 7.89 | 1.91 | 2.36 | 0.68 | — |
| TG-002 | 1.71 | 1.68 | 1.88 | 1.21 | 0.44 | 0.73 | — |
| TG-003 | 0.96 | 3.56 | 4.69 | 3.12 | 1.39 | 0.56 | — |
| TG-005 | 0.91 | 0.36 | 2.64 | 1.15 | 1.3 | 2.39 | — |
| TG-006 | 3.86 | 1.92 | 2.48 | 0.70 | 0.48 | 0.44 | — |
| TG-004 | 0.9 | 0.4 | 0.73 | 1.11 | 4.29 | 2.66 | — |
| TG-033 | 0.95 | 1.87 | 38.85 | 3.76 | 0.99 | 0.04 | — |
| TG-007 | 4.38 | 1.67 | 1.42. | 2.87 | 0.65 | 0.99 | — |
| TG-008 | 3.34 | 1.38 | 1.42 | 0.61 | 6.28 | 5.46 | — |
| TG-009 | 1.29 | 1.28 | 0.95 | 1 | 1.61 | 5.94 | — |
| TG-036 | 1.19 | 1.39 | 0.32 | 1.09 | 0.43 | 1.75 | — |
| TG-045 | 0.62 | 0.99 | 0.62 | 0.73 | 1.78 | 0.35 | — |
| TG-035 | 1.66 | 0.44 | 1.72 | 1.06 | 0.55 | 0.2 | — |
| TG-037 | 1.3 | 0.62 | 1.77 | 1.69 | 1.8 | 3.23 | — |
| TG-038 | 0.79 | 1.06 | 0.96 | 1.71 | 1.32 | 1.29 | — |
| TG-012 | 1.99 | 2.31 | 3.14 | 0.5 | 2.08 | 4.38 | — |
| TG-011 | 1.75 | 1.18 | 1.3 | 0.46 | 1.24 | 0.55 | — |
| TG-010 | 0.98 | 0.68 | 0.69 | 1.48 | 5.31 | 9.78 | — |
| TG-024 | 1.82 | 1.14 | 1.64 | 4.86 | 8.38 | 4.32 | — |
| TG-041 | 0.62 | 0.84 | 1.97 | 8.17 | 0.16 | 0.23 | — |
| TG-040 | 2.09 | 3.97 | 1.46 | 0.81 | 0.22 | 0.28 | — |
| TG-039 | 1.18 | 2.67 | 9.43 | 1.7 | 0.3 | 0.18 | — |
| TG-042 | 10.98 | 7.25 | 9.86 | 1.11 | 0.63 | 0.84 | — |
| TG-044 | 0.65 | 1.18 | 1.56 | 1.04 | 0.79 | 0.95 | — |
| TG-022 | 2.31 | 0.91 | 1.43 | 1.68 | 1.89 | 0.66 | — |
| TG-013 | 1.44 | 2.51 | 3.98 | 3.3 | 3.23 | 2.44 | — |
| TG-015 | 1.58 | 1.26 | 2.18 | 4.3 | 1.65 | 1.53 | — |
| TG-029 | 2.21 | 1.51 | 1.02 | 1.54 | 2.6 | 2.30 | — |
| TG-043 | 1.16 | 1.52 | 2.0'3 | 3.36 | 4.09 | 4.29 | — |
| TG-016 | 3.09 | 1.00 | 1.34 | 1.54 | 2.77 | 17.07 | — |
| TG-017 | 1.54 | 1.29 | 2.55 | 5.9 | 2.29 | 2.48 | — |
| TG-018 | 0.88 | 3.62 | 4.15 | 5.26 | 7.24 | 6.53 | — |
| TG-019 | 0.74 | 0.72 | 1.03 | 5.20 | 7.03 | 2.92 | — |
| TG-020 | 0.88 | 0.93 | 2.80 | 3.90 | 2.24 | 2.56 | — |
| TG-021 | 0.87 | 2.69 | 3.81 | 4.24 | 9.20 | 7.96 | — |
| TG-025 | 1.62 | 1.78 | 1.43 | 2.15 | 9.69 | 2.06 | — |
| TG-026 | 1.44 | 6.85 | 7.92 | 8.13 | 7.92 | 8.16 | — |
| TG-051 | 1.1 | 4.49 | 6.76 | 7.89 | 11.16 | 8.18 | — |
| TG-027 | 1.66 | 6.36 | 3.83 | 3.93 | 1.07 | 0.43 | — |
| TG-049 | 1.29 | 1.86 | 3.33 | 2.62. | 0.63 | 13.29 | — |
| TG-050 | 1.27 | 2.81 | 1.85 | 2.16 | 1.74 | 15.14 | — |
| TG-047 | 2.12 | 1.93 | 2.34 | 2.84 | 2.6 | 3.45 | — |
| TG-048 | 1.43 | 1.26 | 4.73 | 11.01 | 3.81 | 2.19 | — |
| TG-046 | 1.86 | 1.96 | 2.14 | 2.27 | 2.25 | 5.32 | — |

"—" denotes not detected.

Effect Example 2: Screening of Active Molecules that Promote VEGF-A mRNA Expression in "Sponge Implanted Animal Model"

The target pro-angiogenic compounds TG-052, TG-053, TG-054, TG-028, and TG-055 obtained in Effect Example 1 that perform well at the cellular level were further screened for the active molecules that promote VEGF-A mRNA expression in the "sponge implanted animal model" of inflammatory angiogenesis. Related research shows that in the "sponge implanted animal model", about 75% of the cells that can be recruited into the sponge in the early stage of inflammation are macrophages. This model can well reflect the expression of VEGF-A mRNA in macrophages recruited around inflammation.

A sponge implanted mouse model was established following the method as described in Zhang J, Modi Y, and Yarovinsky T, et al. Macrophage β2 integrin-mediated, HuR-dependent stabilization of angiogenic factor-encoding mRNAs in inflammatory angiogenesis. [J]. American Journal of Pathology, 2012. 180(4): 1751-1760. The mice used in the present invention was male C57/BL6 mice aged 6-8 weeks and weighing 20-25 g, purchased from Shanghai SLAC Laboratory Animal Co., Ltd, Production License No: SCXK (Shanghai) 2013-0016. The compound screened in Effect Example 1 was weighed according to the amount intended to be used in two weeks, and then mixed with a gel matrix and a solvent to prepare a sustained-release gel of the compound (see Patent Application No.: CN201610168493.9 for the details of the preparation method of the sustained-release gel and the model establishment and detection methods). The specific steps were as follows. A certain amount of the compound obtained in Effect Example 1 was weighed into a 1.5 mL EP tube, and then a certain amount of poly-L-lactic acid (PLLA) with a weight average molecular weight of less than 10,000 was weighed and mixed with the compound (at a weight ratio of the compound to PLLA of 0.5:1 to 2:1). Finally a certain amount of DMSO (less than 100 microliters) was added, spun, mixed well, and then sealed with a sealing film. After continuous ultrasonication at 200 W and 25° C. for 5 h, a sustained-release gel of the compound was obtained, which was stored at 4° C. for later use.

The prepared sustained-release gel can release the drug completely within 2 weeks. The sustained-release gel and sponge were both subcutaneously implanted in the mice at the back. After 2 weeks, the sponge was taken out, and the residual tissue and fur were removed. The sponge was transferred to a cell culture plate containing 10 mL of DMEM medium containing collagenase (Collagenase:D-MEM=10 mg/10 mL), cut, and incubated for 1 h in a cell incubator. Then the culture medium containing sponge debris was filtered, and the resulting filtrate was centrifuged. The supernatant was discarded, and 500 μL of Trizol reagent was added to the pellet, and mixed uniformly by blowing. Then the liquid was transferred to a 1.5 mL EP tube, and stored at −80° C. RNA was extracted according to a conventional method, and the RNA concentration was determined using a microvolume nucleic acid and protein analyzer (Nanodrop2000c). The required volume V of RNA was calculated according to the RNA concentration, and the RNA reverse transcription reaction system was prepared according to Table 1. Then RNA reverse transcription (cDNA synthesis) was carried out according to the conditions described in Table 2. The resulting cDNA was used to prepare a fluorescence quantitative qPCR reaction solution according to Table 3. The fluorescence quantitative qPCR reaction conditions were set according to Table 4, and the fluorescence quantitative PCR reaction was performed using cDNA from the reverse transcription reaction as a template. The relative expression level $2^{-\Delta\Delta Ct}$ of the target gene was calculated from the Ct value of each sample with the blank group as a control and β-Actin as an internal reference. The expression level of VEGF-A mRNA in the cells extracted from the sponge was observed after 2 weeks.

In the "sponge implanted animal model", three different (high, medium and low) dosages of the compound were used, 60 mg/kg/d Salvianolate (purchased from Henan Provincial People's Hospital) was used as a positive control (where experiments have shown that this dose is the optimal dose of Salvianolate in this model to promote VEGF-A mRNA expression, as shown in FIG. 1A), the sustained-release gel without drugs was used as the blank control. FIG. 1 shows the results from RT-qPCR.

Compared with the blank control without drugs, the results show that TG-052 (41.37 mg/kg/d) and TG-055 (19.48 mg/kg/d) allow the expression level of VEGF-A mRNA to increase by about 3 times, so the activity is comparable to that of Salvianolate (60 g/kg/d). The dose of TG-055 (19.48 mg/kg/d) is lower than that of TG-052 (41.37 mg/kg/d), so the activity is higher than TG-052. Compared with Salvianolate (60 g/kg/d), TG-053 and TG-054 have a slightly lower activity in promoting the VEGF-A mRNA expression. At a dose of 11.74 mg/kg/d and 23.48 mg/kg/d, TG-028 promote the VEGF-A mRNA to express at a level that is more than 6 times that of the blank control without drugs, so the activity is significantly higher than that of Salvianolate (60 mg/kg/d). Therefore, the activity results can be expressed as: TG-028>TG-055>TG-052>Danshen dofenate>TG-053>TG-054. The results show that most of the compounds screened by the in-vitro cell experiment in Effect Example 1 have an activity that is superior or comparable to that of commercially available Salvianolate in the in-vivo animal model.

Figure 19:
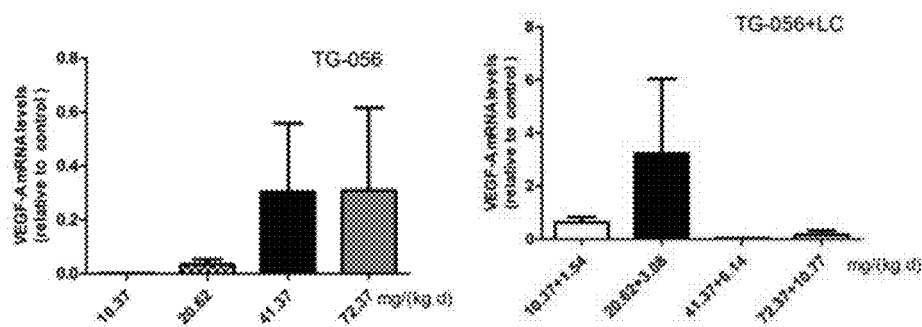
FIG. 19 shows the effect of various doses of salidroside (TG-056) alone on the expression of VEGF-A mRNA in a sponge implanted animal model.

As shown in FIG. 19, the use of various doses of salidroside (TG-056) leads to a very low expression of VEGF-A mRNA in the sponge implanted animal model. Also, the effect of salidroside and tyrosol LC (a main component in salidroside injection) on the expression of VEGF-A mRNA was investigated in the sponge implanted animal model. It is found that salidroside (20.62 mg/(kg·d))+tyrosol (3.08 mg/(kg·d)) can promote the expression of VEGF-A mRNA with an effect that is not as good as Salvianolate. Therefore, in the subsequent experiments the effect of salidroside will not be investigated.

Effect Example 3: Verification of Inhibition on Cerebral Infarction and Neuroprotection for Brain Injury of Screened Active Molecules After obtaining the active molecules that can promote the expression of VEGF-A mRNA in the animal model of inflammatory angiogenesis, a rat model of cerebral infarction was used for further verification. Following the method as described in Longa, E. Z., Longa, E. Z., Weinstein, P. R., Carlson, S. & Commin, R. Reversible middle cerebral artery occlusion without craniectomy in rats. [J]. Stroke, 1989. 1: 84-91, an acute cerebral infarction model was established in rats with middle cerebral artery occlusion (MCAO); and following the method as described in C. dela Torre, T. Fortin, G. A. S. Park, K. S. Butler, P. Kozlowski, B. A. Pappas, H. de Socarraz, J. K. Saunders and M. T. Richard. [J]. Brain Research, 1992. 582:186-195, a chronic cerebral ischemia model was established in rats with permanent ligation of bilateral common carotid arteries (2VO). The inhibition on cerebral infarction and neuroprotection for brain injury of the active molecules screened in Effect Example 2 were verified.

In the acute cerebral infarction model in rats with MCAO, TG-028 and TG-055, which showed higher activity in Effect Example 2, were selected for activity verification. The control drugs were: Edaravone (purchased from Zhejiang Shengtong Biotechnology Co., Ltd.), Clopidogrel bisulfate (purchased from Wuhan Yuancheng Gongchuang Technology Co., Ltd.), and Salvianolate (purchased from Henan Provincial People's Hospital). Clopidogrel bisulfate is a platelet aggregation inhibitor, and Edaravone is a brain protectant (free radical scavenger). The MCAO model of rats was made by the thread occlusion method. The rats used in this effect example were male SD rats weighing 280-320 grams, purchased from Shanghai SLAC Laboratory Animal Co., Ltd. Five SD (Sprague Dawley) rats in each group were administered by intraperitoneal injection, 2 h before surgery, and every 24 h after modeling. The specific dosage is shown in Table 7.

TABLE 7

Dosage of drugs used

| Drug name | Dosage of drugs used (mg/kg) | | | | |
|---|---|---|---|---|---|
| TG-028 | 1 | 3 | 5 | 7 | 10 |
| TG-055 | 10 | 30 | 60 | 80 | 100 |
| Clopidogrel bisulfate | 3 | 7 | 10 | 20 | 40 |
| Edaravone | 3 | 10 | 20 | 40 | 60 |
| Salvianolate | 5 | 10 | 15 | 20 | 30 |

Figure 2:
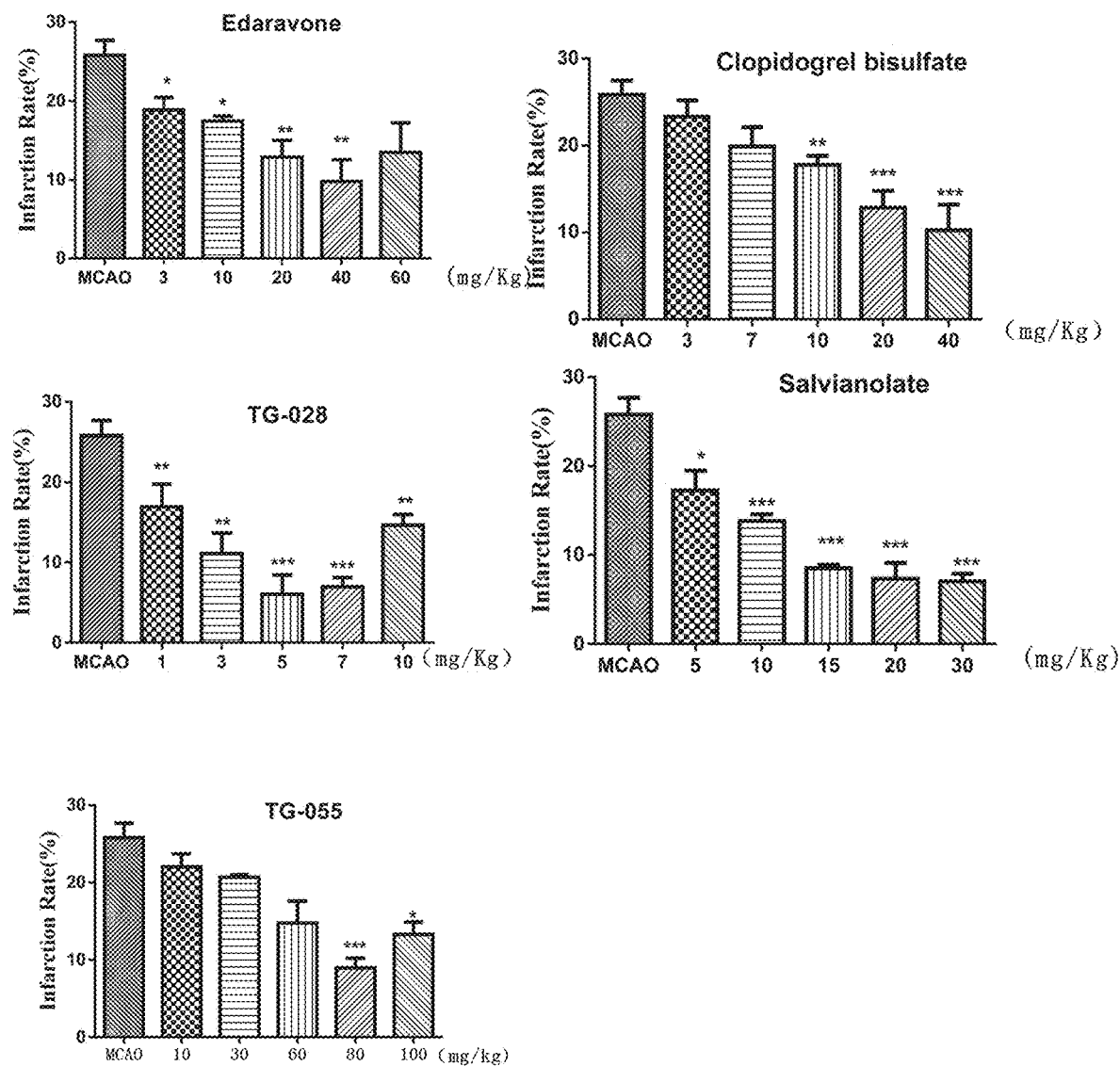
FIG. 2 shows the infarction rates (%) in the presence of different drugs in an acute cerebral infarction model of MCAO.

Three days later, the brain was taken, and the rat brain was stained with TTC (2,3,5-triphenyltetrazolium chloride, to detect the cell viability) and then photographed. Infarction rate (%)=(Non-infarction area of right brain section−non-infarction area of left brain section)/total area of brain section*100%. According to t tests, *$P<0.05$, $P<0.01$, *$P<0.001$ compared with the model group (MCAO). The results are shown in FIG. 2. Infarction inhibition rate (%) at different doses=(infarction rate of model group-infarction rate of treatment group)/infarction rate of model group*100%. The infarction inhibition rate at different doses was plotted, and the ED50 of the drug was calculated. The results are shown in Table 8.

TABLE 8

ED50 of different drugs for infarction inhibition rate (%) in acute cerebral infarction model of MCAO

| Drug | TG-028 | TG-055 | Edaravone | Clopidogrel bisulfate | Salvianolate |
|---|---|---|---|---|---|
| $ED_{50}$ (mg/kg) | 2.61 | 65.30 | 25.67 | 28.07 | 10.85 |

It can be seen from the results in Table 8 that Compound TG-028 has the most potent effect on inhibiting cerebral infarction in rats in the acute cerebral infarction model of middle cerebral artery occlusion (MCAO), and is thus superior to the commonly used drugs available from the market.

Figure 3:
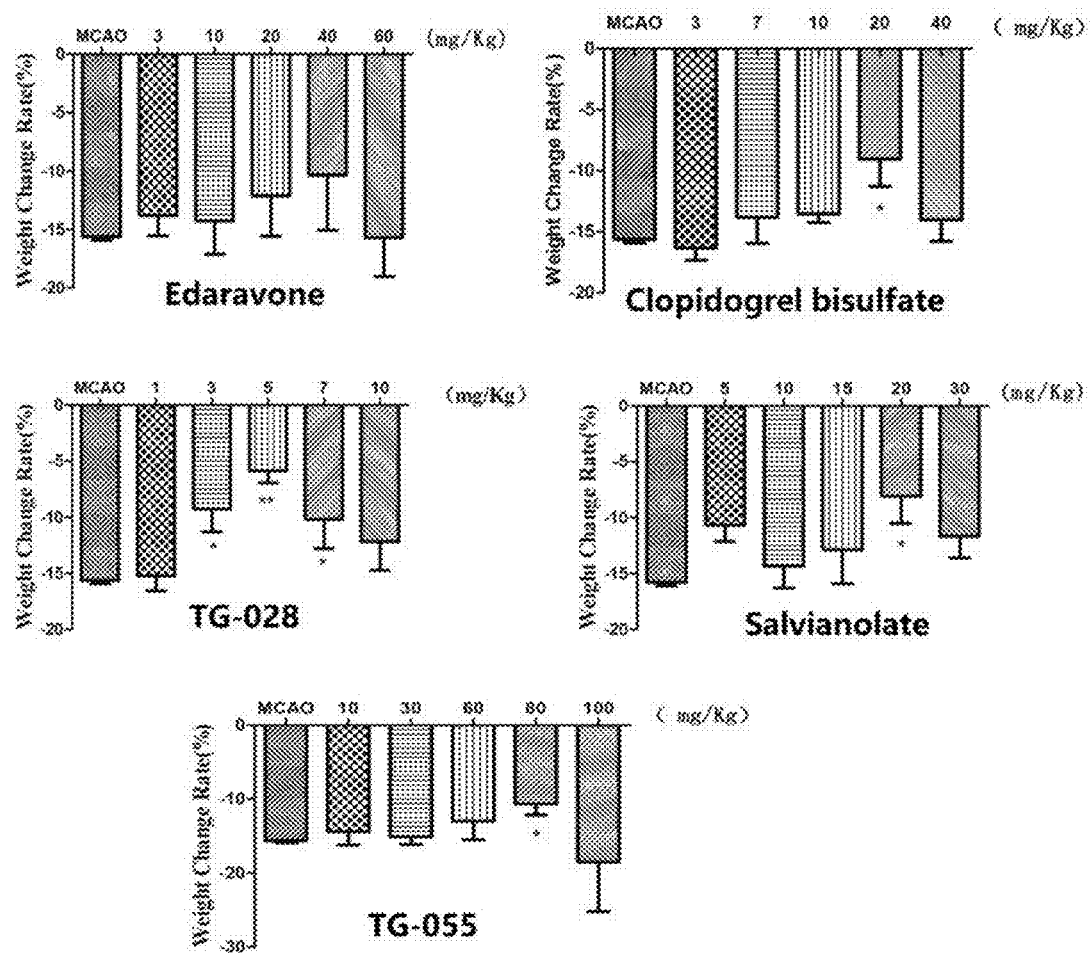
FIG. 3 shows the rates (%) of body weight change in the presence of different drugs in an acute cerebral infarction model of MCAO.

Moreover, the body weight of the rats was recorded. The rate of body weight change was calculated according to a formula: Rate of body weight change (%)=(final weight-initial weight)/final weight*100%. The rate of body weight change at various doses of different drugs is obtained, as shown in FIG. 3. It can be seen from the rate of body weight change of rats three days after brain injury that TG-028 has a significant protection for rats in terms of the body weight after brain injury, which is superior to TG-055, Edaravone, Clopidogrel bisulfate, and Salvianolate.

Figure 4:
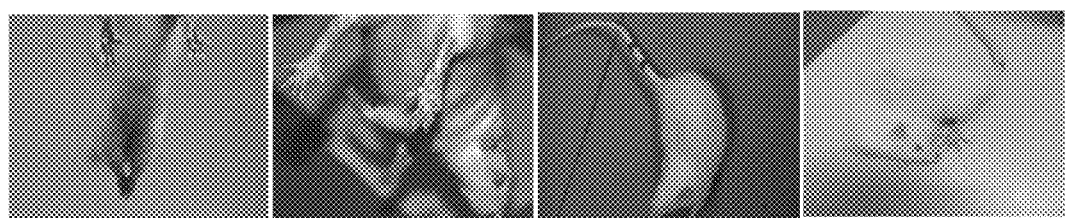
FIG. 4 is a schematic diagram of the Longa nerve scoring criteria. From left to right: Score 1, indicating that the forepaws at both sides cannot be fully extended; Score 2, indicating turning to the opposing side; Score 3, indicating toppling to the opposing side; and Score 4, indicating that it is not possible to spontaneously walk, with loss of consciousness.

Three days after the acute cerebral infarction model was established in rats with MCAO, the test rats were scored for neurological function according to the Longa nerve scoring standard. The schematic diagram of the scoring standard is shown in FIG. 4. Score 0 indicates normal without nerve damage; Score 1 indicates that the forepaws at both sides cannot be fully extended; Score 2 indicates turning to the opposing side; Score 3 indicates toppling to the opposing side; Score 4 indicates that it is not possible to spontaneously walk, with loss of consciousness.

Figure 5:
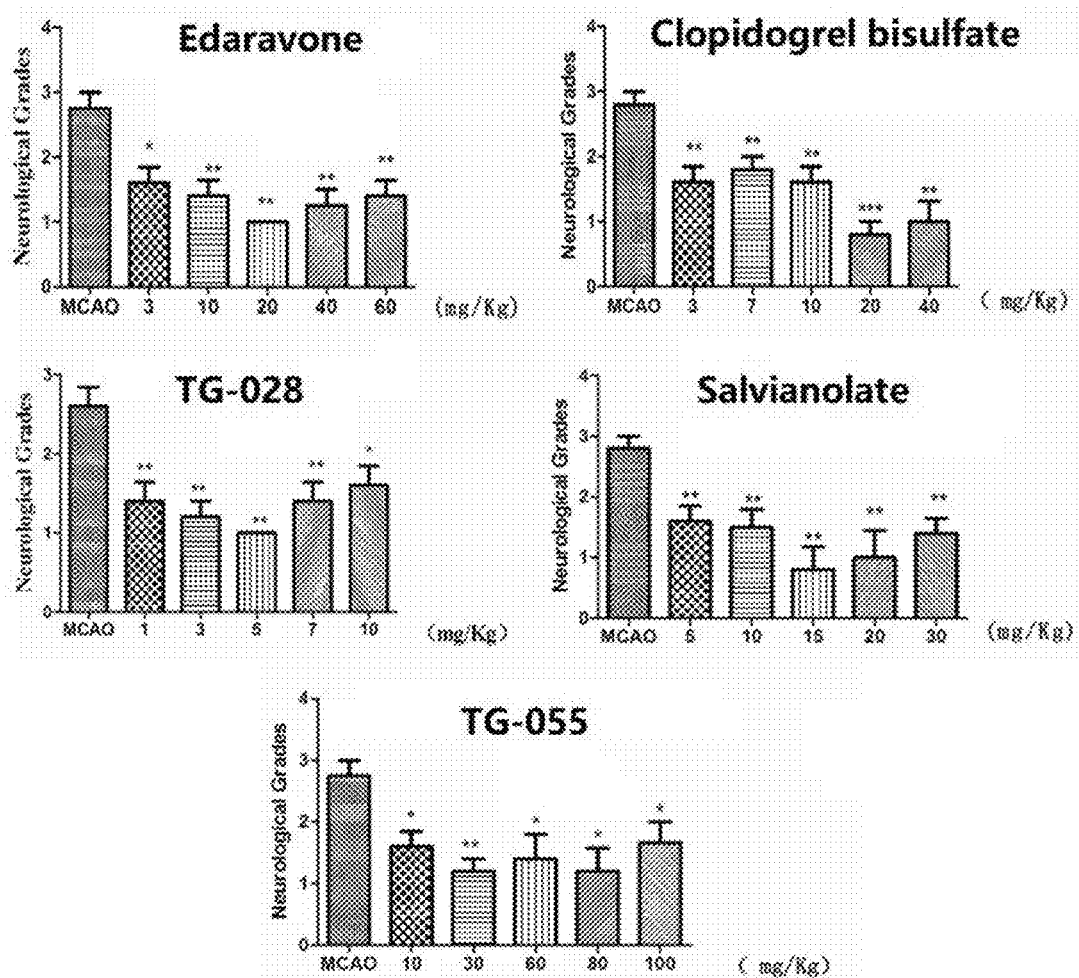
FIG. 5 is a schematic diagram showing the Longa nerve scores in the presence of different drugs in an acute cerebral infarction model of MCAO.

According to the Longa nerve scoring standard, the rats were scored for neurological function, and Longa nerve scores for different drugs at various doses were obtained. The results are shown in FIG. 5. The Longa nerve scoring results show that the protective effect of TG-028 and TG-055 on nerves in rats after brain injury is equivalent to that of Edaravone, Clopidogrel bisulfate, and Salvianolate.

In the acute cerebral infarction model in rats with MCAO, the results with respect to the infarction inhibition rate (%), rate of body weight change and Longa nerve scoring show that TG-028 is obviously more potent than TG-055, which is consistent with the previous experimental results in sponge implanted animal model, indicating the reliability of the screening model of the present invention.

Figure 20:
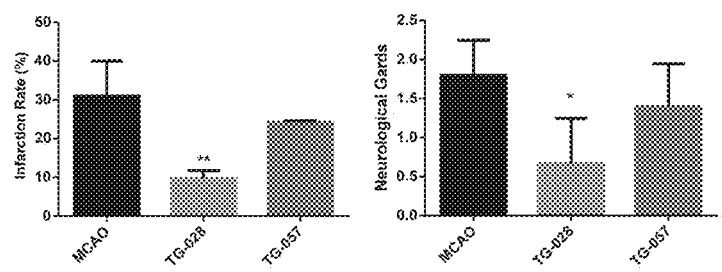
FIG. 20 shows the infarction rate and Longa nerve score in the presence of TG-028 and TG-057 in an acute cerebral infarction model of MCAO.

On the basis of the above experiments, the activity of TG-057 was also tested. As shown in FIG. 20, TG-057 also has the effect of inhibiting cerebral infarction in the rats at the same dosage (5 mg/kg) as that of TG-028. Longa nerve scoring results show that TG-057 has a protective effect on nerves in rats after brain injury, but the effect is not as strong as that of TG-028.

Figure 6:
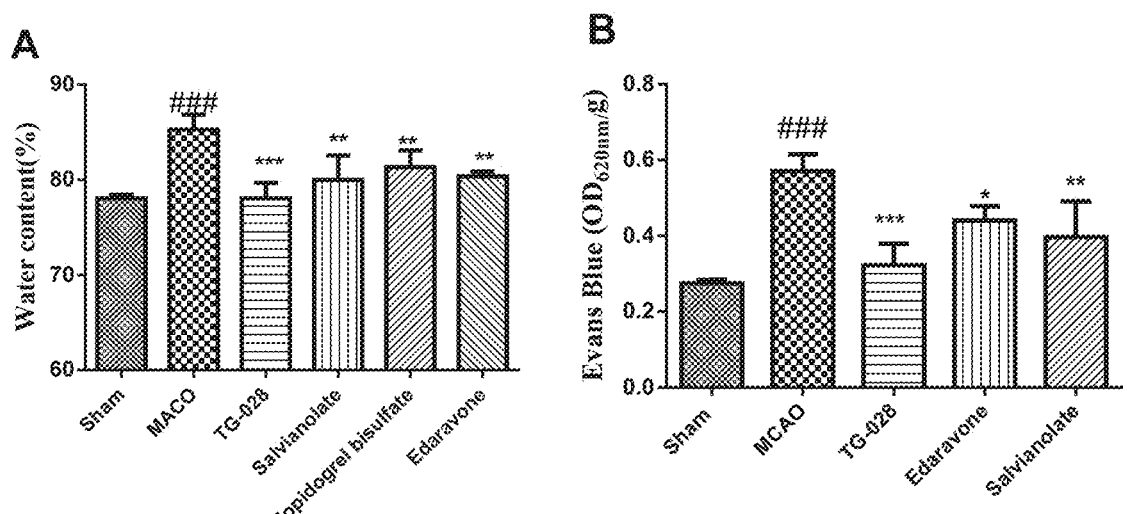
FIG. 6 shows the water content in brain and integrity of blood-brain barrier determined in the presence of different drugs in an acute cerebral infarction model of MCAO.

Three days after the acute cerebral infarction model of MCAO was established in rats, the intact brain tissue was taken out, olfactory bulb and the brain tissue that is 4 mm in front of the frontal pole was removed, and the immediately adjacent brain tissue of 2 mm thick was taken for water content measurement in the brain. The results are shown in FIG. 6A. The water content in brain tissue is calculated by the formula: (WW−DW)/WW×100%, where WW is the wet weight and DW is the dry weight. Three days after the acute cerebral infarction model of MCAO was established in rats, the brain tissue was stained with Evans Blue (EB, a commonly used azo dye preparation) to evaluate the permeability across the blood-brain barrier (BBB), so as to evaluate the integrity of blood-brain barrier. The results are shown in FIG. 6B. Both experiments were tested with the optimal dose of each drug previously determined: TG-028 (5 mg/Kg), Salvianolate (20 mg/Kg), Clopidogrel bisulfate (40 mg/Kg), Edaravone (40 mg/Kg).

FIG. 6A (where Sham is a sham operation group) shows that TG-028 has a better effect on reducing cerebral edema after acute brain injury of MCAO in rats than Edaravone, Clopidogrel bisulfate, and Salvianolate. FIG. 6B shows that TG-028 has a better protective effect on blood-brain barrier after acute brain injury of MCAO in rats than Edaravone and Salvianolate.

In the later period of the present invention, a chronic cerebral ischemia model was established in rats with permanent ligation of bilateral common carotid arteries (2VO). TG-028 (5 mg/kg) was administered to 5 rats in each group daily by intraperitoneal injection for 3 weeks. The effects of TG-028 and the control drug Edaravone (40 mg/kg) in the rat model of chronic cerebral ischemia were observed.

Figure 7:
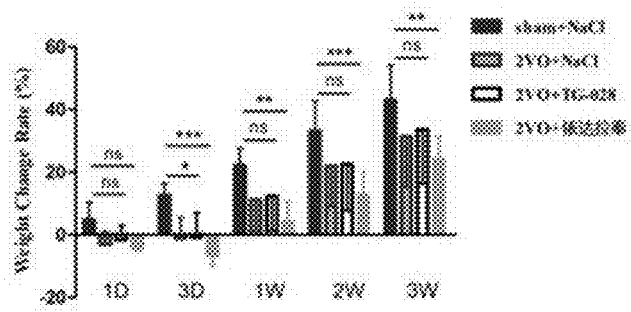
FIG. 7 shows the rates of body weight change in the presence of different drugs in a chronic cerebral ischemia model in rats with 2VO.

The changes in the body weight of the rats within 3 weeks are shown in FIG. 7 (where Sham is a sham operation group). 3 days after chronic ischemic brain injury in rats, the treatment groups with TG-028 and Edaravone both have weight loss compared with the sham operation group. However, after 1 week, there is no difference in weight change between the treatment group with TG-028 and the sham operation group, indicating that TG-028 had a protective effect on body weight. The Edaravone group has no significant weight increase compared with the sham operation group, so the protective effect on body weight is low.

Figure 8:
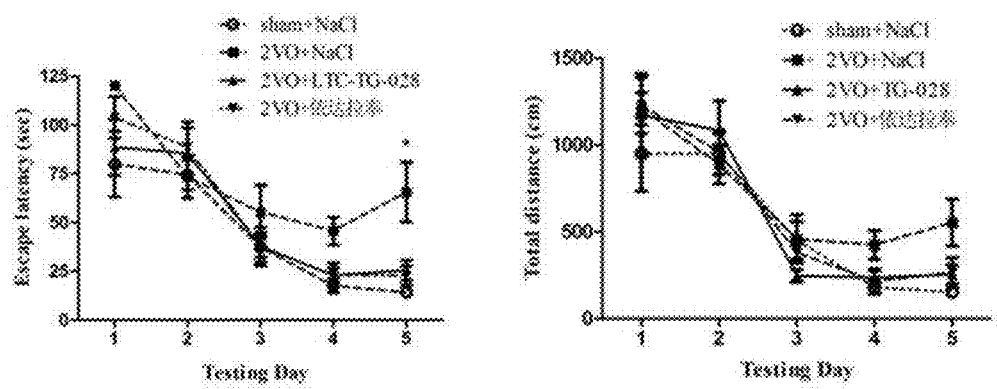
FIG. 8 shows the results of the Morris water maze positioning and navigation experiment with different drugs in a chronic cerebral ischemia model in rats with 2VO.

3 weeks after the establishment of the rat model of 2VO chronic cerebral ischemia, the Morris water maze experiment was performed on the test rats to determine the effects of drugs on animal learning and memory. The test rats were subjected to ambient positioning and memory training for 5 days. On Day 5 of the training, a positioning navigation experiment was carried out, and the duration for each group of rats from the time of entering the water from different water entry points facing the pool wall to the time of finding the platform, that is, the escape incubation period, was recorded. On Day 6, the platform was removed and a space exploration experiment was carried out. The swimming time of the rats in the target quadrant, the dwell time in the target quadrant, the distance in the target quadrant, and the number of passes through the platform were recorded in 120 s from the time of entering water from a quadrant opposing the target quadrant. The results of the water maze positioning and navigation experiment are shown in FIG. 8 (where Sham is a sham operation group). The results of the Morris water maze positioning and navigation experiment after 3 weeks of administration in rats with 2VO chronic cerebral ischemia show that after training, the duration of the escape incubation period and the total distance traveled by the rats in the 2VO+TG-028 group and the 2VO+Edaravone group are different from those of the 2VO+NaCl group on Day 3 of the experiment, and the highest difference is exhibited on Day 5. Compared with the Edaravone group, the TG-028 group has a comparable effect, indicating that the memory ability and cognitive ability of the rats were improved.

After permanent ligation of the bilateral common carotid arteries, a 5-day positioning training was carried out, and three weeks of Morris water maze space exploration experiment was performed after the training.

Figure 9:
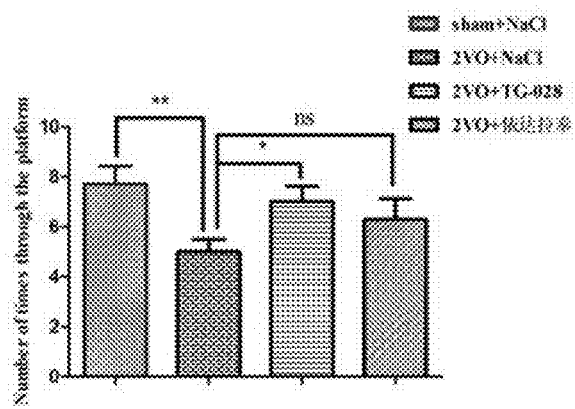
FIG. 9 shows the results of the Morris water maze space exploration experiment with different drugs in a chronic cerebral ischemia model in rats with 2VO.

The results are shown in FIG. 9 (where Sham is a sham operation group). Compared with the 2VO+NaCl group, the number of passes through the platform of the 2VO+TG-028 group increases significantly, but the 2VO+Edaravone group has no significant difference, indicating that after the administration, the rats in the 2VO+TG-028 group have enhanced ability to explore the space and has improved cognitive ability. Data were Mean±SEM (n=7).**P<0.01, *P<0.05, ns: No Significant Different.

Figure 10:
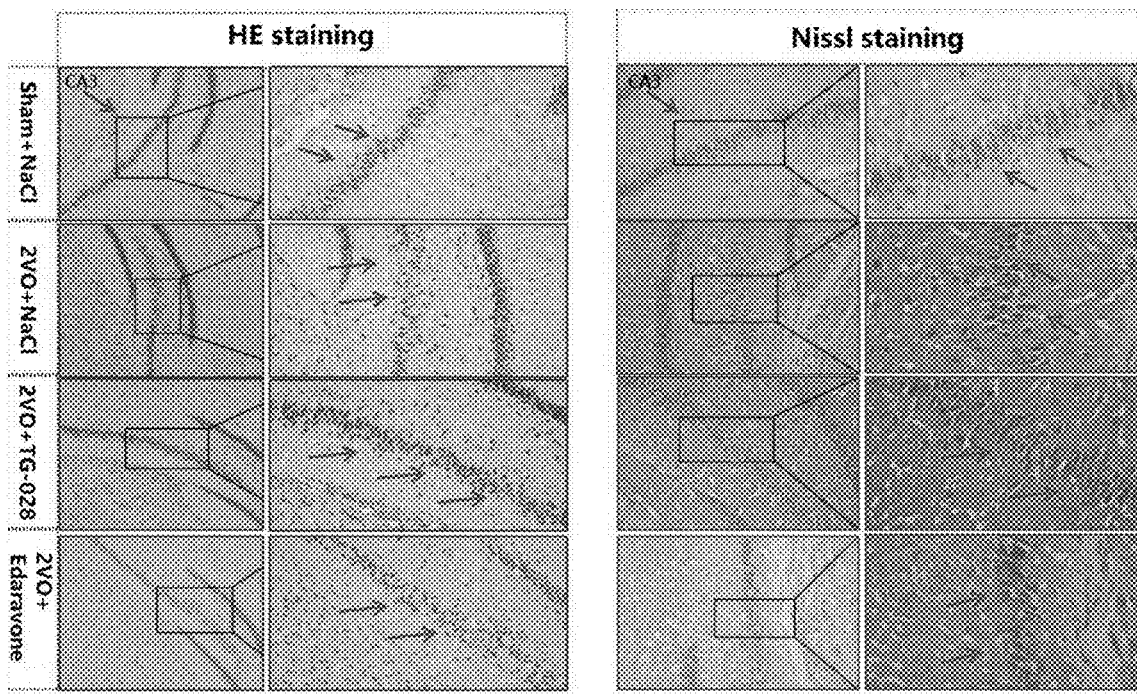
FIG. 10 shows the results of HE staining and Nissl staining of brain sections after chronic cerebral ischemia.

The results of HE staining (hematoxylin-eosin staining) and Nissl staining of brain sections 3 weeks after chronic cerebral ischemia are shown in FIG. 10 (where Sham is a sham operation group). The results show that compared with the 2VO+NaCl group, the neurons in the rat hippocampal CA3 area in the 2VO+TG-028 group are neatly and densely arranged, and the granules have uniform size and are sharp; and the cell morphology in the 2VO+Edaravone group is also improved. It indicates that TG-028 and Edaravone both have protection and can repair damaged neurons to improve the nerve function.

In addition, an acute toxicity test of TG-028 was conducted. The LD50 is measured to be 616.59 mg/kg, and the therapeutic index LD50/ED50=616.59/2.61=236, which indicates that TG-028 has a large treatment window and good safety.

Figure 11:
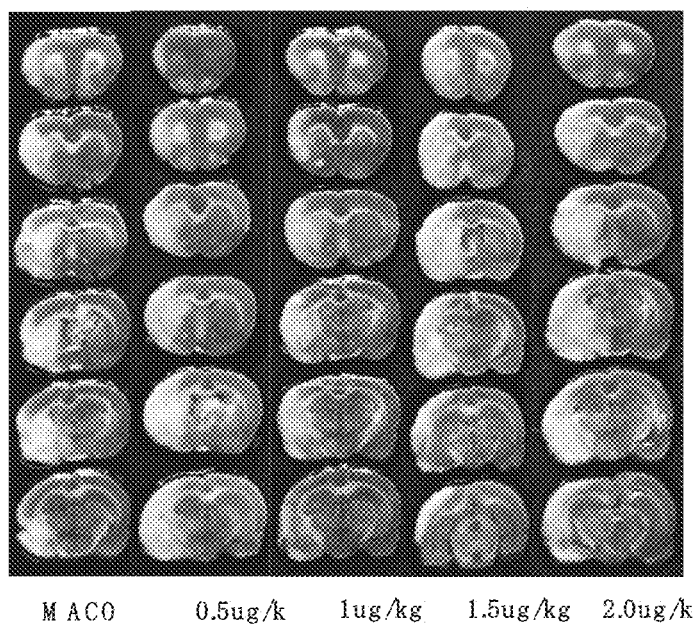
FIG. 11 shows the result of TTC staining showing the inhibitory effect of VEGF protein on cerebral infarction 3 days after administration in an acute cerebral infarction model of MCAO.
Figure 12:
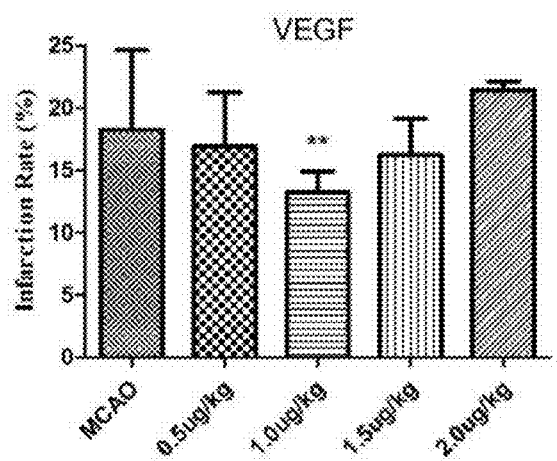
FIG. 12 shows the infarction rate in the presence of VEGF protein in an acute cerebral infarction model of MCAO.
Figure 13:
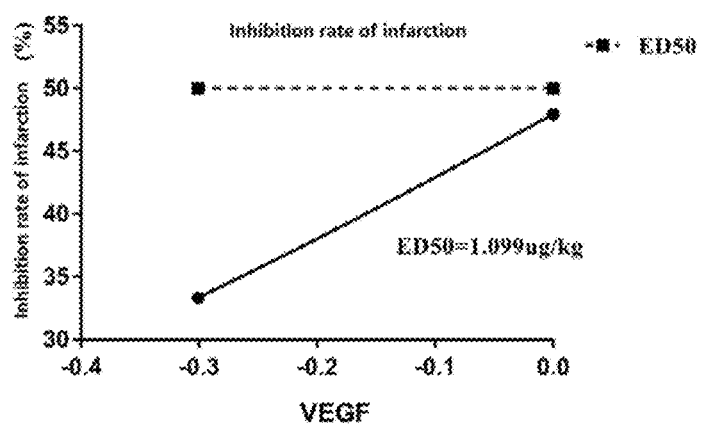
FIG. 13 shows the infarction inhibition rate of VEGF protein in an acute cerebral infarction model of MCAO.

Finally, Recombinant Human VEGF165 protein (PEPROTECH, USA) was also directly used in a rat model of middle cerebral artery occlusion (MCAO), and the inhibitory effect on cerebral infarction was observed after 3 days. The preparation method of the rat model of MCAO, animals used in related experiments and the experimental procedures are the same as described above. The specific dosage and TTC staining results are shown in FIG. 11. The related results of infarction rate and infarction inhibition rate are shown in FIGS. 12 and 13. The results show that VEGF can inhibit cerebral infarction in rats, which directly proves that VEGF is an important factor for promoting angiogenesis after cerebral ischemia.

Effect Example 4: After Acting on Macrophages, TG-028 can Promote the Proliferation, Migration and Tubule Formation of Endothelial Cells, Thus Affecting the Formation of New Blood Vessels In addition, it was further confirmed through in-vitro cell experiment that after acting on macrophages, TG-028 can promote the proliferation, migration and tubule formation of endothelial cells, thus affecting the formation of new blood vessels The experiment included seven groups. In Group 1, HUVEC-12 endothelial cells (purchased from Shanghai RongChuang Biotech Co., Ltd.) were treated directly with simple DMEM medium (Gibcol, Shanghai) containing 10% FBS (SERANA, Germany) (control). In Group 2, the endothelial cells were treated with the supernatant obtained 24 h after macrophages were cultured with DMEM medium containing 10% FBS (s-control). In Group 3, the endothelial cells cultured with DMEM medium containing 10% FBS were treated directly with TG-028 (TG-028, 10 μM). In Group 4, the endothelial cells were treated with the supernatant obtained after macrophages cultured with DMEM medium containing 10% FBS were treated and co-incubated with TG-028 for 24 h (s-TG-028, 10 M). In Group 5, the endothelial cells cultured with DMEM medium containing 10% FBS were treated directly with Cpd-18 (Salvianolate) (cpd-18, 10 μM). In Group 6, the endothelial cells were treated with the supernatant obtained after macrophages cultured with DMEM medium containing 10% FBS were treated and co-incubated with Cpd-18 (Salvianolate, 10 μM) for 24 h (s-cpd18). In Group 7, the endothelial cells cultured with DMEM medium containing 10% FBS were treated directly with VEGFD (Recombinant Human VEGF165, 10 ng/mL).

Figure 14:
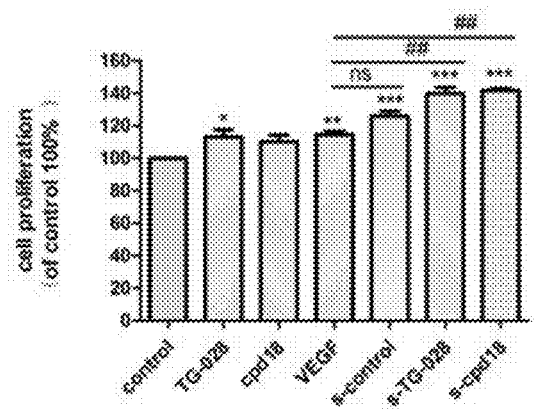
FIG. 14 shows the effect of each group of samples on the proliferation of HUVEC-12 cells in Effect Example 4.

(1) Effect of Supernatant Obtained 24 h after Macrophages were Treated with TG-028 on Proliferation of Endothelial Cells Human umbilical vein endothelial cells HUVEC-12 in logarithmic growth phase were counted, adjusted to a cell density of $2.5 \times 10^4$ cells/mL, and inoculated in 100 μL per well in a 96-well plate. The cells were cultured in an incubator overnight until the cells were completely adhered to the wall. Based the above different groups, HUVEC-12 endothelial cells were treated, and the 96-well plate was incubated for 24 h in an incubator at 37° C. and 5% CO2. The 96-well plate was removed, and 20 L/well of 5 mg/mL MTT was added and cultured for another 4 h. After 4 h, the supernatant was discarded, and 150 μL/well of DMSO was added, and shaken for 10 min on a shaker to fully dissolve the purple crystals. The OD value at a wavelength of 570 nm was measured on an ELISA Reader (Microplate Reader, Thermo Fisher) 10 min after dissolution in DMSO. Based on the measured absorbance (OD), the HUVEC-12 endothelial cells treated directly with simple DMEM medium (control) were used as a blank control (Group 1), the percentage of cell proliferation in each group was calculated, and compared. As can be seen from the results, except that the direct treatment of endothelial cells with Cpd-18 (Salvianolate, 10 μM) (i.e. Group 5) shows no significant promotion on the proliferation of endothelial cells, the other groups all have significant promotion on the proliferation of endothelial cells. The treatment of endothelial cells with the supernatant obtained after macrophages were treated and co-incubated with TG-028 for 24 h (s-TG-028, 10 μM) (i.e. Group 4) and the treatment of endothelial cells with the supernatant obtained after macrophages were treated and co-incubated with Cpd-18 (Salvianolate, 10 μM) (i.e. Group 6) both have a more potent promotion on the proliferation of endothelial cells than the direct treatment of endothelial cells with VEGF (i.e. Group 7), and there is significant difference (##$P<0.01$). The treatment of endothelial cells with the supernatant obtained after macrophages were cultured for 24 hrs (s-control) (i.e. Group 2) has no significant (ns) promotion on the proliferation of endothelial cells compared with the direct treatment of endothelial cells with VEGF (i.e. Group 7). These indicate that TG-028 and Cpd-18 (Salvianolate) can promote the proliferation of endothelial cells by acting on macrophages, which is different from the direct effect of VEGF on the proliferation of endothelial cells, as shown in FIG. 14.

(2) Effect of Supernatant Obtained 24 h after Macrophages were Treated with TG-028 on Migration of Endothelial Cells Human umbilical vein endothelial cells HUVEC-12 in logarithmic growth phase were counted, adjusted to a cell density of $5\times10^5$ cells/mL, and inoculated in 1 mL per well in a 6-well plate. The cells were conventionally cultured in an incubator to to form monolayer cells of 90% confluency. The 6-well plate fully plated with cells was scratched perpendicular to the cell surface with a 200 μL pipette tip from one end to the other end of the well. The scratches were made transversely with the pipette tip being as perpendicular as possible to the bottom of the plate. In this case, cross scratches on the cell surface can be clearly seen from the surface of the cell culture plate.

Figure 15:
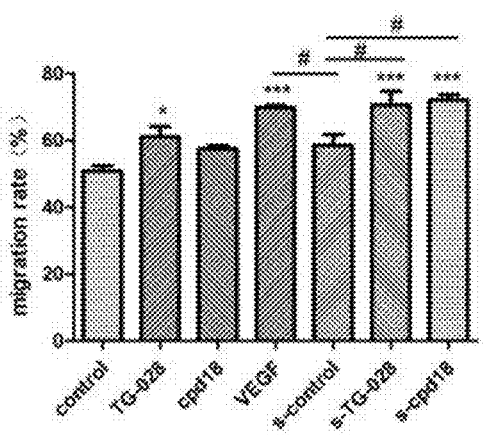
FIG. 15 shows the effect of each group of samples on the migration of HUVEC-12 cells in Effect Example 4.
Figure 16:
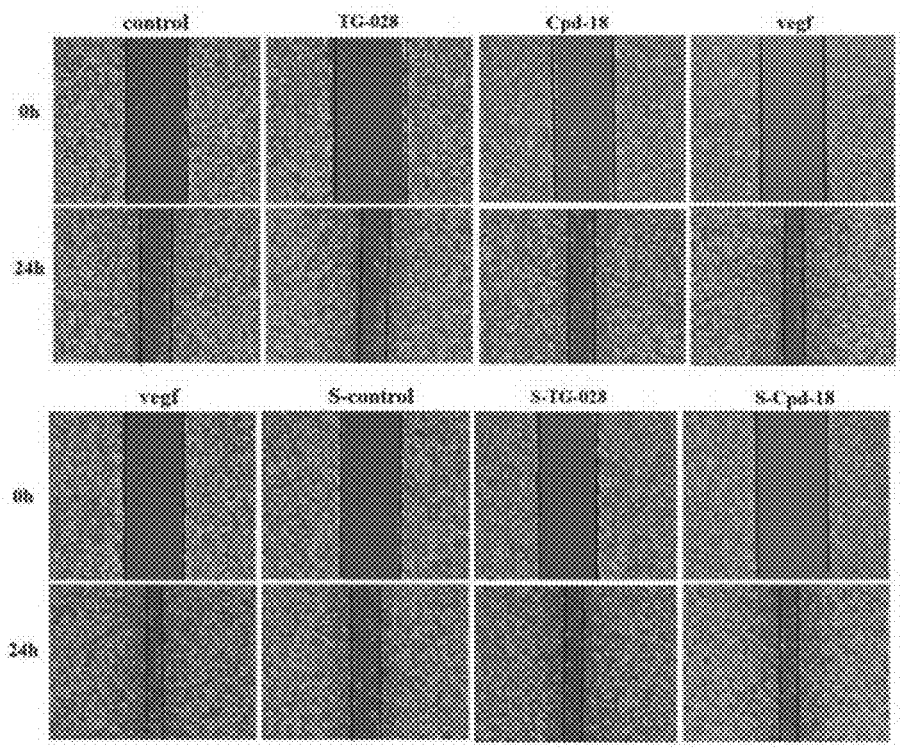
FIG. 16 shows the scratch test results of each group of samples in Effect Example 4.

The medium was aspirated and the cells scratched off were washed off with PBS. Similarly, based on the above seven groups, the HUVEC-12 cells cultured were treated. Each group had two replicate wells, and the cells were cultured in an incubator at 37° C., and 5% $CO_2$. Samples were taken at 0 h and 24 h, and photographed to observe the width of scratches in different treatment groups. The migration of endothelial cells was detected according to the cell scratch method and the relative migration rate was calculated. Relative migration rate=(scratch width at 0 h−scratch width at 24 h)/scratch width at 0 h. The results of the scratch experiment are shown in FIGS. 15 and 16.

Compared with the group where HUVEC-12 endothelial cells were treated directly with simple DMEM medium (control) (i.e. Group 1), the TG-028 group (i.e. Group 3), VEGF group (i.e. Group 7), s-TG-028 group (i.e. Group 4), and s-cpd18 group (i.e. Group 6) have significant effect on the migration of endothelial cells in 24 h (*$P<0.05$, ***$P<0.001$), and s-TG-028 and s-cpd18 have comparable effect on the migration of endothelial cells as VEGF. Compared with the group where endothelial cells were treated with the supernatant obtained 24 h after the macrophages were cultured (s-control) (i.e. Group 2), the VEGF group, s-TG-028 group, and s-cpd18 group have better effect on the migration of endothelial cells than s-control group, indicating that Compound TG-028 and Salvianolate can promote the migration of endothelial cells by acting on macrophages.

Figure 17:
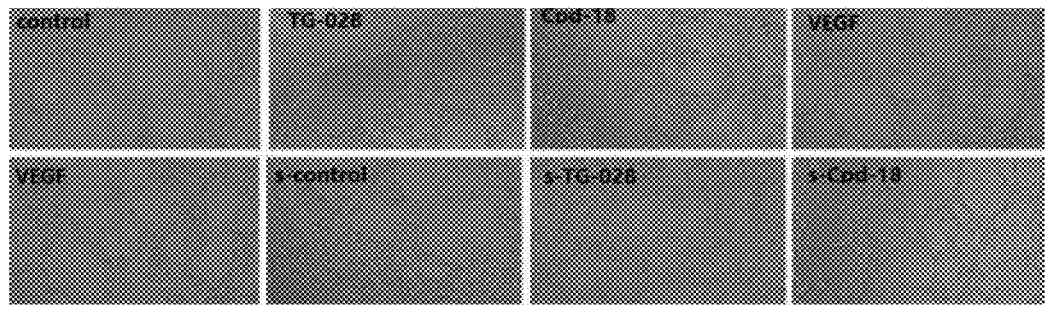
FIG. 17 is an inverted micrograph showing the effect of each group of samples on the tubule formation of HUVEC-12 cells in Effect Example 4.
Figure 18:
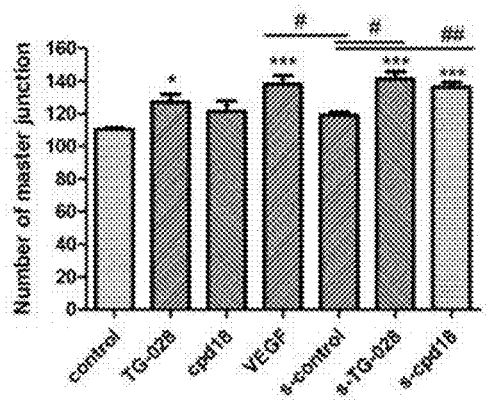
FIG. 18 shows the effect of each group of samples on the tubule formation of HUVEC-12 cells in Effect Example 4.

(3) Effect of Supernatant Obtained 24 h after Macrophages were Treated with TG-028 on Tubule Formation of Endothelial Cells A 96-well plate and sterile yellow pipette tip were stored overnight in a refrigerator at −20° C. The packed Matrigel was thawed overnight in a refrigerator at 4° C. before the experiment. On the following day, the Matrigel thawed was centrifuged for a few minutes. 60 μL per well of the pre-cooled Matrigel was added to a 96-well plate in an ice bath on a ultra-clean bench, and then allowed to stand in an incubator for 1 h. After Matrigel was solidified, HUVEC-12 cells in logarithmic growth phase were taken and adjusted for the cell density. The cells were well mixed with each group of medium at a density of $5\times10^4$ cells/well and inoculated into a 96-well plate. The plate was incubated for 3 h in an incubator at 37° C. and 5% $CO_2$. Then the cell culture plate was removed and observed and photographed successively under an inverted microscope (magnification 50×, Leica DMi inverted microscope). 5 fields of view per well were selected at random to take pictures to observe the tube-like structure formed by attachment between the cells. The tube-like structure was analyzed by ImageJ image-analysis software, and the tube formation ability was evaluated using number of master junction as a quantitative index. The results are shown in FIGS. 17 and 18.

In the tube formation experiment, compared with the group where HUVEC-12 endothelial cells were treated directly with simple DMEM medium (control), the TG-028 group, VEGF group, s-TG-028 group, and s-cpd18 group have significant effect on the tube formation of endothelial cells (*$P<0.05$, ***$P<0.001$), and s-TG-028 and s-cpd18 have comparable effect on the tube formation of endothelial cells as VEGF. In the group where endothelial cells were treated with simply the supernatant obtained 24 h after the macrophages were cultured (s-control), no effect on tube formation of endothelial cells is exhibited. However, in the s-TG-028, and s-cpd18 groups where the drug TG-028 or Salvianolate is added, the tube formation activity of endothelial cells is greatly improved, indicating that Compound TG-028 and Salvianolate can promote the tube formation of endothelial cells by activation by macrophages.

Therefore, Compound TG-028 screened by the activity screening method of the present invention can promote the proliferation, migration and tubule formation of endothelial cells by acting on macrophages, thus affecting the formation of new blood vessels.

As can be seen from the results of the above effect examples, preliminary target angiogenic active compounds are screened out from a large number of compounds to be tested by the in vitro macrophage experiment in the present invention, which are shown to have good angiogenic activity in subsequent semi-in vivo animal screening models. Among them, Compound TG-028 is even better in activity than Salvianolate. That is, the present invention can screen out the target angiogenic active compounds at the molecular level, and further subsequent in-vivo experiments in animal models have verified the accuracy and stability of the activity screening method of the present invention. In addition, it is confirmed that Compound TG-028 promotes the proliferation, migration, and tubule formation of endothelial cells mainly by acting on macrophages, thus affecting the formation of new blood vessels. This principally demonstrates in turn the reliability of in-vitro macrophage experiment and sponge implanted animal model in the detection of VEGF-A mRNA as a screening model for angiogenic active compounds. The compounds screened according to the activity screening method of the present invention are the expected compounds, which can achieve the effects of promoting angiogenesis to inhibit cerebral infarction, neuroprotection, reducing brain edema, protecting the integrity of the blood-brain barrier after injury, protecting body weight after brain injury, improving the memory function of rats, protecting and repairing damaged neurons to promote the improvement of nerve function.

What is claimed is:

1. A glycoside compound represented by Formula III below:

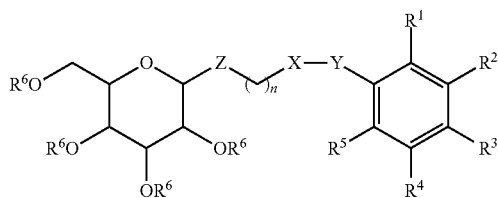

III wherein $R^1$, $R^2$, $R^4$ and $R^5$ are each independently selected from the group consisting of hydrogen, hydroxyl, mercapto, a substituted or unsubstituted $C_1$-$C_{20}$ alkoxy group, nitro or halo;
$R^3$ is selected from the group consisting of hydrogen, mercapto, a substituted or unsubstituted $C_1$-$C_{20}$ alkoxy group, nitro or halo;
or $R^2$ and $R^3$ form, together with carbon atoms on the phenyl ring to which they are attached, a 6-membered heterocyclic ring having a heteroatom that is O or S;
where the substituent in the substituted or unsubstituted $C_1$-$C_{20}$ alkoxy group is selected from the group consisting of a $C_3$-$C_{20}$ cycloalkyl group, a $C_1$-$C_{20}$ alkenyl group, a substituted or unsubstituted $C_6$-$C_{20}$ aryl group, halo, a substituted or unsubstituted $C_2$-$C_{20}$ heteroaryl group, a $C_3$-$C_6$ cycloalkoxy group, a $C_1$-$C_{20}$ alkoxy group, and a $C_1$-$C_{20}$ alkyl group, in which the substituent in the substituted or unsubstituted $C_6$-$C_{20}$ aryl group and the substituted or unsubstituted $C_2$-$C_{20}$ heteroaryl group is each independently halo or a halo-substituted $C_1$-$C_{20}$ alkyl group;
X is $CH_2$;
Y is $CH_2$;
Z is O or S;
each $R^6$ is independently hydrogen or glycosyl; and
n is 2, 3 or 4,
with the provision that:
when X is $CH_2$, Y is $CH_2$, and n=2, 3 or 4, $R^1$-$R^5$ are not all H;
when n=2, $R^1$, $R^4$ and $R^5$ are H, $R^2$ and $R^3$ are not both $OCH_3$ and OH;
when n=2, $R^1$, $R^2$ and $R^5$ are H, $R^3$ and $R^4$ are not both OH and $OCH_3$;
when n=2, $R^2$, $R^4$ and $R^5$ are H, $R^1$ and $R^3$ are not both OH; and
when n=2, $R^1$, $R^2$ and $R^4$ are H, $R^3$ and $R^5$ are not both OH.

2. A glycoside compound represented by Formula I below:

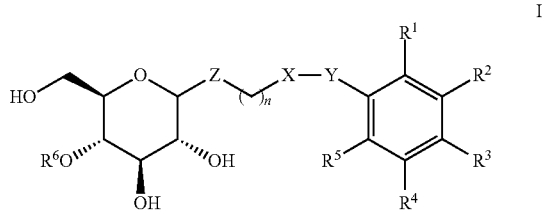

I wherein $R^1$, $R^2$, $R^4$ and $R^5$ are each independently selected from the group consisting of hydrogen, hydroxyl, mercapto, a substituted or unsubstituted $C_1$-$C_{20}$ alkoxy group, nitro or halo;
$R^3$ is selected from the group consisting of hydrogen, mercapto, a substituted or unsubstituted $C_1$-$C_{20}$ alkoxy group, nitro or halo;
or $R^2$ and $R^3$ form, together with carbon atoms on the phenyl ring to which they are attached, a 6-membered heterocyclic ring having a heteroatom that is O or S;
where the substituent in the substituted or unsubstituted $C_1$-$C_{20}$ alkoxy group is selected from the group consisting of a $C_3$-$C_{20}$ cycloalkyl group, a $C_1$-$C_{20}$ alkenyl group, a substituted or unsubstituted $C_6$-$C_{20}$ aryl group, halo, a substituted or unsubstituted $C_2$-$C_{20}$ heteroaryl group, a $C_3$-$C_6$ cycloalkoxy group, a $C_1$-$C_{20}$ alkoxy group, and a $C_1$-$C_{20}$ alkyl group,
in which the substituent in the substituted or unsubstituted $C_6$-$C_{20}$ aryl group and the substituted or unsubstituted $C_2$-$C_{20}$ heteroaryl group is each independently halo or a halo-substituted $C_1$-$C_{20}$ alkyl group;
X is $CH_2$;
Y is $CH_2$;
Z is O or S;
$R^6$ is hydrogen or

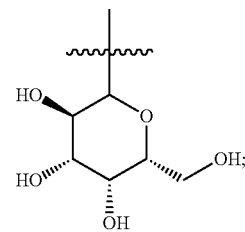

n is 2, 3 or 4,
with the provision that:
when X is $CH_2$, Y is $CH_2$, and n=2, 3 or 4, $R^1$-$R^5$ are not all H;
when n=2, $R^1$, $R^4$ and $R^5$ are H, $R^2$ and $R^3$ are not both $OCH_3$ and OH; and
when n=2, $R^1$, $R^2$ and $R^5$ are H, $R^3$ and $R^4$ are not both OH and $OCH_3$.

3. The glycoside compound according to claim 1, wherein when $R^1$, $R^2$, $R^3$, $R^4$ and $R^5$ are each independently a substituted or unsubstituted $C_1$-$C_{20}$ alkoxy group, the substituted or unsubstituted $C_1$-$C_{20}$ alkoxy group is a substituted or unsubstituted $C_1$-$C_{10}$ alkoxy group;
and/or when $R^1$, $R^2$, $R^3$, $R^4$ and $R^5$ are each independently halo, the halo is fluoro, chloro, bromo, or iodo;

and/or when $R^1$, $R^2$, $R^3$, $R^4$ and $R^5$ are each independently a substituted or unsubstituted $C_1$-$C_{20}$ alkoxy group, and the substituent in the substituted or unsubstituted $C_1$-$C_{20}$ alkoxy group is a $C_3$-$C_{20}$ cycloalkyl group, the $C_3$-$C_{20}$ cycloalkyl group is a $C_3$-$C_{10}$ cycloalkyl group;

and/or when $R^1$, $R^2$, $R^3$, $R^4$ and $R^5$ are each independently a substituted or unsubstituted $C_1$-$C_{20}$ alkoxy group, and the substituent in the substituted or unsubstituted $C_1$-$C_{20}$ alkoxy group is a $C_1$-$C_{20}$ alkenyl group, the $C_1$-$C_{ao}$ alkenyl group is a $C_1$-$C_6$ alkenyl group;

and/or when $R^1$, $R^2$, $R^3$, $R^4$ and $R^5$ are each independently a substituted or unsubstituted $C_1$-$C_{20}$ alkoxy group, and the substituent in the substituted or unsubstituted $C_1$-$C_{20}$ alkoxy group is a substituted or unsubstituted $C_6$-$C_{20}$ aryl group, the substituted or unsubstituted $C_6$-$C_{20}$ aryl group is a substituted or unsubstituted $C_6$-$C_{10}$ aryl group;

and/or when $R^1$, $R^2$, $R^3$, $R^4$ and $R^5$ are each independently a substituted or unsubstituted $C_1$-$C_{20}$ alkoxy group, and the substituent in the substituted or unsubstituted $C_1$-$C_{20}$ alkoxy group is halo, the halo is one or more selected from fluoro, chloro, bromo, and iodo;

and/or when $R^1$, $R^2$, $R^3$, $R^4$ and $R^5$ are each independently a substituted or unsubstituted $C_1$-$C_{20}$ alkoxy group, and the substituent in the substituted or unsubstituted $C_1$-$C_{20}$ alkoxy group is a substituted or unsubstituted $C_2$-$C_{20}$ heteroaryl group, the substituted or unsubstituted $C_2$-$C_{20}$ heteroaryl group is a substituted or unsubstituted $C_2$-$C_{10}$ heteroaryl group;

and/or when $R^1$, $R^2$, $R^3$, $R^4$ and $R^5$ are each independently a substituted or unsubstituted $C_1$-$C_{20}$ alkoxy group, and the substituent in the substituted or unsubstituted $C_1$-$C_{20}$ alkoxy group is a $C_1$-$C_{20}$ alkoxy group, the $C_1$-$C_{20}$ alkoxy group is a $C_1$-$C_{10}$ alkoxy group;

and/or when $R^1$, $R^2$, $R^3$, $R^4$ and $R^5$ are each independently a substituted or unsubstituted $C_1$-$C_{20}$ alkoxy group, and the substituent in the substituted or unsubstituted $C_1$-$C_{20}$ alkoxy group is a $C_1$-$C_{20}$ alkyl group, the $C_1$-$C_{20}$ alkyl group is a $C_1$-$C_{10}$ alkyl group;

and/or when $R^1$, $R^2$, $R^3$, $R^4$ and $R^5$ are each independently a substituted or unsubstituted $C_1$-$C_{20}$ alkoxy group, the substituent in the substituted or unsubstituted $C_1$-$C_{20}$ alkoxy group is a substituted or unsubstituted $C_6$-$C_{20}$ aryl group, and the substituent in the substituted or unsubstituted $C_6$-$C_{20}$ aryl group is halo or a halo-substituted $C_1$-$C_{20}$ alkyl group, the halo is fluoro, chloro, bromo or iodo;

and/or when $R^1$, $R^2$, $R^3$, $R^4$ and $R^5$ are each independently a substituted or unsubstituted $C_1$-$C_{20}$ alkoxy group, the substituent in the substituted or unsubstituted $C_1$-$C_{20}$ alkoxy group is a substituted or unsubstituted $C_2$-$C_{20}$ heteroaryl group, and the substituent in the substituted or unsubstituted $C_2$-$C_{20}$ heteroaryl group is halo or a halo-substituted $C_1$-$C_{20}$ alkyl group, the halo is fluoro, chloro, bromo or iodo;

and/or when $R^1$, $R^2$, $R^3$, $R^4$ and $R^5$ are each independently a substituted or unsubstituted $C_1$-$C_{20}$ alkoxy group, the substituent in the substituted or unsubstituted $C_1$-$C_{20}$ alkoxy group is a substituted or unsubstituted $C_6$-$C_{20}$ aryl group, and the substituent in the substituted or unsubstituted $C_6$-$C_{20}$ aryl group is a halo-substituted $C_1$-$C_{20}$ alkyl group, the halo-substituted $C_1$-$C_{20}$ alkyl group is a halo-substituted $C_1$-$C_{10}$ alkyl group;

and/or when $R^1$, $R^2$, $R^3$, $R^4$ and $R^5$ are each independently a substituted or unsubstituted $C_1$-$C_{20}$ alkoxy group, the substituent in the substituted or unsubstituted $C_1$-$C_{20}$ alkoxy group is a substituted or unsubstituted $C_2$-$C_{20}$ heteroaryl group, and the substituent in the substituted or unsubstituted $C_2$-$C_{20}$ heteroaryl group is a halo-substituted $C_1$-$C_{20}$ alkyl group, the halo-substituted $C_1$-$C_{20}$ alkyl group is a halo-substituted $C_1$-$C_{10}$ alkyl group;

and/or when $R^1$, $R^2$, $R^3$, $R^4$ and $R^5$ are each independently selected from hydrogen, hydroxyl, mercapto, a substituted or unsubstituted $C_1$-$C_{20}$ alkoxy group, nitro or halo, one substituted or unsubstituted $C_1$-$C_{20}$ alkoxy group is present;

and/or the optical isomer of

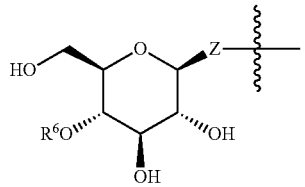

in the compound represented by Formula I is:

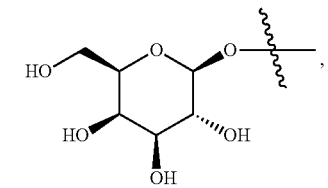,

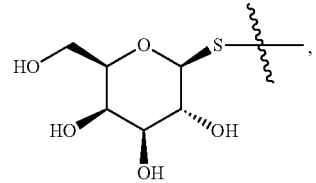,

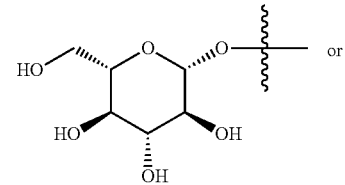 or

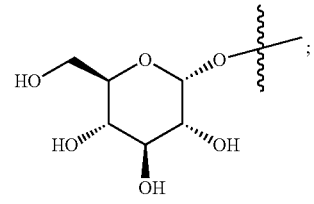;

and/or $R^1$, $R^2$, $R^3$, $R^4$ and $R^5$ are each independently selected from the group consisting of hydrogen, a substituted or unsubstituted $C_1$-$C_{20}$ alkoxy group, nitro and halo.

4. The glycoside compound according to claim 1, wherein when $R^1$, $R^2$, $R^3$, $R^4$ and $R^5$ are each independently a substituted or unsubstituted $C_1$-$C_{20}$ alkoxy group, the substituted or unsubstituted $C_1$-$C_{20}$ alkoxy group is a substituted or unsubstituted $C_1$-$C_6$ alkoxy group;

and/or when $R^1$, $R^2$, $R^3$, $R^4$ and $R^5$ are each independently halo, the halo is fluoro, chloro, or bromo;

and/or when $R^1$, $R^2$, $R^3$, $R^4$ and $R^5$ are each independently a substituted or unsubstituted $C_1$-$C_{20}$ alkoxy group, and the substituent in the substituted or unsubstituted $C_1$-$C_{20}$ alkoxy group is a $C_3$-$C_{20}$ cycloalkyl group, the $C_3$-$C_{20}$ cycloalkyl group is a $C_3$-$C_6$ cycloalkyl group;

and/or when $R^1$, $R^2$, $R^3$, $R^4$ and $R^5$ are each independently a substituted or unsubstituted $C_1$-$C_{20}$ alkoxy group, and the substituent in the substituted or unsubstituted $C_1$-$C_{20}$ alkoxy group is a $C_1$-$C_{20}$ alkenyl group, the $C_1$-$C_{20}$ alkenyl group is a $C_1$-$C_4$ alkenyl group;

and/or when $R^1$, $R^2$, $R^3$, $R^4$ and $R^5$ are each independently a substituted or unsubstituted $C_1$-$C_{20}$ alkoxy group, and the substituent in the substituted or unsubstituted $C_1$-$C_{20}$ alkoxy group is a substituted or unsubstituted $C_6$-$C_{20}$ aryl group, the substituted or unsubstituted $C_6$-$C_{20}$ aryl group is a substituted or unsubstituted aryl group or naphthyl;

and/or when $R^1$, $R^2$, $R^3$, $R^4$ and $R^5$ are each independently a substituted or unsubstituted $C_1$-$C_{20}$ alkoxy group, and the substituent in the substituted or unsubstituted $C_1$-$C_{20}$ alkoxy group is halo, the halo is one or more selected from fluoro, chloro, or bromo;

and/or when $R^1$, $R^2$, $R^3$, $R^4$ and $R^5$ are each independently a substituted or unsubstituted $C_1$-$C_{20}$ alkoxy group, and the substituent in the substituted or unsubstituted $C_1$-$C_{20}$ alkoxy group is a substituted or unsubstituted $C_2$-$C_{20}$ heteroaryl group, the substituted or unsubstituted $C_2$-$C_{20}$ heteroaryl group is a substituted or unsubstituted $C_2$-$C_6$ heteroaryl group;

and/or when $R^1$, $R^2$, $R^3$, $R^4$ and $R^5$ are each independently a substituted or unsubstituted $C_1$-$C_{20}$ alkoxy group, and the substituent in the substituted or unsubstituted $C_1$-$C_{20}$ alkoxy group is a $C_1$-$C_{20}$ alkoxy group, the $C_1$-$C_{20}$ alkoxy group is a $C_1$-$C_6$ alkoxy group;

and/or when $R^1$, $R^2$, $R^3$, $R^4$ and $R^5$ are each independently a substituted or unsubstituted $C_1$-$C_{20}$ alkoxy group, and the substituent in the substituted or unsubstituted $C_1$-$C_{20}$ alkoxy group is a $C_1$-$C_{20}$ alkyl group, the $C_1$-$C_{20}$ alkyl group is a $C_1$-$C_6$ alkyl group;

and/or when $R^1$, $R^2$, $R^3$, $R^4$ and $R^5$ are each independently a substituted or unsubstituted $C_1$-$C_{20}$ alkoxy group, the substituent in the substituted or unsubstituted $C_1$-$C_{20}$ alkoxy group is a substituted or unsubstituted $C_6$-$C_{20}$ aryl group, and the substituent in the substituted or unsubstituted $C_6$-$C_{20}$ aryl group is halo or a halo-substituted $C_1$-$C_{20}$ alkyl group, the halo is fluoro, chloro, or bromo;

and/or when $R^1$, $R^2$, $R^3$, $R^4$ and $R^5$ are each independently a substituted or unsubstituted $C_1$-$C_{20}$ alkoxy group, the substituent in the substituted or unsubstituted $C_1$-$C_{20}$ alkoxy group is a substituted or unsubstituted $C_2$-$C_{20}$ heteroaryl group, and the substituent in the substituted or unsubstituted $C_2$-$C_{20}$ heteroaryl group is halo or a halo-substituted $C_1$-$C_{20}$ alkyl group, the halo is fluoro, chloro, or bromo;

and/or when $R^1$, $R^2$, $R^3$, $R^4$ and $R^5$ are each independently a substituted or unsubstituted $C_1$-$C_{20}$ alkoxy group, the substituent in the substituted or unsubstituted $C_1$-$C_{20}$ alkoxy group is a substituted or unsubstituted $C_6$-$C_{20}$ aryl group, and the substituent in the substituted or unsubstituted $C_6$-$C_{20}$ aryl group is a halo-substituted $C_1$-$C_{20}$ alkyl group, the halo-substituted $C_1$-$C_{20}$ alkyl group is a halo-substituted $C_1$-$C_6$ alkyl group;

and/or when $R^1$, $R^2$, $R^3$, $R^4$ and $R^5$ are each independently a substituted or unsubstituted $C_1$-$C_{20}$ alkoxy group, the substituent in the substituted or unsubstituted $C_1$-$C_{20}$ alkoxy group is a substituted or unsubstituted $C_2$-$C_{20}$ heteroaryl group, and the substituent in the substituted or unsubstituted $C_2$-$C_{20}$ heteroaryl group is a halo-substituted $C_1$-$C_{20}$ alkyl group, the halo-substituted $C_1$-$C_{20}$ alkyl group is a halo-substituted $C_1$-$C_6$ alkyl group.

5. The glycoside compound according to claim 1, wherein when $R^1$, $R^2$, $R^3$, $R^4$ and $R^5$ are each independently a substituted or unsubstituted $C_1$-$C_{20}$ alkoxy group, the substituted or unsubstituted $C_1$-$C_{20}$ alkoxy group is

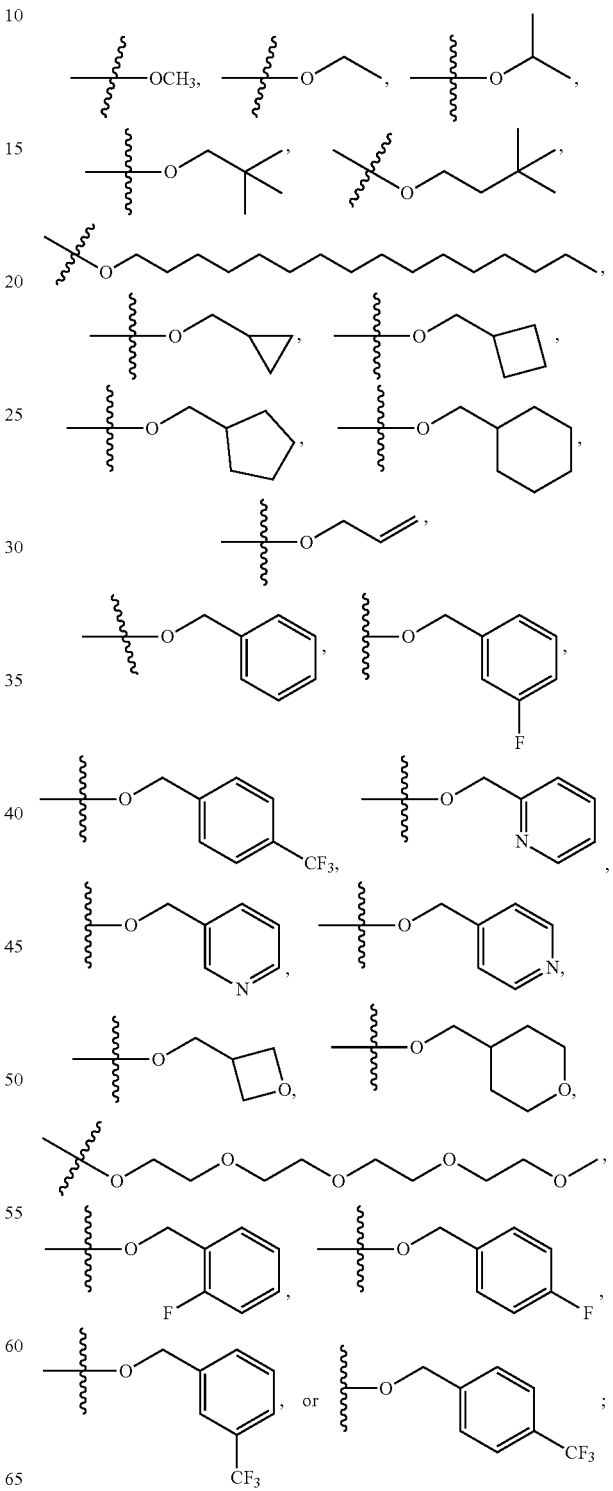

and/or when $R^1$, $R^2$, $R^3$, $R^4$ and $R^5$ are each independently a substituted or unsubstituted $C_1$-$C_{20}$ alkoxy group, and the substituent in the substituted or unsubstituted $C_1$-$C_{20}$ alkoxy group is a $C_3$-$C_{20}$ cycloalkyl group, the $C_3$-$C_{20}$ cycloalkyl group is cyclopropyl, cyclobutyl, cyclopentyl or cyclohexyl;

and/or when $R^1$, $R^2$, $R^3$, $R^4$ and $R^5$ are each independently a substituted or unsubstituted $C_1$-$C_{20}$ alkoxy group, and the substituent in the substituted or unsubstituted $C_1$-$C_{20}$ alkoxy group is a $C_2$-$C_{20}$ alkenyl group, the $C_2$-$C_{20}$ alkenyl group is

;

and/or when $R^1$, $R^2$, $R^3$, $R^4$ and $R^5$ are each independently a substituted or unsubstituted $C_1$-$C_{20}$ alkoxy group, and the substituent in the substituted or unsubstituted $C_1$-$C_{20}$ alkoxy group is a substituted or unsubstituted $C_6$-$C_{20}$ aryl group, the substituted or unsubstituted $C_6$-$C_{20}$ aryl group is

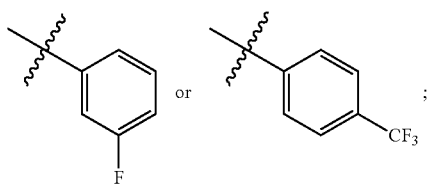 [SMILES: *c1cccc(F)c1 ; *c1ccc(C(F)(F)F)cc1];

and/or when $R^1$, $R^2$, $R^3$, $R^4$ and $R^5$ are each independently a substituted or unsubstituted $C_1$-$C_{20}$ alkoxy group, and the substituent in the substituted or unsubstituted $C_1$-$C_{20}$ alkoxy group is a substituted or unsubstituted $C_2$-$C_{20}$ heteroaryl group, the substituted or unsubstituted $C_2$-$C_{20}$ heteroaryl group is substituted or unsubstituted pyrrolyl, substituted or unsubstituted furyl, substituted or unsubstituted thienyl, substituted or unsubstituted pyrazolyl, substituted or unsubstituted imidazolyl, substituted or unsubstituted oxazolyl, substituted or unsubstituted thiazolyl, substituted or unsubstituted isoxazolyl, substituted or unsubstituted pyridinyl, substituted or unsubstituted pyridazinyl, substituted or unsubstituted pyrimidinyl, or substituted or unsubstituted pyrazinyl;

and/or when $R^1$, $R^2$, $R^3$, $R^4$ and $R^5$ are each independently a substituted or unsubstituted $C_1$-$C_{20}$ alkoxy group, and the substituent in the substituted or unsubstituted $C_1$-$C_{20}$ alkoxy group is a $C_1$-$C_{20}$ alkoxy group, the $C_1$-$C_{20}$ alkoxy group is methoxy, ethoxy or propoxy;

and/or when $R^1$, $R^2$, $R^3$, $R^4$ and $R^5$ are each independently a substituted or unsubstituted $C_1$-$C_{20}$ alkoxy group, and the substituent in the substituted or unsubstituted $C_1$-$C_{20}$ alkoxy group is a $C_1$-$C_{20}$ alkyl group, the $C_1$-$C_{20}$ alkyl group is a $C_1$-$C_3$ alkyl group;

and/or

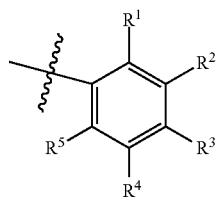

has a structure selected from:

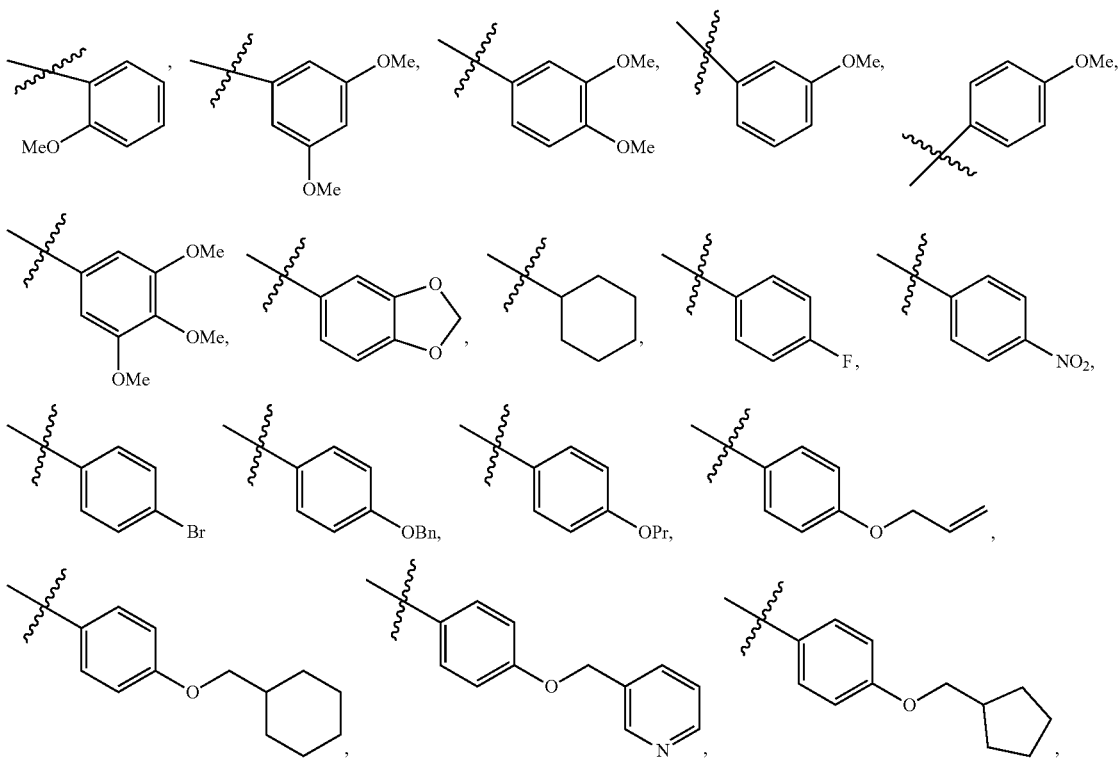

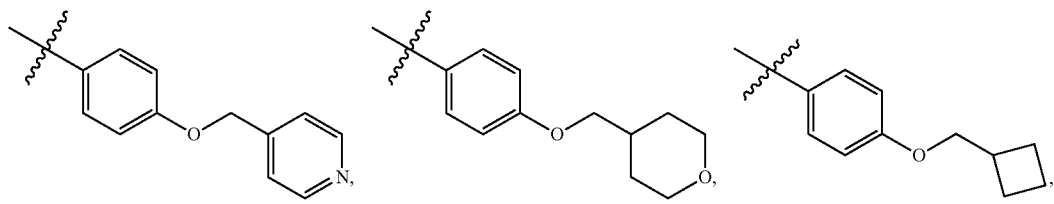
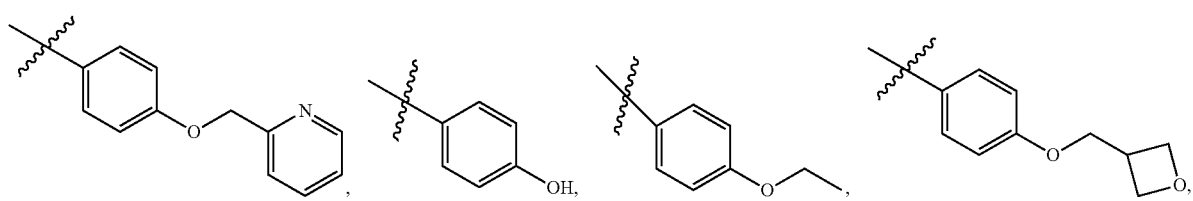
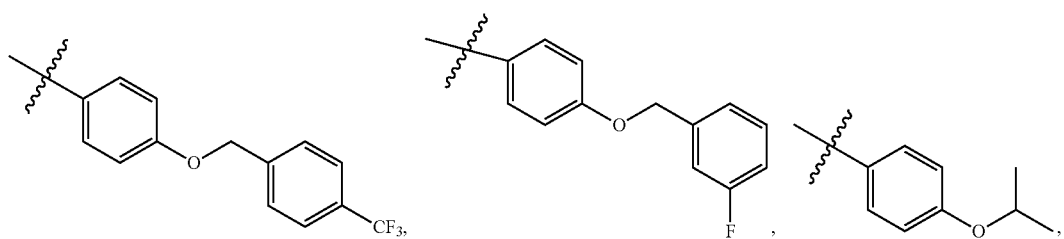
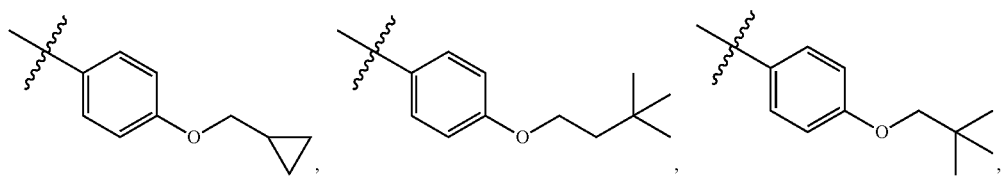
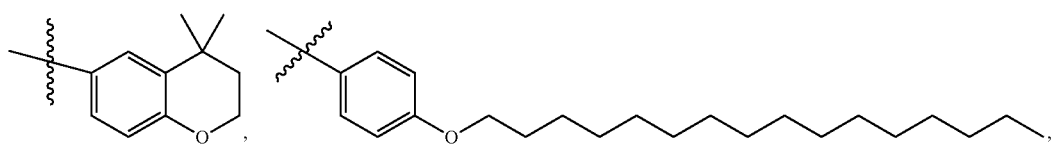
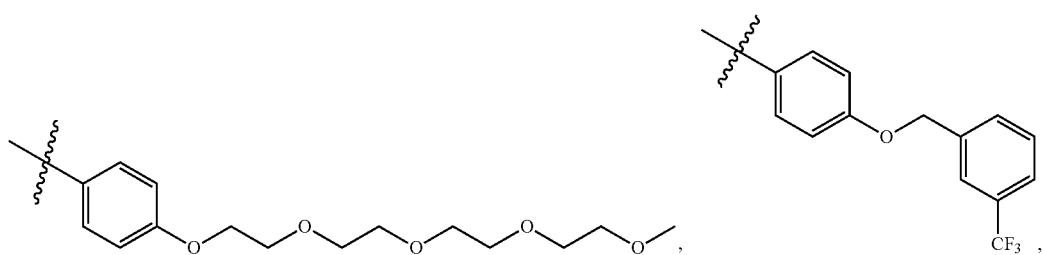

-continued

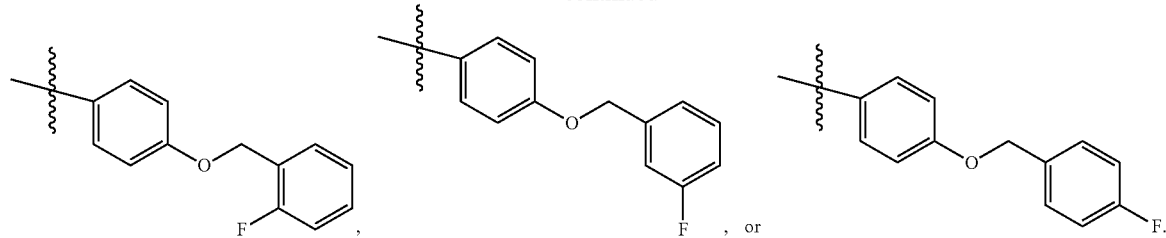

6. The glycoside compound according to claim 1, wherein $R^1$ is hydrogen;

and/or $R^3$ is hydrogen, mercapto, a substituted or unsubstituted $C_1$-$C_{20}$ alkoxy group, hydroxyl, nitro or halo;
and/or $R^4$ is hydrogen, or a substituted or unsubstituted $C_1$-$C_{20}$ alkoxy group;
and/or $R^5$ is hydrogen;
and/or X is $CH_2$; and Y is $CH_2$, $NR^8$, S or O, in which $R^8$ is hydrogen, an aryl-substituted alkoxycarbonyl group or an alkoxycarbonyl group;
and/or X is $NR^7$; and Y is $CH_2$, in which $R^7$ is hydrogen, an aryl-substituted alkoxycarbonyl group or an alkoxycarbonyl group;
and/or X is O or S, and Y is $CH_2$;
and/or $R^6$ is hydrogen;

and/or the optical isomer of

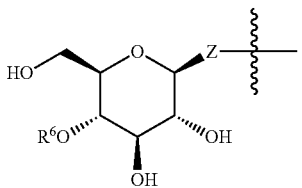

in the compound represented by Formula I is:

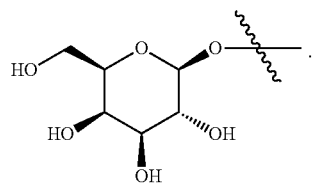 [SMILES: *O[C@@H]1O[C@H](CO)[C@H](O)[C@H](O)[C@H]1O]

7. A glycoside compound selected from:

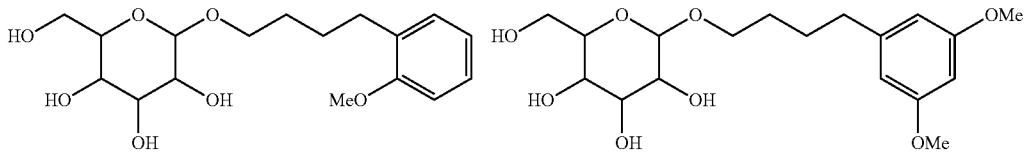

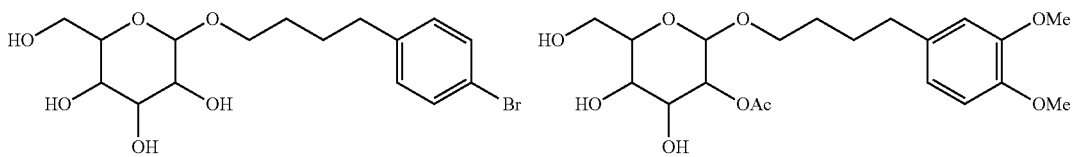

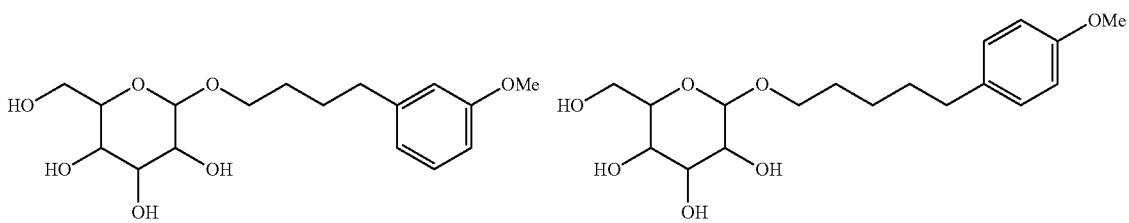

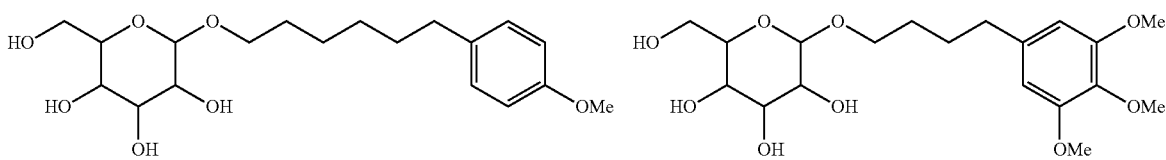

-continued
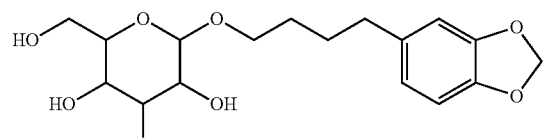
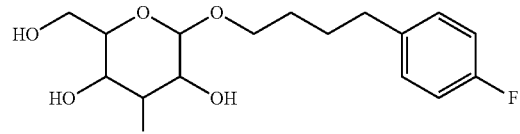
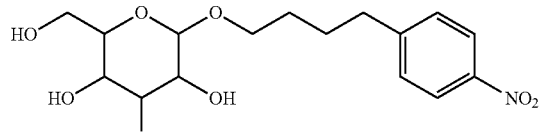
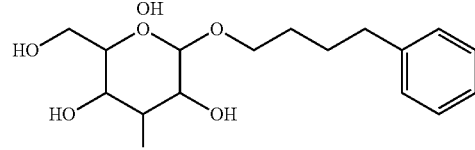
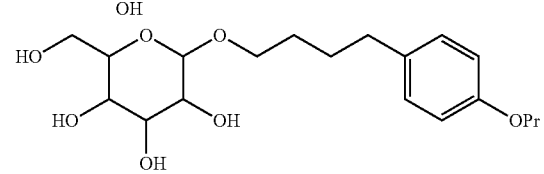
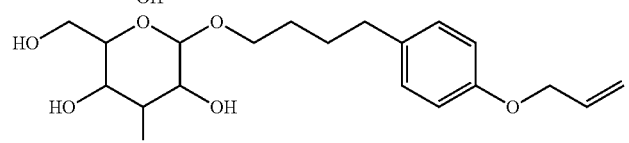
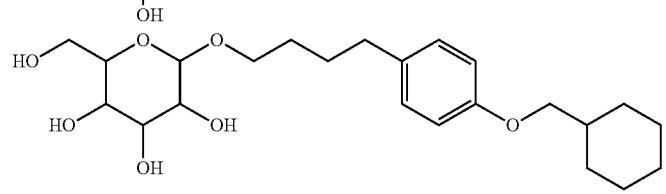
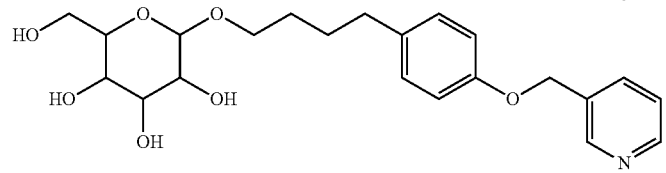
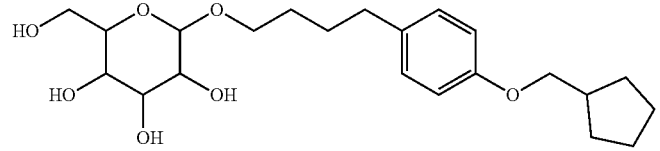
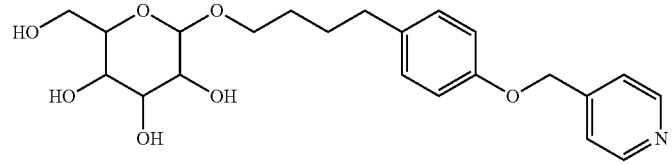
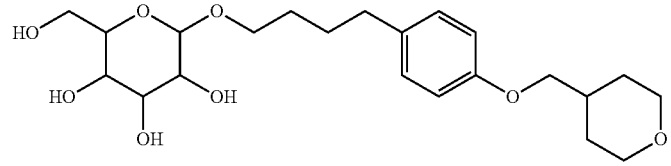
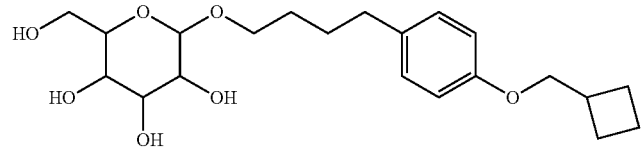
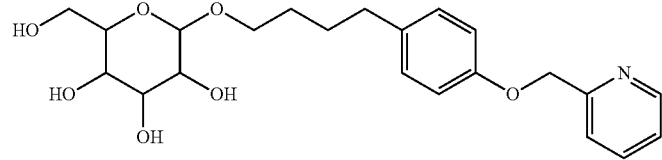

131
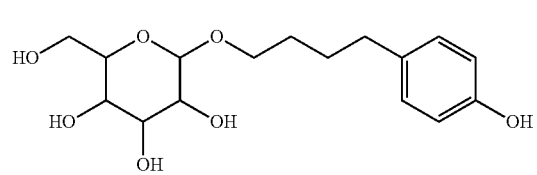
132
-continued
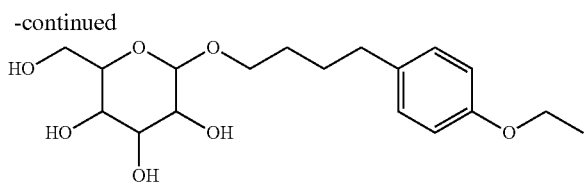
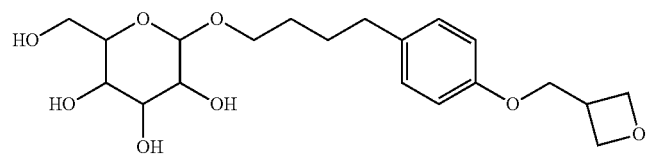
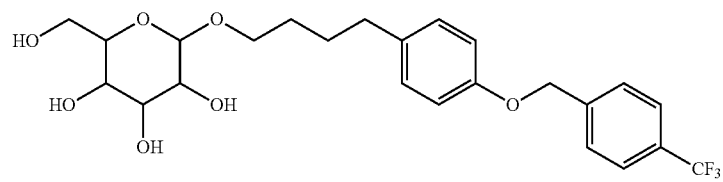
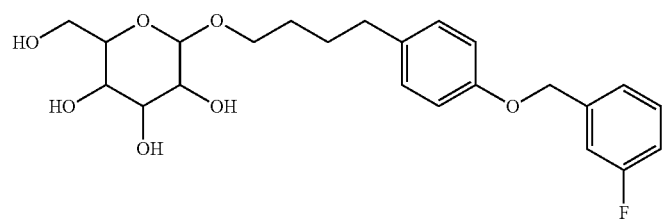
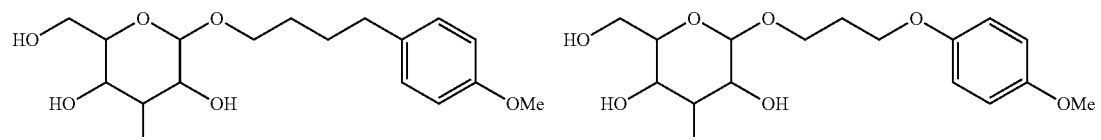
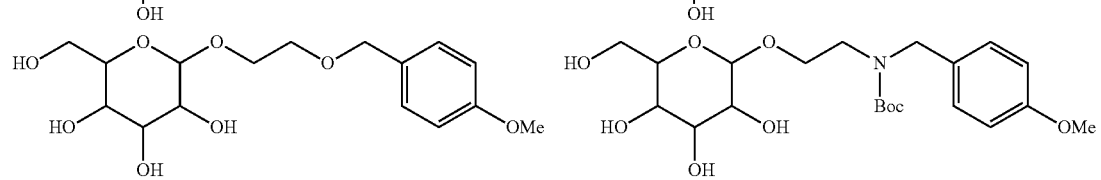
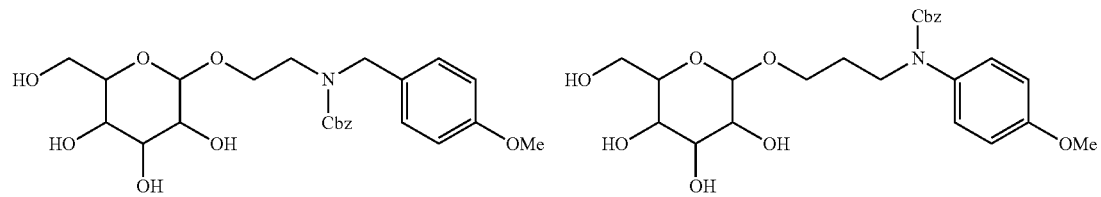
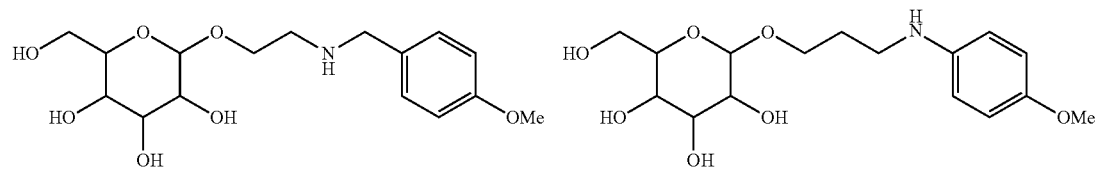
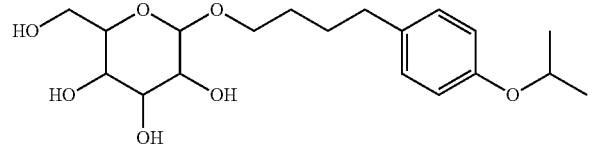
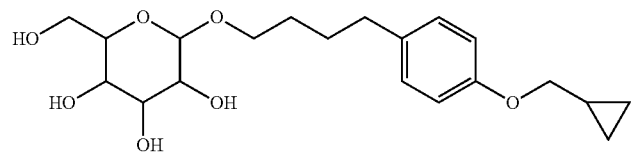

133
-continued
134
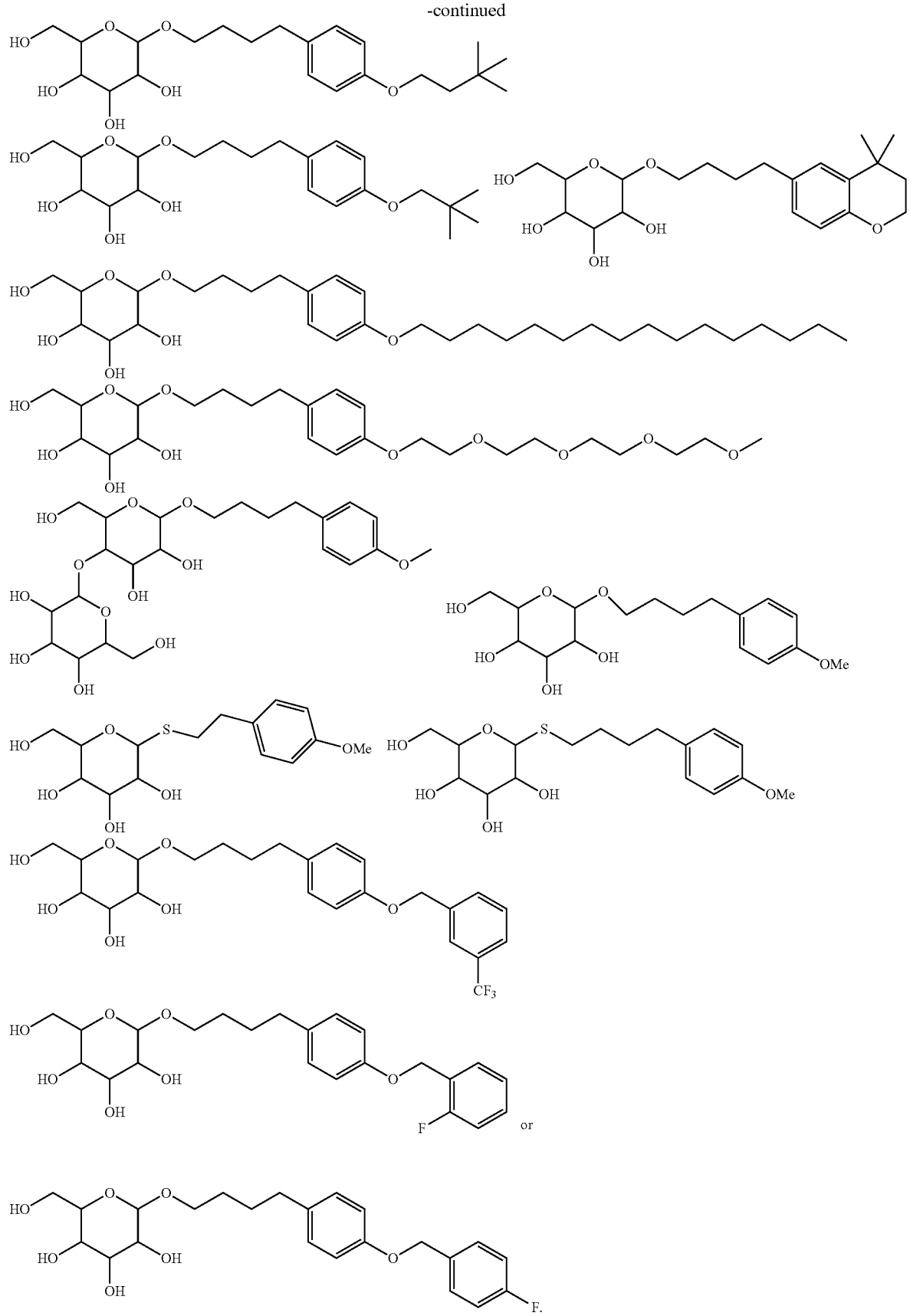

8. A glycoside compound selected from:
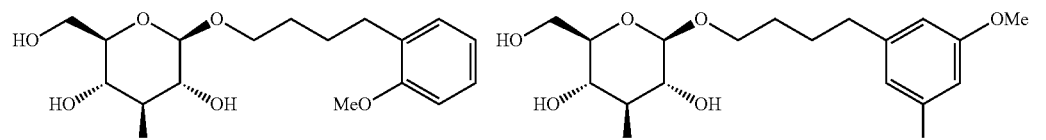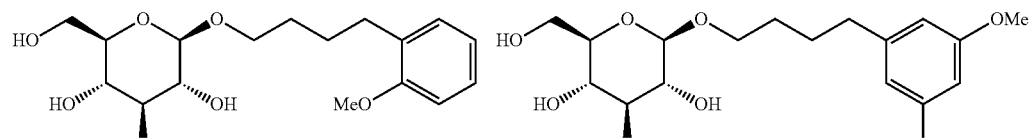
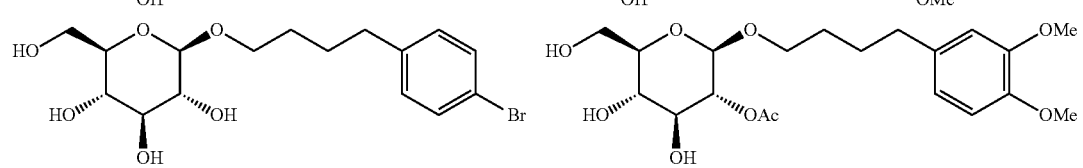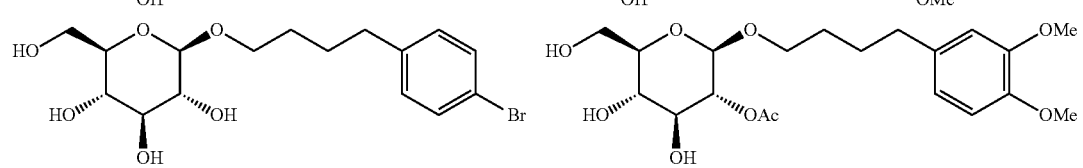
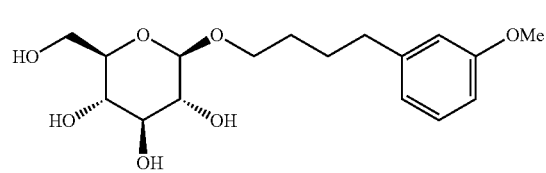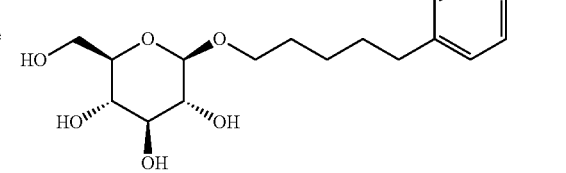
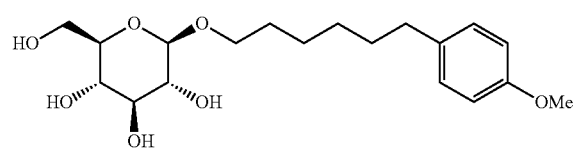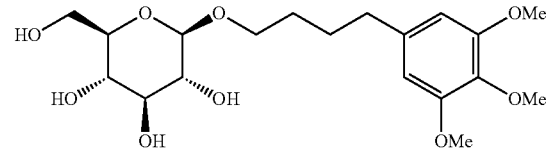
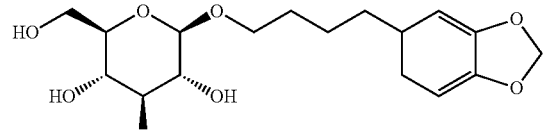
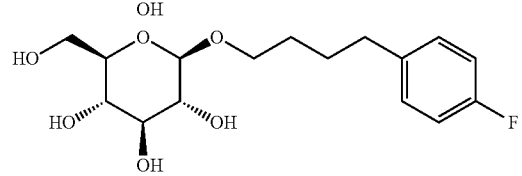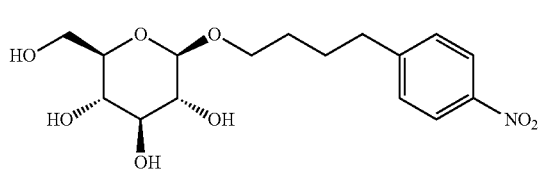
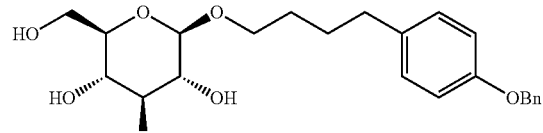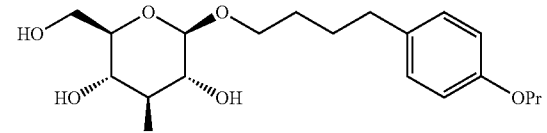
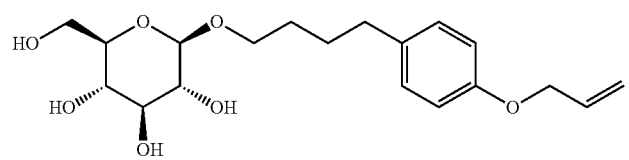
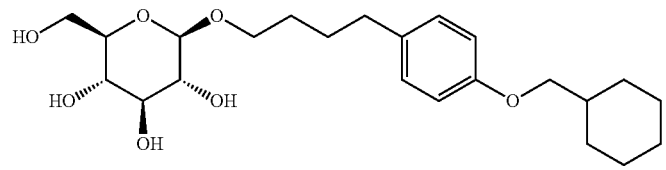
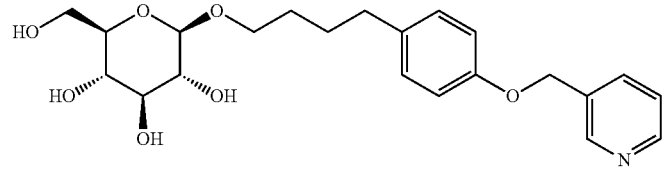

137 138
-continued
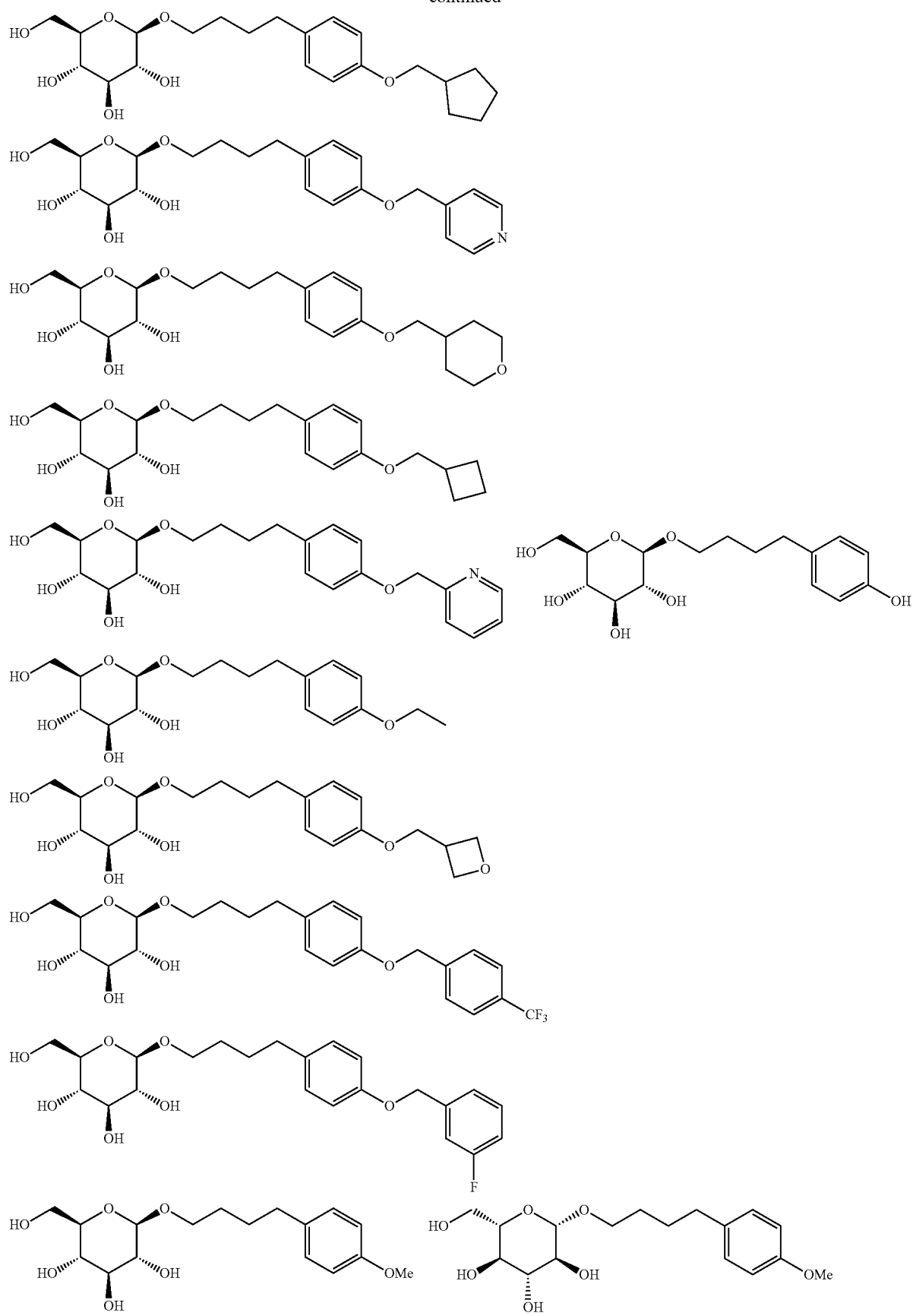

139
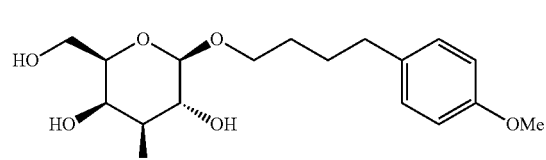
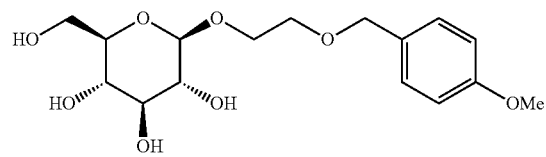
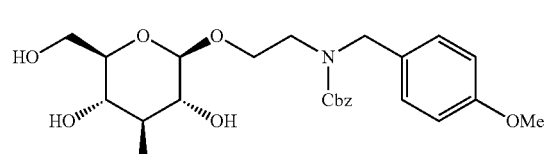
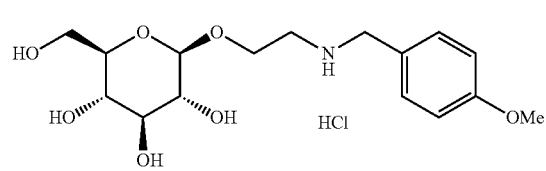
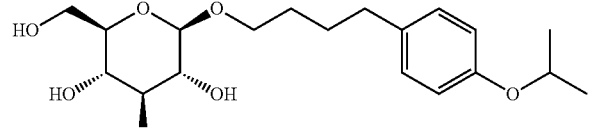
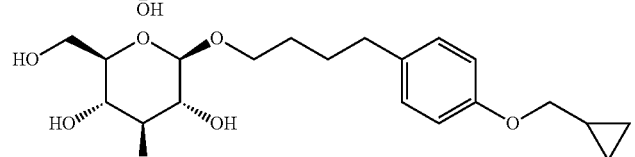
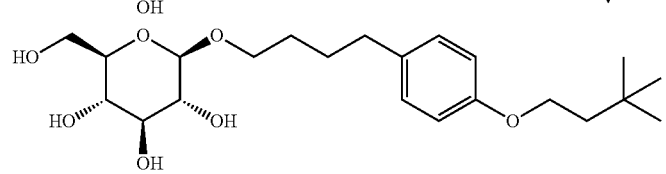
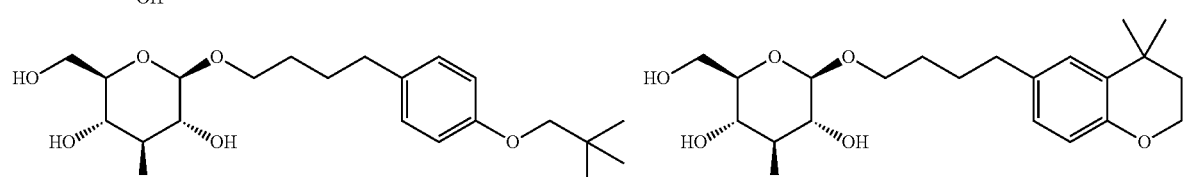
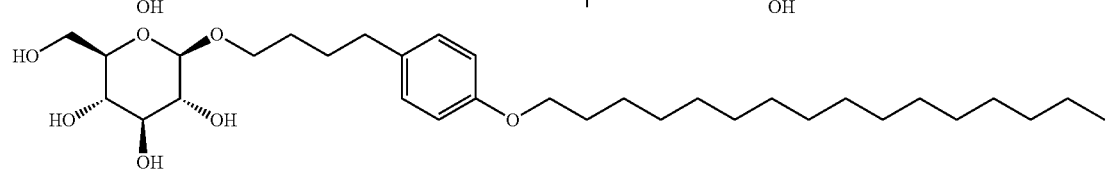
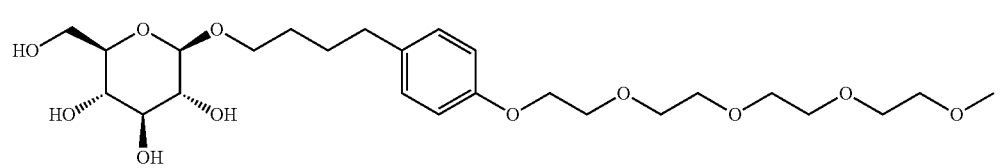
140
-continued
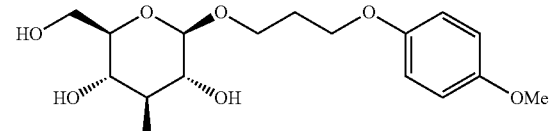
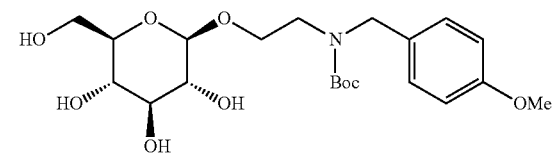
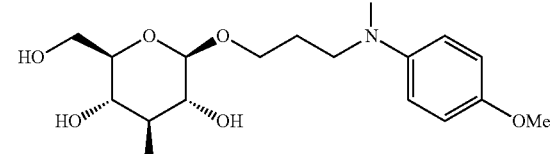
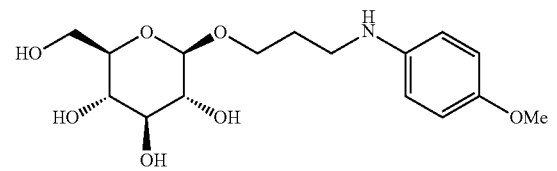

-continued

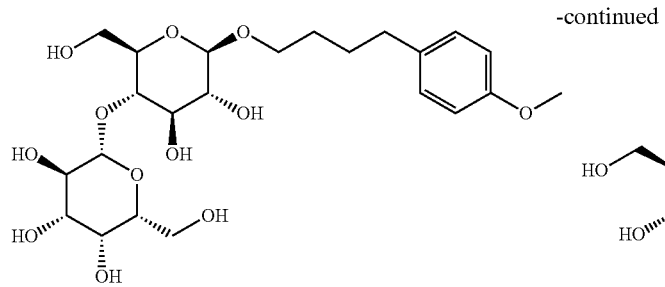
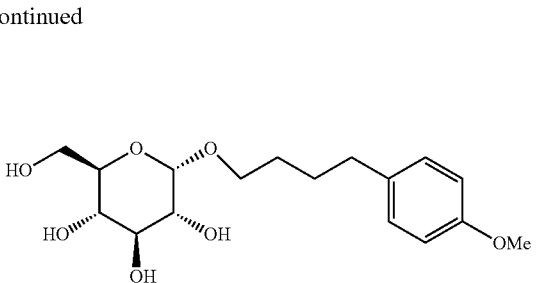
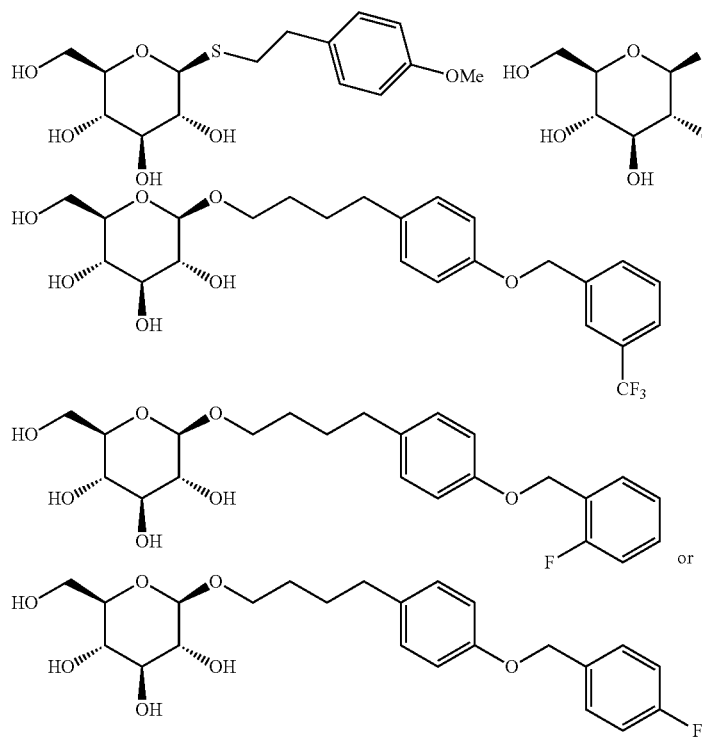
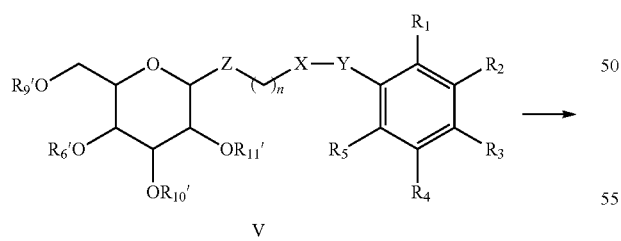
or
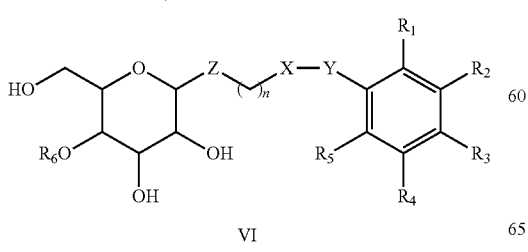

9. A method for preparing a glycoside compound according to claim 1, comprising the steps of: reducing a compound represented by Formula V in a solvent to obtain a compound represented by Formula VI:

where $R^{9'}$, $R^{10'}$ and $R^{11'}$ are each independently hydrogen or Ac, and at least one of them is Ac; $R^{6'}$ is hydrogen, Ac or

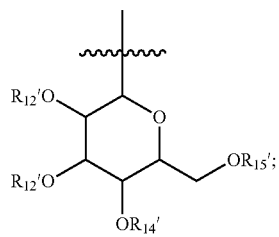

$R^{12'}$, $R^{13'}$, $R^{14'}$, and $R^{15'}$ are each independently hydrogen, Bz or Ac; when $R^{6'}$ is hydrogen or Ac, $R^6$ is hydrogen; and when $R^{6'}$ is

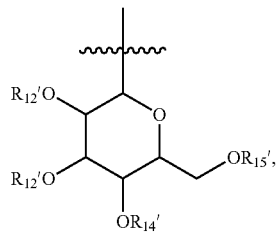

$R^6$ is

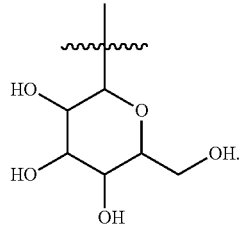 [SMILES: *C1OC(CO)C(O)C(O)C1O]

10. A method for preparing a glycoside compound according to claim 1, comprising the steps of: reducing a compound represented by Formula II in a solvent to obtain a compound represented by Formula I:

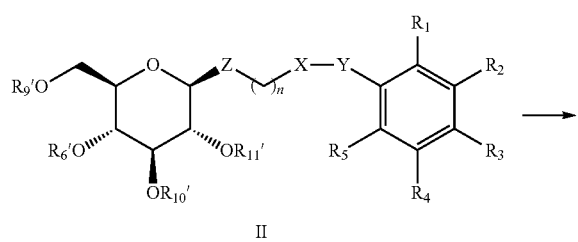

II

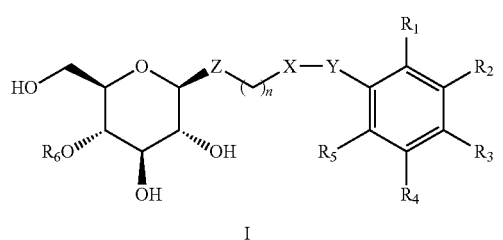

I where $R^{9'}$, $R^{10'}$ and $R^{11'}$ are each independently hydrogen or Ac, and at least one of them is Ac; $R^{6'}$ is hydrogen, Ac

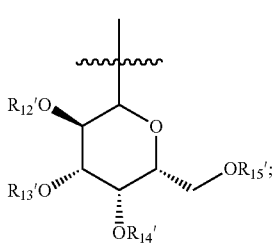

$R^{12'}$, $R^{13'}$, $R^{14'}$, and $R^{15'}$ are each independently hydrogen, Bz or Ac; when $R^{6'}$ is hydrogen or Ac, $R^6$ is hydrogen; and when $R^{6'}$ is

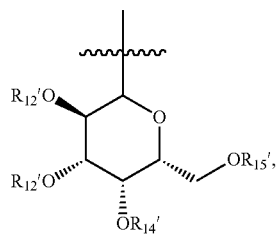

$R^6$ is

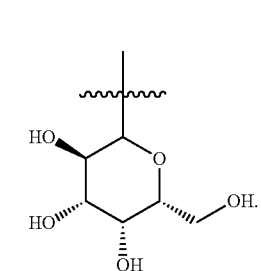 [SMILES: *C1O[C@H](CO)[C@H](O)[C@H](O)[C@H]1O]

11. A method to prepare a pro-angiogenic drug with a glycoside compound according to claim 1; or a compound selected from:

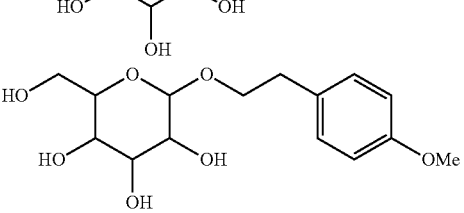

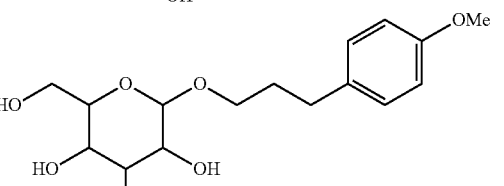

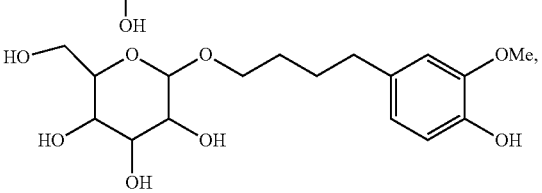

the method comprising combining a therapeutically effective amount of the compound with a pharmaceutically acceptable excipient or carrier.

12. A method to prepare a pro-angiogenic drug with a glycoside compound according to claim 1; or a compound selected from:

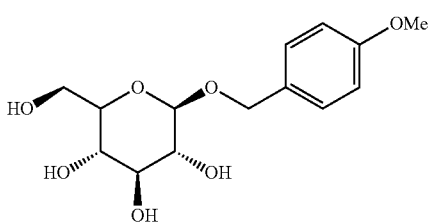

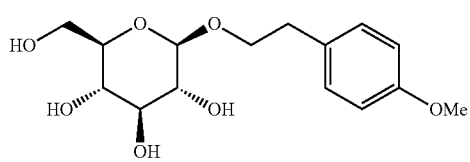

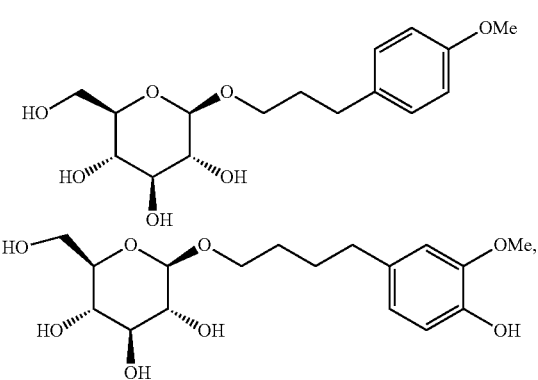

the method comprising combining a therapeutically effective amount of the compound with a pharmaceutically acceptable excipient or carrier.

13. A method to prepare drugs for treating ischemic cardio-cerebrovascular diseases and ischemic microcirculatory disturbance of lower limbs, with a glycoside compound according to claim 1, or a compound selected from:

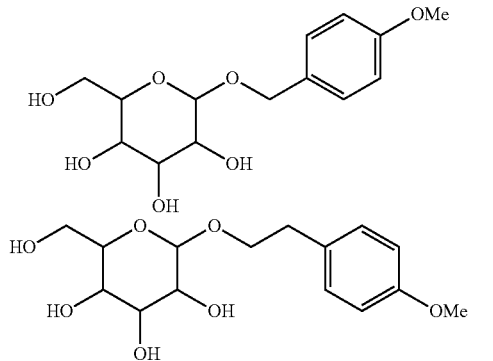

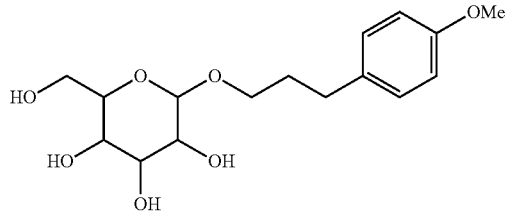

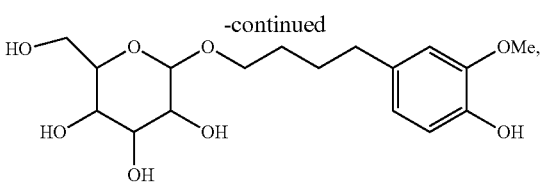

the method comprising combining a therapeutically effective amount of the compound with a pharmaceutically acceptable excipient or carrier.

14. A method to prepare drugs for treating ischemic cardio-cerebrovascular diseases and ischemic microcirculator disturbance of lower limbs, with a glycoside compound represented by Formula I according to claim 2, or a compound selected from:

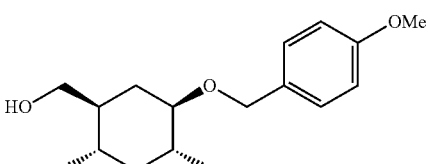

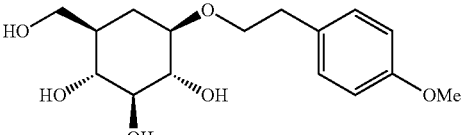

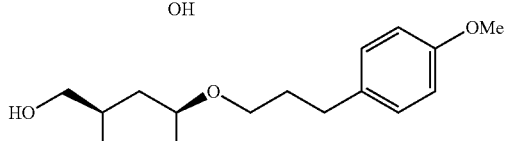

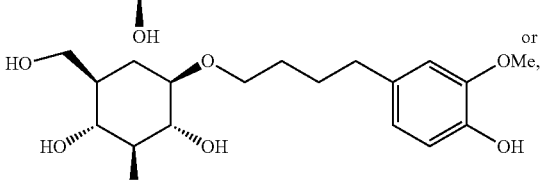

the method comprising combining a therapeutically effective amount of the compound with a pharmaceutically acceptable excipient or carrier.

15. A method for treating ischemic cardio-cerebrovascular diseases and ischemic microcirculatory disturbance of lower limbs comprising administering the glycoside compound of claim 1 to a patient.

16. The method according to claim 15, wherein the treatment comprises administering, as a sole active ingredient, the glycoside compound.

17. The method according to claim 15, wherein the treatment comprises administering in a combined therapy an additional therapeutic agent selected from the group consisting of another glycoside compound, antihypertensive drugs, lipid-lowering drugs, thrombolytic drugs, platelet aggregation inhibitors, anticoagulants, neuroprotective drugs, calcium antagonists, glutamate antagonists, glutamate release inhibitors, GABA receptor agonists, free radical scavengers, and cell membrane stabilizers.

18. The method according to claim 17, wherein the additional therapeutic agent is selected from the group consisting of Reteplase, Lanoteplase, Monteplase, Douchi Fibrinolytic Enzyme, new earthworm fibrinolytic enzyme, Nattokinase, snake venom plasminogen activator, Aspirin, Ticlopidine, Clopidogrel, Prasugrel, Ticagrelor, Cangrelor, sarpogrelate hydrochloride, vorapaxar, atopaxar, heparin, low molecular weight heparin, warfarin, Rivaroxaban, Bivalirudin, Pradaxa, Edaravone, and Statins.

19. The method according to claim 17, wherein the combined therapy further comprises simultaneously, sequentially or separately administering the glycoside compound, and the additional therapeutic agent, to a subject.

20. The method according to claim 14, wherein the pharmaceutically acceptable prodrug or derivative thereof is in the form of tablets, granules, injections, gels, pills, capsules, suppositories, implants, or nano-preparations.

21. An intermediate represented by a formula below:

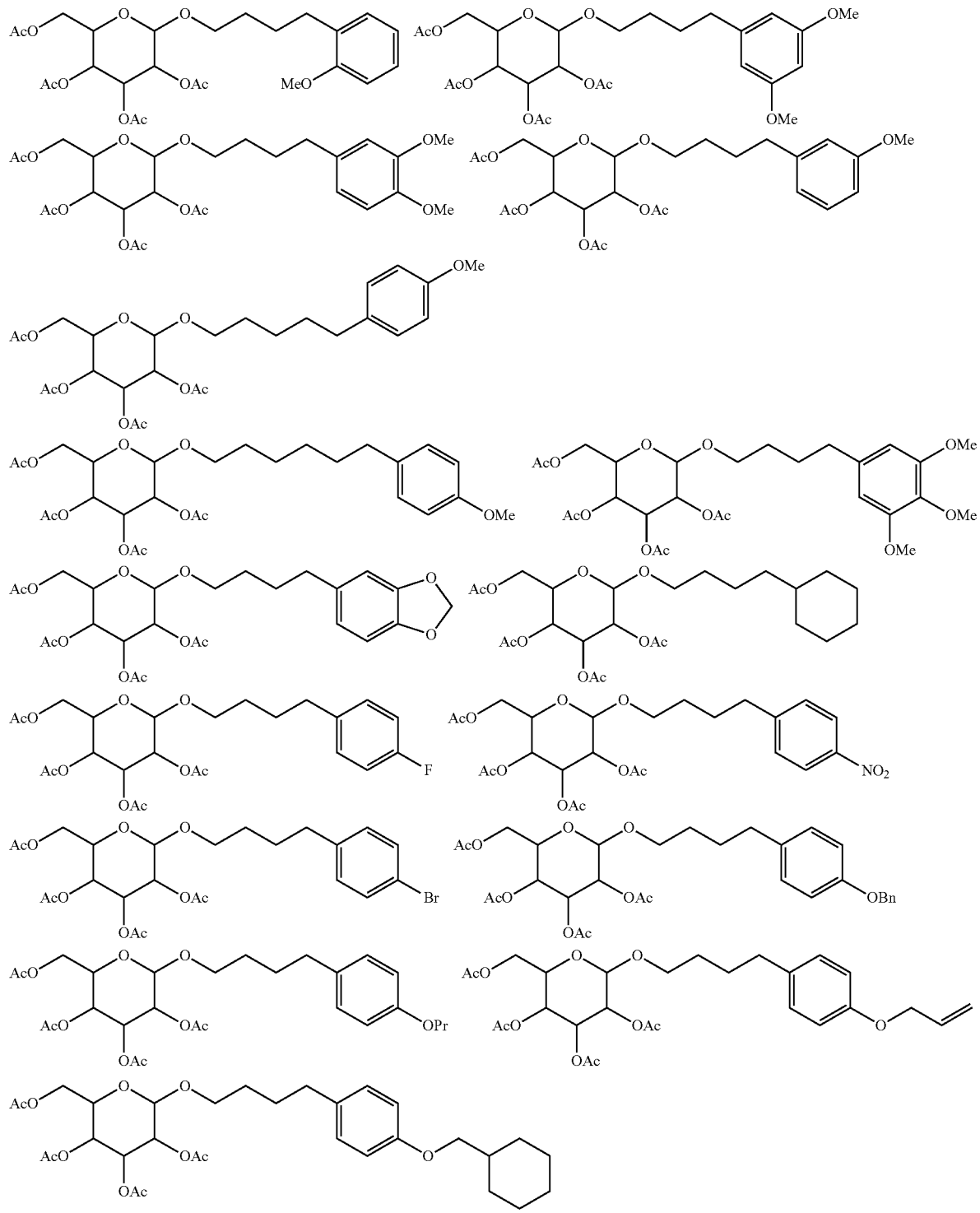

-continued
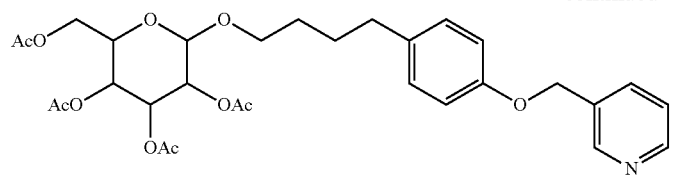
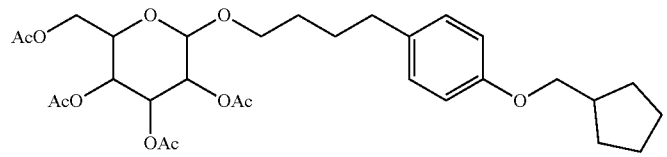
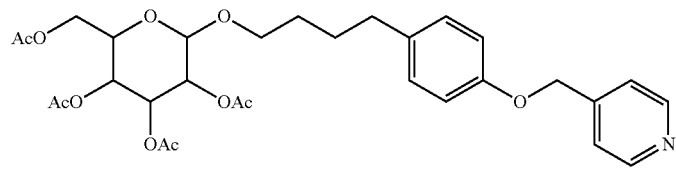
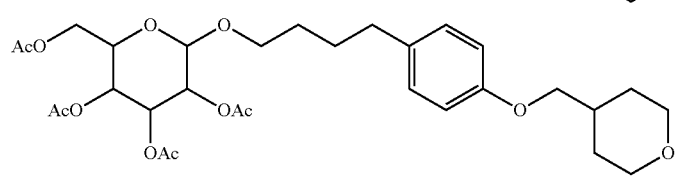
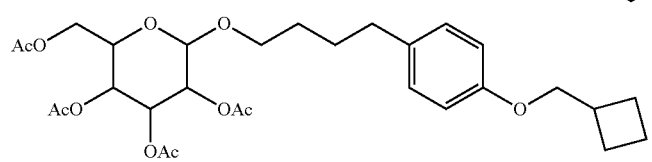
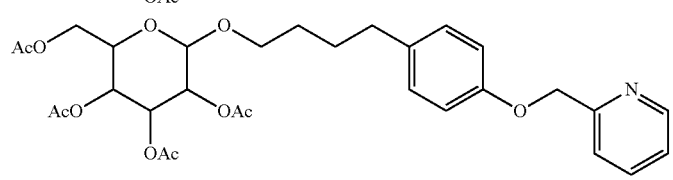
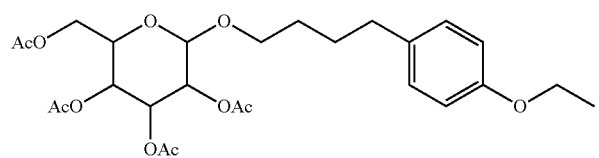
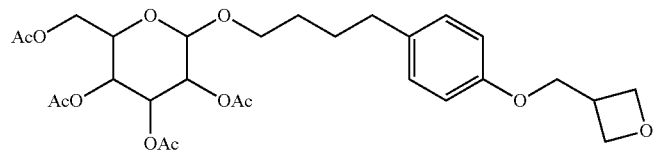
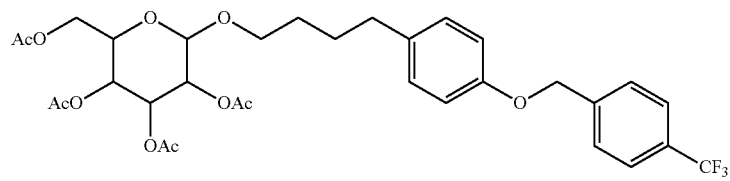
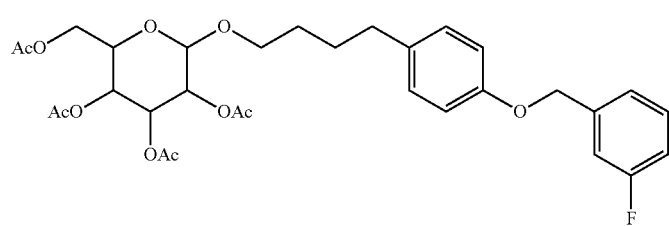

-continued
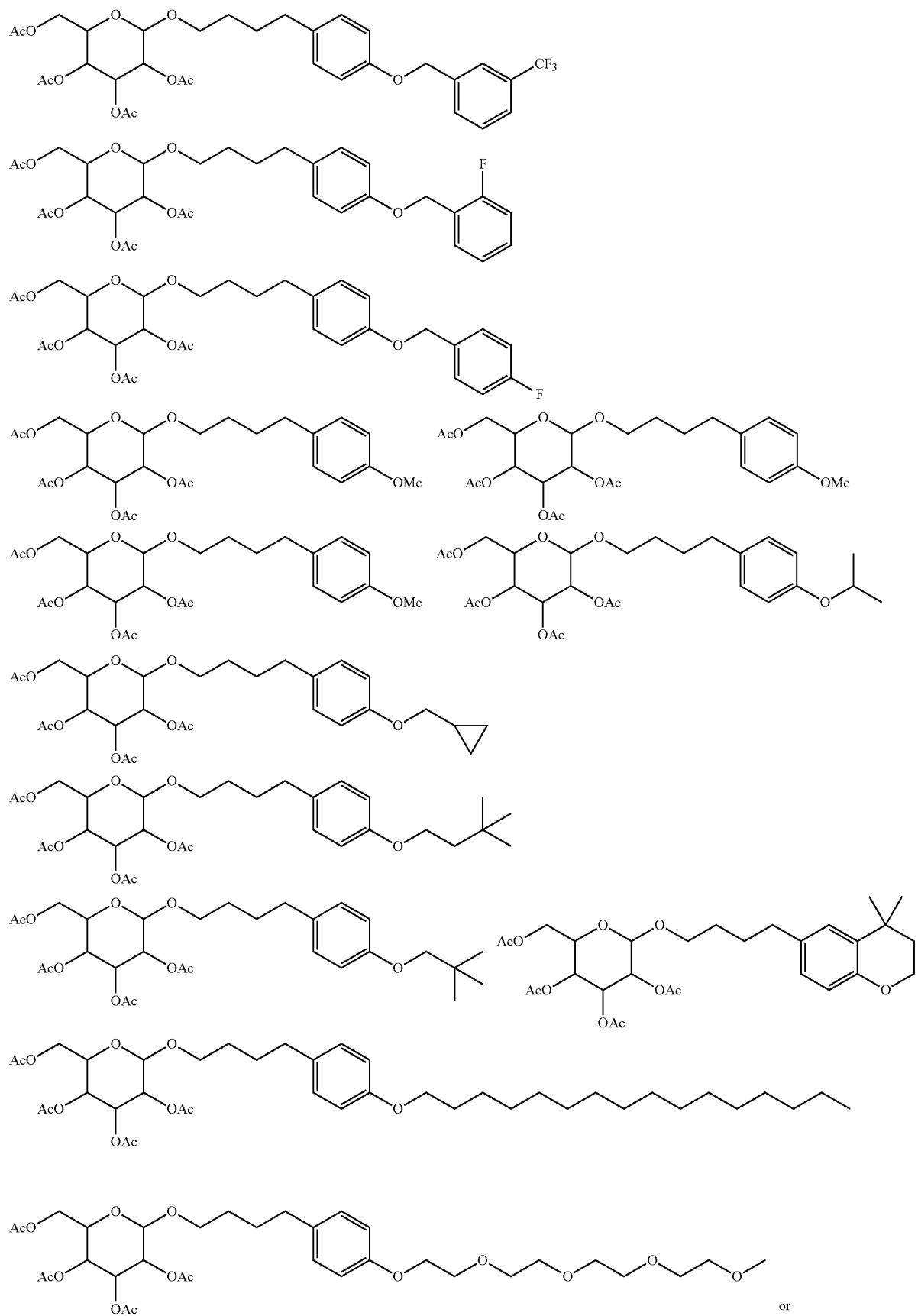
or

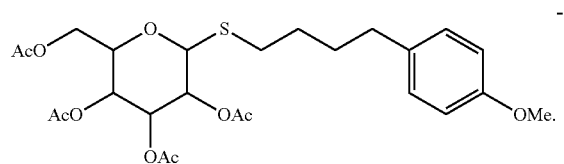
22. An intermediate represented by a formula below:
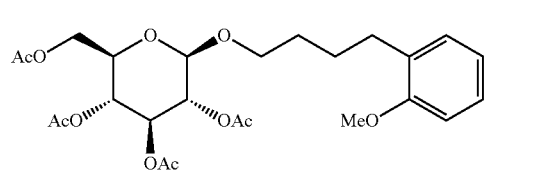 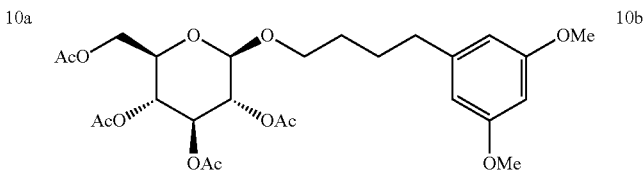
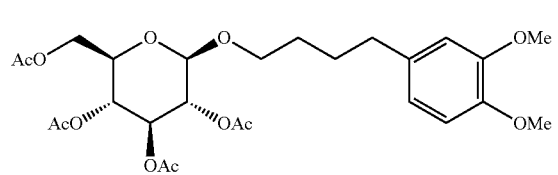 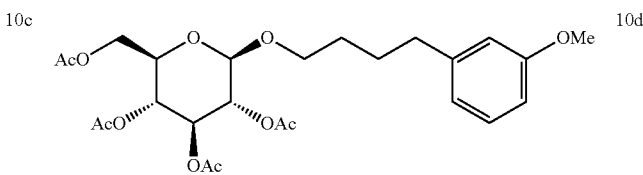
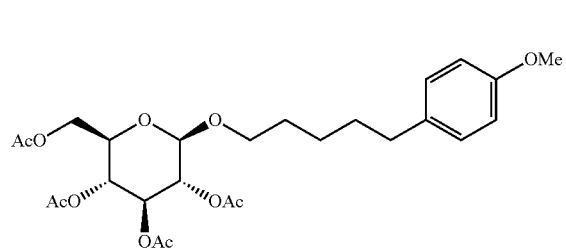 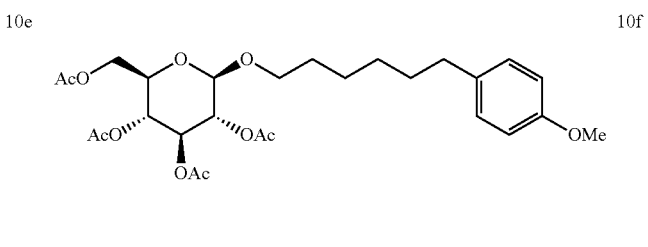
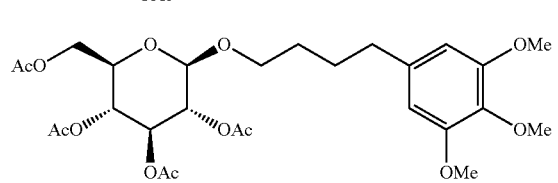 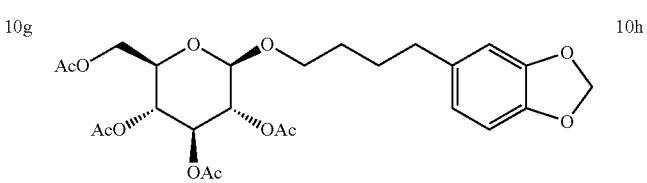
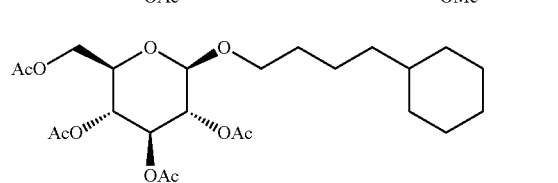 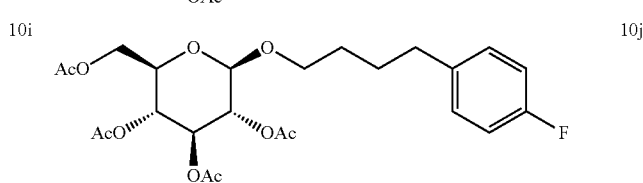
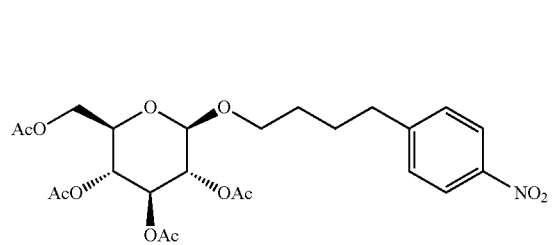 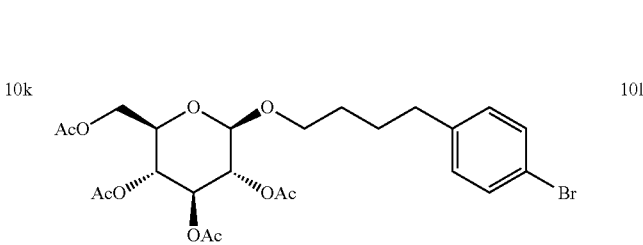
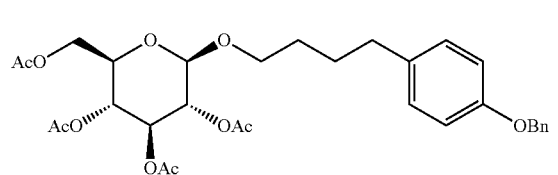 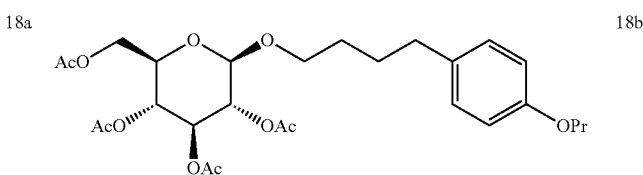

-continued
| 18c | 18d |
|---|---|
| 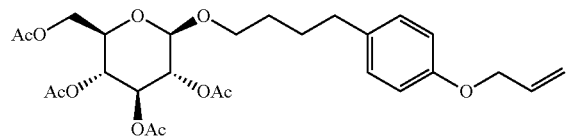 | 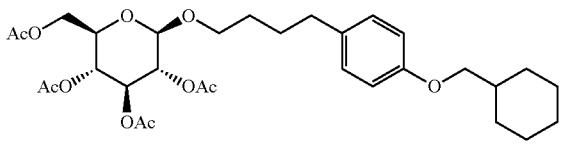 |
| 18e | 18f |
| 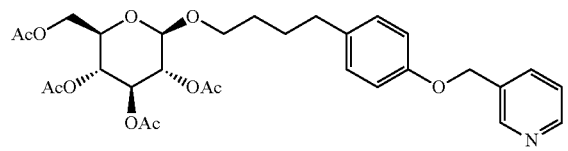 | 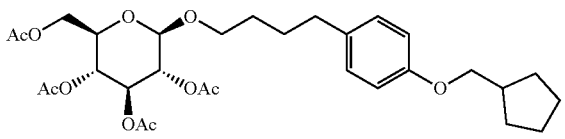 |
| 18g | 18h |
| 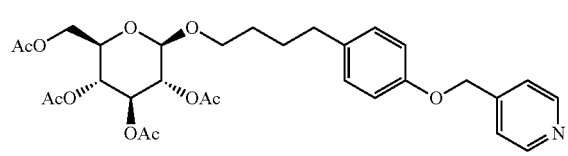 | 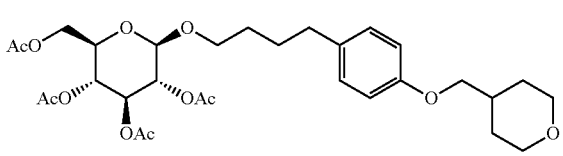 |
| 18i | 18j |
| 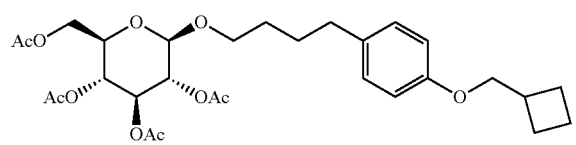 | 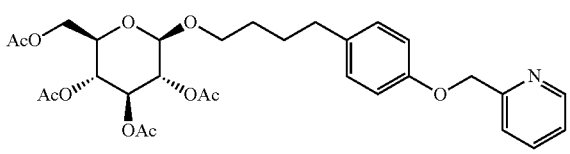 |
| 18k | 18l |
| 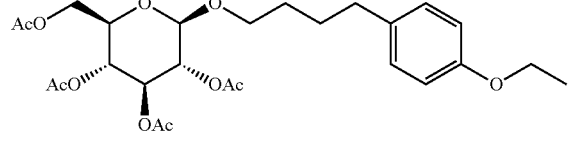 | 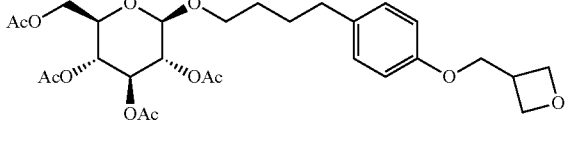 |
| 18m | 18n |
| 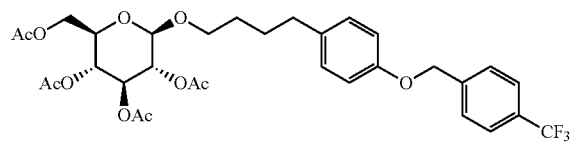 | 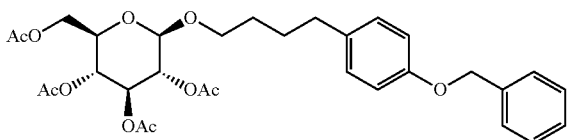 |
| 18o | 18p |
| 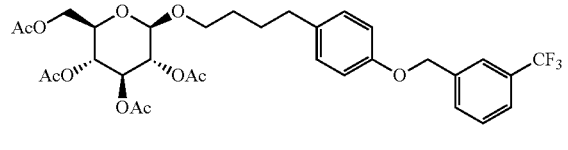 | 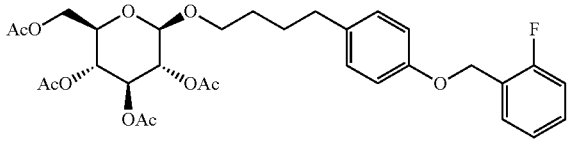 |
| 18q | 22a |
| 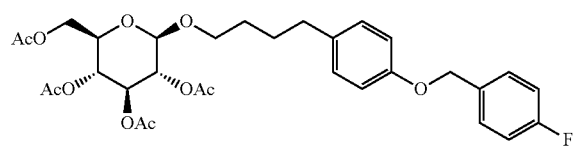 | 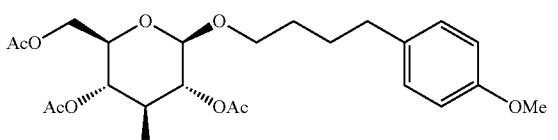 |
| 22b | 22c |
| 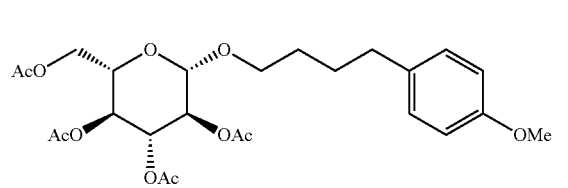 | 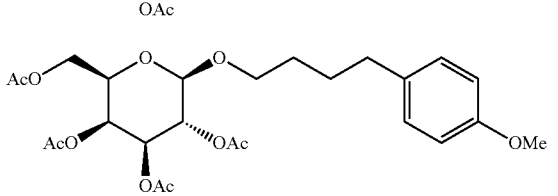 |

-continued
| | | |
|---|---|---|
| 39a 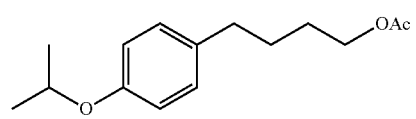 | | 39b 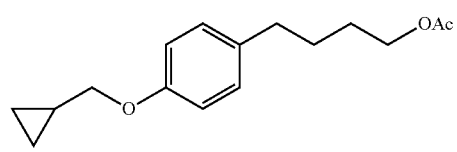 |
| 39c 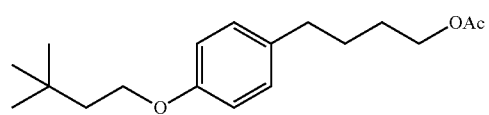 | | 39d 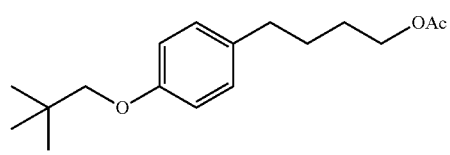 |
| 39e 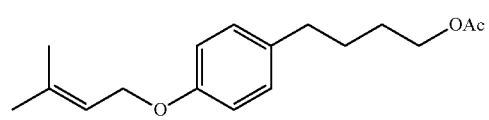 | | |
| 39f 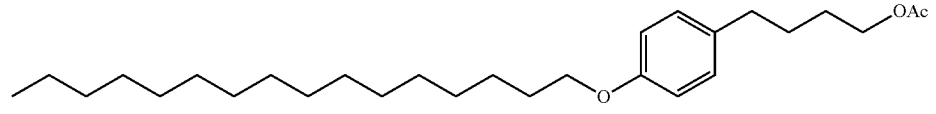 | | |
| 39g 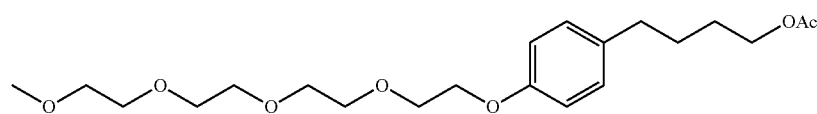 | | |
| 40b 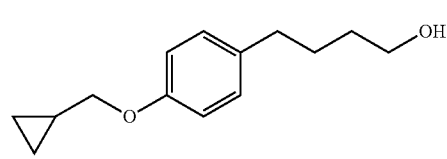 | | 40c 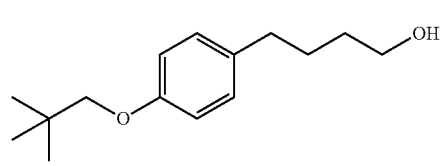 |
| 40d 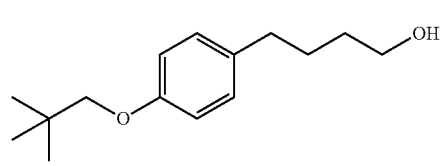 | | 40e |
| 40f 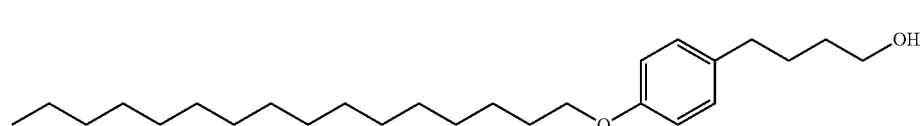 | | |
| 40g 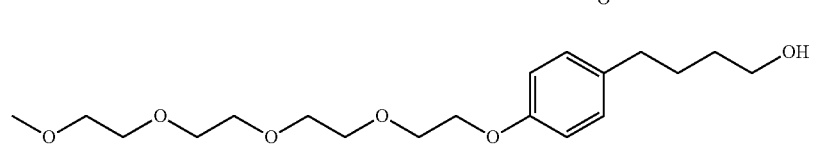 | | |
| 43a 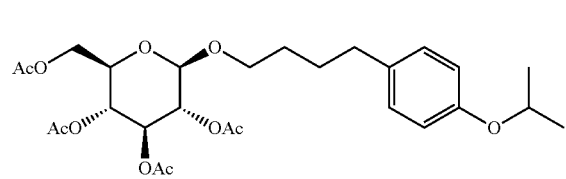 | | 43b 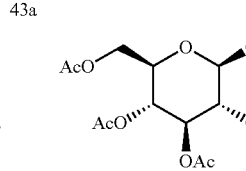 |
| 43c 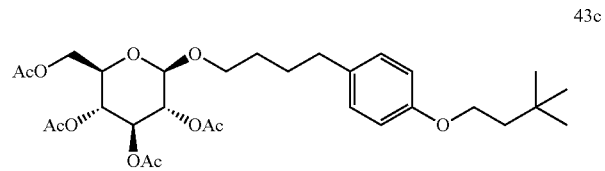 | | 43d 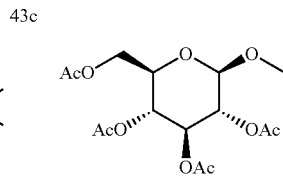 |

-continued

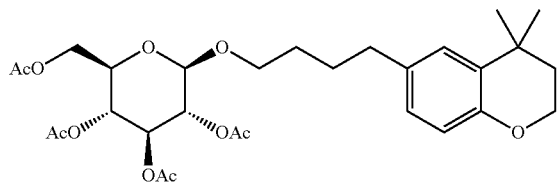

43e

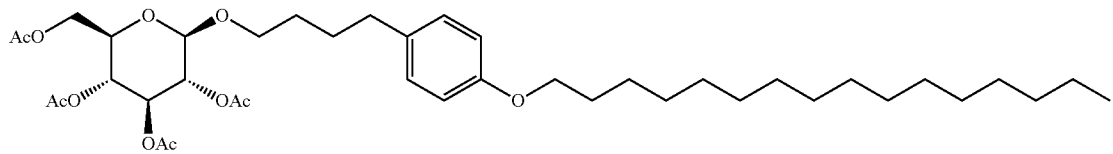

43f

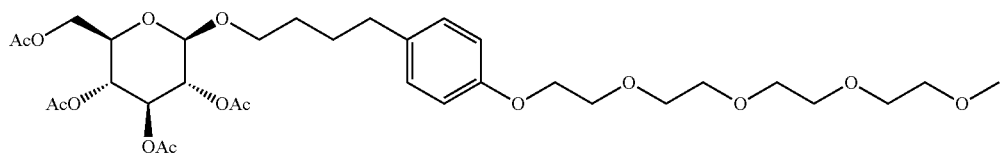

43g or

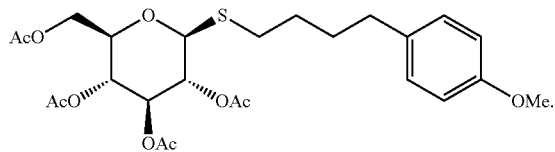

55

23. A pharmaceutical composition, comprising the glycoside compound according to claim 1, and optionally a pharmaceutically acceptable carrier and/or an additional active agent.

24. A method for promoting angiogenesis, comprising administering, to a patient, the glycoside compound according to claim 1.

25. A method for treating cardio-cerebrovascular diseases, and ischemic microcirculatory disturbance of lower limbs, comprising administering, to a patient, the glycoside compound according to claim 1.

26. A method for treating cardio-cerebrovascular diseases, and ischemic microcirculatory disturbance of lower limbs, comprising administering, to a patient, the glycoside compound represented by Formula III below:

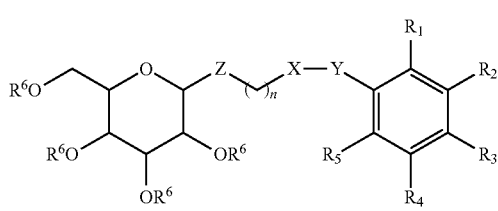

III wherein $R^1$, $R^2$, $R^4$ and $R^5$ are each independently selected from the group consisting of hydrogen, hydroxyl, mercapto, a substituted or unsubstituted $C_1$-$C_{20}$ alkoxy group, nitro or halo;

$R^3$ is selected from the group consisting of hydrogen, mercapto, a substituted or unsubstituted $C_1$-$C_{20}$ alkoxy group, nitro or halo;

or $R^2$ and $R^3$ form, together with carbon atoms on the phenyl ring to which they are attached, a 6-membered heterocyclic ring having a heteroatom that is O or S;

where the substituent in the substituted or unsubstituted $C_1$-$C_{20}$ alkoxy group is selected from the group consisting of a $C_3$-$C_{20}$ cycloalkyl group, a $C_1$-$C_{20}$ alkenyl group, a substituted or unsubstituted $C_6$-$C_{20}$ aryl group, halo, a substituted or unsubstituted $C_2$-$C_{20}$ heteroaryl group, a $C_3$-$C_6$ cycloalkoxy group, a $C_1$-$C_{20}$ alkoxy group, and a $C_1$-$C_{20}$ alkyl group, in which the substituent in the substituted or unsubstituted $C_6$-$C_{20}$ aryl group and the substituted or unsubstituted $C_2$-$C_{20}$ heteroaryl group is each independently halo or a halo-substituted $C_1$-$C_{20}$ alkyl group;

X is $CH_2$;

Y is $CH_2$;

Z is O or S;

each $R^6$ is independently hydrogen or glycosyl; and n is 2, 3 or 4, with the provision that:

when X is $CH_2$, Y is $CH_2$, and n=2, 3 or 4, $R^1$-$R^5$ are not all H;

when n=2, $R^1$, $R^4$ and $R^5$ are H, $R^2$ and $R^3$ are not both $OCH_3$ and OH;

when n=2, $R^1$, $R^2$ and $R^5$ are H, $R^3$ and $R^4$ are not both OH and $OCH_3$;

when n=2, $R^2$, $R^4$ and $R^5$ are H, $R^1$ and $R^3$ are not both OH; and when n=2, $R^1$, $R^2$ and $R^4$ are H, $R^3$ and $R^5$ are not both OH;

and optionally a pharmaceutically acceptable carrier and/or an additional active agent.

27. A method for promoting angiogenesis, comprising administering, to a patient, the glycoside compound represented by Formula III below:

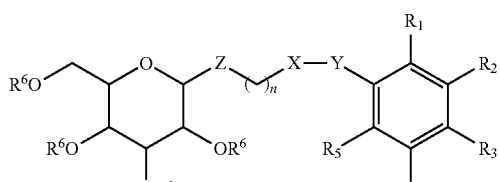

III wherein $R^1$, $R^2$, $R^4$ and $R^5$ are each independently selected from the group consisting of hydrogen, hydroxyl, mercapto, a substituted or unsubstituted $C_1$-$C_{20}$ alkoxy group, nitro or halo;

$R^3$ is selected from the group consisting of hydrogen, mercapto, a substituted or unsubstituted $C_1$-$C_{20}$ alkoxy group, nitro or halo;

or $R^2$ and $R^3$ form, together with carbon atoms on the phenyl ring to which they are attached, a 6-membered heterocyclic ring having a heteroatom that is O or S;

where the substituent in the substituted or unsubstituted $C_1$-$C_{20}$ alkoxy group is selected from the group consisting of a $C_3$-$C_{20}$ cycloalkyl group, a $C_1$-$C_{20}$ alkenyl group, a substituted or unsubstituted $C_6$-$C_{20}$ aryl group, halo, a substituted or unsubstituted $C_2$-$C_{20}$ heteroaryl group, a $C_3$-$C_6$ cycloalkoxy group, a $C_1$-$C_{20}$ alkoxy group, and a $C_1$-$C_{20}$ alkyl group, in which the substituent in the substituted or unsubstituted $C_6$-$C_{20}$ aryl group and the substituted or unsubstituted $C_2$-$C_{20}$ heteroaryl group is each independently halo or a halo-substituted $C_1$-$C_{20}$ alkyl group;

X is $CH_2$;
Y is $CH_2$;
Z is O or S;
each $R^6$ is independently hydrogen or glycosyl; and
n is 2, 3 or 4,
with the provision that:
when X is $CH_2$, Y is $CH_2$, and n=2, 3 or 4, $R^1$-$R^5$ are not all H;
when n=2, $R^1$, $R^4$ and $R^5$ are H, $R^2$ and $R^3$ are not both $OCH_3$ and OH;
when n=2, $R^1$, $R^2$ and $R^5$ are H, $R^3$ and $R^4$ are not both OH and $OCH_3$;
when n=2, $R^2$, $R^4$ and $R^5$ are H, $R^1$ and $R^3$ are not both OH; and
when n=2, $R^1$, $R^2$ and $R^4$ are H, $R^3$ and $R^5$ are not both OH;
and optionally a pharmaceutically acceptable carrier and/or an additional active agent.

28. The method according to claim 15, wherein the ischemic cerebrovascular diseases are selected from cerebral stroke, atherosclerotic cerebral thrombosis, cardiogenic cerebral embolism, acute ischemic cerebrovascular syndrome, small vessel disease, multiple cerebral infarction, massive cerebral infarction, cerebral watershed infarction, hemorrhagic infarction, asymptomatic cerebral infarction, cerebral venous and cerebral venous sinus thrombosis, Moyamoya disease, and ischemic cerebral stroke due to other causes.

* * * * *